US008815875B2

(12) United States Patent
Shipps, Jr. et al.

(10) Patent No.: US 8,815,875 B2
(45) Date of Patent: Aug. 26, 2014

(54) INHIBITORS OF FATTY ACID BINDING PROTEIN (FABP)

(75) Inventors: Gerald W. Shipps, Jr., Stoneham, MA (US); Cliff C. Cheng, Cambridge, MA (US); Xiaohua Huang, Malden, MA (US); Abdelghani Abe Achab, Melrose, MA (US); Peter Orth, Maplewood, NJ (US); Johannes H. Voigt, Cranford, NJ (US); Kyle Ann Soucy, Dracut, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 274 days.

(21) Appl. No.: 13/128,099

(22) PCT Filed: Nov. 10, 2009

(86) PCT No.: PCT/US2009/063787
§ 371 (c)(1),
(2), (4) Date: Jun. 8, 2011

(87) PCT Pub. No.: WO2010/056631
PCT Pub. Date: May 20, 2010

(65) Prior Publication Data
US 2011/0237575 A1   Sep. 29, 2011

Related U.S. Application Data

(60) Provisional application No. 61/113,802, filed on Nov. 12, 2008.

(51) Int. Cl.
*A61K 31/519* (2006.01)

(52) U.S. Cl.
USPC .................................................. 514/259.31

(58) Field of Classification Search
USPC .................................................. 514/259.31
See application file for complete search history.

(56) References Cited

U.S. PATENT DOCUMENTS

| 2002/0077340 A1 | 6/2002 | Sulsky et al. |
| 2004/0220186 A1 | 11/2004 | Bell et al. |
| 2006/0089362 A1 | 4/2006 | Seno et al. |
| 2010/0069407 A1 * | 3/2010 | Press et al. ............... 514/259.31 |

FOREIGN PATENT DOCUMENTS

| WO | 00/15320 | 3/2000 |
| WO | 01/00185 A2 | 1/2001 |
| WO | 01/00186 | 1/2001 |
| WO | 01/54694 | 8/2001 |
| WO | 2008/057601 A2 | 5/2008 |
| WO | 2010/056630 A1 | 5/2010 |
| WO | 2011/043994 A1 | 4/2011 |

OTHER PUBLICATIONS

Search Report of Taiwan Patent Appln. 098138298, dated Jun. 21, 2012.
Allen, "Structure of certain polyazaindenes", J. Org. Chem. (1959), vol. 24, pp. 779-786.
Wagner, Database Chem. Abstr. XP002566063, "Glycosides of heterocycle, 53, Glucosides of 7-hydroxy- . . . ", database accession No. 1975:479537.
Database Chem. Abstr. XP992566964, Ryan scientific screening library, database accession No. ASN13828393, BAS12534455, BAS12534448, BAS07100587, Jan. 5, 2008.
Database Chem, Abstr. XP002566065, "New chemistry horizons laboratories screening", database accession No. ON:NCHSC3-01833, Mar. 30, 2008.
International Search Report in PCT/US2009/063787, dated Feb. 25, 2010.
Int'l Preliminary Report on Patentability of PCT/US2009/063787, dated May 17, 2011.
Lan, "Small-molecule inhibitors of FABP4/5 ameliorate dyslipidemia . . . ", J. Lipid Res. (2011), vol. 52, pp. 646-656.
van Dongen, et al., "Structure-Based Screening As Applied to Human FABP4: A Highly Efficient Alternative to HTS for Hit Generation", J. Amer. Chem. Soc., vol. 124, pp. 11874-11880 (2002).

\* cited by examiner

*Primary Examiner* — San-Ming Hui
(74) *Attorney, Agent, or Firm* — Anna L. Cocuzzo; Catherine D. Fitch

(57) ABSTRACT

The present invention relates to novel heterocyclic compounds as Fatty Acid Binding Protein ("FABP") inhibitors, pharmaceutical compositions comprising the heterocyclic compounds and the use of the compounds for treating or preventing a cardiovascular disease, a metabolic disorder, obesity or an obesity-related disorder, diabetes, dyslipidemia, a diabetic complication, impaired glucose tolerance or impaired fasting glucose. An illustrative compound of the present invention is shown below: (I)

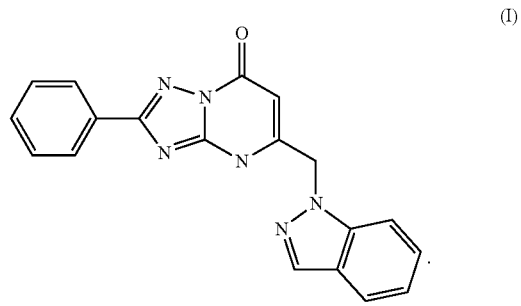

11 Claims, No Drawings

INHIBITORS OF FATTY ACID BINDING PROTEIN (FABP)

FIELD OF THE INVENTION

The present invention relates to certain triazolopyrimidinones useful as Fatty Acid Binding Protein ("FABP") inhibitors, pharmaceutical compositions containing the compounds, and methods of treatment using the compounds and compositions to treat or prevent various diseases including cardiovascular disease, metabolic disorder, dyslipedemia, obesity and diabetes (e.g., Type 2 diabetes).

BACKGROUND OF THE INVENTION

The global prevalence of obesity is increasing epidemically. Obesity causes an array of health problems, reduces life expectancy, and costs over US$100 billion annually. More than a quarter of the population suffers from an aggregation of co-morbidities, including obesity, atherosclerosis, insulin resistance, dyslipidemias, coagulapathies, hypertension, and a pro-inflammatory state known as the metabolic syndrome. Patients with metabolic syndrome have high risk of atherosclerosis as well as type 2 diabetes and other health problems. Like obesity, atherosclerosis has very limited therapeutic options.

Atherosclerosis is the leading cause of death in the United States. At the core of this syndrome is the dysregulation of lipid metabolism and aberrant inflammatory responses. Although mechanistic roles for fatty acids have been put forward in the formation of obesity and diabetes by modifying glucose and lipid metabolism as well as inflammatory cascades, little is known about the mechanisms that link fatty acids or other lipid signals to inflammatory responses and the formation of atherosclerotic lesions. The biology of fatty acid binding proteins (FABPs) in several mouse models with targeted mutations in adipocyte/macrophage isoforms of these proteins has been investigated. Although serum fatty acid levels are not reduced in these FABP-deficient models, they are strikingly and paradoxically protected from obesity, insulin resistance, type 2 diabetes, fatty liver disease and atherosclerosis. This phenotype emphasizes the fact that total fatty acids may not be the primary pathogenic indicator, and that individual fatty acid or metabolite action at the intracellular level and the specific responses evoked by these signals are more relevant to the pathophysiology and outcomes of atherosclerotic disease than parameters classically measured.

Lipids and lipid signals are critical in the integration of metabolic and integration of metabolic and inflammatory response systems and consequently play significant parts in the pathogenesis of a cluster of chronic metabolic diseases, including type 2 diabetes, fatty liver disease and atherosclerosis. However, how lipids couple to target signaling pathways or metabolic processes and how their intracellular trafficking is regulated are poorly understood. Cytoplasmic fatty-acid-binding proteins (FABPs) are a family of 14-15-kDa proteins that bind with high affinity to hydrophobic ligands such as saturated and unsaturated long-chain fatty acids and eicosanoids such as hydroxyeicosatetra-enoic acid, leukotrienes and prostaglandins. The adipocyte FABP, aP2 (FABP4), is highly expressed in adipocytes and regulated by peroxisome-proliferator-activated receptor-γ (PPAR γ) agonists, insulin and fatty acids.

Impared insulin action at its target tissues, a phenomenon termed insulin resistance, is typical in obesity, type 2 diabetes, and associated atherosclerosis but also occurs during inflammatory and neoplastic processes. The development of insulin resistance has been linked to augmented availability of lipids and other nutrients. Specifically, plasma concentrations of free fatty acids (FFAs) are elevated in insulin resistance and even predict type 2 diabetes. Over past years, evidence has accumulated that FFAs induce insulin resistance by raising intracellular lipid metabolites.

The concentrations of FFAs can increase either in the circulating blood due to high-fat diet and release by adipocytes or within cells consequent to lipolysis or de novo synthesis. FFAs traffic through the body mainly while bound to fatty acid transport proteins, whereas fatty acid-binding proteins (FABPs) regulate their intracellular fate. In this regard, FABPs include, for example FABP2, FABP3, FABP4, FABP5, etc. Specifically, the adipocyte-specific isoform (FABP4, A-FABP, ALBP or aP2) has gained attention for its proposed role in metabolic disorders and atherosclerosis.

There is a need for additional ways of treating diseases associated metabolic syndrome such as, for example, dyslipedemia, obesity and diabetes (e.g., Type 2 diabetes).

Furthermore, Fatty acid binding proteins integrate metabolic and immune responses and link the inflammatory and lipid-mediated pathways that are critical in the metabolic syndrome.

The link between FABPs and the various diseases stated above is discussed by Roden et al, *Cell Metabolism* (2007) 6, pp. 89-91; Furuhashi et al, *Nature* (2007) 447, pp. 959-965; and Makowski et al, *Current Opinion Lipidology* (2005) 16, pp. 543-547.

A need exits in the art, however, for FABP inhibitors, especially FABP4 inhibitors, that have efficacy for the treatment of metabolic disorders such as, for example, obesity, type II diabetes mellitus and metabolic syndrome.

A need exits in the art, however, for FABP inhibitors, especially FABP5 inhibitors, that have efficacy for the treatment of metabolic disorders such as, for example, obesity, type II diabetes mellitus and metabolic syndrome.

A need exits in the art, however, for FABP inhibitors, especially FABP3 inhibitors, that have efficacy for the treatment of metabolic disorders such as, for example, obesity, type II diabetes mellitus and metabolic syndrome.

A need exits in the art also for dual FABP inhibitors that have efficacy for the treatment and/or prevention of cardiovascular conditions.

SUMMARY OF THE INVENTION

In an embodiment, this invention discloses a compound, or pharmaceutically acceptable salt, solvate, ester or prodrug of said compound, or pharmaceutically acceptable salt, solvate or ester of said prodrug, the compound being represented by the general Formula I:

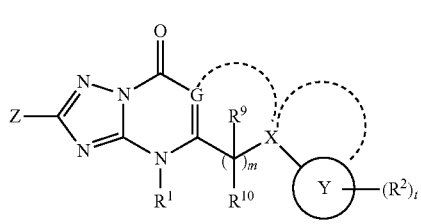

wherein:
Y is a ring as described below;
X is either:

(i) C(R$^7$R$^8$), N(R$^3$), S, S(O$_2$), or O, and both ⌒ are absent; or (ii) C(R$^7$), and X is linked, either to the ring marked Y as shown by the ⌒ towards the right of X, or to the position marked G on the triazolopyrimidinone ring as shown by the ⌒ towards the left of X, to form a 3-8 membered cycloalkyl or a 4-8 membered heterocyclyl ring containing 1-3 heteroatoms independently selected from N, O and S, or (iii) N (with R$^3$ being absent), and X is linked, either to the ring marked Y as shown by the ⌒ towards the right of X, or to the position marked G on the triazolopyrimidinone ring as shown by the ⌒ towards the left of X, to form a 4-8 membered heterocyclyl ring containing 1-3 heteroatoms independently selected from N, O and S, including the nitrogen atom of X;

further wherein ⌒ shown to the right of X is mutually exclusive of ⌒ shown to the left of X;

G is C(R$^6$) when ⌒ shown to the left of X is absent, and G is C when ⌒ shown to the left of X is present;

Ring Y is aryl, heteroaryl, heterocyclyl or cycloalkyl, and when ⌒ shown to the right of X is present, a ring atom on Y is the point of attachment for said ⌒ shown to the right of X, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and CF$_3$;

R$^3$ may be present or absent as stated above, and when R$^3$ is present, R$^3$ is H, alkyl or cycloalkyl, wherein each of said alkyl and cycloalkyl may be unsubstituted or optionally independently substituted with one or more substituents which can be the same or different, each substituent being independently selected from the group consisting of halo, hydroxyl, alkoxy, CN and CF$_3$;

R$^1$ is H, alkyl, -alkyl-OR$^4$, haloalkyl, haloalkoxy or -alkyl-CN;

m is 1-2;

t is 0-4;

each R$^2$ is independently selected from the group consisting of halo, CN, —OR$^5$, alkyl, haloalkyl, haloalkoxy, aryl, heteroaryl, heterocyclyl, cycloalkyl, —NH$_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—NH$_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—NH$_2$, —C(O)R$^5$, and —C(O)OR$^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R$^5$, CN and CF$_3$;

Z is H, —OR$^5$, —C(O)OR$^5$, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, —C(O)R$^5$, and —C(O)OR$^5$;

R$^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)R$^4$, CN and CF$_3$;

R$^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^7$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF$_3$;

R$^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF$_3$;

R$^9$ is H, halo, alkyl, cycloalkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$; and R$^{10}$ is H, halo, alkyl, cycloalkyl, aryl or heteroaryl, —C(O)OH, —C(O)—NH$_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)N(alkyl)(cycloalkyl), —C(O)N(cycloalkyl)(aryl), —C(O)N(cycloalkyl)(heterocyclyl), —NH—C(O)—NH$_2$, —C(O)R$^5$, and —C(O)OR$^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R$^5$, CN and CF$_3$;

or alternatively, R$^9$ and R$^{10}$ can together form =O or R$^9$ and R$^{19}$ can be joined to form a spirocyclyl group;

with the proviso that the compound represented by Formula I excludes the following compounds:

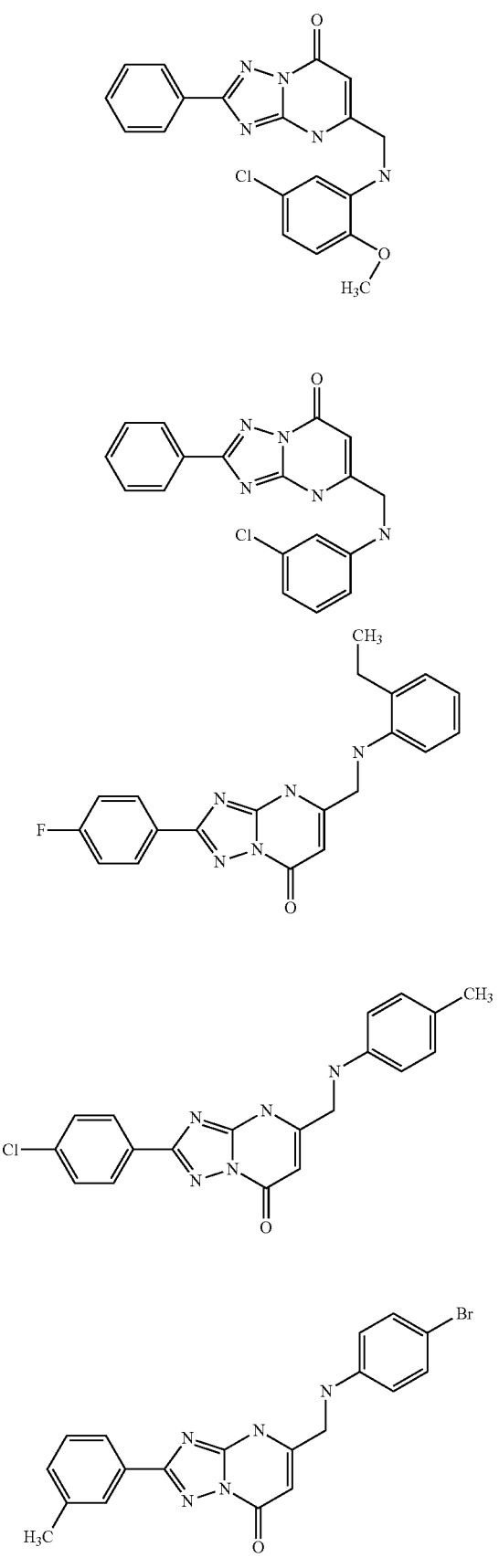
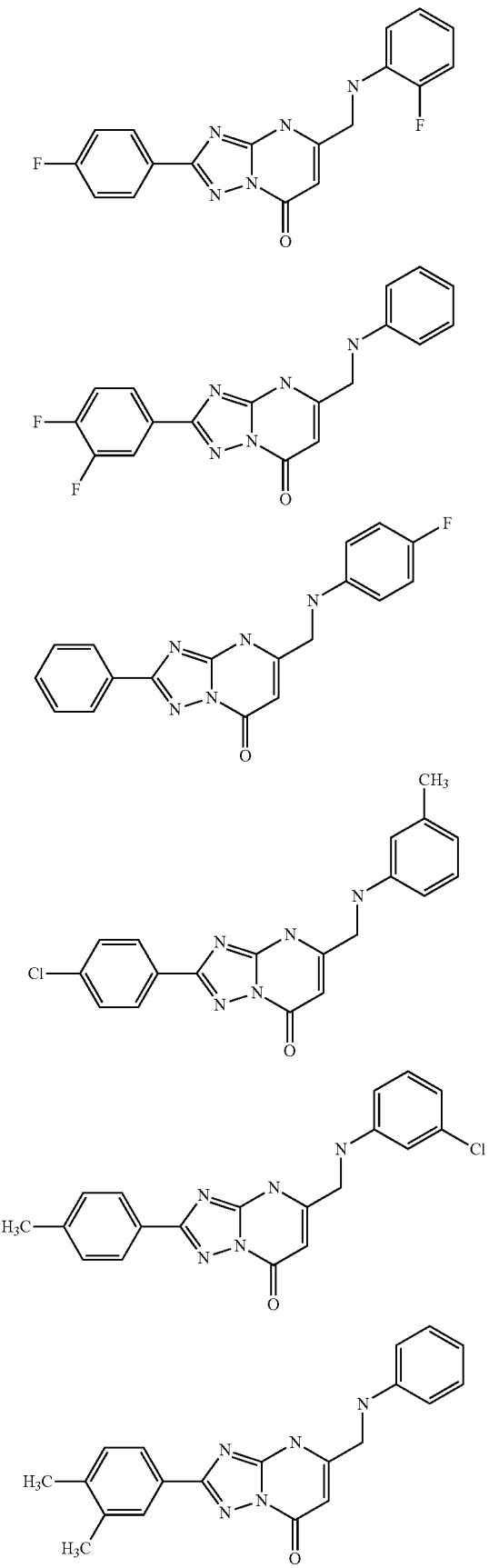

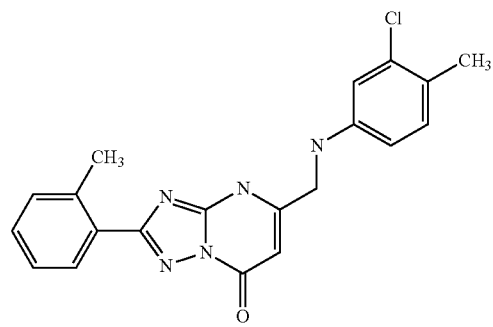
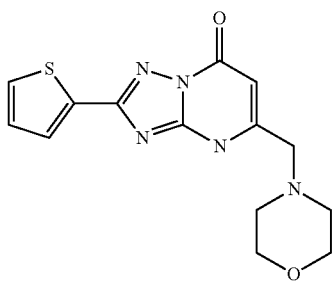
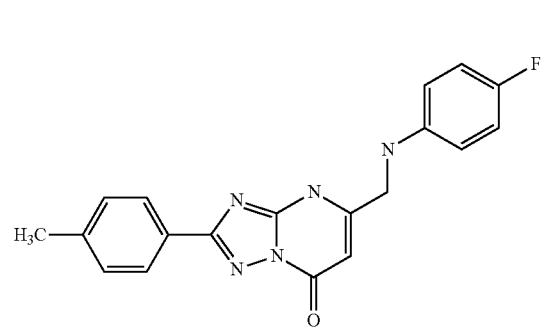
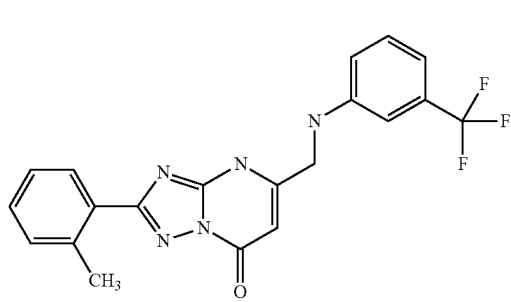
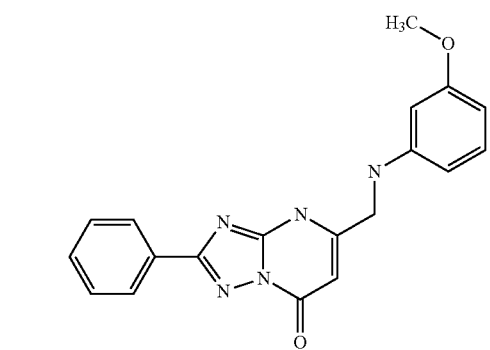
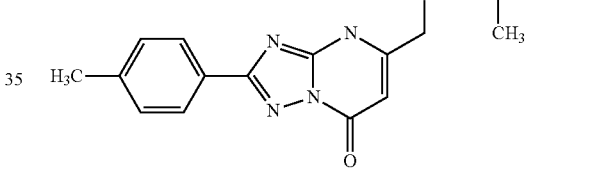
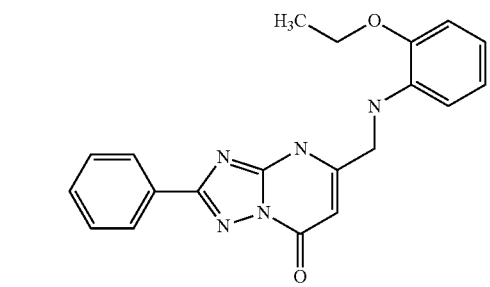
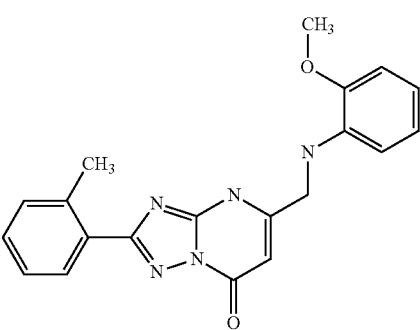
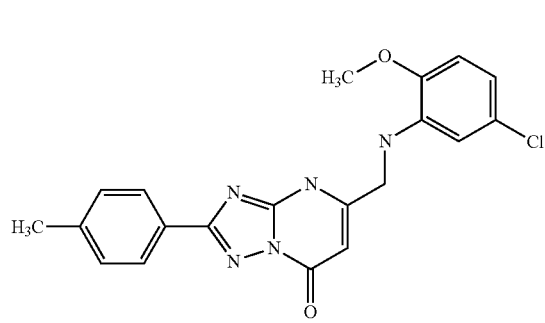
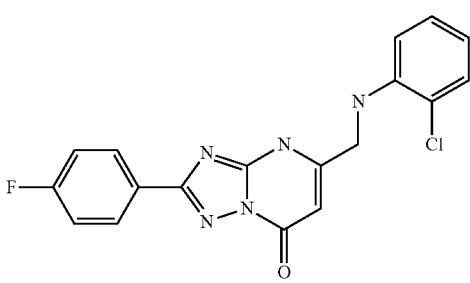

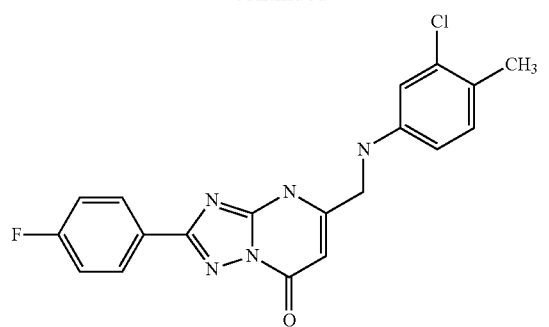
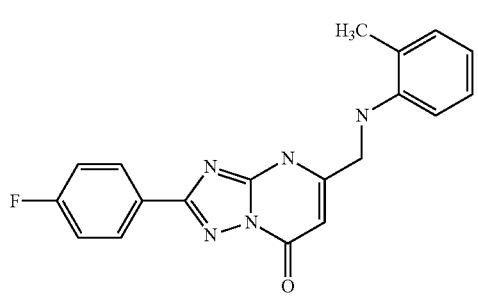
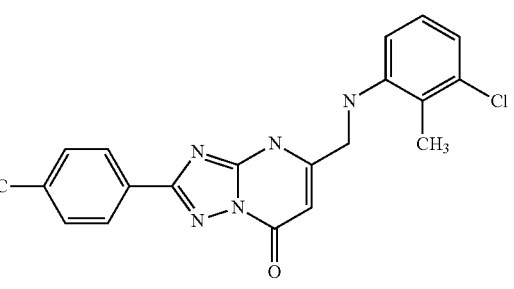
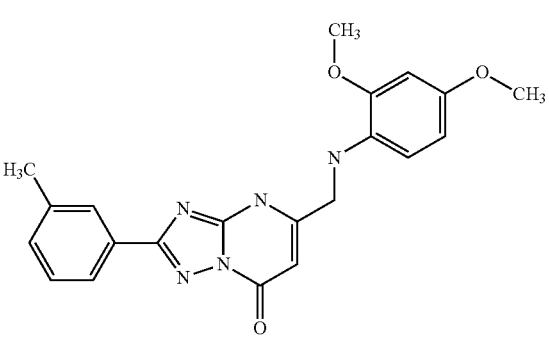
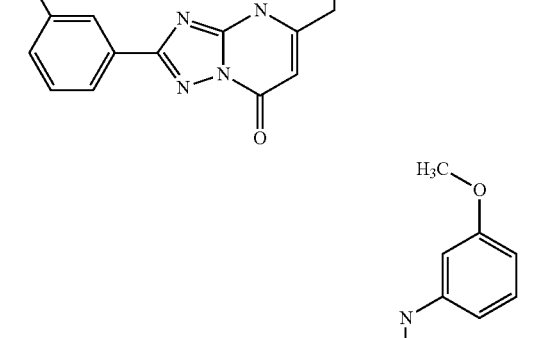
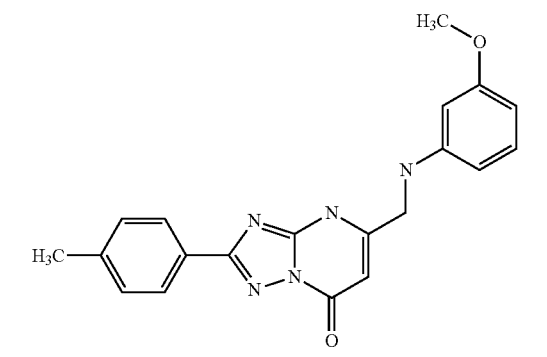
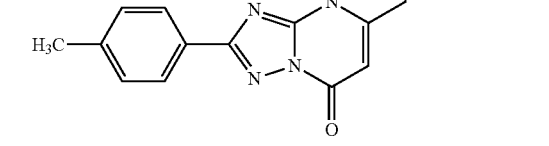
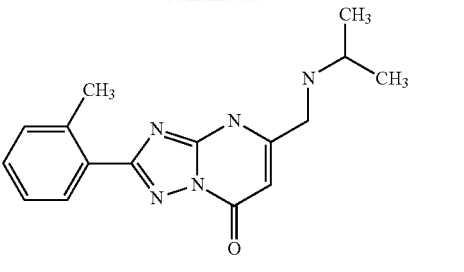
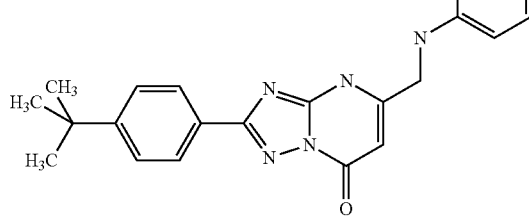
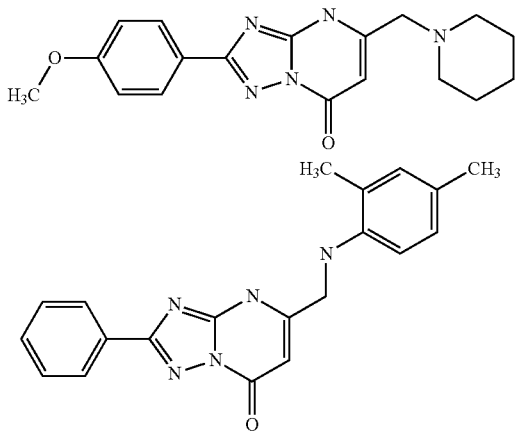
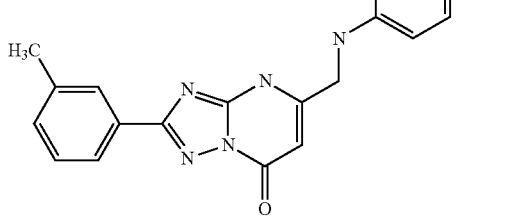
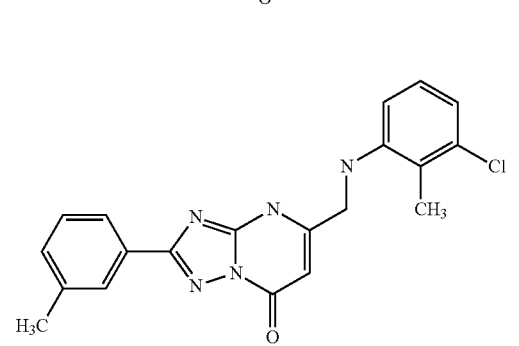

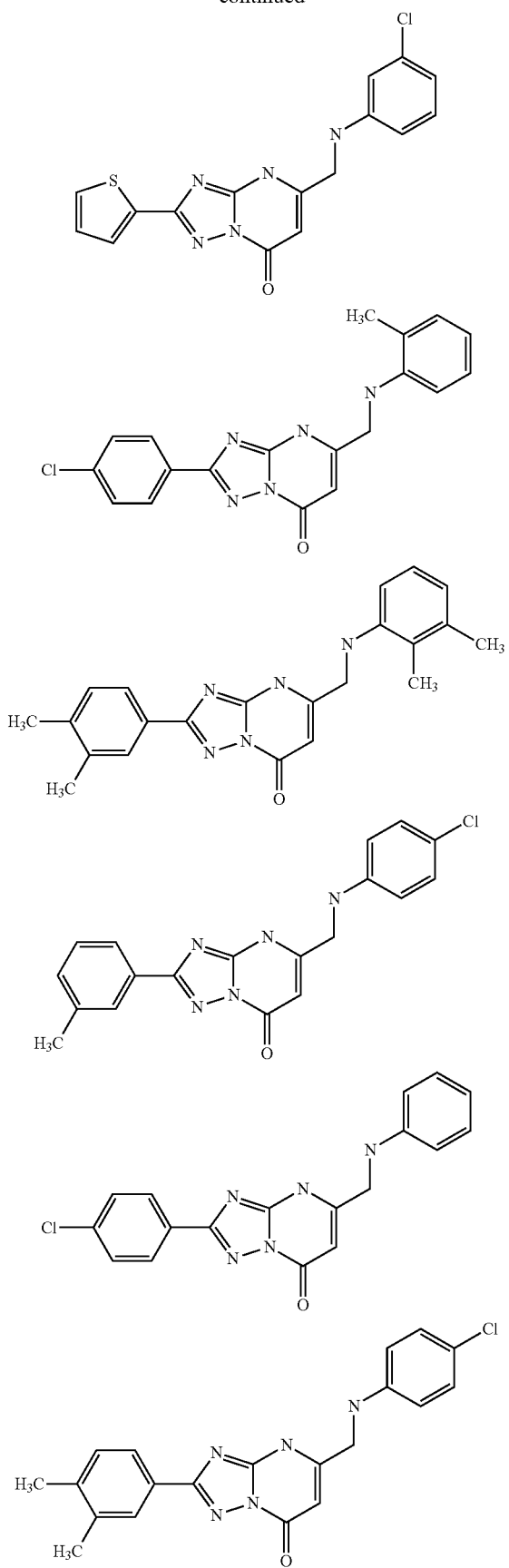
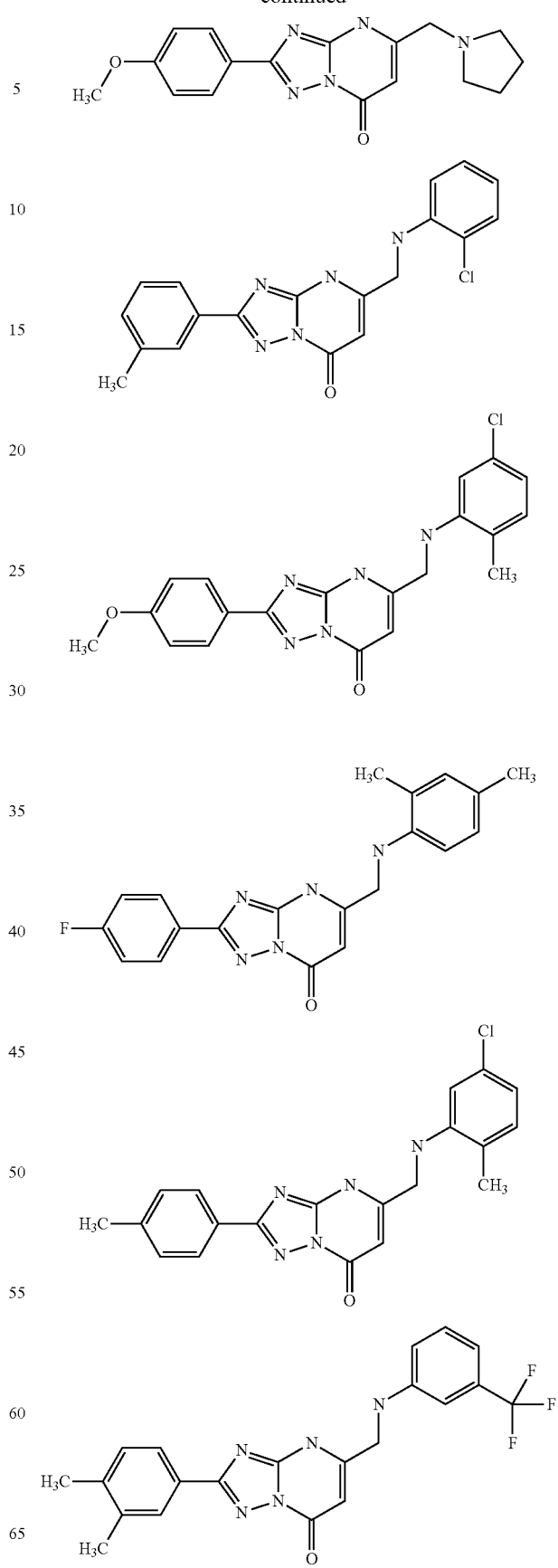

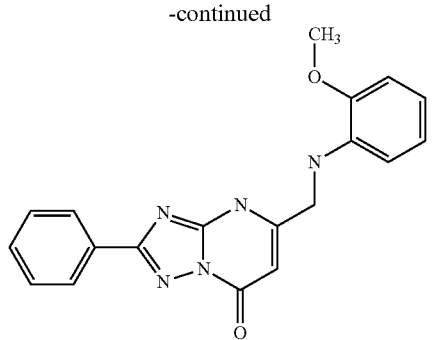
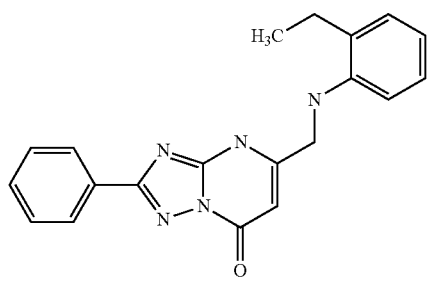
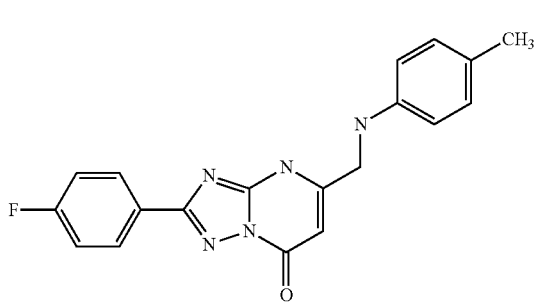
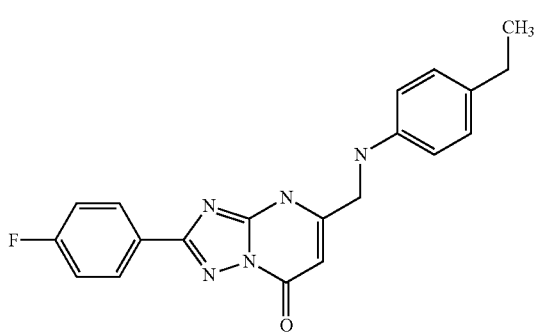
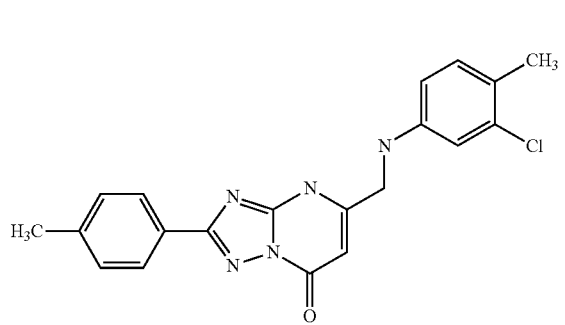
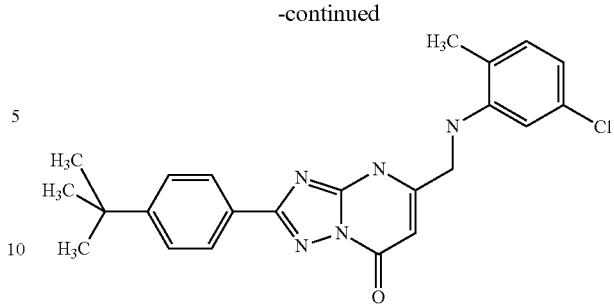
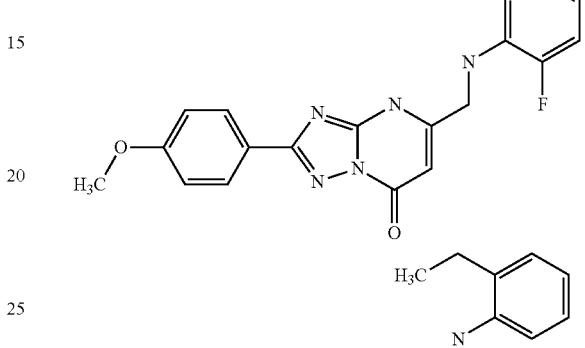
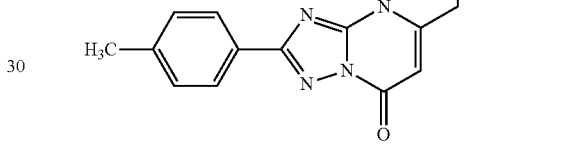
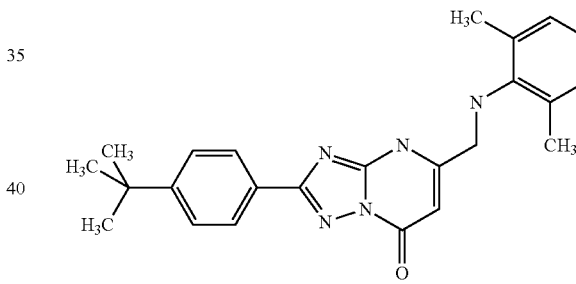
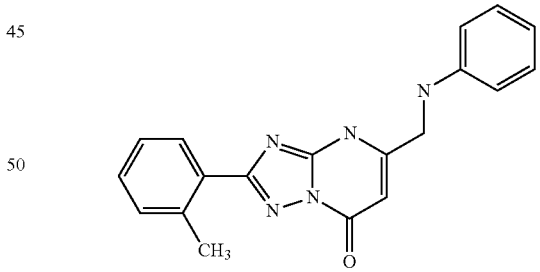
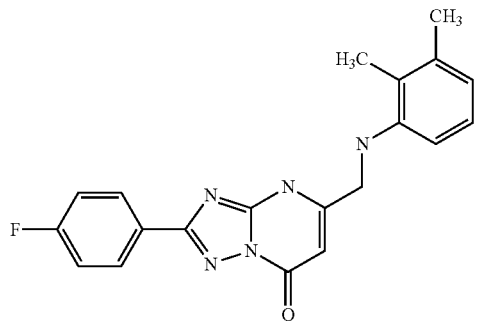

-continued
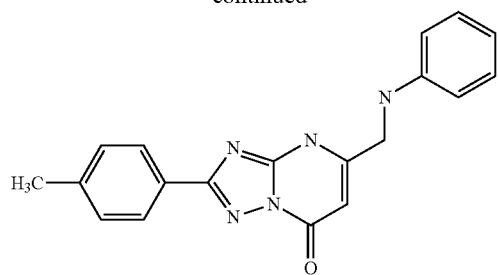
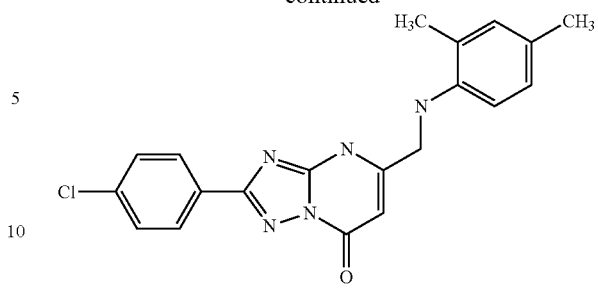
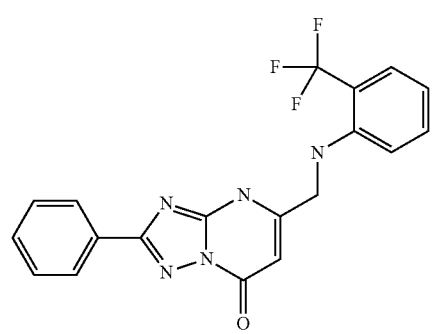
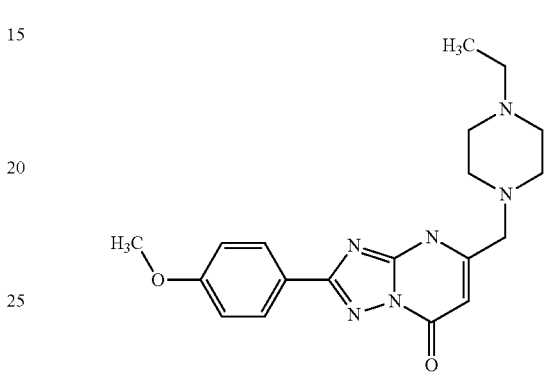
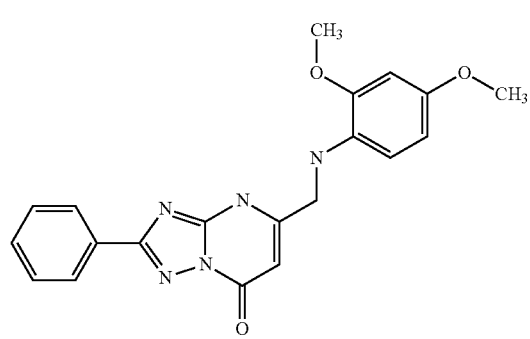
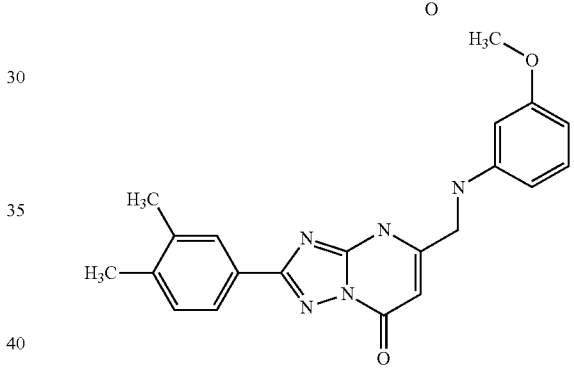
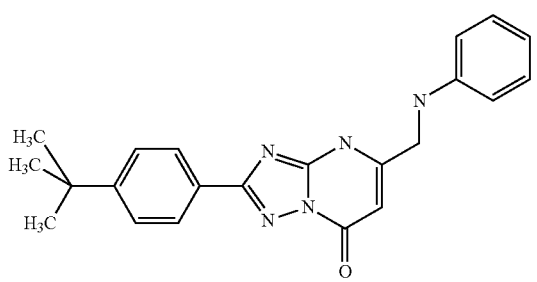
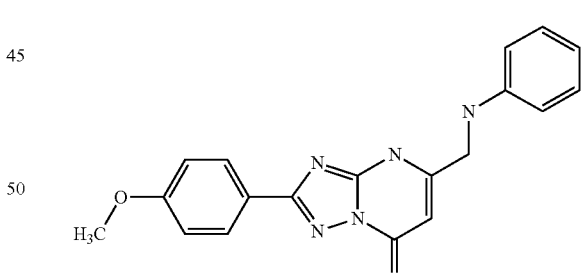
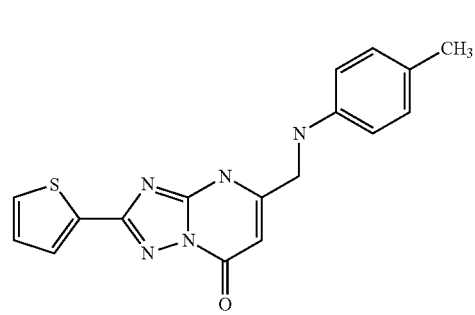
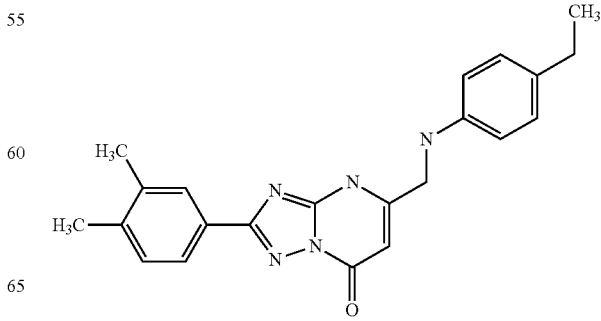

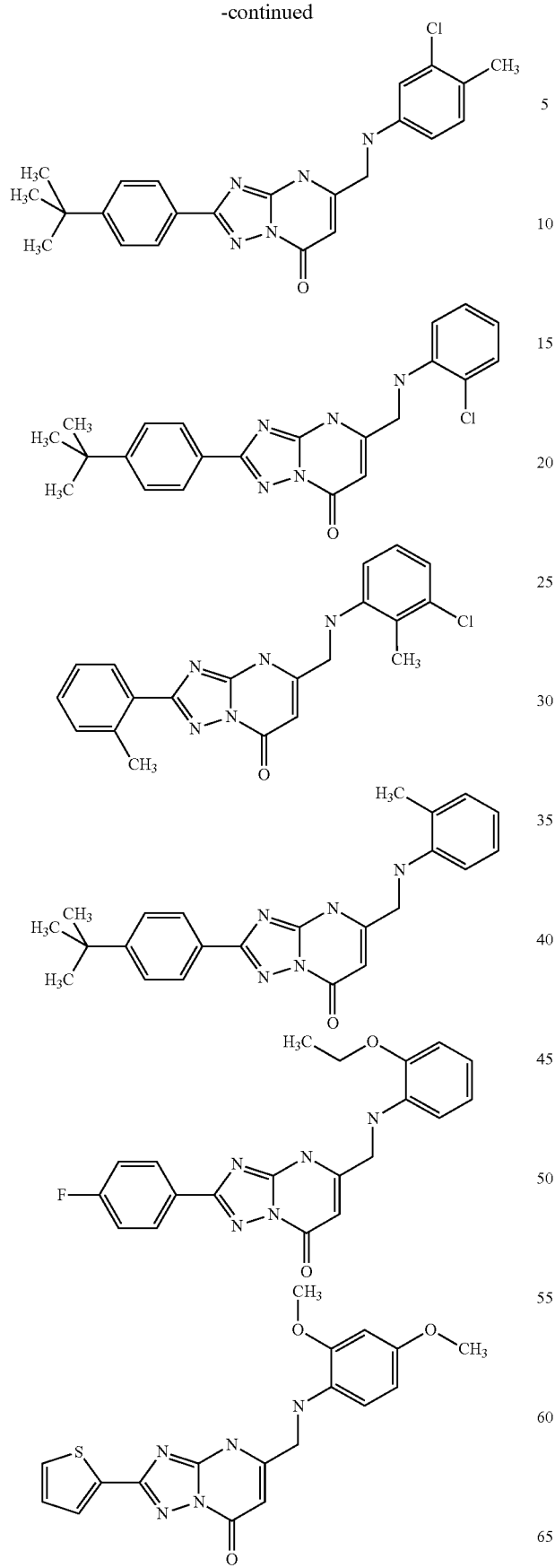
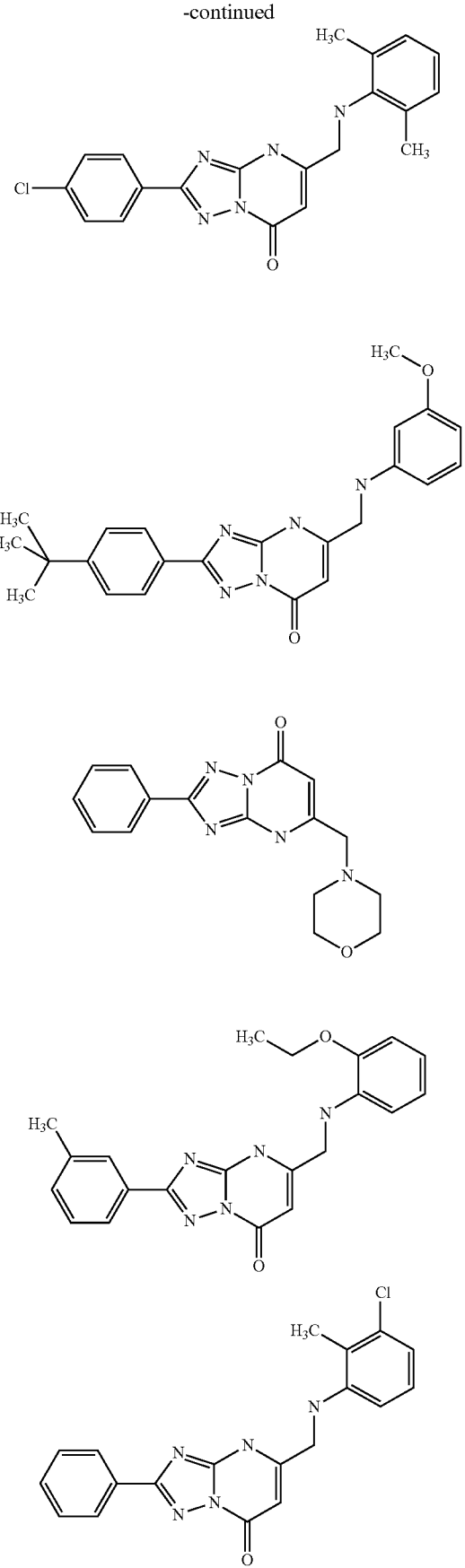

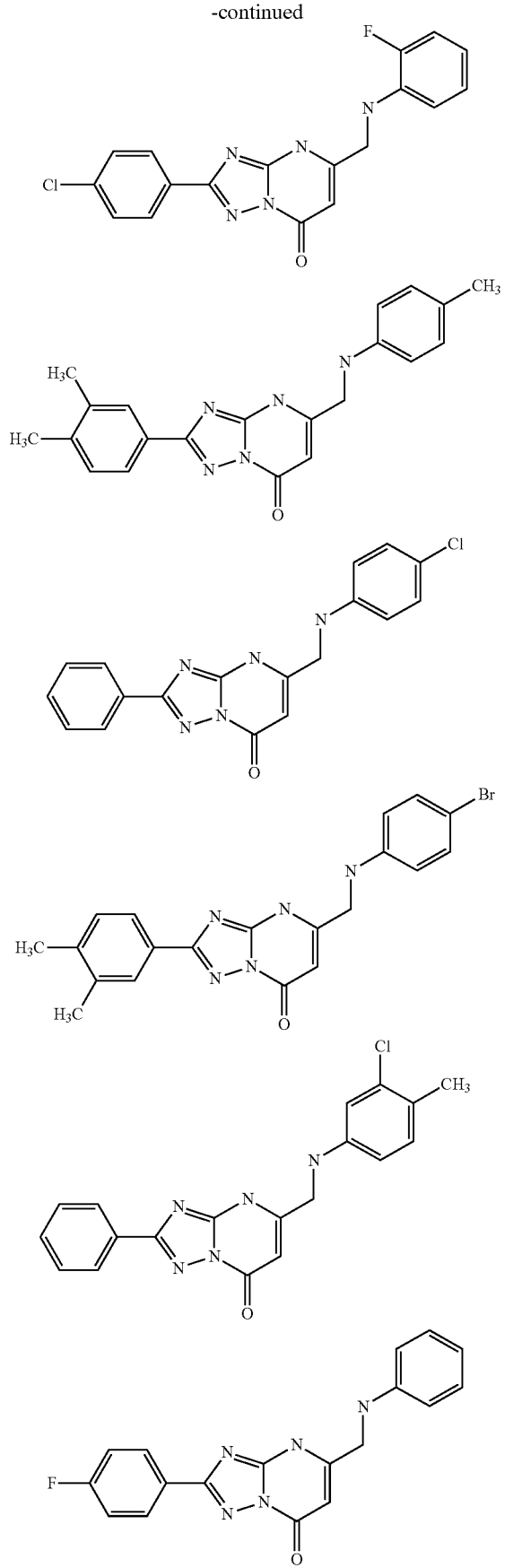
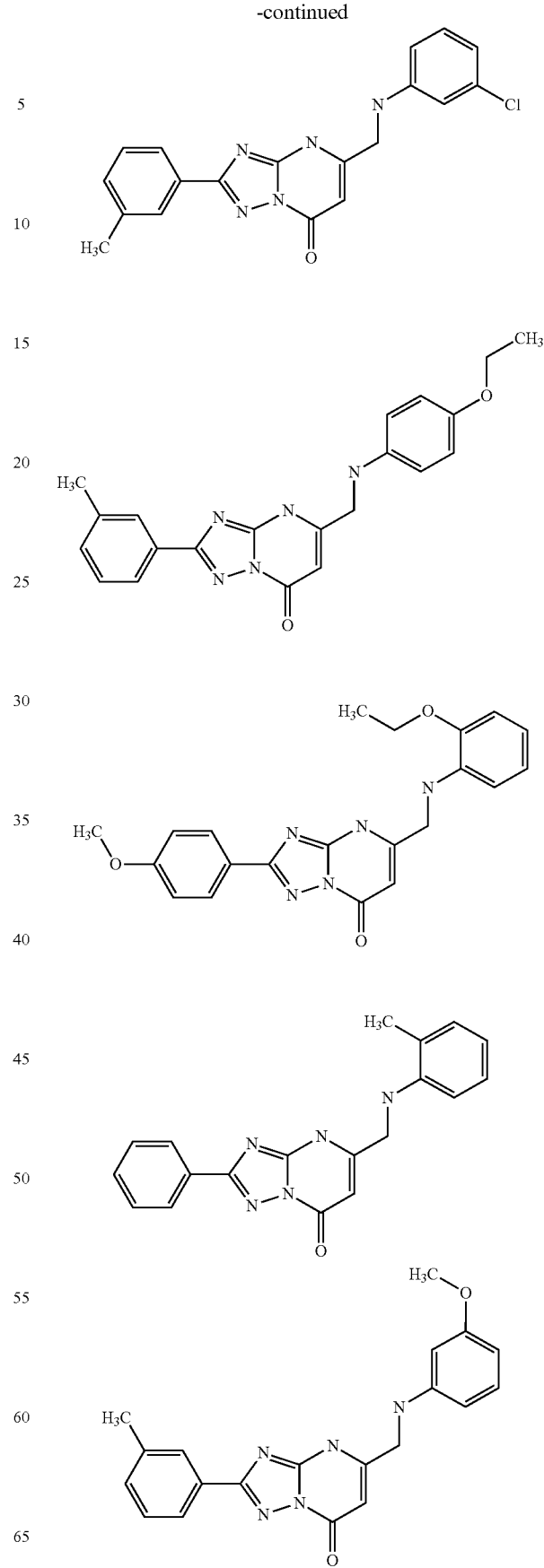

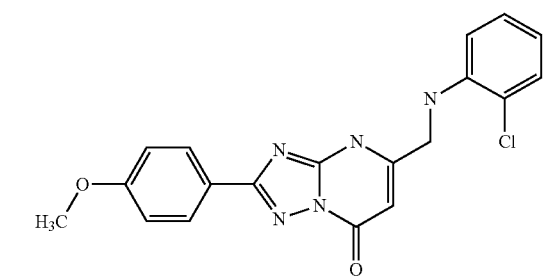
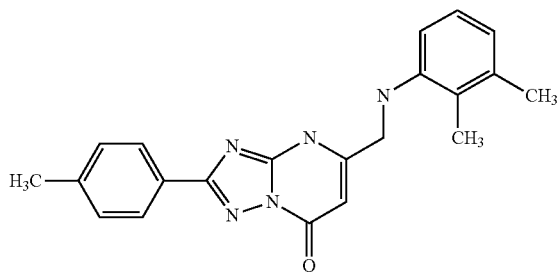
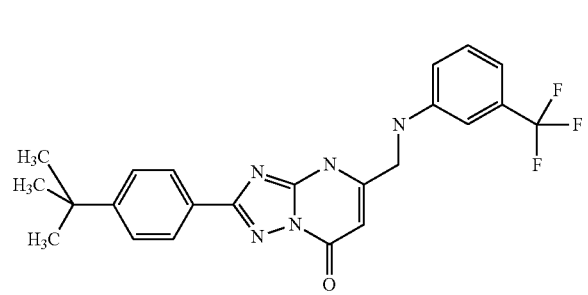
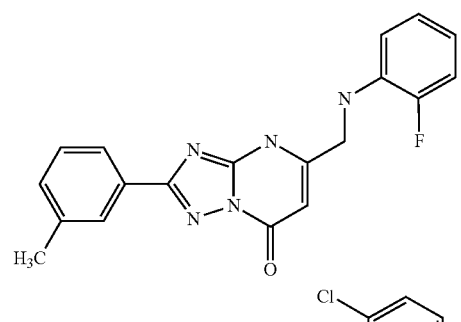
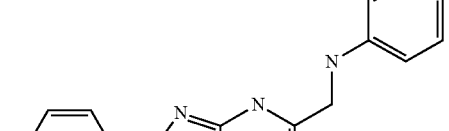
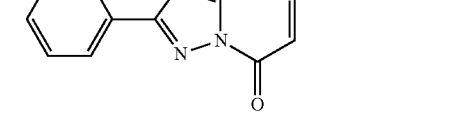
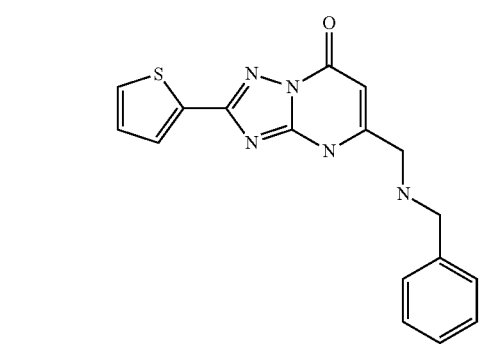
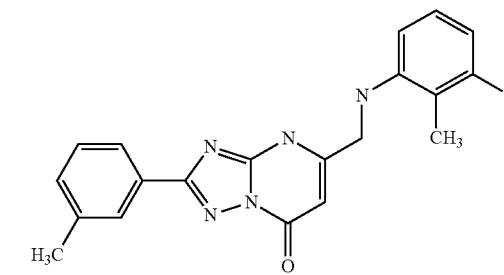
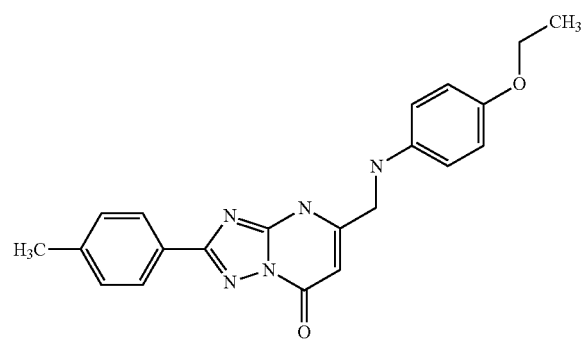
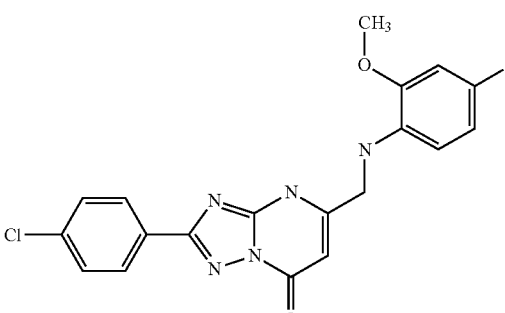
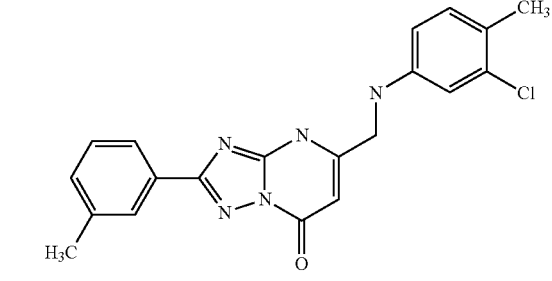
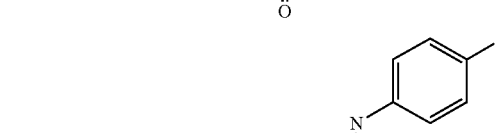
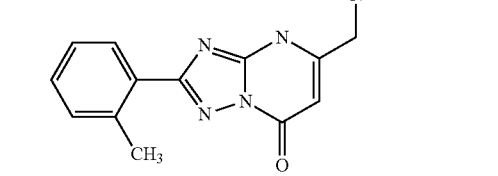

23
-continued
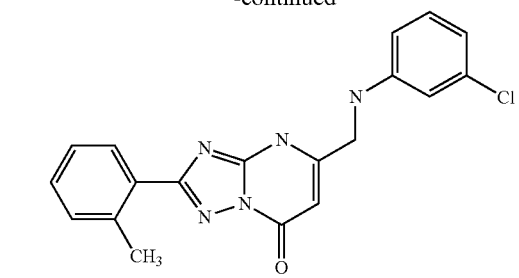
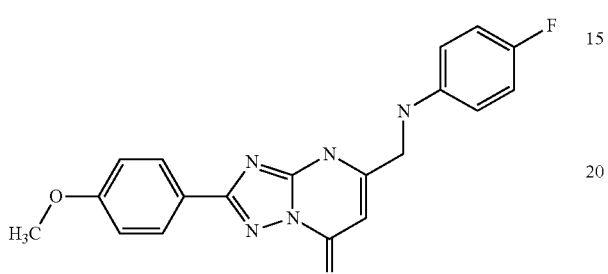
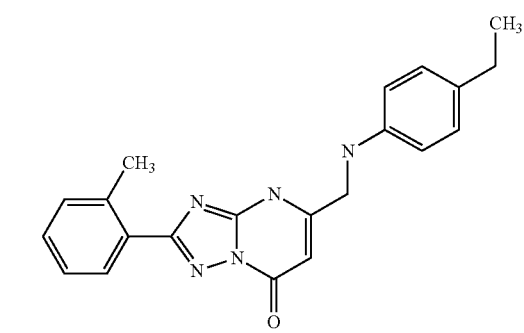
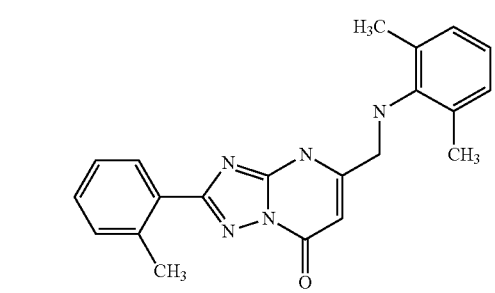
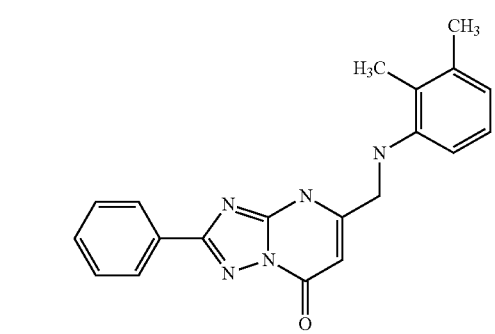
24
-continued
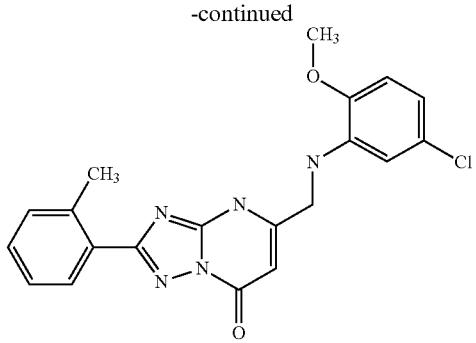
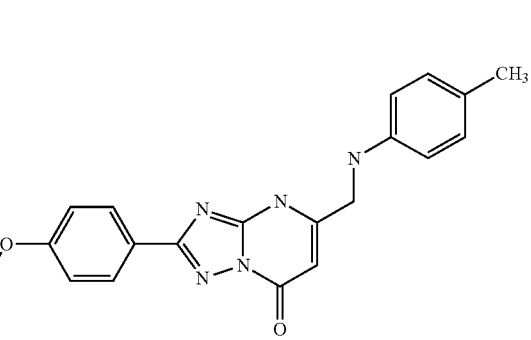
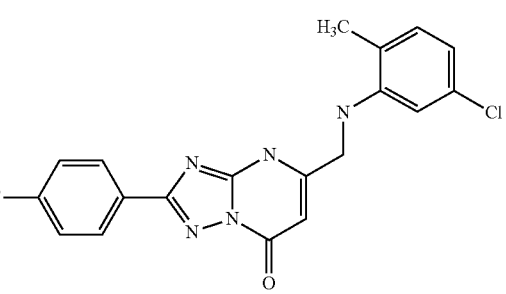
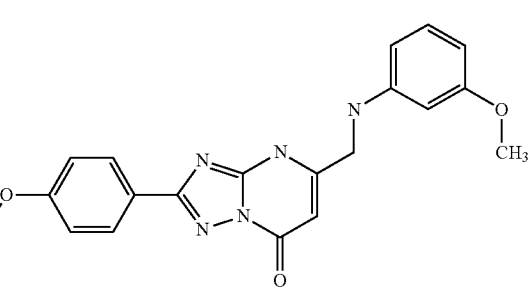
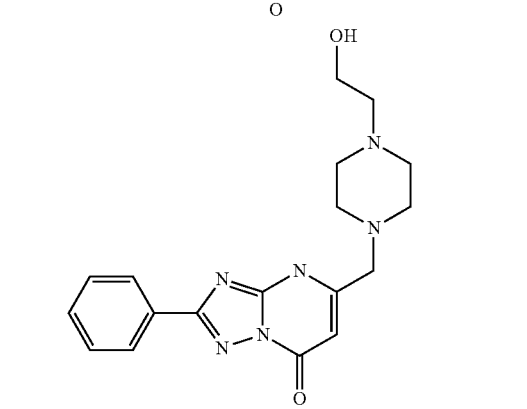

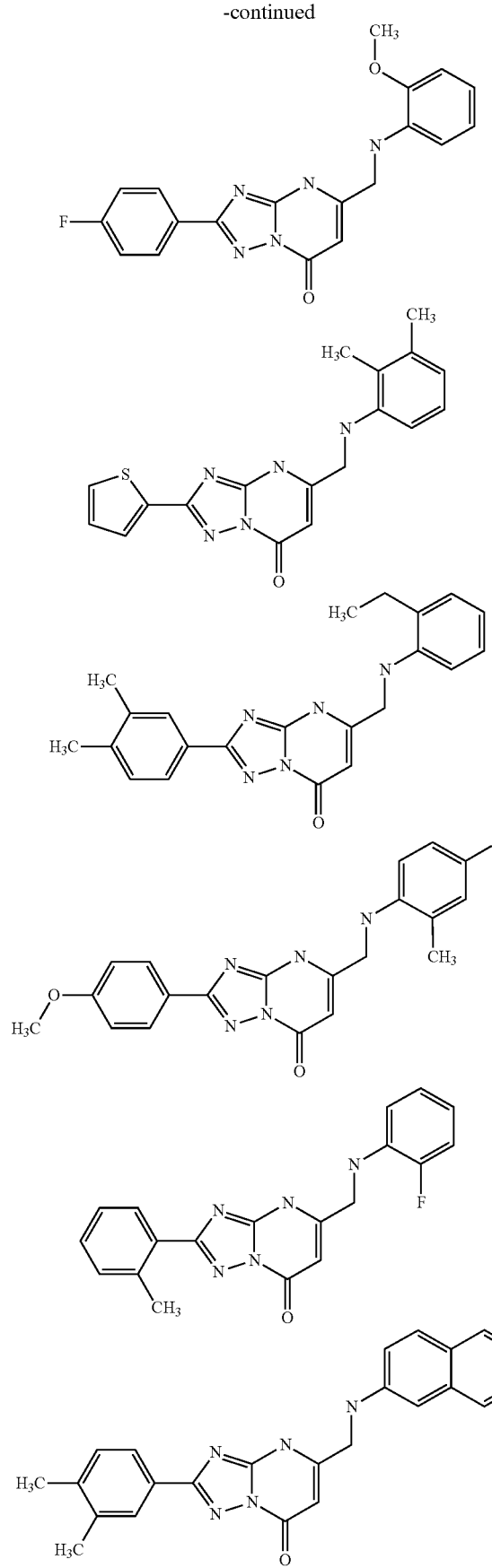
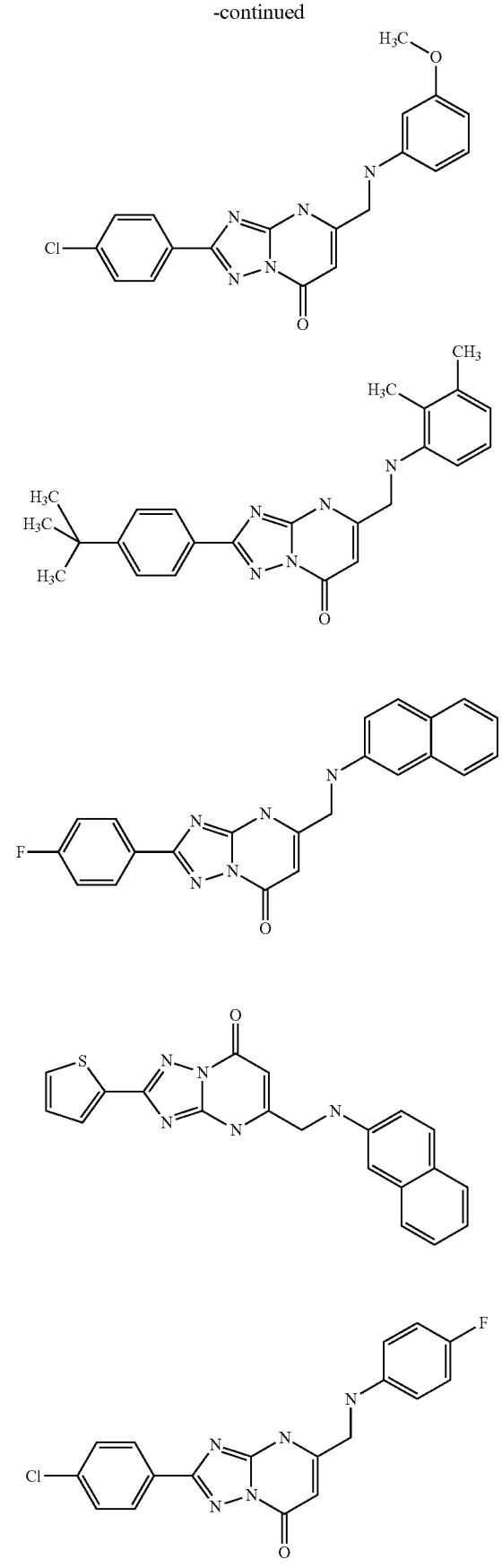

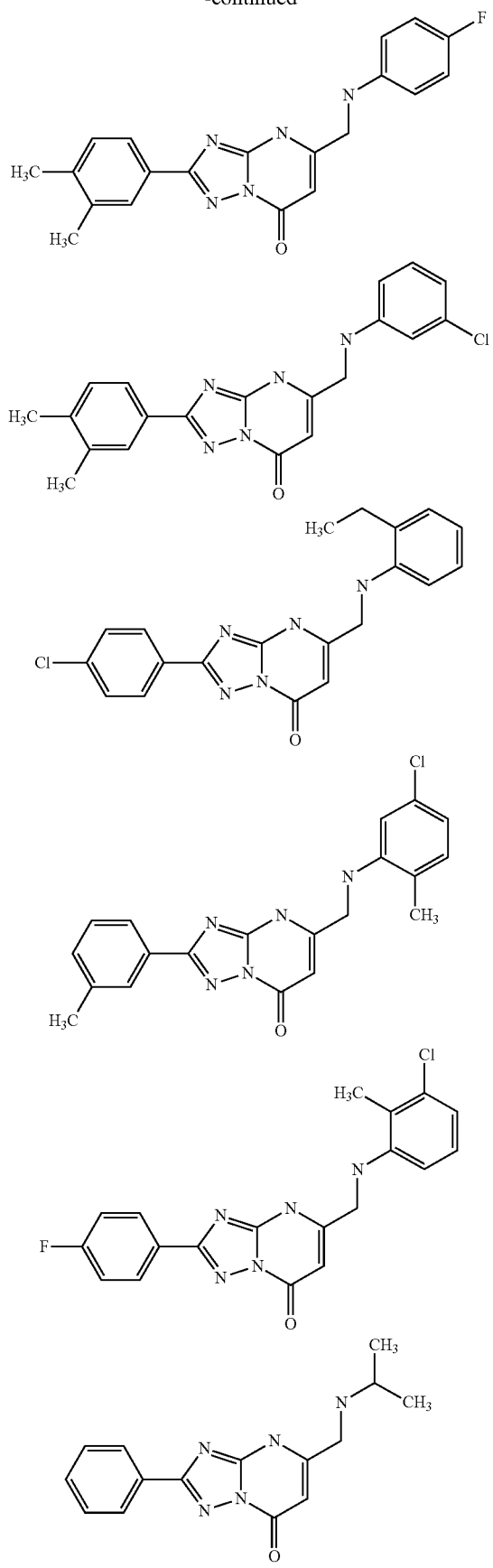
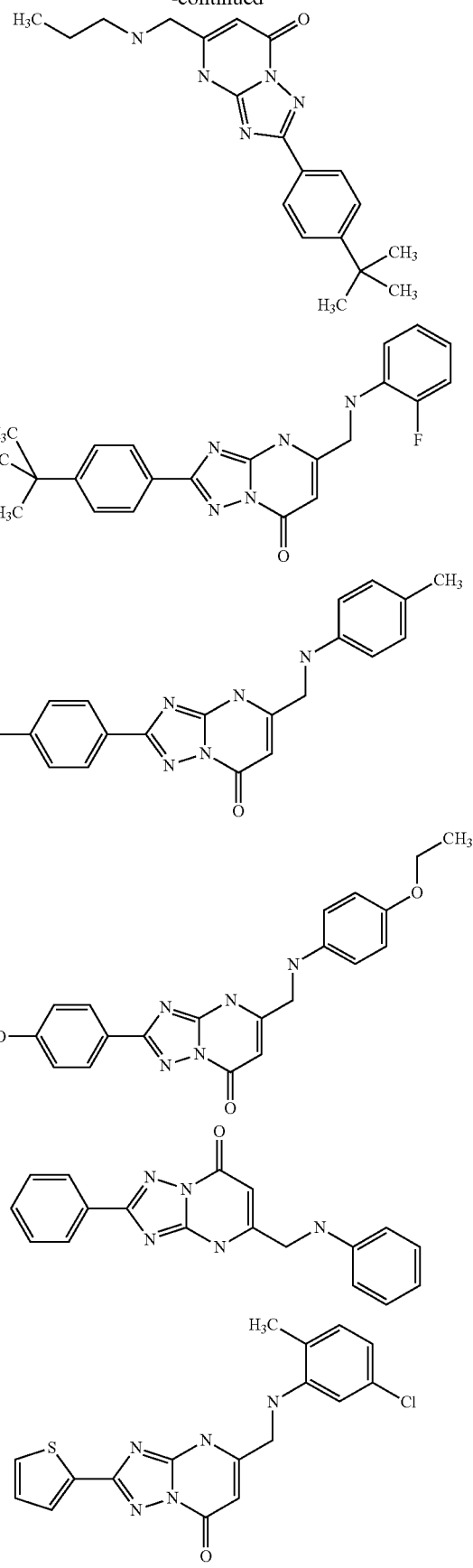

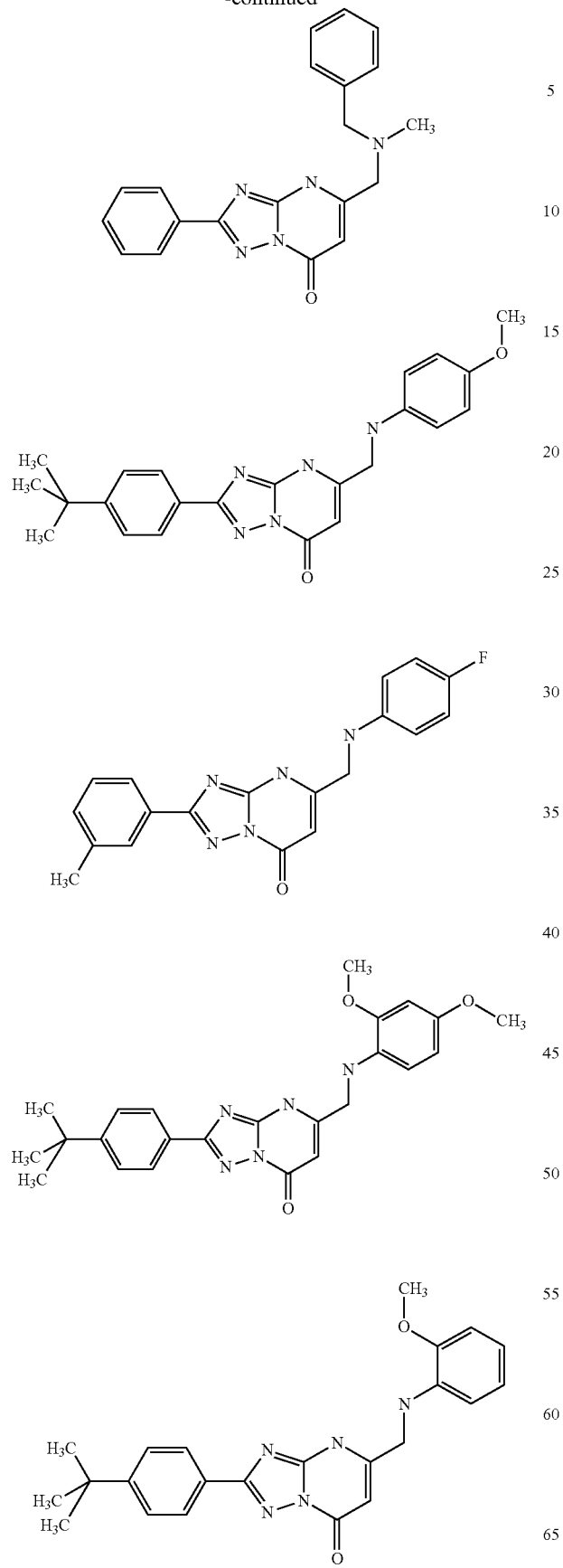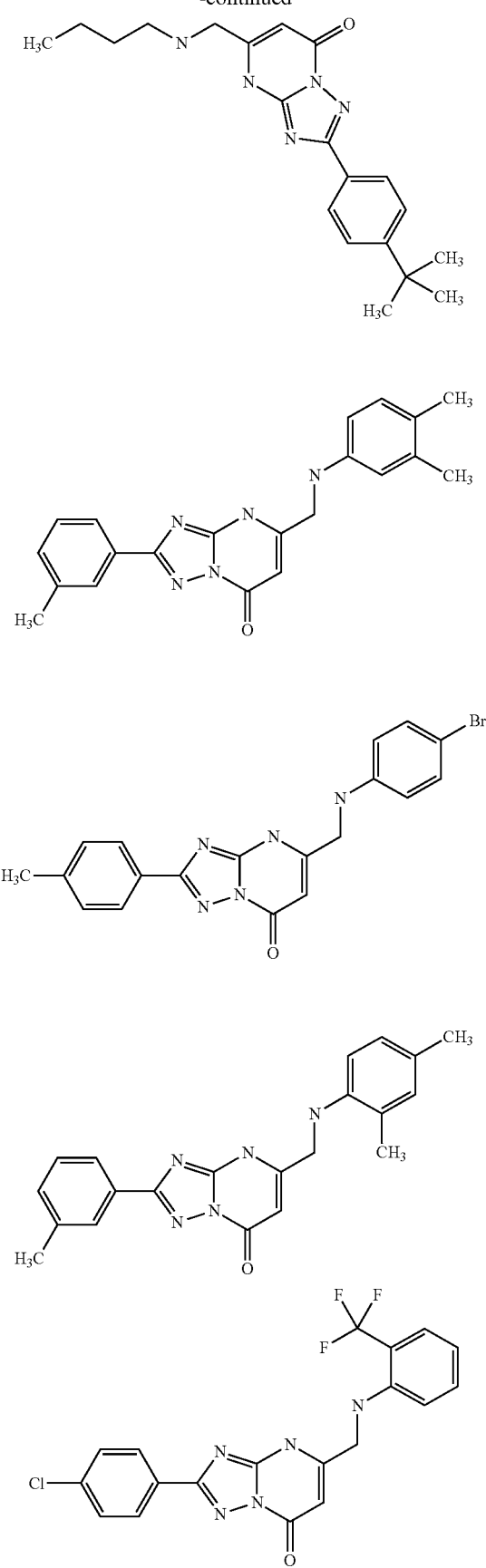

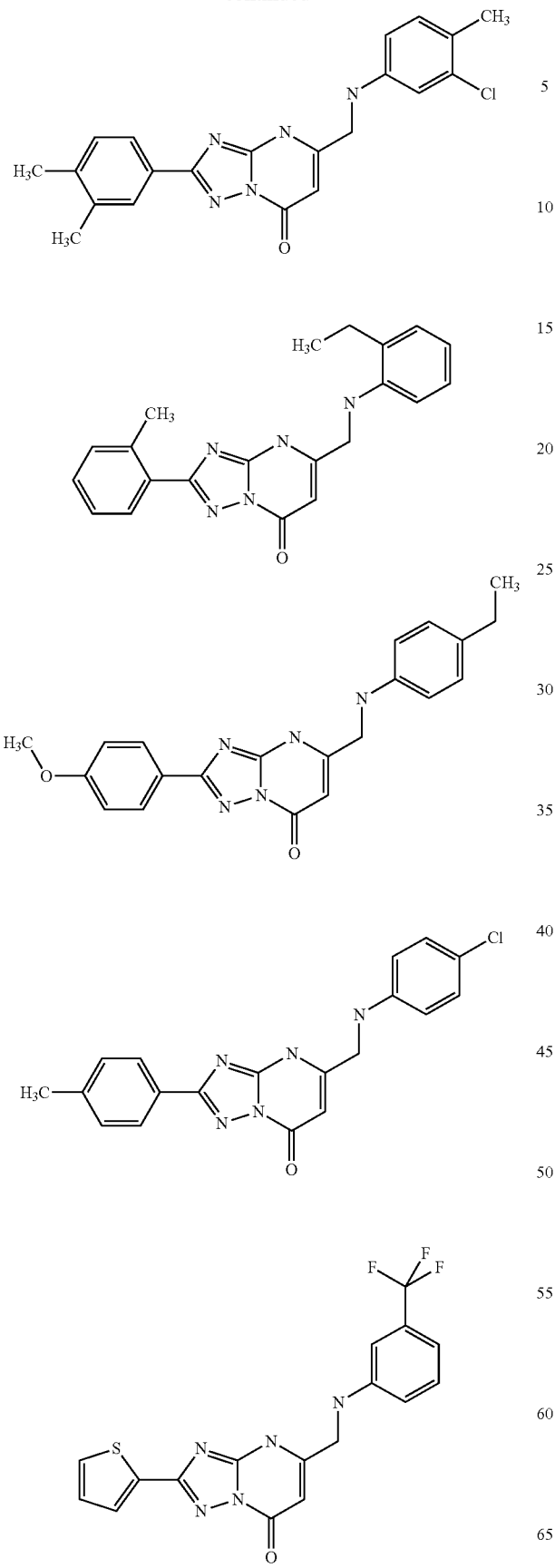
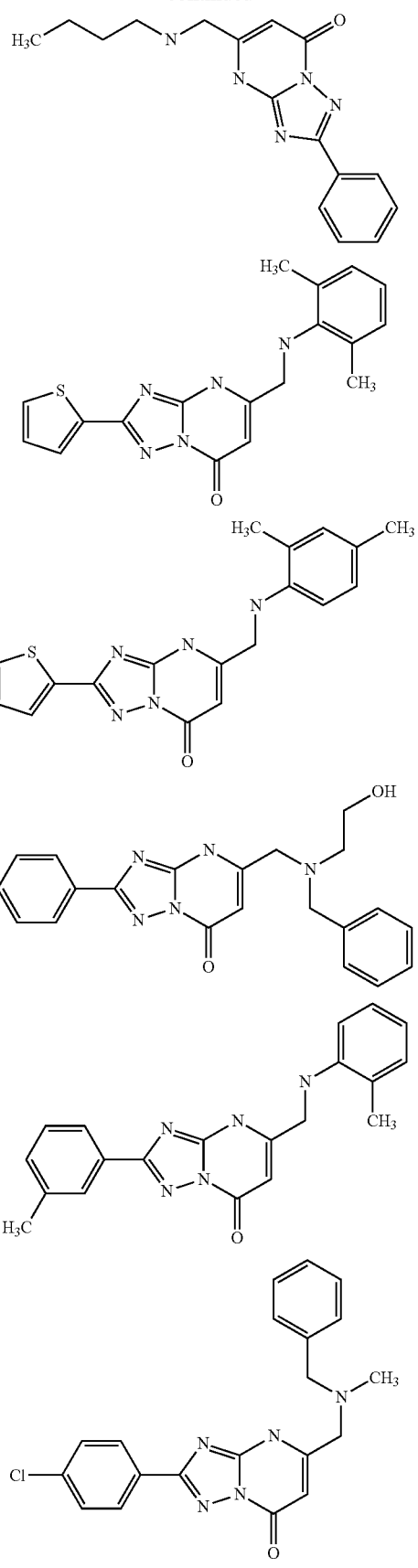

33
-continued
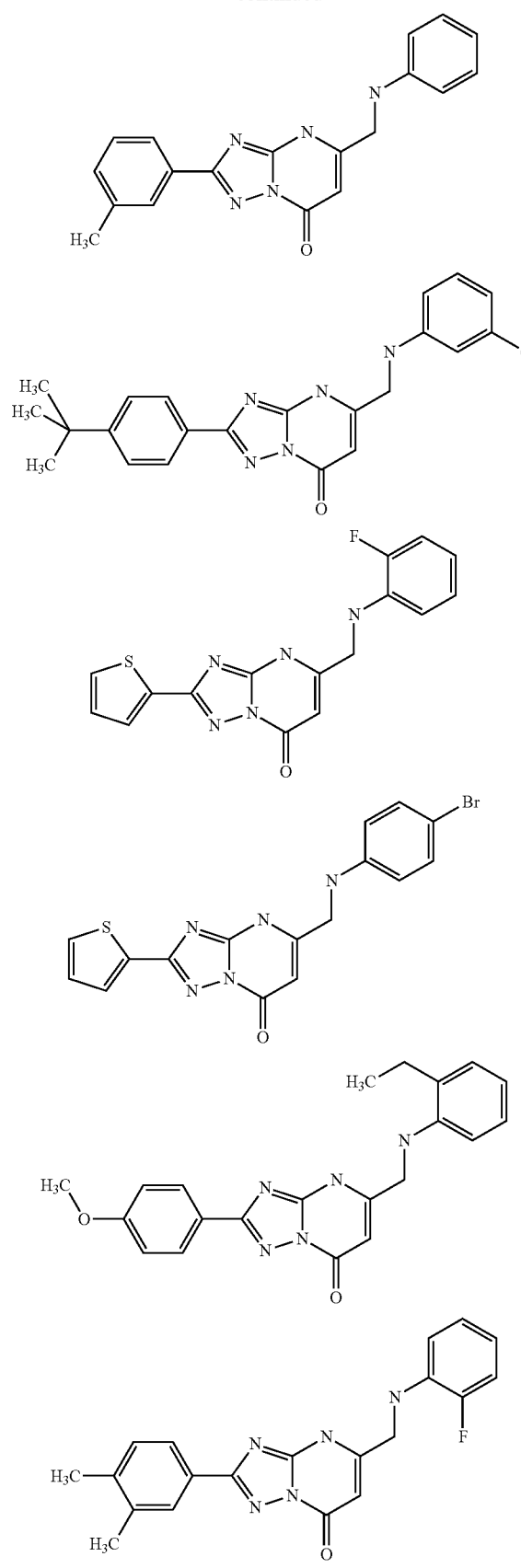
34
-continued
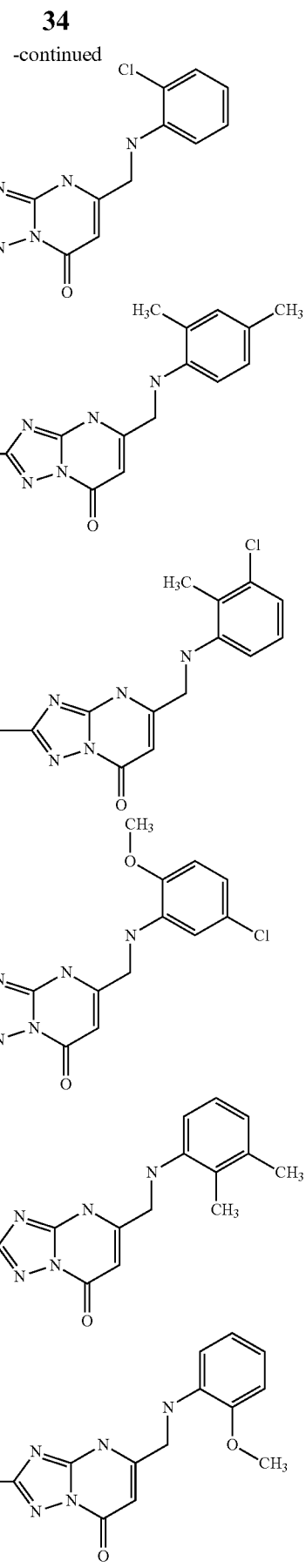

-continued
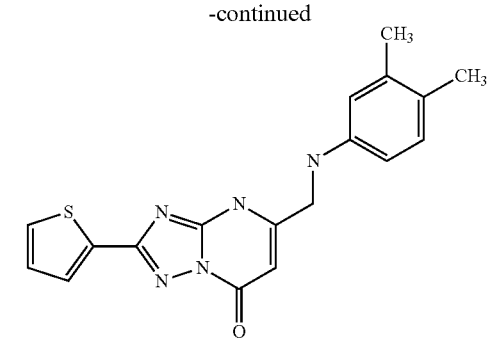
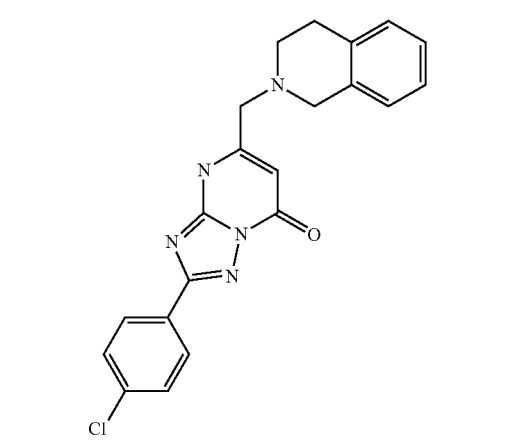
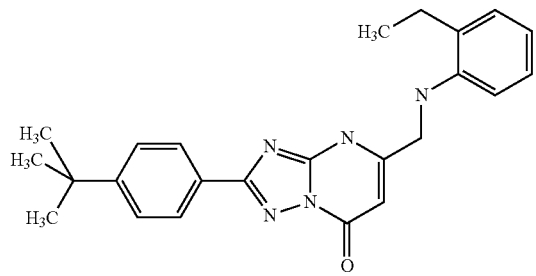
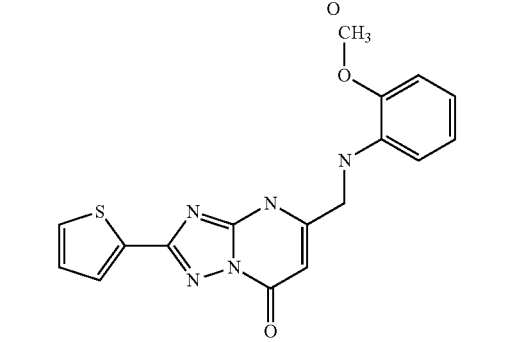
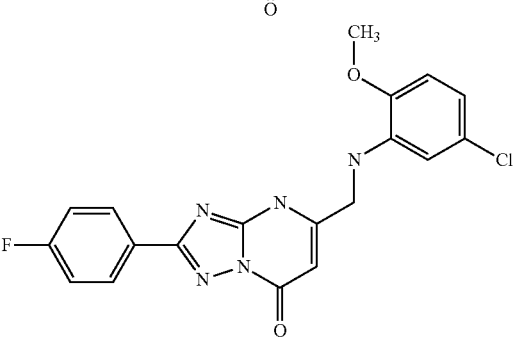
-continued
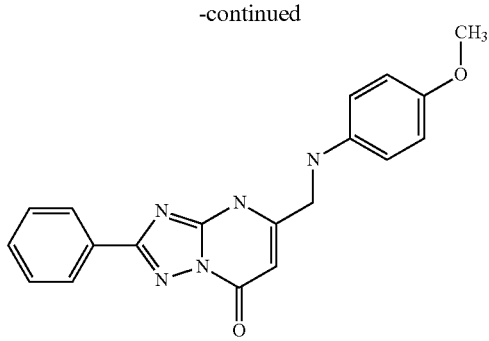
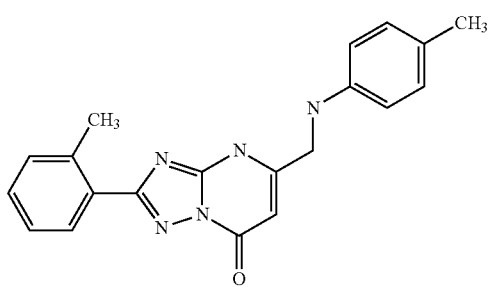
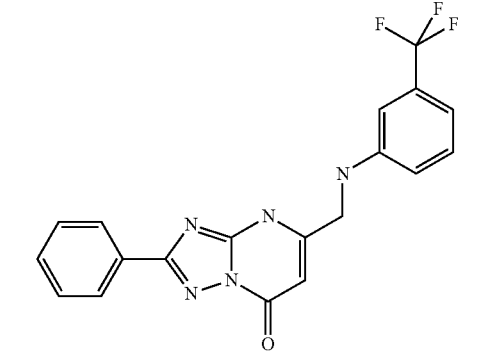
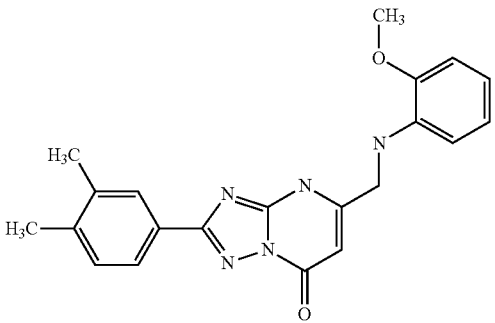
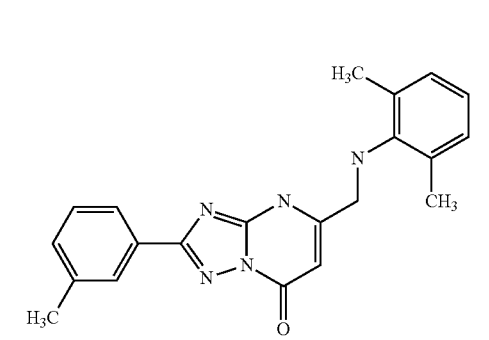

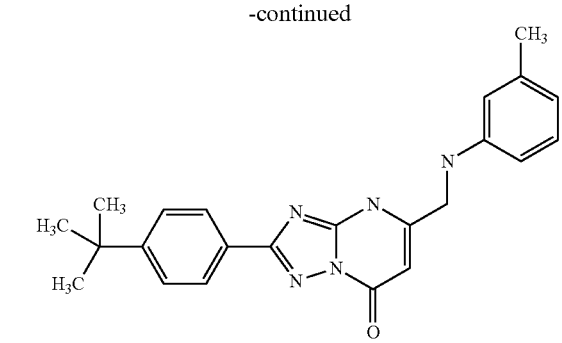
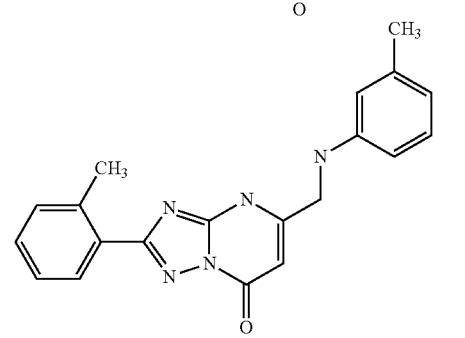
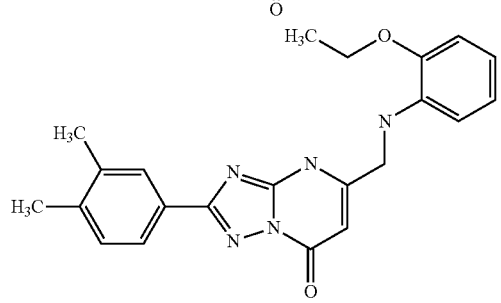
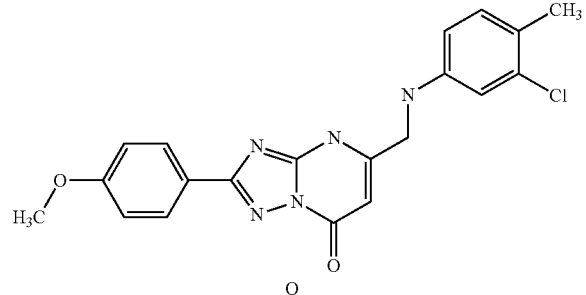
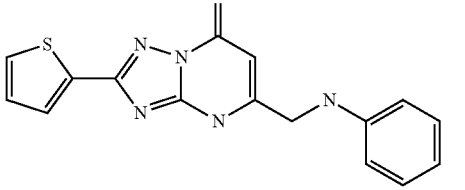
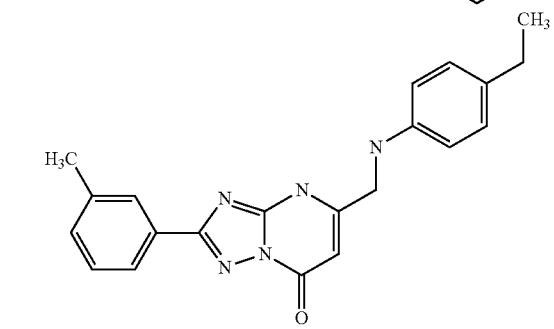
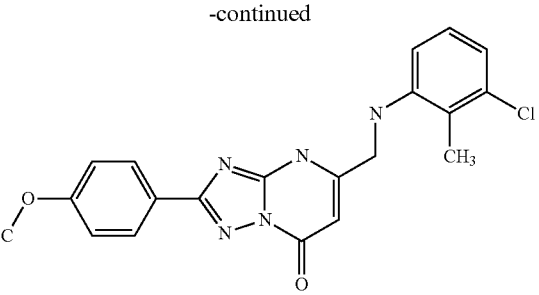
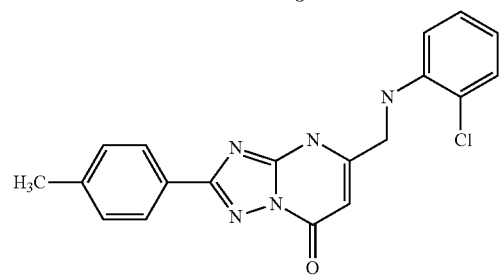

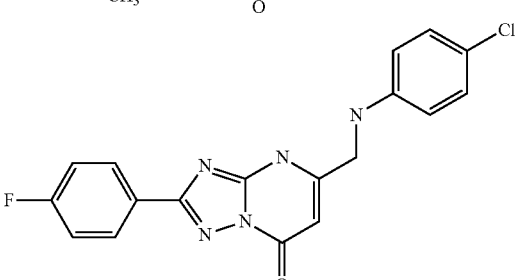
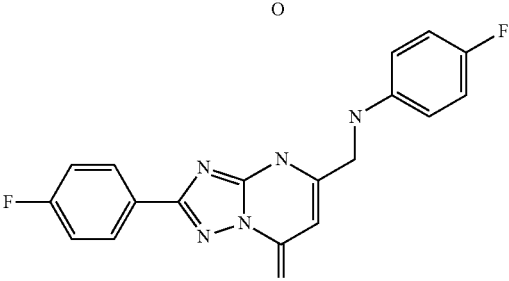
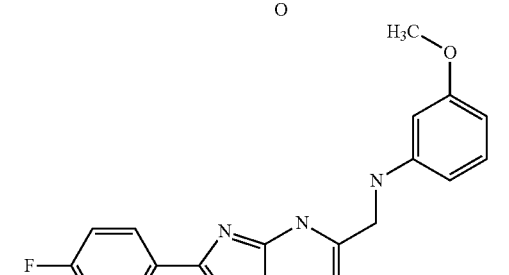
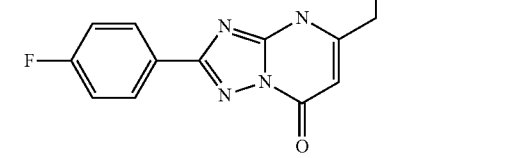

39
-continued
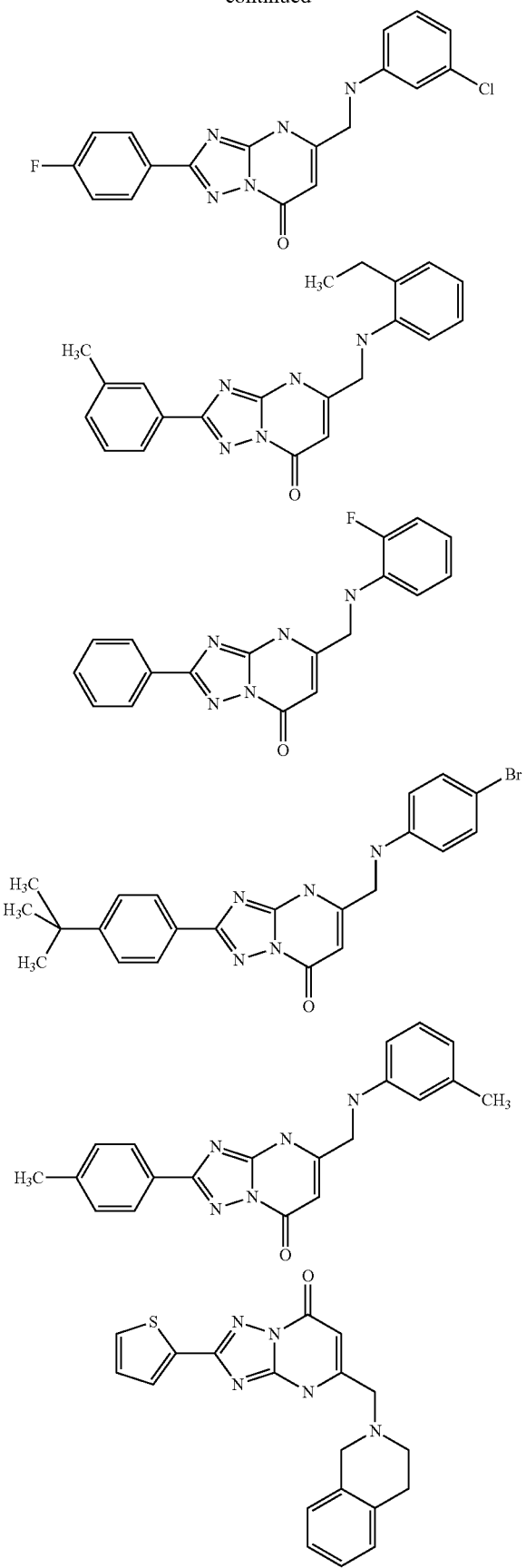
40
-continued
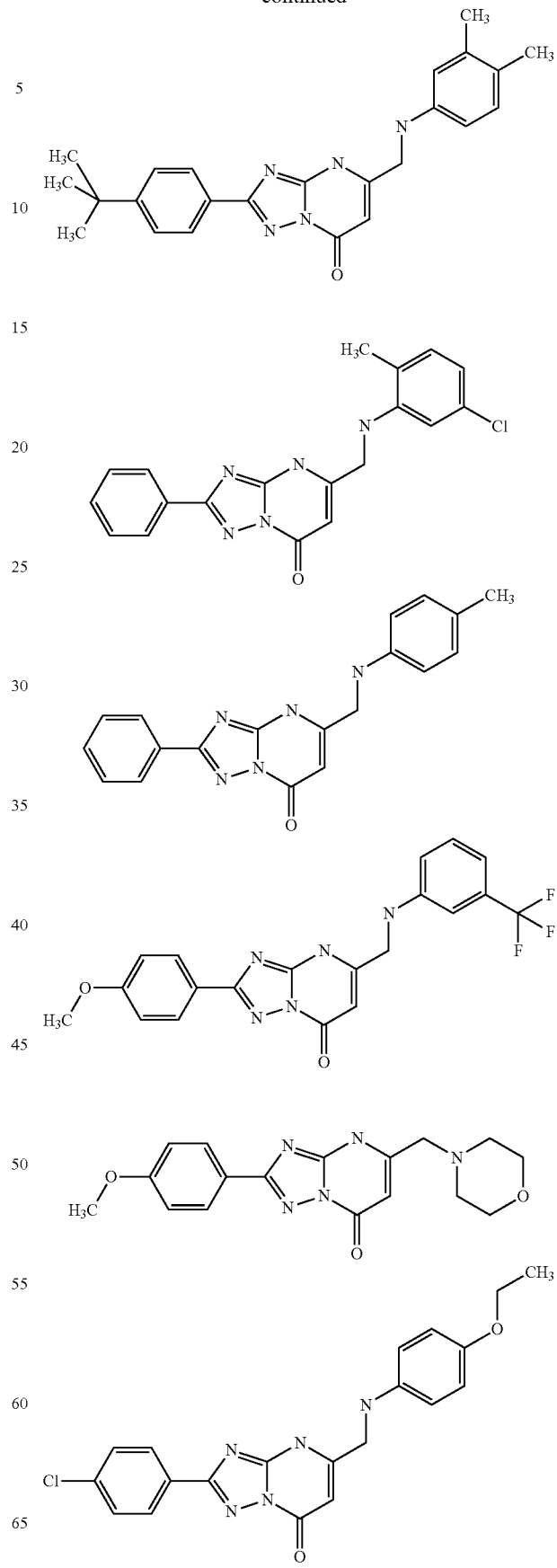

41
-continued
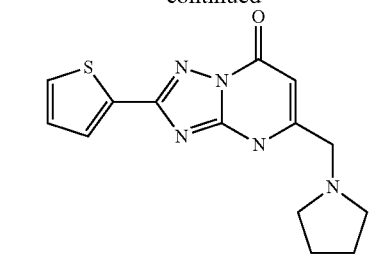
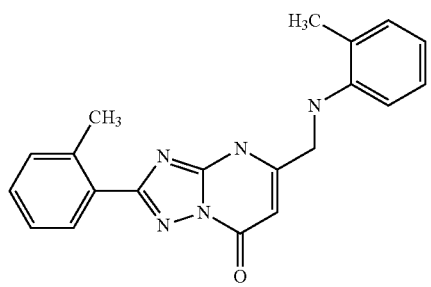
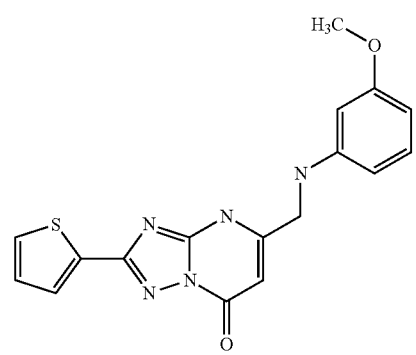
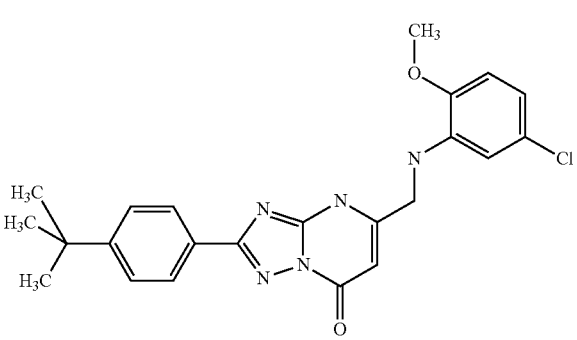
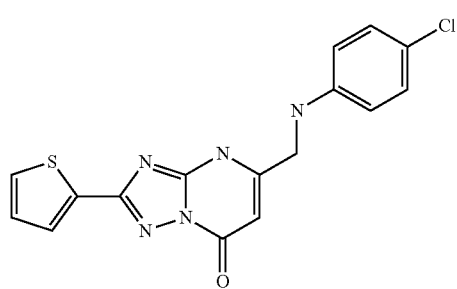
42
-continued
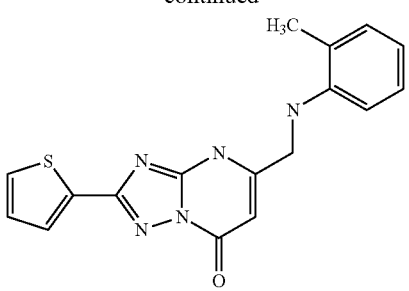
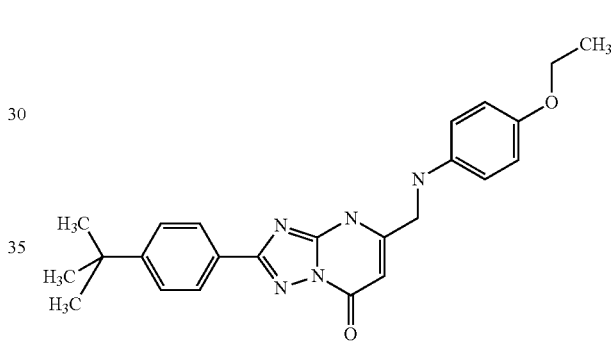

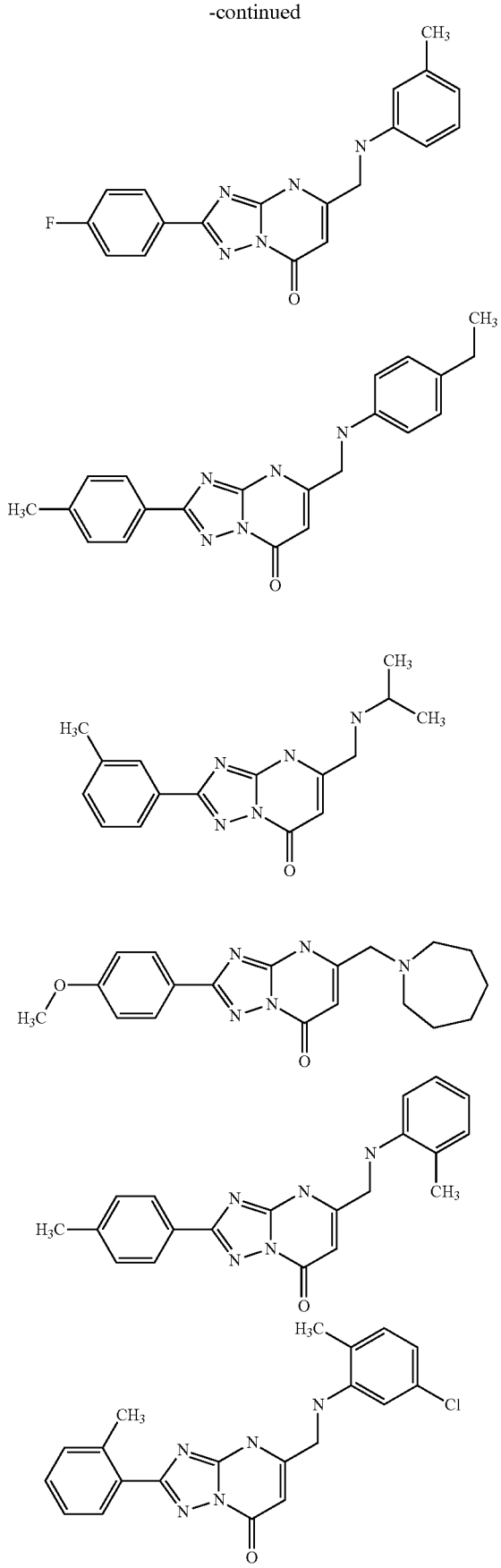
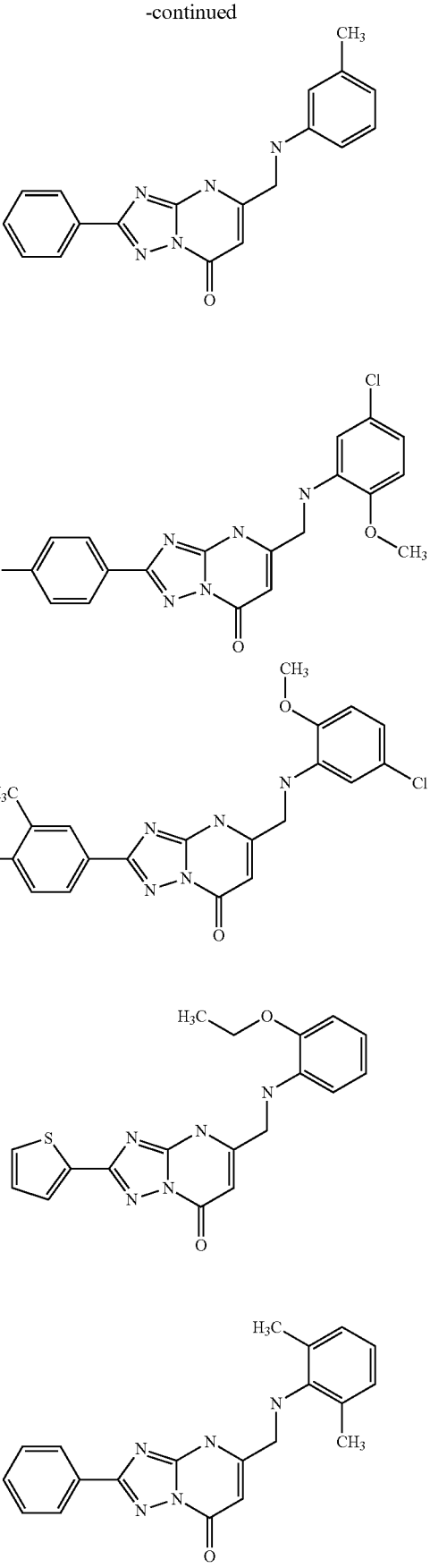

45
-continued
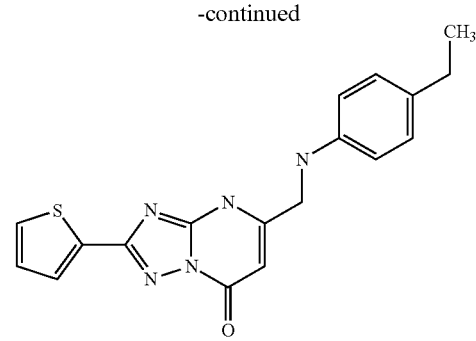
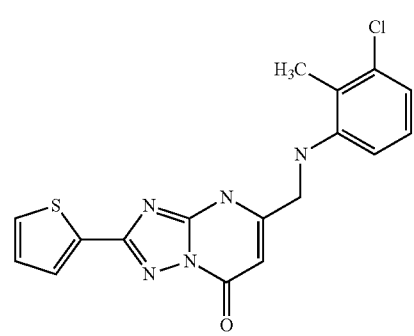
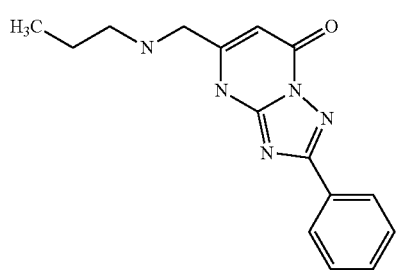
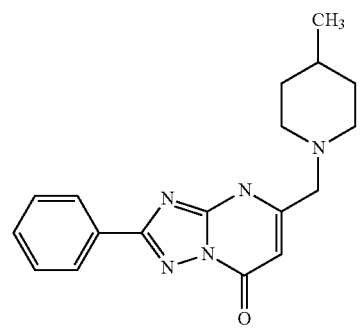
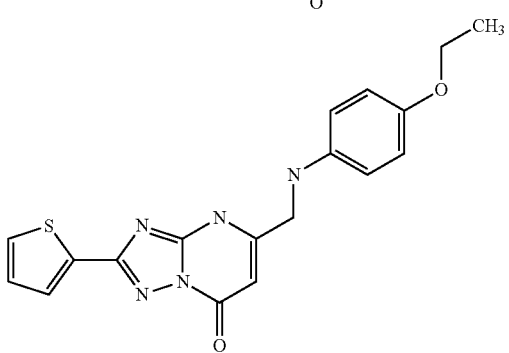
46
-continued
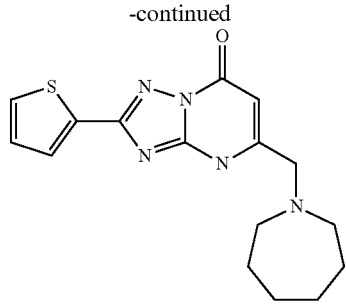
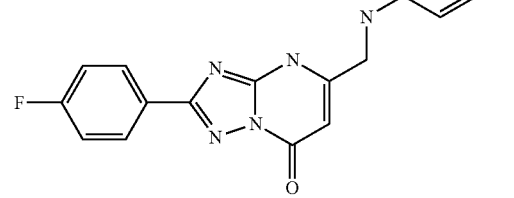
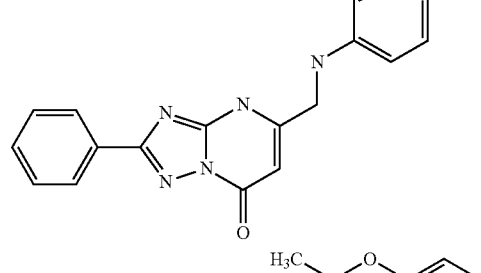
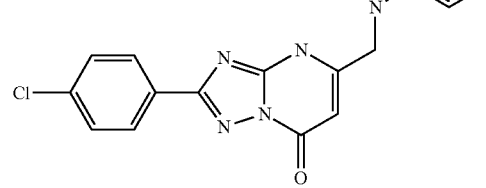
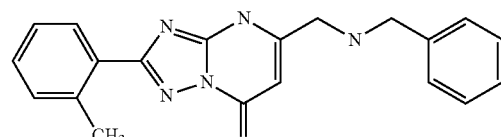
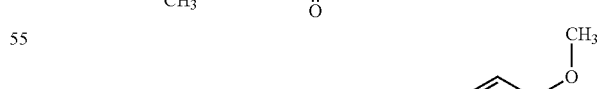
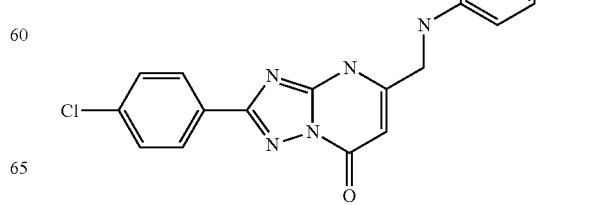

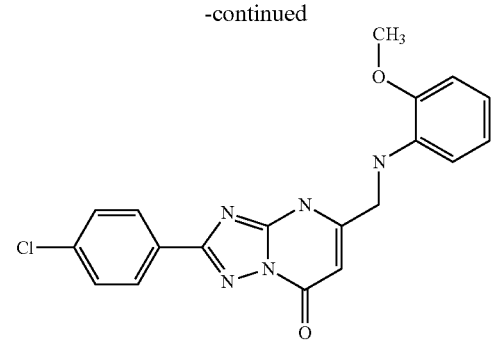
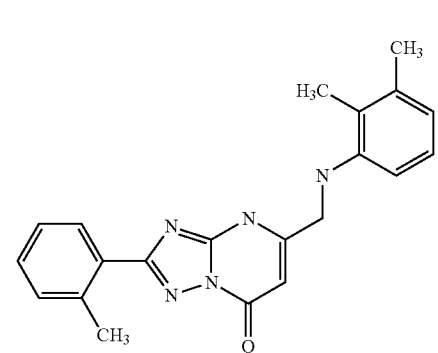
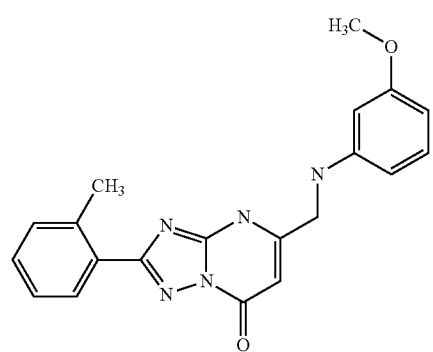
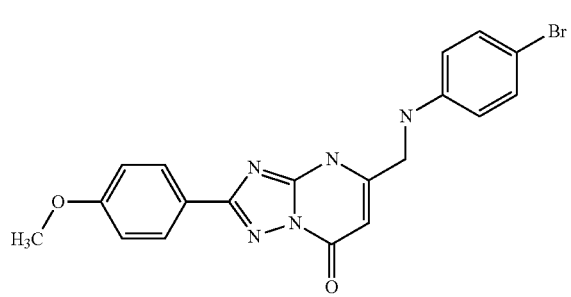
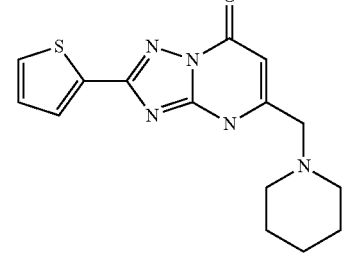
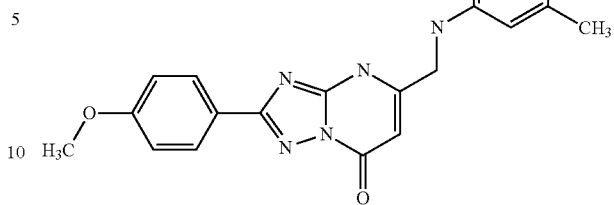
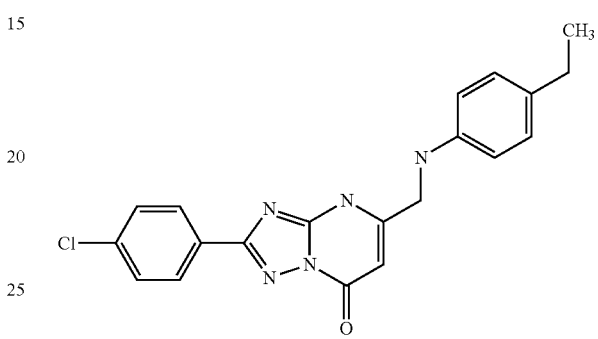
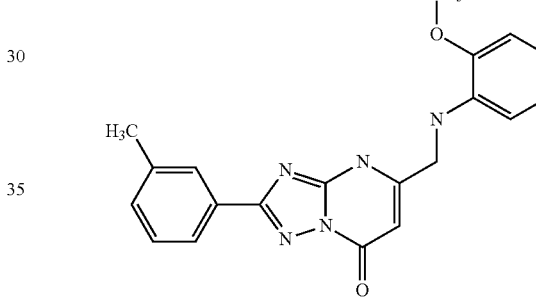
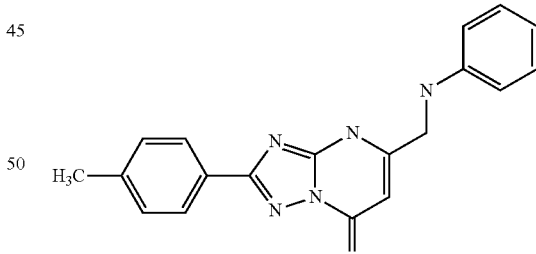
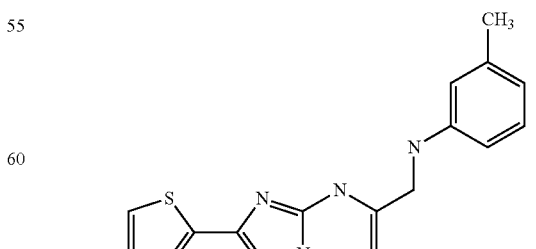

49
-continued
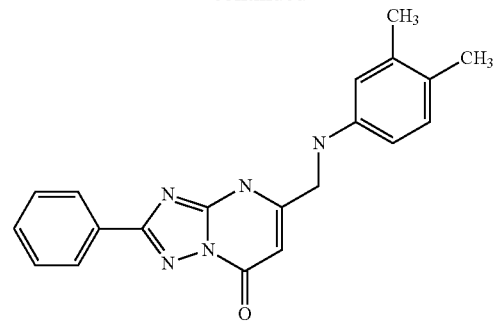
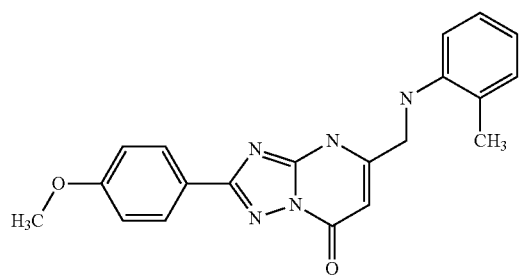
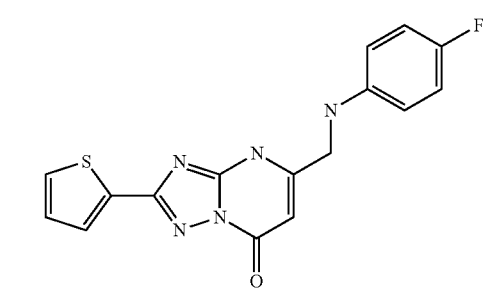
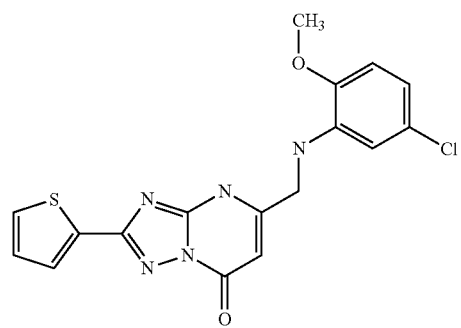
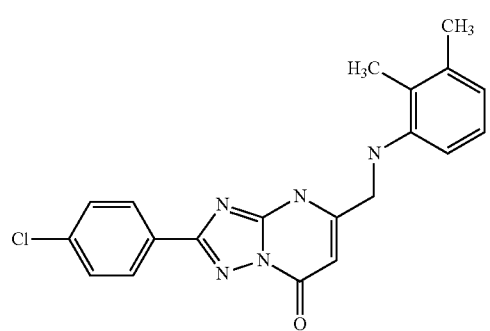
50
-continued
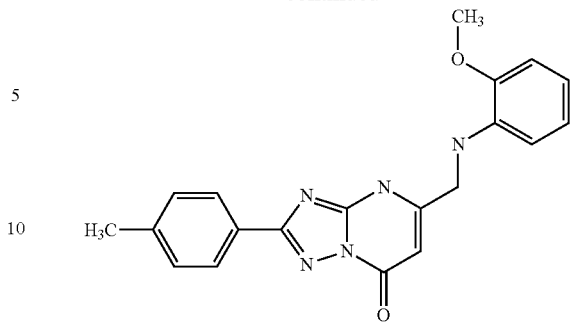
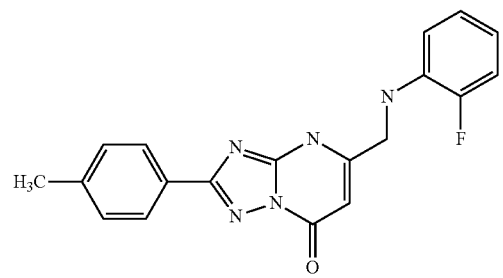
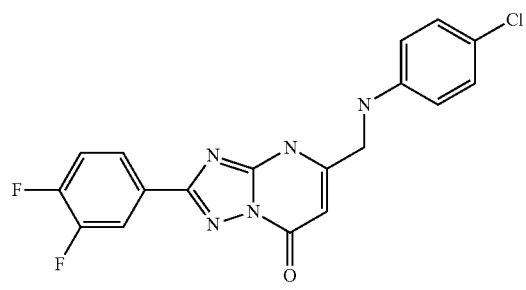
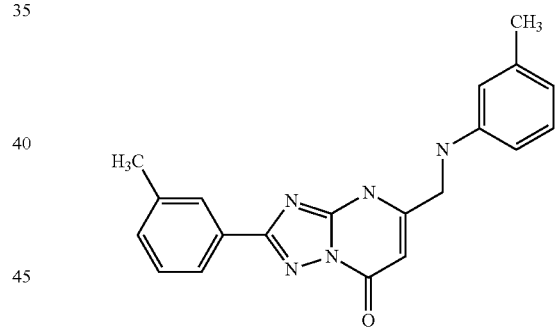
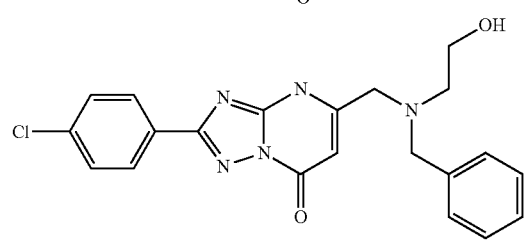
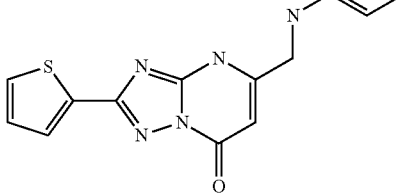

-continued

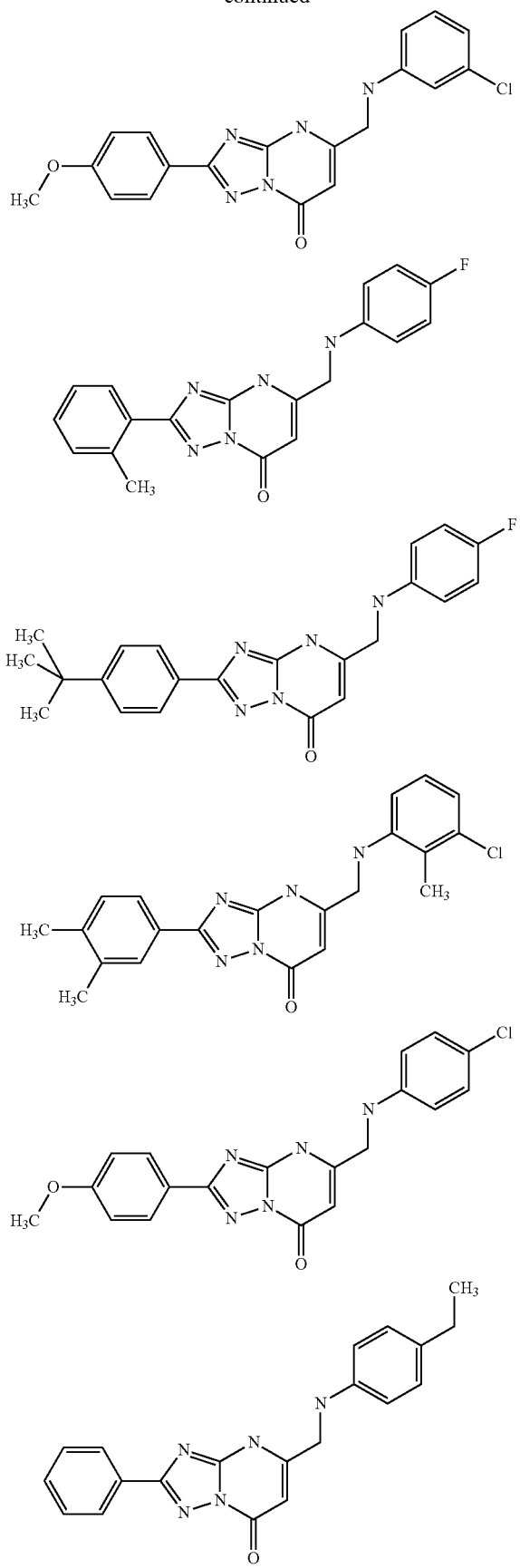

-continued

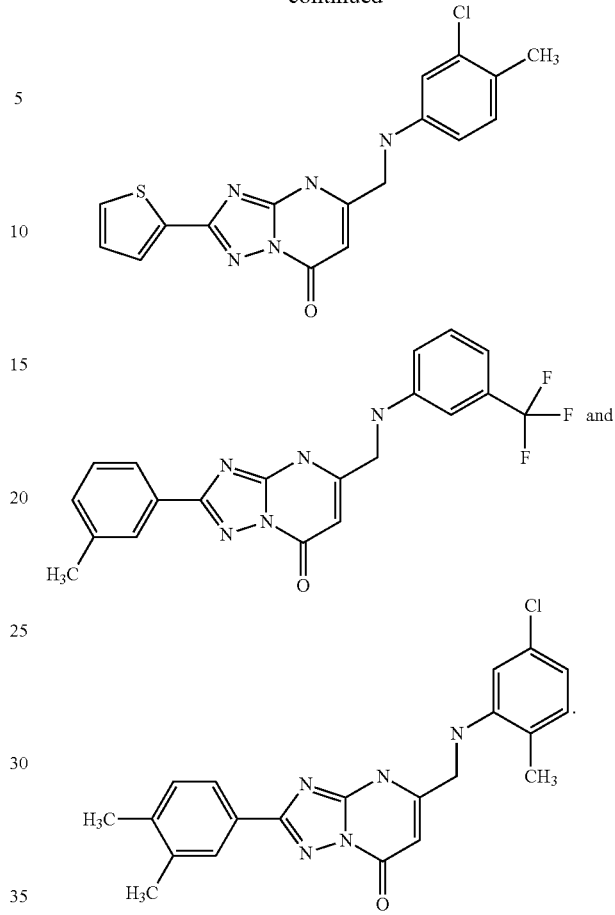

In another aspect, this invention provides compositions comprising at least one compound of Formula I.

In another aspect, this invention provides pharmaceutical compositions comprising at least one compound of Formula I and at least one pharmaceutically acceptable carrier.

In another aspect, this invention provides a method of treating diabetes in a patient in need of such treatment using therapeutically effective amounts of at least one compound of Formula I, or of a composition comprising at least one compound of Formula I.

In another aspect, this invention provides a method of treating diabetes in a patient in need of such treatment, e.g., Type 2 diabetes, using therapeutically effective amounts of at least one compound of Formula I, or of a composition comprising at least one compound of Formula I.

In another aspect, this invention provides a method of treating metabolic syndrome in a patient in need of such treatment, using therapeutically effective amounts of at least one compound of Formula I, or of a composition comprising at least one compound of Formula I.

In another aspect, this invention provides a method of treating dyslipidemia in a patient in need of such treatment, using therapeutically effective amounts of at least one compound of Formula I, or of a composition comprising at least one compound of Formula I.

In another aspect, this invention provides a method of treating or preventing a cardiovascular condition in a patient in need of such treatment, using therapeutically effective amounts of at least one compound of Formula I, or of a composition comprising at least one compound of Formula I.

In another aspect, this invention provides a method of treating obesity in a patient in need of such treatment, using therapeutically effective amounts of at least one compound of Formula I, or of a composition comprising at least one compound of Formula I.

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 5 ("FABP5").

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 4 ("FABP4").

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP4 and FABP5.

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 3 ("FABP3").

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP3 and FABP4.

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP3 and FABP5.

This invention further provides methods of using at least one compound of Formula I, or pharmaceutically acceptable salt, solvate, ester or prodrug of said compound, or pharmaceutically acceptable salt, solvate or ester of said prodrug, for inhibiting FABP3, FABP4 and FABP5.

In another aspect, this invention provides a method of inhibiting FABP using therapeutically effective amounts of a composition comprising at least one compound of Formula I.

In another aspect, this invention provides a method of inhibiting FABP4, or FABP3, or FABP5, using therapeutically effective amounts of a composition comprising at least one compound of Formula I.

In another aspect, this invention provides a method of inhibiting both FABP4 and FABP5 using therapeutically effective amounts of a composition comprising at least one compound of Formula I.

In another aspect, this invention provides a method of inhibiting both FABP3 and FABP5 using therapeutically effective amounts of a composition comprising at least one compound of Formula I.

In another aspect, this invention provides a method of inhibiting both FABP3 and FABP4 using therapeutically effective amounts of a composition comprising at least one compound of Formula I.

In another aspect, this invention provides a method of inhibiting FABP3, FABP4 and FABP5 using therapeutically effective amounts of a composition comprising at least one compound of Formula I.

In another aspect, this invention provides a method of inhibiting FABP using therapeutically effective amounts of at least one compound of Formula I, and therapeutically effective amounts of at least one other therapeutic agent.

In another aspect, this invention provides a method of inhibiting FABP4, or FABP3 or FABP5, using therapeutically effective amounts of at least one compound of Formula I, and therapeutically effective amounts of at least one other therapeutic agent.

In another aspect, this invention provides a method of inhibiting both FABP4 and FABP5 using therapeutically effective amounts of a composition comprising at least one compound of Formula I, and therapeutically effective amounts of at least one other therapeutic agent.

In another aspect, this invention provides a method of inhibiting both FABP3 and FABP5 using therapeutically effective amounts of a composition comprising at least one compound of Formula I, and therapeutically effective amounts of at least one other therapeutic agent.

In another aspect, this invention provides a method of inhibiting both FABP4 and FABP3 using therapeutically effective amounts of a composition comprising at least one compound of Formula I, and therapeutically effective amounts of at least one other therapeutic agent.

In another aspect, this invention provides a method of inhibiting FABP3, FABP4 and FABP5, using therapeutically effective amounts of a composition comprising at least one compound of Formula I, and therapeutically effective amounts of at least one other therapeutic agent.

In another aspect, this invention provides a method of treating or preventing a cardiovascular condition in a patient in need of such treatment, using therapeutically effective amounts of at least one compound of Formula I, and therapeutically effective amounts of at least one other therapeutic agent.

In another aspect, this invention provides a method of treating diabetes in a patient in need of such treatment using therapeutically effective amounts of at least one compound of Formula I, and therapeutically effective amounts of at least one other therapeutic agent.

In another aspect, this invention provides a method of treating diabetes in a patient in need of such treatment, e.g., Type 2 diabetes, using therapeutically effective amounts of at least one compound of Formula I, and therapeutically effective amounts of at least one other therapeutic agent.

In another aspect, this invention provides a method of inhibiting both FABP4 and FABP5 using therapeutically effective amounts of at least one compound of Formula I, or of a composition comprising at least one compound of Formula I.

DESCRIPTION OF THE INVENTION

In an embodiment, the present invention discloses compounds of Formula I, or pharmaceutically acceptable salts, solvates, esters or prodrugs thereof.

In another embodiment, for Formula I, this invention discloses a compound, or pharmaceutically acceptable salt, solvate, ester or prodrug of said compound, or pharmaceutically acceptable salt, solvate or ester of said prodrug, the compound being represented by the general Formula:

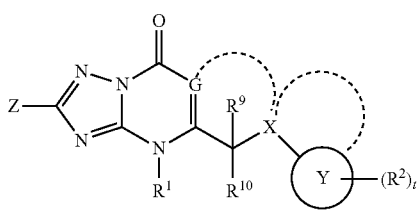

wherein:
Y is a ring as described below;
X is either:
(i) C($R^7R^8$), N($R^3$), S, S($O_2$), or O, and both ⌢ are absent; or
(ii) C($R^7$), and X is linked, either to the ring marked Y as shown by the ⌢ towards the right of X, or to the position marked G on the triazolopyrimidinone ring as shown by the ⌢ towards the left of X, to form a 3-8 membered cycloalkyl or a 4-8 membered heterocyclyl ring containing 1-3 heteroatoms independently selected from N, O and S, or
(iii) N (with $R^3$ being absent), and X is linked, either to the ring marked Y as shown by the ⌢ towards the right of X, or to the position marked G on the triazolopyrimidinone ring as shown by the ⌢ towards the left of X, to form a 4-8 membered heterocyclyl ring containing 1-3 heteroatoms independently selected from N, O and S, including the nitrogen atom of X;
further wherein ⌢ shown to the right of X is mutually exclusive of ⌢ shown to the left of X;
G is C($R^6$) ⌢ when shown to the left of X is absent, and G is C when ⌢ shown to the left of X is present;
Ring Y is aryl, heteroaryl, heterocyclyl or cycloalkyl, and when ⌢ shown to the right of X is present, a ring atom on Y is the point of attachment for said ⌢ shown to the right of X, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and $CF_3$;
$R^3$ may be present or absent as stated above, and when $R^3$ is present, $R^3$ is H, alkyl or cycloalkyl, wherein each of said alkyl and cycloalkyl may be unsubstituted or optionally independently substituted with one or more substituents which can be the same or different, each substituent being independently selected from the group consisting of halo, hydroxyl, alkoxy, CN and $CF_3$;
$R^1$ is H, alkyl, -alkyl-$OR^4$, haloalkyl, haloalkoxy or -alkyl-CN;
t is 0-4;
each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$;
Z is H, —$OR^5$, —C(O)$OR^5$, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—$NH_2$, —C(O)N(H)($CH_3$), —NH—C(O)—$NH_2$, —C(O)$R^5$, and —C(O)$OR^5$;
$R^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;
$R^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)$R^4$, CN and $CF_3$;
$R^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;
$R^7$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$;
$R^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$;
$R^9$ is H, halo, alkyl, cycloalkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; and
$R^{10}$ is H, halo, alkyl, cycloalkyl, aryl or heteroaryl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R$^5$, CN and CF$_3$, or alternatively, R$^9$ and R$^{10}$ can together form =O or R$^9$ and R$^{19}$ can be joined to form a spirocyclyl group;

with the same proviso that is shown above under Formula I.

In another embodiment, for Formula I, the present invention discloses compounds of Formula IA, or pharmaceutically acceptable salts, solvates, esters or prodrugs thereof:

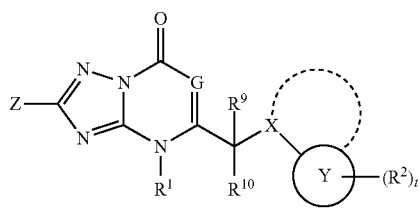

IA wherein:

G is C(R$^6$);

Y is a ring as described below;

X is either:
  (i) C(R$^7$R$^8$), N(R$^3$), S, S(O$_2$), or O, and ⁀ is absent; or
  (ii) X is C(R$^7$), and X is linked to the ring marked Y as shown by the ⁀ towards the right of X to form a 3-8 membered cycloalkyl ring or a 4-8 membered heterocyclyl ring containing 1-3 heteroatoms independently selected from N, O and S; or
  (iii) X is N (with R$^3$ being absent), and X is linked to the ring marked Y as shown by the ⁀ towards the right of X to form a 4-8 membered heterocyclyl ring containing 1-3 heteroatoms independently selected from N, O and S, including the nitrogen of X;

Ring Y is aryl, heteroaryl, heterocyclyl or cycloalkyl, and when ⁀ shown to the right of X is present, one ring atom on Y is the point of attachment for said ⁀ to the right of X, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and CF$_3$;

R$^3$ may be present or absent as stated above, and when R$^3$ is present, R$^3$ is H, alkyl or cycloalkyl, wherein each of said alkyl and cycloalkyl may be unsubstituted or optionally independently substituted with one or more substituents which can be the same or different, each substituent being independently selected from the group consisting of halo, hydroxyl, alkoxy, CN and CF$_3$;

R$^1$ is H, alkyl, -alkyl-OR$^4$, -alkyl-halo, haloalkyl, haloalkoxy or -alkyl-CN;

t is 0-4;

each R$^2$ is independently selected from the group consisting of halo, CN, —OR$^5$, alkyl, haloalkyl, haloalkoxy, aryl, heteroaryl, heterocyclyl, cycloalkyl, —NH$_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—NH$_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—NH$_2$, —C(O)R$^5$, and —C(O)OR$^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R$^5$, CN and CF$_3$;

Z is H, —OR$^5$, —C(O)OR$^5$, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, —C(O)R$^5$, and —C(O)OR$^5$;

R$^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)R$^4$, CN and CF$_3$;

R$^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^7$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF$_3$;

R$^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF$_3$; and R$^9$ and R$^{10}$ are as defined under Formula I, or alternatively, R$^9$ and R$^{19}$ can together form =O or R$^9$ and R$^{10}$ can be joined to form a spirocyclyl group;

with the same proviso as shown earlier under Formula I.

In another embodiment, for Formula I, the present invention discloses compounds of Formula IB, or pharmaceutically acceptable salts, solvates, esters or prodrugs thereof:

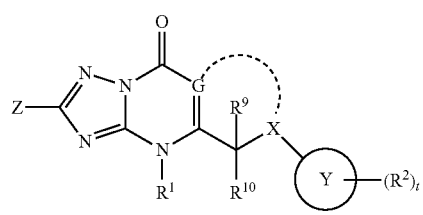

IB wherein:

Y is a ring as described below;

G is $C(R^6)$ when ⌒ shown to the left of X is absent, and G is C when ⌒ shown to the left of X is present;

X is either:
(i) $C(R^7R^8)$, $N(R^3)$, S, $S(O_2)$, or O, and ⌒ is absent; or
(ii) X is $C(R^7)$, and X is linked to the position marked G on the triazolopyrimidinone moiety ring as shown by the ⌒ towards the left of X to form a 3-8 membered cycloalkyl ring or a 4-8 membered heterocyclyl ring containing 1-3 heteroatoms independently selected from N, O and S; or
(iii) X is N (with $R^3$ being absent), and X is linked to the position marked G on the triazolopyrimidinone moiety as shown by the ⌒ towards the left of X to form a 4-8 membered heterocyclyl ring containing 1-3 heteroatoms independently selected from N, O and S, including the nitrogen of X;

Ring Y is aryl, heteroaryl, heterocyclyl or cycloalkyl, and when ⌒ shown to the right is present, one ring atom on Y is the point of attachment for said ⌒ to the right, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and $CF_3$, $R^3$ may be present or absent as stated above, and when $R^3$ is present, $R^3$ is H, alkyl or cycloalkyl, wherein each of said alkyl and cycloalkyl may be unsubstituted or optionally independently substituted with one or more substituents which can be the same or different, each substituent being independently selected from the group consisting of halo, hydroxyl, alkoxy, CN and $CF_3$;

$R^1$ is H, alkyl, -alkyl-$OR^4$, -alkyl-halo, haloalkyl, haloalkoxy or -alkyl-CN;

t is 0-4;

each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)—$NH_2$, —C(O)N(H)($CH_3$), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$;

Z is H, —$OR^5$, —C(O)$OR^5$, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—$NH_2$, —C(O)N(H)($CH_3$), —NH—C(O)—$NH_2$, —C(O)$R^5$, and —C(O)$OR^5$;

$R^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)$R^4$, CN and $CF_3$;

$R^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$, $R^7$ is present, $R^7$ is H or alkyl, wherein said alkyl may be unsubstituted or optionally independently substituted with one or more substituents which can be the same or different, each substituent being independently selected from the group consisting of halo, hydroxyl, alkoxy, CN and $CF_3$;

$R^8$ is present, $R^8$ is H or alkyl, wherein said alkyl may be unsubstituted or optionally independently substituted with one or more substituents which can be the same or different, each substituent being independently selected from the group consisting of halo, hydroxyl, alkoxy, CN and $CF_3$; and $R^9$ and $R^{10}$ are as defined under Formula I, or alternatively, $R^9$ and $R^{10}$ can together form =O or $R^9$ and $R^{10}$ can be joined to form a spirocyclyl group;

with the same proviso as shown earlier under Formula I.

In another embodiment, for Formula I, the present invention discloses compounds of Formula IC, or pharmaceutically acceptable salts, solvates, esters or prodrugs thereof:

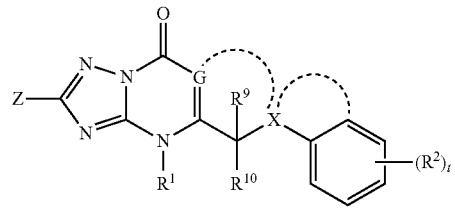

IC wherein:

G is $C(R^6)$ when ⌒ shown to the left of X is absent, and G is C when ⌒ shown to the left of X is present;

X is either:
(i) $C(R^7R^8)$, $N(R^3)$ or O, and both ⌒ are absent; or
(ii) X is $C(R^7)$, and X is linked, either to the phenyl ring as shown by the ⌒ towards the right of X, or to the position marked G on the triazolopyrimidinone ring as shown by the ⌒ towards left of X, to form a 3-8 membered cycloalkyl ring or a 4-8 membered heterocyclyl ring containing 1-3 heteroatoms independently selected from N, O and S; or
(iii) X is N (with $R^3$ being absent), and X is linked, either to the phenyl ring as shown by the ⌒ towards the right of X, or to the triazolopyrimidinone ring as shown by the ⌒ towards left of X, to form a 4-8 membered heterocyclyl ring containing 1-3 heteroatoms independently selected from N, O and S, including the nitrogen of X; further wherein ⌒ shown to the right of X is mutually exclusive of ⌒ shown to the left of X;

$R^3$ may be present or absent as stated above, and when $R^3$ is present, $R^3$ is H or alkyl, wherein said alkyl may be unsubstituted or optionally independently substituted with one or more substituents which can be the same or different, each substituent being independently selected from the group consisting of halo, hydroxyl, alkoxy, CN and $CF_3$;

$R^1$ is H, alkyl, -alkyl-$OR^4$, -alkyl-halo, haloalkyl, haloalkoxy or -alkyl-CN;

t is 0-4;

each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$;

Z is aryl or heteroaryl, wherein each of said alkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—$NH_2$, —C(O)N(H)($CH_3$), —NH—C(O)—$NH_2$, and —C(O)$OR^5$;

$R^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; and $R^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$;

$R^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$; and $R^9$ and $R^{10}$ are as defined under Formula I, or alternatively, $R^9$ and $R^{10}$ can be joined together to form a spirocyclyl group or a =O group;

with the same proviso as shown earlier under Formula I.

In another embodiment, for Formula I, the present invention discloses compounds of Formula ID, or pharmaceutically acceptable salts, solvates, esters or prodrugs thereof:

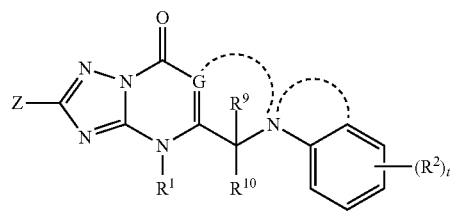

ID wherein:

G is C($R^6$) when shown to the left of N (between the two dotted lines) is absent, and G is C when shown to the left of N (between the two dotted lines) is present;

the N in between the dotted lines is linked, either to the phenyl ring as shown by the towards the right of N, or to the triazolopyrimidinone ring as shown by the towards left of N, to form a 4-8 membered heterocyclyl ring containing 1-3 heteroatoms independently selected from N, O and S, including the nitrogen of N; further wherein shown to the right of X is mutually exclusive of shown to the left of N;

$R^1$ is H, alkyl, -alkyl-$OR^4$, -alkyl-halo, haloalkyl, haloalkoxy or -alkyl-CN;

t is 0-4;

each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$;

Z is aryl, alkenyl, alkynyl, or heteroaryl, wherein each of said alkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—$NH_2$, —C(O)N(H)($CH_3$), —NH—C(O)—$NH_2$, and —C(O)$OR^5$, $R^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; and $R^9$ and $R^{10}$ are as defined under Formula I, or alternatively, $R^9$ and $R^{10}$ can be joined together to form a spirocyclyl group or a =O group;

with the same proviso as shown earlier under Formula I.

In another embodiment, for Formula I, the present invention discloses compounds of Formula IE, or pharmaceutically acceptable salts, solvates, esters or prodrugs thereof:

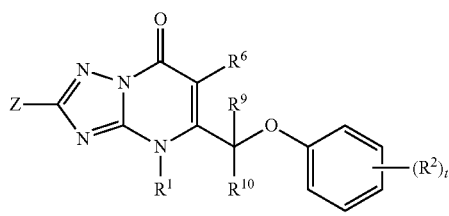

IE wherein:

$R^1$ is H, alkyl, -alkyl-$OR^4$, -alkyl-halo, haloalkyl, haloalkoxy or -alkyl-CN;

t is 0-4;

each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, ON and $CF_3$;

Z is aryl or heteroaryl, wherein each of said alkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—$NH_2$, —C(O)N(H)($CH_3$), —NH—C(O)—$NH_2$, and —C(O)$OR^5$;

$R^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, CN and $CF_3$;

$R^6$ is H, halo, hydroxy, alkoxy, amino, aminoalkyl, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; and $R^9$ and $R^{10}$ are as defined under Formula I, or alternatively, $R^9$ and $R^{10}$ can be joined together to form a spirocyclyl group or a =O group;

with the same proviso as shown earlier under Formula I.

In another embodiment, for Formula I, the present invention discloses compounds of Formula IF, or pharmaceutically acceptable salts, solvates, esters or prodrugs thereof:

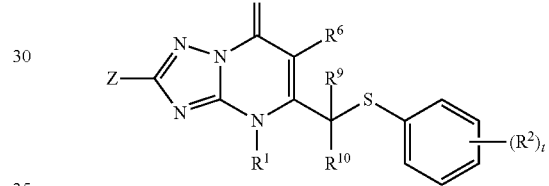

IF wherein:

$R^1$ is H, alkyl, -alkyl-$OR^4$, -alkyl-halo, haloalkyl, haloalkoxy or -alkyl-CN;

t is 0-4;

each $R^2$ is independently selected from the group consisting of halo, CN, —$OR^5$, alkyl, haloalkyl, haloalkoxy, aryl, heteroaryl, heterocyclyl, cycloalkyl, —$NH_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)$OR^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$;

Z is aryl or heteroaryl, wherein each of said alkyl, aryl and heteroaryl may be unsubstituted or optionally independently substituted with one or more substituents which can be the same or different, each substituent being independently selected from the group consisting of halo, CN, —$OR^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$;

R$^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, CN and CF$_3$;

R$^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF$_3$; and R$^9$ and R$^{10}$ are as defined under Formula I, or alternatively, R$^9$ and R$^{10}$ can be joined together to form a spirocyclyl group or a =O group;

with the same proviso as shown earlier under Formula I.

The term 'spirocyclyl" refers to a cyclic group substituted off the same carbon atom. A non-limiting example is:

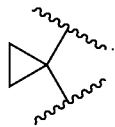 [SMILES: *C1(*)CC1]

The term "or alternatively, R$^9$ and R$^{10}$ can be joined together to form a spirocyclyl group" means that R$^9$ and R$^{10}$ can optionally form a spirocyclyl group having from 1-6 carbon atoms including the carbon that both R$^9$ and R$^{10}$ are shown attached to in Formula I and other Formulas above. Non-limiting examples of such spirocyclyl groups for R$^9$ and R$^{10}$ include the following:

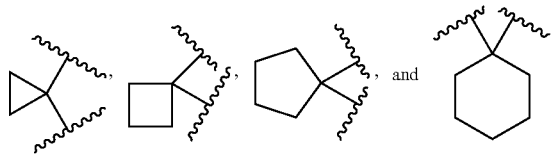

The following embodiments are independent of each other; different such embodiments can be independently selected and combined in various combinations. These embodiments are applicable to Formulas I, IA, IB, IC, ID, IE or IF as suitable and as valences would permit. Such combinations should be considered as part of the invention.

In another embodiment, G is C(R$^6$).
In another embodiment, ring Y is aryl.
In another embodiment, ring Y is heteroaryl.
In another embodiment, ring Y is heterocyclyl.
In another embodiment, ring Y is cycloalkyl.
In another embodiment, X is C(R$^7$R$^8$).
In another embodiment, X is N(R$^3$).
In another embodiment, X is NH.
In another embodiment, X is N(alkyl).
In another embodiment, X is O.

In another embodiment, X is S.

In another embodiment, X is C(R$^7$R$^8$), Y is a phenyl ring, and X is linked to the phenyl ring as shown by the ⌒ towards the right in Formula I to form a 4-8 membered heterocyclyl ring containing 1-3 heteroatoms independently selected from N, O and S, including the nitrogen of X.

In another embodiment, X is C(R$^7$R$^8$), Y is a phenyl ring, and X is linked to the phenyl ring as shown by the ⌒ towards the right in Formula I to form a 5-7 membered heterocyclyl ring containing 1-3 heteroatoms independently selected from N, O and S, including the nitrogen of X.

In another embodiment, X is C(R$^7$R$^8$), Y is a phenyl ring, and X is linked to the phenyl ring as shown by the ⌒ towards the right in Formula I to form a piperidinyl ring including the nitrogen of X.

In another embodiment, X is C(R$^7$R$^8$), Y is a phenyl ring, and X is linked to the phenyl ring as shown by the ⌒ towards the right in Formula I to form a piperazinyl ring including the nitrogen of X.

In another embodiment, X is N, R$^3$ is absent, Y is a phenyl ring, and X is linked to the phenyl ring as shown by the ⌒ towards the right in Formula I to form a 4-8 membered heterocyclyl ring containing 1-3 heteroatoms independently selected from N, O and S, including the nitrogen of X.

In another embodiment, X is N, R$^3$ is absent, Y is a phenyl ring, and X is linked to the phenyl ring as shown by the ⌒ towards the right in Formula I to form a 5-7 membered heterocyclyl ring containing 1-3 heteroatoms independently selected from N, O and S, including the nitrogen of X.

In another embodiment, X is N, R$^3$ is absent, Y is a phenyl ring, and X is linked to the phenyl ring as shown by the ⌒ towards the right in Formula I to form a piperidinyl ring including the nitrogen of X.

In another embodiment, X is N, R$^3$ is absent, Y is a phenyl ring, and X is linked to the phenyl ring as shown by the ⌒ towards the right in Formula I to form a piperazinyl ring including the nitrogen of X.

In another embodiment, X is N and R$^3$ is absent, G is C, Y is as discussed under Formula I, and X is linked to the triazolopyrimidinone ring as shown by the ⌒ towards the left in Formula I to form a 4-8 membered heterocyclyl ring containing 1-3 heteroatoms independently selected from N, and S, including the nitrogen of X.

In another embodiment, X is N and R$^3$ is absent, G is C, Y is as discussed under Formula I, and X is linked to the triazolopyrimidinone ring as shown by the ⌒ towards the left in Formula I to form a 5-7 membered heterocyclyl ring containing 1-3 heteroatoms independently selected from N, O and S, including the nitrogen of X.

In another embodiment, Y is phenyl.
In another embodiment, Y is pyridyl.
In another embodiment, Y is cyclobutyl.
In another embodiment, Y is piperidyl.
In another embodiment, Y is tetrahydronaphthyl.
In another embodiment, R$^1$ is H.
In another embodiment, R$^1$ is methyl.
In another embodiment, R$^1$ is hydroxymethyl.
In another embodiment, R$^1$ is chloromethyl.
In another embodiment, R$^1$ is cyanomethyl.
In another embodiment, R$^1$ is methoxymethyl.
In another embodiment, R$^1$ is CF$_3$.
In another embodiment, t is 0.
In another embodiment, t is 1.
In another embodiment, t is 2.
In another embodiment, t is 3.
In another embodiment, t is 4.
In another embodiment, R$^2$ is halo.

In another embodiment, $R^2$ is CN.
In another embodiment, $R^2$ is —OH.
In another embodiment, $R^2$ is —NH$_2$.
In another embodiment, $R^2$ is —C(O)R$^5$.
In another embodiment, $R^2$ is alkyl.
In another embodiment, $R^2$ is haloalkyl.
In another embodiment, $R^2$ is alkoxy.
In another embodiment, $R^2$ is haloalkoxy.
In another embodiment, $R^2$ is —C(O)—NH$_2$.
In another embodiment, $R^2$ is —C(O)OR$^5$.
In another embodiment, Z is aryl, wherein said aryl may be unsubstituted or optionally independently substituted with one or more substituents which can be the same or different, each substituents being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$.
In another embodiment, Z is cycloalkyl, wherein said cycloalkyl may be unsubstituted or optionally independently substituted with one or more substituents which can be the same or different, each substituents being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$.
In another embodiment, Z is heteroaryl, wherein said heteroaryl may be unsubstituted or optionally independently substituted with one or more substituents which can be the same or different, each substituent being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$.
In another embodiment, Z is phenyl, wherein said phenyl may be unsubstituted or optionally independently substituted with one or more substituents which can be the same or different, each substituent being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$.
In another embodiment, Z is thiophenyl, wherein said thiophenyl may be unsubstituted or optionally independently substituted with one or more substituents which can be the same or different, each substituents being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, and —C(O)OR$^5$.
In another embodiment, $R^4$ is H.
In another embodiment, $R^4$ is methyl.
In another embodiment, $R^4$ is alkyl.
In another embodiment, $R^5$ is H.
In another embodiment, $R^5$ is alkyl.
In another embodiment, $R^5$ is methyl.
In another embodiment, $R^6$ is H.
In another embodiment, $R^6$ is alkyl.
In another embodiment, $R^6$ is halo.
In another embodiment, $R^7$ is absent.
In another embodiment, $R^7$ is H.
In another embodiment, $R^7$ is alkyl.
In another embodiment, $R^8$ is absent.
In another embodiment, $R^8$ is H.
In another embodiment, $R^8$ is alkyl.
In another embodiment, $R^9$ is H.
In another embodiment, $R^9$ is halo.
In another embodiment, $R^9$ is fluoro.
In another embodiment, $R^9$ is alkyl.
In another embodiment, $R^9$ is cycloalkyl.
In another embodiment, $R^{10}$ is H.
In another embodiment, $R^{10}$ is halo.
In another embodiment, $R^{10}$ is fluoro.
In another embodiment, $R^{10}$ is alkyl.
In another embodiment, $R^{10}$ is cycloalkyl.
In another embodiment, $R^9$ and $R^{10}$ form a 3-membered spirocyclyl group (cyclopropyl).
In another embodiment, $R^9$ and $R^{10}$ form a =O.
In another embodiment, —C(R$^9$R$^{10}$)—X— is a —C(=O)—NH—.
In another embodiment, $R^9$ and $R^{10}$ form a 4-membered spirocyclyl group (cyclobutyl).
In another embodiment, $R^9$ and $R^{10}$ form a 5-membered spirocyclyl group (cyclopentyl).
In another embodiment, wherein X, t, $R^1$, Z, $R^1$, $R^3$, $R^4$, $R^5$ and the other moieties are independently selected, X is NH, Z is aryl, $R^1$ is H, and the other moieties are as previously described.
In another embodiment, wherein X, t, $R^1$, Z, $R^1$, $R^3$, $R^4$, $R^5$ and the other moieties are independently selected, X is NH, Z is phenyl, $R^1$ is H, and the other moieties are as previously described.
In another embodiment, wherein X, t, $R^1$, Z, $R^1$, $R^3$, $R^4$, $R^5$ and the other moieties are independently selected, X is N(alkyl), Z is aryl, $R^1$ is H, and the other moieties are as previously described.
In another embodiment, wherein X, t, $R^1$, Z, $R^1$, $R^3$, $R^4$, $R^5$ and the other moieties are independently selected, X is N(alkyl), Z is phenyl, $R^1$ is H, and the other moieties are as previously described.
In another embodiment, wherein X, t, $R^1$, Z, $R^1$, $R^3$, $R^4$, $R^5$ and the other moieties are independently selected, X is N(methyl), Z is phenyl, $R^1$ is H, and the other moieties are as previously described.
In another embodiment, wherein X, t, $R^1$, Z, $R^1$, $R^4$, $R^5$ and the other moieties are independently selected, X is O, Z is aryl, $R^1$ is H, and the other moieties are as previously described.
In another embodiment, wherein X, t, $R^1$, Z, $R^1$, $R^3$, $R^4$, $R^5$ and the other moieties are independently selected, X is O, Z is phenyl, $R^1$ is H, and the other moieties are as previously described.
In another embodiment, wherein X, t, $R^1$, Z, $R^1$, $R^3$, $R^4$, $R^5$ and the other moieties are independently selected, X is O, Z is heteroaryl, $R^1$ is H, and the other moieties are as previously described.
In another embodiment, wherein X, t, $R^1$, Z, $R^1$, $R^3$, $R^4$, $R^5$ and the other moieties are independently selected, X is O, Z is thiophenyl, $R^1$ is H, and the other moieties are as previously described.
In another embodiment, wherein X, t, $R^1$, Z, $R^1$, $R^3$, $R^4$, $R^5$ and the other moieties are independently selected, X is NH, Z is heteroaryl, $R^1$ is H, and the other moieties are as previously described.
In another embodiment of, wherein X, t, $R^1$, Z, $R^1$, $R^3$, $R^4$, $R^5$ and the other moieties are independently selected, X is NH, Z is thiophenyl, $R^1$ is H, and the other moieties are as previously described.

In another embodiment, wherein X, t, $R^1$, Z, $R^1$, $R^3$, $R^4$, $R^5$ and the other moieties are independently selected, X is N(alkyl), Z is heteroaryl, $R^1$ is H, and the other moieties are as previously described.

In another embodiment, wherein X, t, $R^1$, Z, $R^1$, $R^3$, $R^4$, $R^5$ and the other moieties are independently selected, X is N(methyl), Z is heteroaryl, $R^1$ is H, and the other moieties are as previously described.

In another embodiment, wherein X, t, $R^1$, Z, $R^1$, $R^3$, $R^4$, $R^5$ and the other moieties are independently selected, X is N(alkyl), Z is thiophenyl, $R^1$ is H, and the other moieties are as previously described.

In another embodiment, wherein X, t, $R^1$, Z, $R^1$, $R^4$, $R^5$ and the other moieties are independently selected, X is O, Z is heteroaryl, $R^1$ is H, and the other moieties are as previously described.

In another embodiment, wherein X, t, $R^1$, Z, $R^1$, $R^3$, $R^4$, $R^5$ and the other moieties are independently selected, X is NH, Z is phenyl, $R^1$ is H, and the other moieties are as previously described.

In another embodiment, wherein X, t, $R^1$, Z, $R^1$, $R^3$, $R^4$, $R^5$ and the other moieties are independently selected, X is N(alkyl), Z is phenyl, $R^1$ is H, and the other moieties are as previously described.

In another embodiment, wherein X, t, $R^1$, Z, $R^1$, $R^4$, $R^5$ and the other moieties are independently selected, X is O, Z is phenyl, $R^1$ is H, and the other moieties are as previously described.

In another embodiment, wherein X, t, $R^1$, Z, $R^1$, $R^3$, $R^4$, $R^5$ and the other moieties are independently selected, X is NH, Z is thiophenyl, $R^1$ is H, and the other moieties are as previously described.

In another embodiment, wherein X, t, $R^1$, Z, $R^1$, $R^3$, $R^4$, $R^5$ and the other moieties are independently selected, X is N(alkyl), Z is thiophenyl, $R^1$ is H, and the other moieties are as previously described.

In another embodiment, wherein X, t, $R^1$, Z, $R^1$, $R^4$, $R^5$ and the other moieties are independently selected, X is O, Z is thiophenyl, $R^1$ is H, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is alkoxy, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is methoxy, and the other moieties are as previously described.

In another embodiment, wherein X, t, $R^1$, Z, $R^1$, $R^2$, $R^4$, $R^5$ and the other moieties are independently selected, X is NH, Z is unsubstituted phenyl, $R^1$ is H, t is 2, one $R^2$ is Cl and the other $R^2$ is alkoxy, and the other moieties are as previously described.

In another embodiment, wherein X, t, $R^1$, Z, $R^1$, $R^2$, $R^4$, $R^5$ and the other moieties are independently selected, X is NH, Z is unsubstituted phenyl, $R^1$ is H, t is 2, one $R^2$ is Cl and the other $R^2$ is methoxy, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is cycloalkyl, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is cyclopropyl, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is alkyl, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is methyl, and the other moieties are as previously described.

In another embodiment, wherein X, t, $R^1$, Z, $R^1$, $R^2$, $R^4$, $R^5$ and the other moieties are independently selected, X is NH, Z is unsubstituted phenyl, $R^1$ is H, t is 2, one $R^2$ is Cl and the other $R^2$ is cycloalkyl, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is cyclopropyl, and the other moieties are as previously described.

In another embodiment, wherein X, t, $R^1$, Z, $R^1$, $R^2$, $R^4$, $R^5$ and the other moieties are independently selected, X is NH, Z is phenyl, $R^1$ is H, t is 2, one $R^2$ is Cl and the other $R^2$ is cyclobutyl, and the other moieties are as previously described.

In another embodiment, wherein X, t, $R^1$, Z, $R^1$, $R^2$, $R^4$, $R^5$ and the other moieties are independently selected, X is NH, Z is unsubstituted phenyl, $R^1$ is H, t is 2, one $R^2$ is Cl and the other $R^2$ is cyclobutyl, and the other moieties are as previously described.

Several non-limiting examples of the compounds of the invention are shown in the Examples section. Many of the compounds exhibited FABP binding affinities (Kd, nM) less than 3 µM in the assay described later below. Several compounds exhibited Kd values less than 1 µM. Still additional compounds exhibited Kd values less than 100 nM. A representative non-limiting list of compounds and their activity are shown in a Table after the Assay section.

In another aspect, this invention provides pharmaceutical compositions comprising at least one compound of Formula I, IA, IB, IC, ID, IE or IF, and at least one pharmaceutically acceptable carrier.

In another aspect, this invention provides a method of treating diabetes in a patient in need of such treatment using therapeutically effective amounts of at least one compound of Formula I, IA, IB, IC, ID, IE or IF, or of a composition comprising at least one compound of Formula I.

In another aspect, this invention provides a method of treating diabetes in a patient in need of such treatment, e.g., Type 2 diabetes, using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of treating metabolic syndrome in a patient in need of such treatment, using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of treating dyslipidemia in a patient in need of such treatment, using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of treating or preventing a cardiovascular condition in a patient in need of such treatment, using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of treating obesity in a patient in need of such treatment, using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of inhibiting FABP using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of inhibiting FABP4 using therapeutically effective amounts of at least one compound of Formula I, IA, IB, IC, ID, IE or IF, or of a composition comprising at least one compound of Formula I, IA, IB, IC, ID, IE or IF.

In another aspect, this invention provides a method of inhibiting FABP using therapeutically effective amounts of at least one compound of Formula I, IA, IB, IC, ID, IE or IF, and therapeutically effective amounts of at least one other therapeutic agent.

In another aspect, this invention provides a method of inhibiting FABP4 using therapeutically effective amounts of at least one compound of Formula I, IA, IB, IC, ID, IE or IF, and therapeutically effective amounts of at least one other therapeutic agent.

In another aspect, this invention provides a method of treating or preventing a cardiovascular condition in a patient in need of such treatment, using therapeutically effective amounts of at least one compound of Formula I, IA, IB, IC, ID, IE or IF, and therapeutically effective amounts of at least one other therapeutic agent.

In another aspect, this invention provides a method of treating diabetes in a patient in need of such treatment using therapeutically effective amounts of at least one compound of Formula I, IA, IB, IC, ID, IE or IF, and therapeutically effective amounts of at least one other therapeutic agent.

In another aspect, this invention provides a method of treating diabetes in a patient in need of such treatment, e.g., Type 2 diabetes, using therapeutically effective amounts of at least one compound of Formula I, IA, IB, IC, ID, IE or IF, and therapeutically effective amounts of at least one other therapeutic agent.

In another aspect, this invention provides a method of inhibiting both FABP4 and FABP5 using therapeutically effective amounts of at least one compound of Formula I, IA, IB, IC, ID, IE or IF, or of a composition comprising at least one compound of Formula I, IA, IB, IC, ID, IE or IF.

As used above, and throughout this disclosure, the following terms, unless otherwise indicated, shall be understood to have the following meanings:

"Patient" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylhet-eroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)—alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

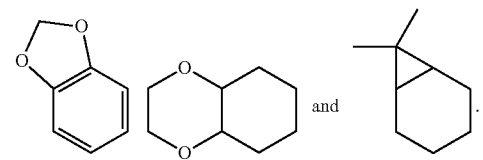

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like. "Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

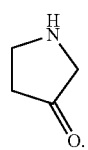

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

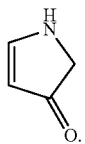

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

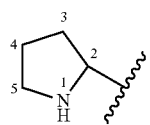

there is no —OH attached directly to carbons marked 2 and 5.

It should also be noted that tautomeric forms such as, for example, the moieties:

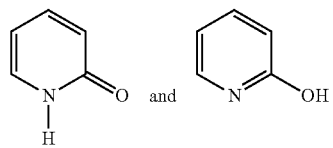 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

The present invention further includes the compound of Formula I, IA, IB, IC, ID, IE or IF in all its isolated forms. Thus, for example, the compound of Formula I, IA, IB, IC, ID, IE or IF is intended to encompass all forms of the compound such as, for example, any solvates, hydrates, stereoisomers, tautomers etc.

The present invention further includes the compound of Formula I, IA, IB, IC, ID, IE or IF in its purified form.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, IA, IB, IC, ID, IE or IF, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula I, IA, IB, IC, ID, IE or IF or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, IA, IB, IC, ID, IE or IF, or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula I, IA, IB, IC, ID, IE or IF contains an alcohol functional group, a prodrug can be formed by the replacement of the hydrogen atom of the alcohol group with a group such as, for example, ($C_1$-$C_8$)alkanoyloxymethyl, 1-(($C_1$-$C_8$)alkanoyloxy)ethyl, 1-methyl-1-(($C_1$-$C_6$)alkanoyloxy)ethyl, ($C_1$-$C_8$)alkoxycarbonyloxymethyl, N—($C_1$-$C_8$)alkoxycarbonylaminomethyl, succinoyl, ($C_1$-$C_8$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_8$)alkyl)$_2$ or glycosyl (the radical resulting from the removal of a hydroxyl group of the hemiacetal form of a carbohydrate), and the like.

If a compound of Formula I, IA, IB, IC, ID, IE or IF incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$) alkyl, carboxy($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al., *J. Pharmaceutical Sci.*, (2004) 93(3), pp. 601-611 describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, (2004) 5(1), article 12; and A. L. Bingham et al., *Chem. Commun.*, (2001) pp. 603-604. A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective" or 'therapeutically effective" is used herein, unless otherwise indicated, to describe an amount of a compound or composition which, in context, is used to produce or effect an intended result or therapeutic effect as understood in the common knowledge of those skilled in the art.

The compounds of Formula I, IA, IB, IC, ID, IE or IF can form salts which are also within the scope of this invention. Reference to a compound of Formula I, IA, IB, IC, ID, IE or IF herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I, IA, IB, IC, ID, IE or IF contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I, IA, IB, IC, ID, IE or IF may be formed, for example, by reacting a compound of Formula I, IA, IB, IC, ID, IE or IF with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) pp. 1-19; P. Gould, *International J. of Pharmaceutics* (1986) (2001) 33 pp. 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, IA, IB, IC, ID, IE or IF, and salts, solvates, esters and prodrugs thereof, may exist in their tautomeric form (for example, as an amide or imino ether). All such tautomeric forms are contemplated herein as part of the present invention.

The compounds of Formula I, IA, IB, IC, ID, IE or IF may contain asymmetric or chiral centers, and, therefore, exist in different stereoisomeric forms. It is intended that all stereoisomeric forms of the compounds of Formula I, IA, IB, IC, ID, IE or IF as well as mixtures thereof, including racemic mixtures, form part of the present invention. In addition, the present invention embraces all geometric and positional isomers. For example, if a compound of Formula I, IA, IB, IC, ID, IE or IF incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I, IA, IB, IC, ID, IE or IF may be atropisomers (e.g., substituted biaryls) and are considered as part of this invention. Enantiomers can also be separated by use of chiral HPLC column.

It is also possible that the compounds of Formula I, IA, IB, IC, ID, IE or IF may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I, IA, IB, IC, ID, IE or IF incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I, IA, IB, IC, ID, IE or IF (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I, IA, IB, IC, ID, IE or IF can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, IA, IB, IC, ID, IE or IF, and of the salts, solvates, esters and prodrugs of the compounds of Formula I, IA, IB, IC, ID, IE or IF are intended to be included in the present invention.

The compounds according to the invention have pharmacological properties. The compounds of Formula I, IA, IB, IC, ID, IE or IF are inhibitors of FABP, particularly FABP4, and can be useful for the therapeutic and/or prophylactic treatment of diseases that are modulated by FABP, particularly by FABP4, such as, for example, metabolic syndrome, diabetes (e.g., Type 2 diabetes mellitus), obesity and the like.

The invention also includes methods of treating diseases that are modulated by FABP, particularly by FABP4.

The invention also includes methods of treating metabolic syndrome, diabetes (e.g., Type 2 diabetes mellitus), and obesity in a patient by administering at least one compound of Formula I, IA, IB, IC, ID, IE or IF to said patient.

Diabetes refers to a disease process derived from multiple causative factors and is characterized by elevated levels of plasma glucose, or hyperglycemia in the fasting state or after administration of glucose during an oral glucose tolerance test. Persistent or uncontrolled hyperglycemia is associated with increased and premature morbidity and mortality. Abnormal glucose homeostasis is associated with alterations of the lipid, lipoprotein and apolipoprotein metabolism and other metabolic and hemodynamic disease. As such, the diabetic patient is at especially increased risk of macrovascular and microvascular complications, including coronary heart disease, stroke, peripheral vascular disease, hypertension, nephropathy, neuropathy, and retinopathy. Accordingly, therapeutic control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissue (muscle, liver and adipose tissue), and the plasma insulin levels, while elevated, are insufficient to overcome the pronounced insulin resistance.

Insulin resistance is not associated with a diminished number of insulin receptors but rather to a post-insulin receptor binding defect that is not well understood. This resistance to insulin responsiveness results in insufficient insulin activation of glucose uptake, oxidation and storage in muscle, and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic [beta]-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a class of agents that can increase insulin sensitivity and bring about some degree of correction of hyperglycemia. However, the biguanides can induce lactic acidosis and nausea/diarrhea.

The glitazones (i.e. 5-benzylthiazolidine-2,4-diones) are a separate class of compounds with potential for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have been noted in some patients treated with glitazone drugs, such as troglitazone.

Additional methods of treating the disease are currently under investigation. New biochemical approaches include treatment with alpha-glucosidase inhibitors (e.g. acarbose) and protein tyrosine phosphatase-1B (PTP-1B) inhibitors.

Compounds that are inhibitors of the dipeptidyl peptidase-IV (DPP-IV) enzyme are also under investigation as drugs that may be useful in the treatment of diabetes, and particularly type 2 diabetes.

The invention includes compositions, e.g., pharmaceutical compositions, comprising at least one compound of Formula I, IA, IB, IC, ID, IE or IF. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Other carriers include Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intrathecal, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient. Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preferably the compound is administered orally, intraperitoneally, or intravenously or intrathecally or some suitable combination(s) thereof.

Methods of administering small molecule therapeutic agents are well-known in the art.

The therapeutic agents described in the present disclosure can be administered to a subject alone or together (coadministered, optionally but not necessarily, in a single formulation) with other active agents as described herein, and are preferably administered with a pharmaceutically acceptable buffer. The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, IA, IB, IC, ID, IE or IF, or a pharmaceutically acceptable salt, solvate, ester or prodrug of said compound and a pharmaceutically acceptable carrier, vehicle or diluent.

Another aspect of the invention includes pharmaceutical compositions comprising at least one compound of Formula I, IA, IB, IC, ID, IE or IF and at least one other therapeutic agent in combination. Non-limiting examples of such combination agents are described below. The agents in the combination can be administered together as a joint administration (e.g., joint single pill), separately, one after the other in any order and the like as is well known in the art.

In the combination therapies of the present invention, an effective amount can refer to each individual agent or to the combination as a whole, wherein the amounts of all agents administered are together effective, but wherein the component agent of the combination may not be present individually in an effective amount.

Combination Therapy

Accordingly, in one embodiment, the present invention provides methods for treating a Condition in a patient, the method comprising administering to the patient one or more Compounds of Formula I, IA, IB, IC, ID, IE or IF, or a pharmaceutically acceptable salt or solvate thereof and at least one additional therapeutic agent that is not a Compound of Formula I, IA, IB, IC, ID, IE or IF, wherein the amounts administered are together effective to treat or prevent a Condition.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Compounds of Formula I, IA, IB, IC, ID, IE or IF is administered during at time when the additional therapeutic agent(s) exert their prophylactic or therapeutic effect, or vice versa.

In another embodiment, the one or more Compounds of Formula I, IA, IB, IC, ID, IE or IF and the additional therapeutic agent(s) are administered in doses commonly employed when such agents are used as monotherapy for treating a Condition.

In another embodiment, the one or more Compounds of Formula I, IA, IB, IC, ID, IE or IF and the additional therapeutic agent(s) are administered in doses lower than the doses commonly employed when such agents are used as monotherapy for treating a Condition.

In still another embodiment, the one or more Compounds of Formula I, IA, IB, IC, ID, IE or IF and the additional therapeutic agent(s) act synergistically and are administered in doses lower than the doses commonly employed when such agents are used as monotherapy for treating a Condition.

In one embodiment, the one or more Compounds of Formula I, IA, IB, IC, ID, IE or IF and the additional therapeutic agent(s) are present in the same composition. In one embodiment, this composition is suitable for oral administration. In another embodiment, this composition is suitable for intravenous administration.

The one or more Compounds of Formula I, IA, IB, IC, ID, IE or IF and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Compounds of Formula I, IA, IB, IC, ID, IE or IF and the additional therapeutic agent(s) may inhibit the resistance of a Condition to these agents.

In one embodiment, when the patient is treated for diabetes, a diabetic complication, impaired glucose tolerance or impaired fasting glucose, the other therapeutic is an antidiabetic agent which is not a Compound of Formula I, IA, IB, IC, ID, IE or IF. In another embodiment, when the patient is treated for pain, the other therapeutic agent is an analgesic agent which is not a Compound of Formula I, IA, IB, IC, ID, IE or IF.

In another embodiment, the other therapeutic agent is an agent useful for reducing any potential side effect of a Compound of Formula I, IA, IB, IC, ID, IE or IF. Such potential side effects include, but are not limited to, nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

Examples of antidiabetic agents useful in the present methods for treating diabetes or a diabetic complication include a sulfonylurea; an insulin sensitizer (such as a PPAR agonist, a DPP-IV inhibitor, a PTP-1B inhibitor and a glucokinase activator); a glucosidase inhibitor; an insulin secretagogue; a hepatic glucose output lowering agent; an anti-obesity agent; an antihypertensive agent; a meglitinide; an agent that slows or blocks the breakdown of starches and sugars in vivo; an histamine $H_3$ receptor antagonist; an antihypertensive agent, a sodium glucose uptake transporter 2 (SGLT-2) inhibitor; a peptide that increases insulin production; and insulin or any insulin-containing composition.

In one embodiment, the antidiabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

Non-limiting examples of insulin sensitizers include PPAR activators, such as troglitazone, rosiglitazone, pioglitazone and englitazone; biguanidines such as metformin and phenformin; DPP-IV inhibitors; PTP-1B inhibitors; and □-glucokinase activators, such as miglitol, acarbose, and voglibose.

Non-limiting examples of DPP-IV inhibitors useful in the present methods include sitagliptin, saxagliptin (Januvia™, Merck), denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of hepatic glucose output lowering agents include Glucophage and Glucophage XR.

Non-limiting examples of histamine $H_3$ receptor antagonist agents include the following compound:

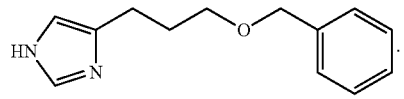 [SMILES: c1ccc(COCCCc2c[nH]cn2)cc1]

Non-limiting examples of insulin secretagogues include sulfonylurea and non-sulfonylurea drugs such as GLP-1, a GLP-1 mimetic, exendin, GIP, secretin, glipizide, chlorpropamide, nateglinide, meglitinide, glibenclamide, repaglinide and glimepiride.

Non-limiting examples of GLP-1 mimetics useful in the present methods include Byetta-Exanatide, Liraglutinide, CJC-1131 (ConjuChem, Exanatide-LAR (Amylin), BIM-51077 (Ipsen/LaRoche), ZP-10 (Zealand Pharmaceuticals), and compounds disclosed in International Publication No. WO 00/07617.

The term "insulin" as used herein, includes all pyridinones of insulin, including long acting and short acting forms of insulin.

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the antidiabetic agent is anti-obesity agent.

Non-limiting examples of anti-obesity agents useful in the present methods for treating diabetes include a 5-HT2C agonist, such as lorcaserin; a neuropeptide γ antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

Non-limiting examples of antihypertensive agents useful in the present methods for treating diabetes include □-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), pyridi inhibitors and endothelin receptor antagonists (for example sitaxsentan).

Non-limiting examples of meglitinides useful in the present methods for treating diabetes include repaglinide and nateglinide.

Non-limiting examples of insulin sensitizing agents include biguanides, such as metformin, metformin hydrochloride (such as GLUCOPHAGE® from Bristol-Myers Squibb), metformin hydrochloride with glyburide (such as GLUCOVANCE™ from Bristol-Myers Squibb) and buformin; glitazones; and thiazolidinediones, such as rosiglitazone, rosiglitazone maleate (AVANDIA™ from GlaxoSmithKline), pioglitazone, pioglitazone hydrochloride (ACTOS™, from Takeda) ciglitazone and MCC-555 (Mitsubishi Chemical Co.)

In one embodiment, the insulin sensitizer is a thiazolidinedione.

In another embodiment, the insulin sensitizer is a biguanide.

In another embodiment, the insulin sensitizer is a DPP-IV inhibitor.

In a further embodiment, the antidiabetic agent is a SGLT-2 inhibitor.

Non-limiting examples of antidiabetic agents that slow or block the breakdown of starches and sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Non-limiting examples of other analgesic agents useful in the present methods for treating pain include acetaminophen, an NSAID, an opiate or a tricyclic antidepressant.

In one embodiment, the other analgesic agent is acetaminophen or an NSAID.

In another embodiment, the other analgesic agent is an opiate.

In another embodiment, the other analgesic agent is a tricyclic antidepressant.

Non-limiting examples of NSAIDS useful in the present methods for treating pain include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizole or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Non-limiting examples of opiates useful in the present methods for treating pain include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Non-limiting examples of tricyclic antidepressants useful in the present methods for treating pain include amitryptyline, carbamazepine, gabapentin or pregabalin.

The Compounds of Formula I, IA, IB, IC, ID, IE or IF can be combined with an $H_1$ receptor antagonist (i.e., the Compounds of Formula I, IA, IB, IC, ID, IE or IF can be combined with an $H_1$ receptor antagonist in a pharmaceutical composition, or the Compounds of Formula I, IA, IB, IC, ID, IE or IF can be administered with one or more $H_1$ receptor antagonists).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of a compound of Formula I, IA, IB, IC, ID, IE or IF is administered with a $H_1$ antagonist, the antagonists can be administered simultaneously or sequentially (first one and then the other over a period of time). In general, but not always, when the antagonists are administered sequentially, the compound of Formula I, IA, IB, IC, ID, IE or IF is administered first.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Compound(s) of Formula I, IA, IB, IC, ID, IE or IF, and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Compounds of Formula I, IA, IB, IC, ID, IE or IF and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

SYNTHESIS

Purification Conditions
General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from $Me_4Si$ with number of protons, multiplicities, and coupling constants in Hz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. The retention time and observed parent ion are given. MS data were obtained using Agilent Technologies LC/MSD SL or 1100 series LC/MSD mass spectrometer. Final compounds were purified by PrepLC using the column of Varian Pursuit XRs C18 10 μm 250×21.2 mm and an eluent mixture of mobile phase A and B. The mobile phase A is composed of 0.1% TFA in $H_2O$ and the mobile phase B is composed of $CH_3CN$ (95%)/$H_2O$ (5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 μm 150×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/min at a temperature of 60° C. Intermediate compounds were characterized by LCMS using a Higgins Haisil HL C18 5 μm 50×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/min at a column temperature of 60° C.

Post Purification

To each Vial was added 1 mL of acetonitrile and 1 mL of 1 N hydrochloric acid standard solution in water. The vials were shaken for few minutes and transferred into a bar-coded 4 mL scintillation vial previously tarred. The tubes were lyophilized overnight then weighed, yields were calculated.

Example 1

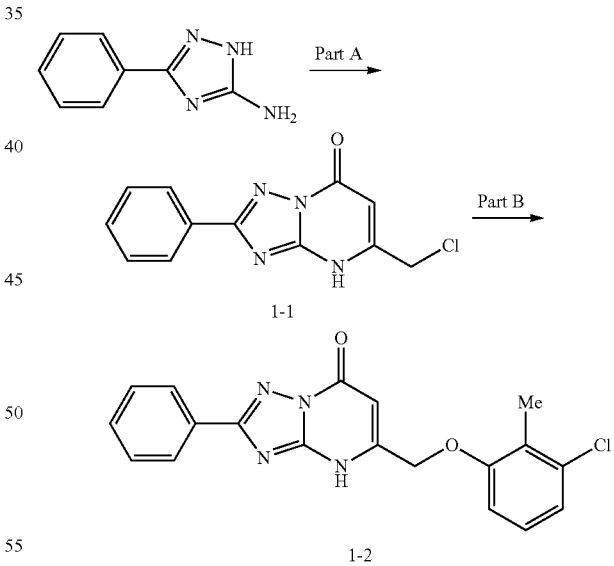

Part A:

To the solution of 3-phenyl-1H-1,2,4-triazol-5-amine (0.8 g, 5 mmol) in acetic acid (6 mL) was added ethyl 4-chloro-3-oxobutanoate (0.75 mL, 5.5 mmol). The reaction mixture was stirred for 24 hours at 80° C., and then cooled to room temperature. The reaction mixture was filtered. The precipitates were washed with ACN and dried to give compound 1-1 in a white powder (872 mg, 67% yield). $^1$H NMR (400 MHz, $CD_3OD$) δ 8.24-8.18 (m, 2H), 7.54-7.46 (m, 3H), 6.21 (s, 1H), 4.65 (s, 2H).

Part B:

A reaction mixture of 3-chloro-2-methylphenol (356.5 mg, 2.5 mmol) and sodium hydride (60% in oil, 120 mg, 3.0 mmol) in DMA (3 mL) was stirred at room temperature for 15 minutes. To the resultant clear solution was added compound 1-1 (390 mg, 1.5 mmol). The reaction mixture was stirred in microwave at 210° C. for 30 minutes. Recrystallization from a mixture of DMSO/ACN (4/1) gave compound 1-2 in a white solid (170.8 mg, 31% yield). $^1$H NMR (400 MHz, CD$_3$OD) δ 8.25-8.15 (m, 2H), 7.55-7.45 (m, 3H), 7.20-7.12 (m, 1H), 7.09-7.03 (m, 1H), 7.01-6.95 (m, 1H), 6.24 (s, 1H), 5.15 (s, 2H), 2.37 (m, 3H).

The following compounds may be synthesized using this procedure:

| ID | Structure | EMW | MS m/z (M$^+$ + H) | Retention Time (RT, min) |
|---|---|---|---|---|
| 1-2 | 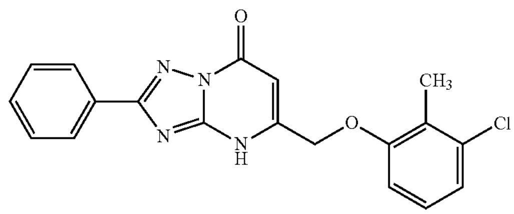 [SMILES: Cc1c(Cl)cccc1OCc1cc(=O)n2nc(-c3ccccc3)nc2[nH]1] | 366.09 | 367.25 | 4.93 |
| 1-3 | 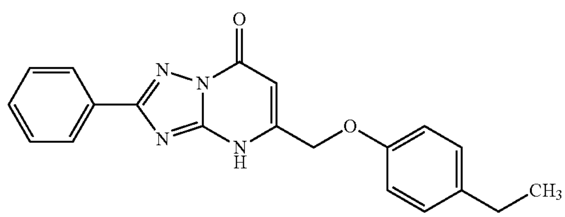 | 346.14 | 347.29 | 4.83 |
| 1-5 | 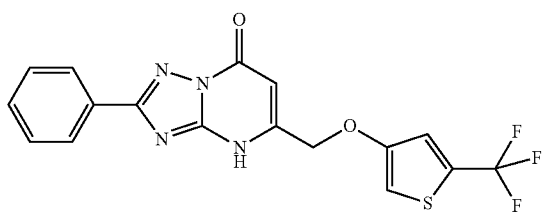 [SMILES: O=c1cc(COc2csc(C(F)(F)F)c2)[nH]c2nc(-c3ccccc3)nn12] | 392.06 | 393.23 | 4.75 |
| 1-6 | 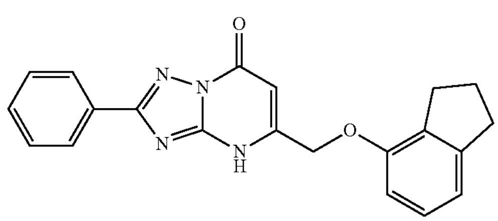 [SMILES: O=c1cc(COc2cccc3c2CCC3)[nH]c2nc(-c3ccccc3)nn12] | 358.14 | 359.31 | 4.86 |
| 1-7 | 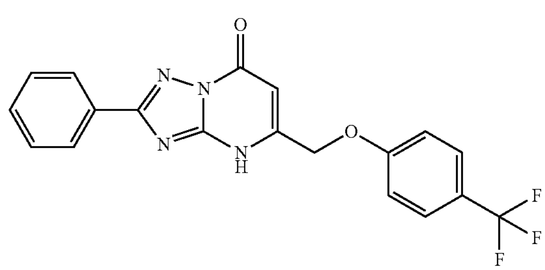 [SMILES: O=c1cc(COc2ccc(C(F)(F)F)cc2)[nH]c2nc(-c3ccccc3)nn12] | 386.1 | 387.27 | 4.76 |
| 1-8 | 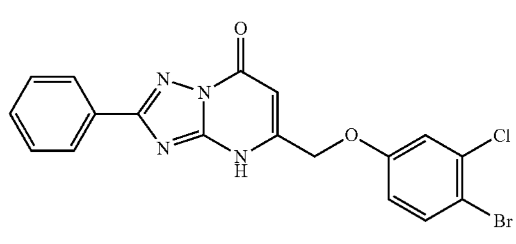 [SMILES: O=c1cc(COc2ccc(Br)c(Cl)c2)[nH]c2nc(-c3ccccc3)nn12] | 429.98 | 431.11 | 4.97 |

| ID | Structure | EMW | MS m/z (M⁺ + H) | Retention Time (RT, min) |
|---|---|---|---|---|
| 1-9 | 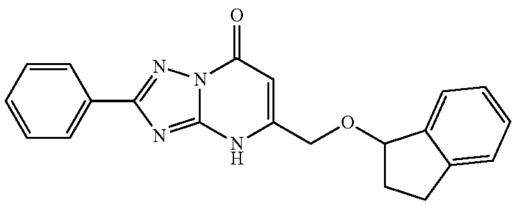 [SMILES: O=c1cc(COC2CCc3ccccc32)[nH]c2nc(-c3ccccc3)nn12] | 358.14 | 359.32 | 4.53 |
| 1-10 | 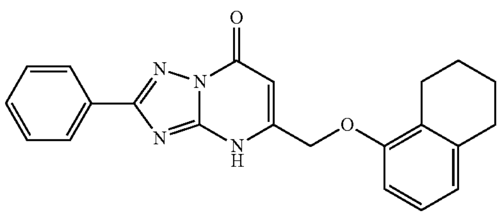 [SMILES: O=c1cc(COc2cccc3c2CCCC3)[nH]c2nc(-c3ccccc3)nn12] | 372.16 | 373.27 | 5.24 |
| 1-11 | 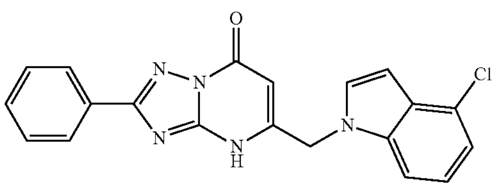 [SMILES: O=c1cc(Cn2ccc3c(Cl)cccc32)[nH]c2nc(-c3ccccc3)nn12] | 375.09 | 376.28 | 4.74 |
| 1-12 | 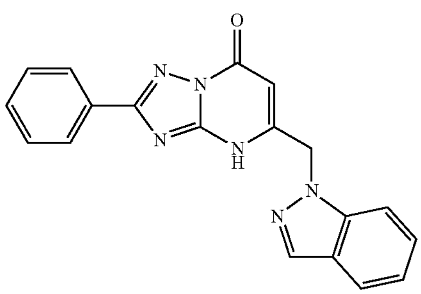 [SMILES: O=c1cc(Cn2ncc3ccccc32)[nH]c2nc(-c3ccccc3)nn12] | 342.3541 | 343.35406 | 3.62 |
| 1-13 | 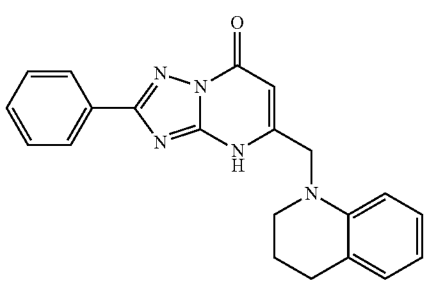 [SMILES: O=c1cc(CN2CCCc3ccccc32)[nH]c2nc(-c3ccccc3)nn12] | 357.4085 | 358.40846 | 4.58 |
| 1-14 | 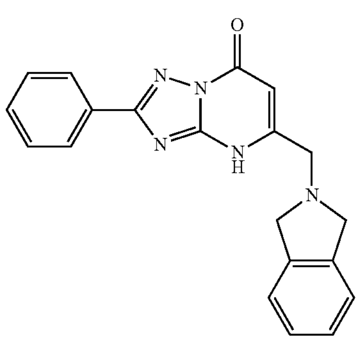 [SMILES: O=c1cc(CN2Cc3ccccc3C2)[nH]c2nc(-c3ccccc3)nn12] | 343.3819 | 344.38188 | 2.46 |

-continued

| ID | Structure | EMW | MS m/z (M⁺ + H) | Retention Time (RT, min) |
|---|---|---|---|---|
| 1-15 | 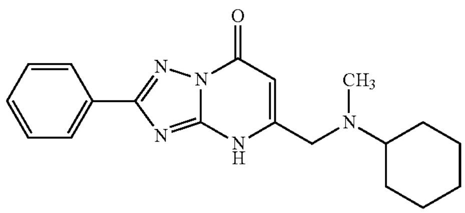 [SMILES: CN(Cc1cc(=O)n2nc(-c3ccccc3)nc2[nH]1)C1CCCCC1] | 337.4188 | 338.41882 | 2.58 |
| 1-16 | 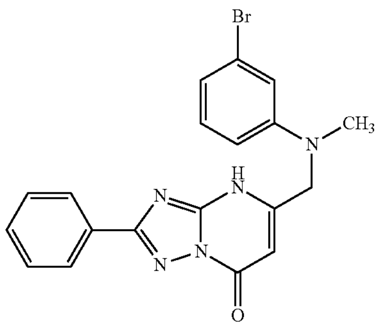 [SMILES: CN(Cc1cc(=O)n2nc(-c3ccccc3)nc2[nH]1)c1cccc(Br)c1] | 410.2672 | 411.26724 | 4.7 |
| 1-17 | 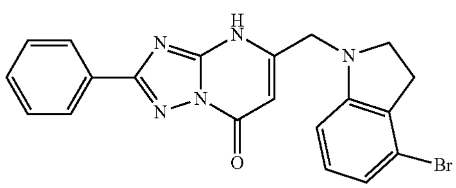 [SMILES: O=c1cc(CN2CCc3c(Br)cccc32)[nH]c2nc(-c3ccccc3)nn12] | 422.2779 | 423.27794 | 4.94 |
| 1-18 | 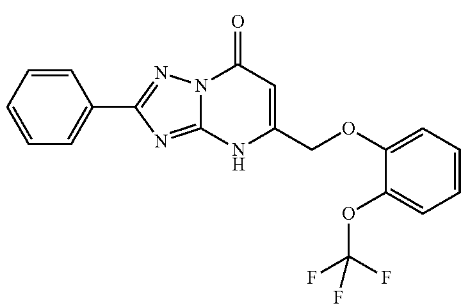 [SMILES: O=c1cc(COc2ccccc2OC(F)(F)F)[nH]c2nc(-c3ccccc3)nn12] | 402.3267 | 403.32672 | 4.69 |
| 1-19 | 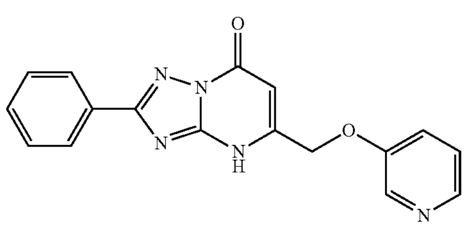 [SMILES: O=c1cc(COc2cccnc2)[nH]c2nc(-c3ccccc3)nn12] | 319.3174 | 320.31742 | 1.99 |
| 1-20 | 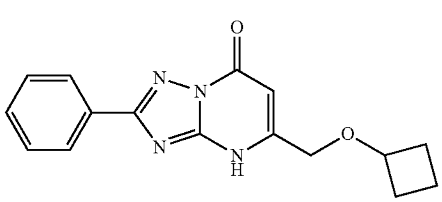 [SMILES: O=c1cc(COC2CCC2)[nH]c2nc(-c3ccccc3)nn12] | 296.3238 | 297.32384 | 3.71 |

-continued

| ID | Structure | EMW | MS m/z (M⁺ + H) | Retention Time (RT, min) |
|---|---|---|---|---|
| 1-21 | 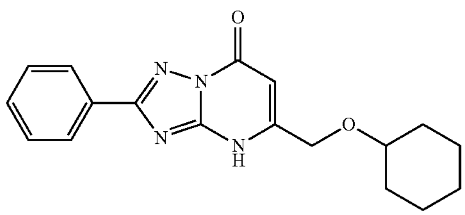 [SMILES: O=c1cc(COC2CCCCC2)[nH]c2nc(-c3ccccc3)nn12] | 324.377 | 325.377 | 4.42 |
| 1-22 | 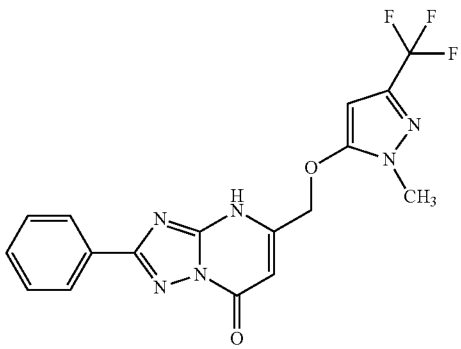 [SMILES: Cn1nc(C(F)(F)F)cc1OCc1cc(=O)n2nc(-c3ccccc3)nc2[nH]1] | 390.3193 | 391.31932 | 3.98 |
| 1-23 | 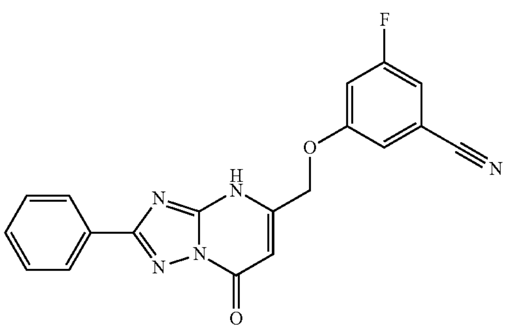 [SMILES: N#Cc1cc(F)cc(OCc2cc(=O)n3nc(-c4ccccc4)nc3[nH]2)c1] | 361.3293 | 362.32928 | 4.02 |
| 1-24 | 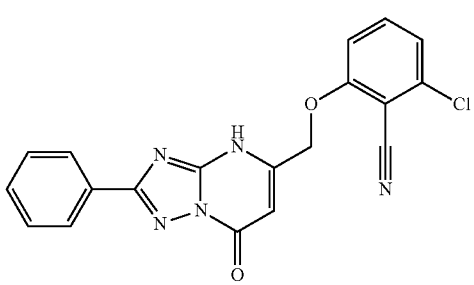 [SMILES: N#Cc1c(Cl)cccc1OCc1cc(=O)n2nc(-c3ccccc3)nc2[nH]1] | 377.7839 | 378.78388 | 4.15 |
| 1-25 | 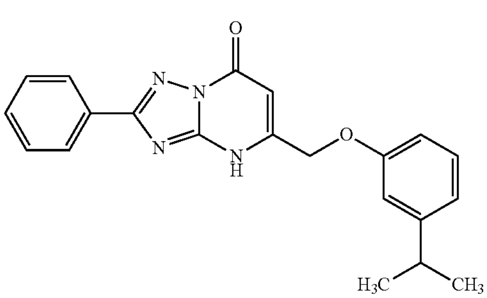 [SMILES: CC(C)c1cccc(OCc2cc(=O)n3nc(-c4ccccc4)nc3[nH]2)c1] | 360.4091 | 361.4091 | 5 |

-continued

| ID | Structure | EMW | MS m/z (M⁺ + H) | Retention Time (RT, min) |
|---|---|---|---|---|
| 1-26 | 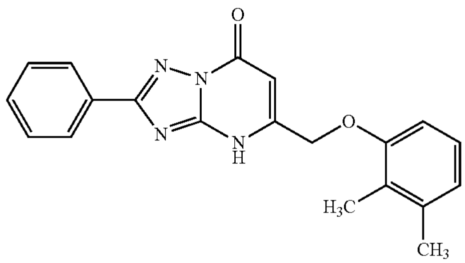 [SMILES: Cc1cccc(OCc2cc(=O)n3nc(-c4ccccc4)nc3[nH]2)c1C] | 346.3825 | 347.38252 | 4.74 |
| 1-27 | 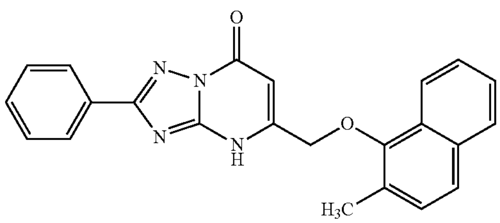 [SMILES: Cc1ccc2ccccc2c1OCc1cc(=O)n2nc(-c3ccccc3)nc2[nH]1] | 382.4146 | 383.41462 | 4.91 |
| 1-28 | | 361.3972 | 362.39716 | 3.02 |
| 1-29 | | 387.3914 | 388.39138 | 3.49 |
| 1-30 | 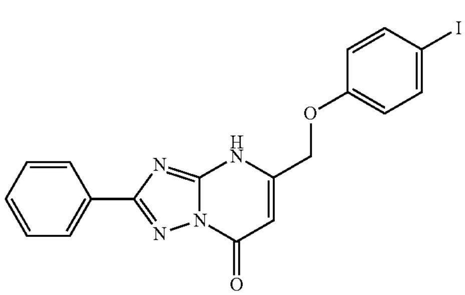 [SMILES: O=c1cc(COc2ccc(I)cc2)[nH]c2nc(-c3ccccc3)nn12] | 444.2259 | 445.22589 | 4.7 |

-continued

| ID | Structure | EMW | MS m/z (M⁺ + H) | Retention Time (RT, min) |
|---|---|---|---|---|
| 1-31 | 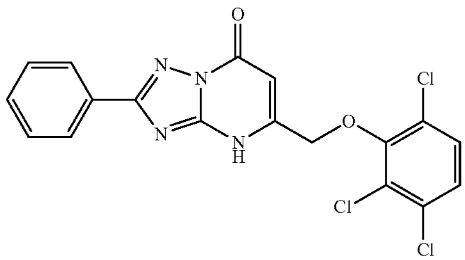 [SMILES: O=c1cc(COc2c(Cl)ccc(Cl)c2Cl)[nH]c2nc(-c3ccccc3)nn12] | 421.6645 | 422.66454 | 4.85 |
| 1-32 | 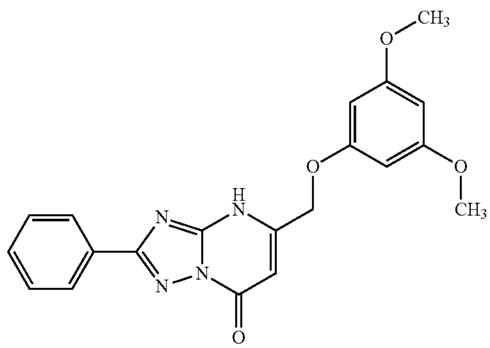 [SMILES: COc1cc(OC)cc(OCc2cc(=O)n3nc(-c4ccccc4)nc3[nH]2)c1] | 378.3813 | 379.38132 | 4.17 |
| 1-33 | 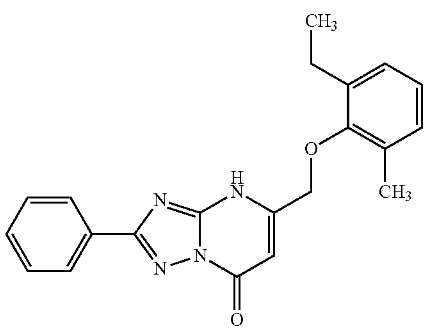 [SMILES: CCc1cccc(C)c1OCc1cc(=O)n2nc(-c3ccccc3)nc2[nH]1] | 360.4091 | 361.4091 | 4.91 |
| 1-34 | 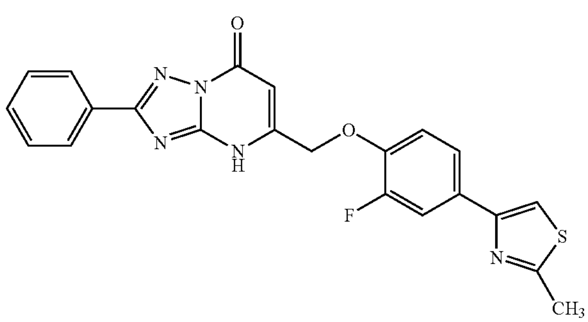 [SMILES: Cc1nc(-c2ccc(OCc3cc(=O)n4nc(-c5ccccc5)nc4[nH]3)c(F)c2)cs1] | 433.4581 | 434.45814 | 4.52 |
| 1-35 | 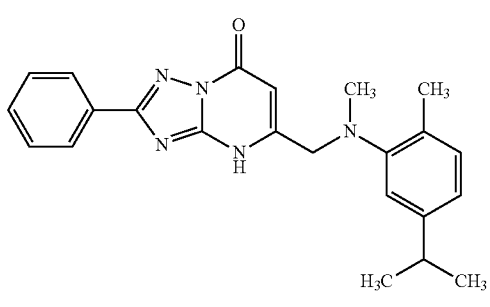 [SMILES: Cc1ccc(C(C)C)cc1N(C)Cc1cc(=O)n2nc(-c3ccccc3)nc2[nH]1] | 387.4775 | 388.4775 | 5.45 |

-continued

| ID | Structure | EMW | MS m/z (M⁺ + H) | Retention Time (RT, min) |
|---|---|---|---|---|
| 1-36 | 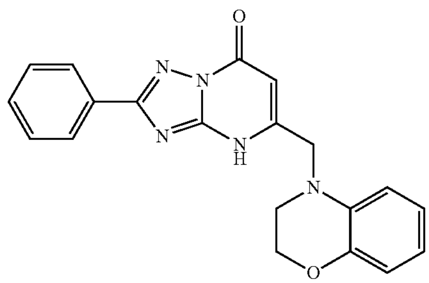 [SMILES: O=c1cc(CN2CCOc3ccccc32)[nH]c2nc(-c3ccccc3)nn12] | 359.3813 | 360.38128 | 4.07 |
| 1-37 | 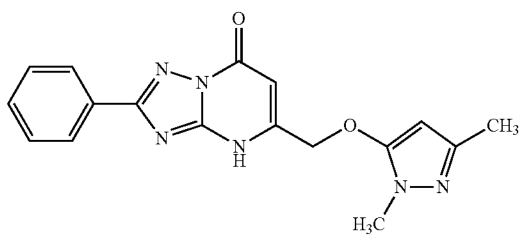 [SMILES: Cc1cc(OCc2cc(=O)n3nc(-c4ccccc4)nc3[nH]2)n(C)n1] | 336.3479 | 337.34794 | 2.56 |
| 1-38 | 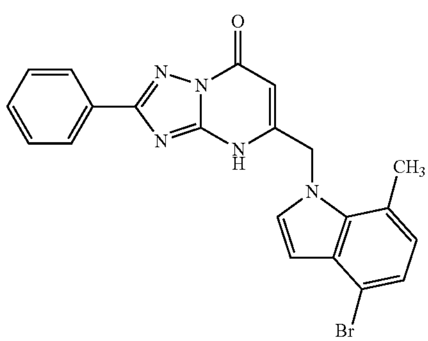 [SMILES: Cc1ccc(Br)c2ccn(Cc3cc(=O)n4nc(-c5ccccc5)nc4[nH]3)c12] | 434.2886 | 435.28864 | 4.94 |
| 1-39 | 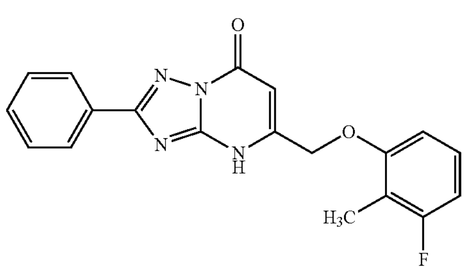 [SMILES: Cc1c(F)cccc1OCc1cc(=O)n2nc(-c3ccccc3)nc2[nH]1] | 350.3464 | 351.3464 | 4.53 |
| 1-40 | 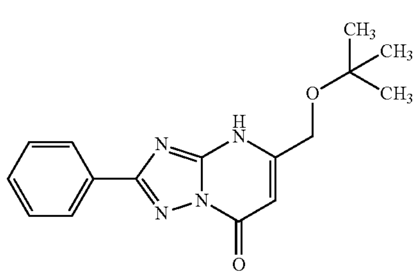 [SMILES: CC(C)(C)OCc1cc(=O)n2nc(-c3ccccc3)nc2[nH]1] | 298.3397 | 299.33972 | 3.87 |

-continued

| ID | Structure | EMW | MS m/z (M⁺ + H) | Retention Time (RT, min) |
|---|---|---|---|---|
| 1-41 | 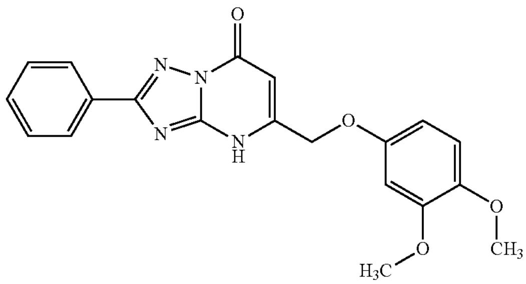 [SMILES: COc1ccc(OCc2cc(=O)n3nc(-c4ccccc4)nc3[nH]2)cc1OC] | 378.3813 | 379.38132 | 3.76 |
| 1-42 | 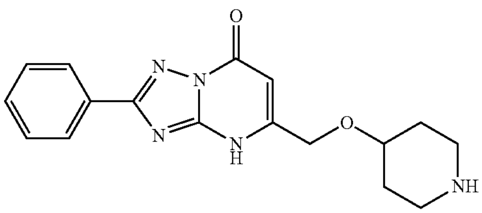 [SMILES: O=c1cc(COC2CCNCC2)[nH]c2nc(-c3ccccc3)nn12] | 325.3651 | 326.36506 | 2.27 |
| 1-43 | 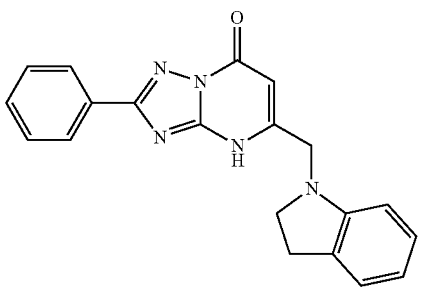 [SMILES: O=c1cc(CN2CCc3ccccc32)[nH]c2nc(-c3ccccc3)nn12] | 343.3819 | 344.38188 | 4.36 |
| 1-44 | 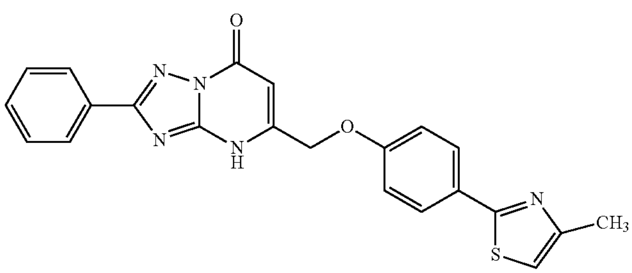 [SMILES: Cc1csc(-c2ccc(OCc3cc(=O)n4nc(-c5ccccc5)nc4[nH]3)cc2)n1] | 415.4677 | 416.46768 | 4.21 |
| 1-45 | 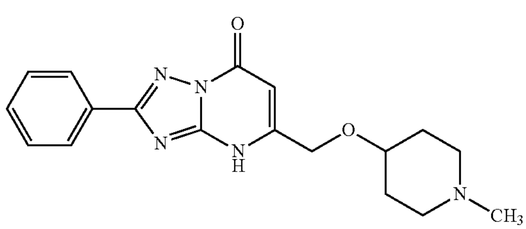 [SMILES: CN1CCC(OCc2cc(=O)n3nc(-c4ccccc4)nc3[nH]2)CC1] | 339.3916 | 340.39164 | 1.92 |
| 1-46 | 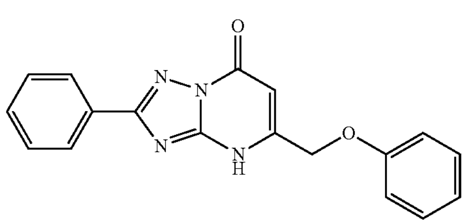 [SMILES: O=c1cc(COc2ccccc2)[nH]c2nc(-c3ccccc3)nn12] | 318.3294 | 319.32936 | 4 |

-continued

| ID | Structure | EMW | MS m/z (M$^+$ + H) | Retention Time (RT, min) |
|---|---|---|---|---|
| 1-47 | 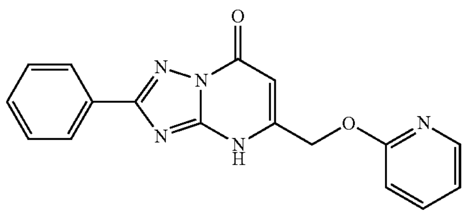 [SMILES: O=c1cc(COc2ccccn2)[nH]c2nc(-c3ccccc3)nn12] | 319.3174 | 320.31742 | 2.68 |
| 1-48 | 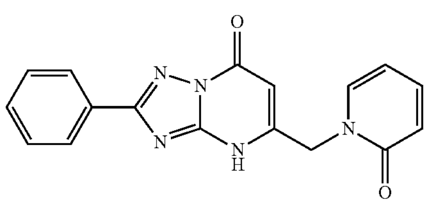 [SMILES: O=c1ccccn1Cc1cc(=O)n2nc(-c3ccccc3)nc2[nH]1] | 319.3174 | 320.31742 | 3.53 |
| 1-49 | 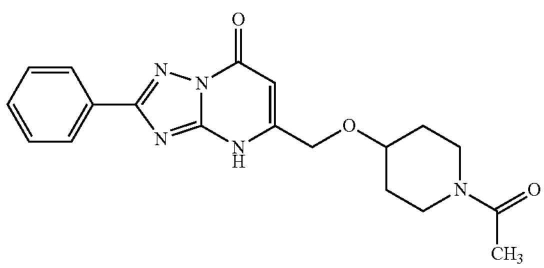 [SMILES: CC(=O)N1CCC(OCc2cc(=O)n3nc(-c4ccccc4)nc3[nH]2)CC1] | 367.4017 | 368.40174 | 2.92 |
| 1-51 | 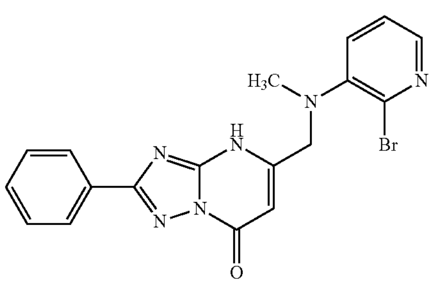 [SMILES: CN(Cc1cc(=O)n2nc(-c3ccccc3)nc2[nH]1)c1cccnc1Br] | 411.2553 | 412.2553 | 3.74 |
| 1-52 | 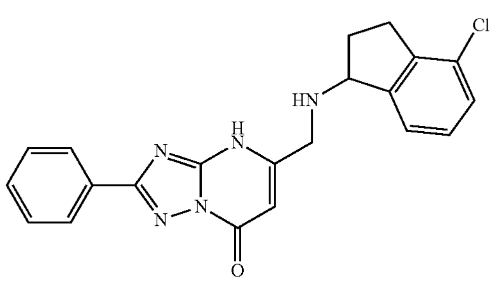 [SMILES: O=c1cc(CNC2CCc3c(Cl)cccc32)[nH]c2nc(-c3ccccc3)nn12] | 391.8535 | 392.85352 | 3.23 |
| 1-54 | 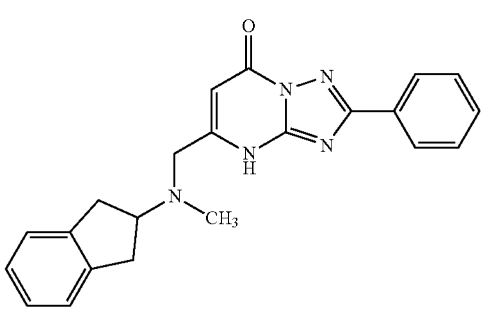 [SMILES: CN(Cc1cc(=O)n2nc(-c3ccccc3)nc2[nH]1)C1Cc2ccccc2C1] | 371.435 | 372.43504 | 2.98 |

-continued

| ID | Structure | EMW | MS m/z (M⁺ + H) | Retention Time (RT, min) |
|---|---|---|---|---|
| 1-55 | 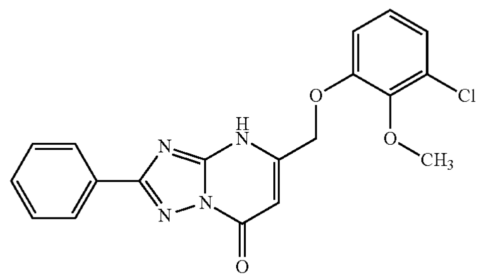 [SMILES: COc1c(Cl)cccc1OCc1cc(=O)n2nc(-c3ccccc3)nc2[nH]1] | 382.8004 | 383.8004 | 4.38 |
| 1-56 | 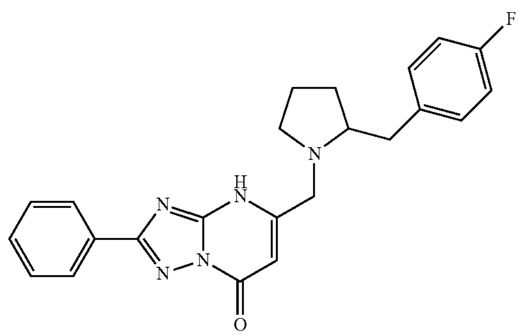 [SMILES: O=c1cc(CN2CCCC2Cc2ccc(F)cc2)[nH]c2nc(-c3ccccc3)nn12] | 403.4521 | 404.45208 | 3.11 |
| 1-57 | 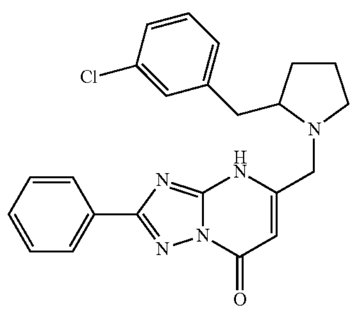 [SMILES: O=c1cc(CN2CCCC2Cc2cccc(Cl)c2)[nH]c2nc(-c3ccccc3)nn12] | 419.9067 | 420.90668 | 3.33 |
| 1-58 | 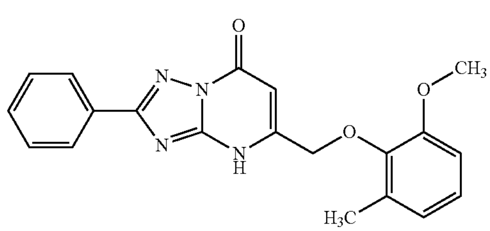 [SMILES: COc1cccc(C)c1OCc1cc(=O)n2nc(-c3ccccc3)nc2[nH]1] | 362.3915 | 363.33 | 4.6 |
| 1-59 | 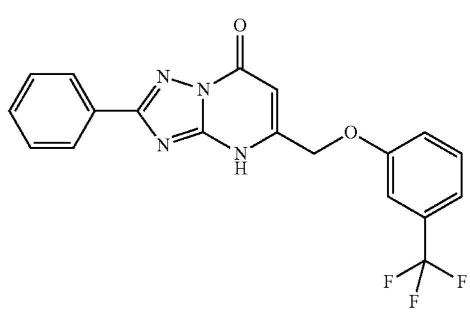 [SMILES: O=c1cc(COc2cccc(C(F)(F)F)c2)[nH]c2nc(-c3ccccc3)nn12] | 386.3363 | 387.26 | 4.8 |

-continued

| ID | Structure | EMW | MS m/z (M+ + H) | Retention Time (RT, min) |
|---|---|---|---|---|
| 1-60 | 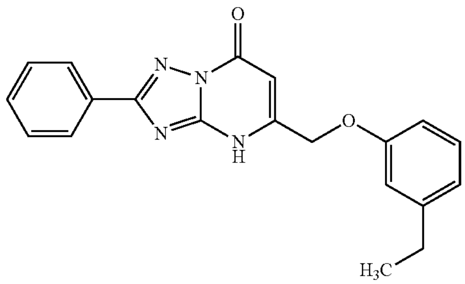 [SMILES: CCc1cccc(OCc2cc(=O)n3nc(-c4ccccc4)nc3[nH]2)c1] | 346.3921 | 347.34 | 4.79 |
| 1-61 | 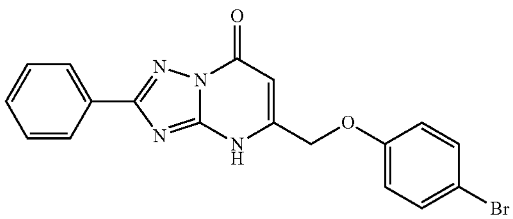 [SMILES: O=c1cc(COc2ccc(Br)cc2)[nH]c2nc(-c3ccccc3)nn12] | 397.2339 | 397.17 | 4.59 |
| 1-62 | 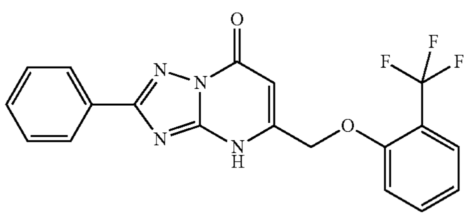 [SMILES: O=c1cc(COc2ccccc2C(F)(F)F)[nH]c2nc(-c3ccccc3)nn12] | 386.3363 | 387.31 | 4.61 |
| 1-63 | 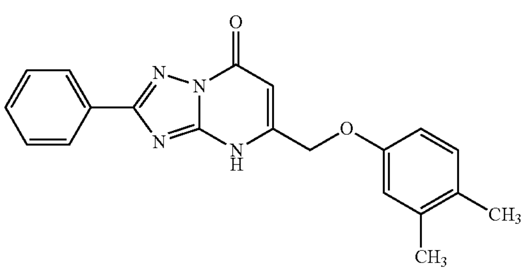 [SMILES: Cc1ccc(OCc2cc(=O)n3nc(-c4ccccc4)nc3[nH]2)cc1C] | 346.3921 | 347.36 | 4.7 |
| 1-64 | 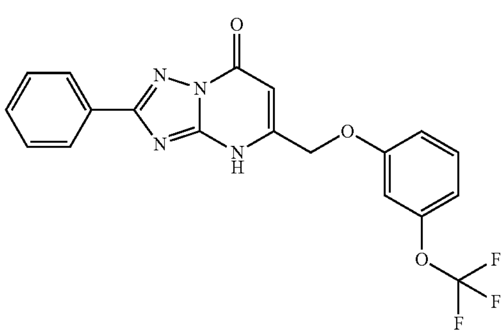 [SMILES: O=c1cc(COc2cccc(OC(F)(F)F)c2)[nH]c2nc(-c3ccccc3)nn12] | 402.3357 | 403.29 | 4.9 |

-continued
| ID | Structure | EMW | MS m/z (M+ + H) | Retention Time (RT, min) |
|---|---|---|---|---|
| 1-65 | 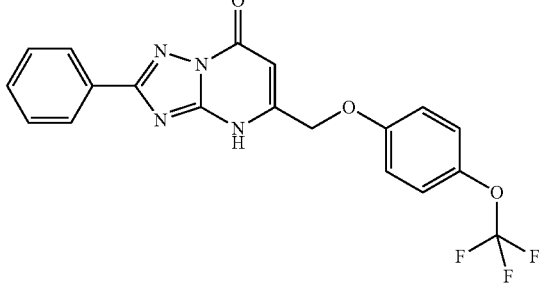 | 402.3357 | 403.3 | 4.89 |
| 1-66 | 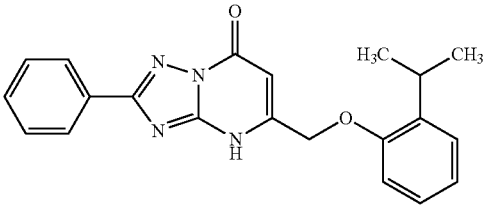 [SMILES: CC(C)c1ccccc1OCc1cc(=O)n2nc(-c3ccccc3)nc2[nH]1] | 360.4192 | 361.38 | 5.07 |
| 1-67 | 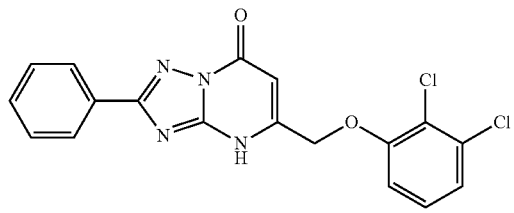 [SMILES: O=c1cc(COc2cccc(Cl)c2Cl)[nH]c2nc(-c3ccccc3)nn12] | 387.2279 | 387.21 | 4.77 |
| 1-68 | 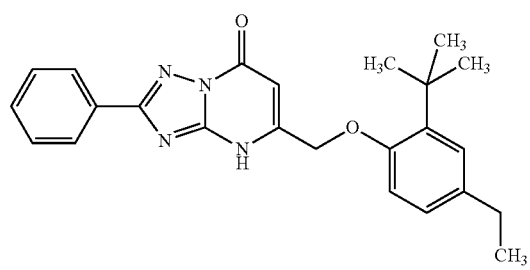 [SMILES: CCc1ccc(OCc2cc(=O)n3nc(-c4ccccc4)nc3[nH]2)c(C(C)(C)C)c1] | 402.5004 | 403.73 | 2.1 |
| 1-69 | 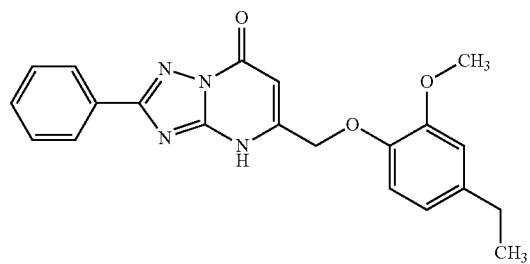 [SMILES: CCc1ccc(OCc2cc(=O)n3nc(-c4ccccc4)nc3[nH]2)c(OC)c1] | 376.4186 | 377.32 | 1.75 |
| 1-70 | 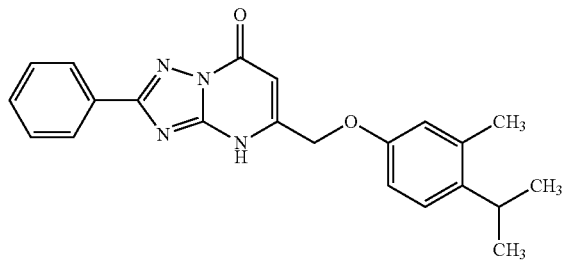 [SMILES: Cc1cc(OCc2cc(=O)n3nc(-c4ccccc4)nc3[nH]2)ccc1C(C)C] | 374.4462 | 375.33 | 5.31 |

-continued

| ID | Structure | EMW | MS m/z (M+ + H) | Retention Time (RT, min) |
|---|---|---|---|---|
| 1-71 | 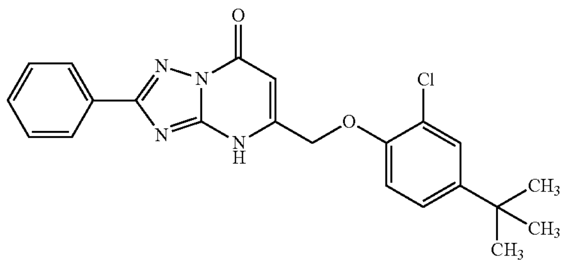 [SMILES: CC(C)(C)c1ccc(OCc2cc(=O)n3nc(-c4ccccc4)nc3[nH]2)c(Cl)c1] | 408.8913 | 409.29 | 5.54 |
| 1-72 | 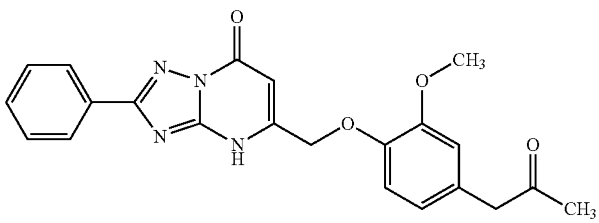 [SMILES: COc1cc(CC(C)=O)ccc1OCc1cc(=O)n2nc(-c3ccccc3)nc2[nH]1] | 404.4291 | 405.29 | 3.78 |
| 1-73 | 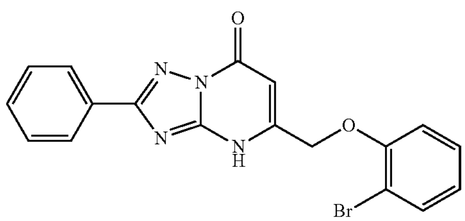 [SMILES: O=c1cc(COc2ccccc2Br)[nH]c2nc(-c3ccccc3)nn12] | 397.2339 | 397.19 | 4.46 |
| 1-74 | 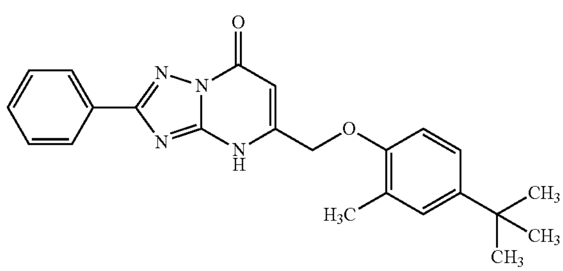 [SMILES: Cc1cc(C(C)(C)C)ccc1OCc1cc(=O)n2nc(-c3ccccc3)nc2[nH]1] | 388.4733 | 389.32 | 5.61 |
| 1-75 | 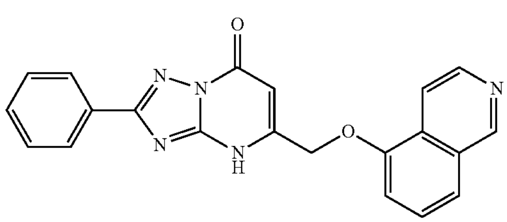 [SMILES: O=c1cc(COc2cccc3cnccc23)[nH]c2nc(-c3ccccc3)nn12] | 369.3761 | 370.3761 | 2.62 |
| 1-76 | 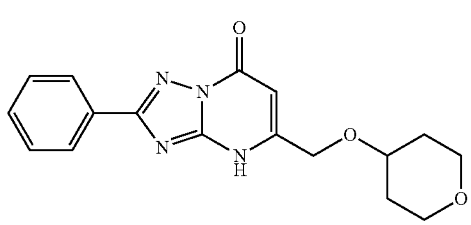 [SMILES: O=c1cc(COC2CCOCC2)[nH]c2nc(-c3ccccc3)nn12] | 326.3498 | 327.34982 | 3.07 |

-continued

| ID | Structure | EMW | MS m/z (M+ + H) | Retention Time (RT, min) |
|---|---|---|---|---|
| 1-77 | 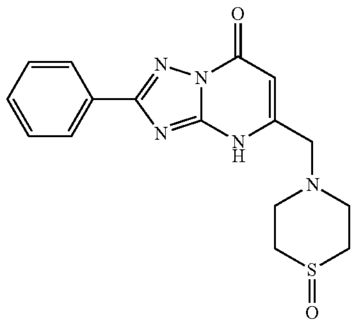 [SMILES: O=c1cc(CN2CCS(=O)CC2)[nH]c2nc(-c3ccccc3)nn12] | 343.4035 | 344.40348 | 2.14 |
| 1-78 | 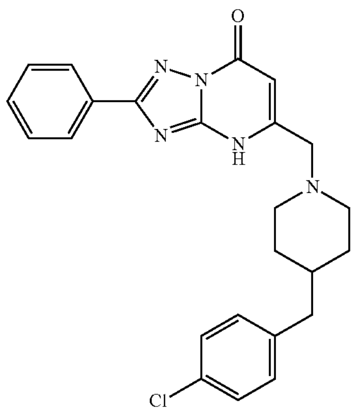 [SMILES: O=c1cc(CN2CCC(Cc3ccc(Cl)cc3)CC2)[nH]c2nc(-c3ccccc3)nn12] | 433.9333 | 434.93326 | 3.77 |
| 1-79 | 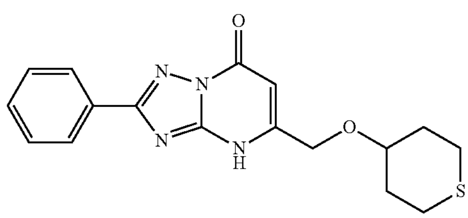 [SMILES: O=c1cc(COC2CCSCC2)[nH]c2nc(-c3ccccc3)nn12] | 342.4154 | 343.41542 | 3.75 |
| 1-80 | 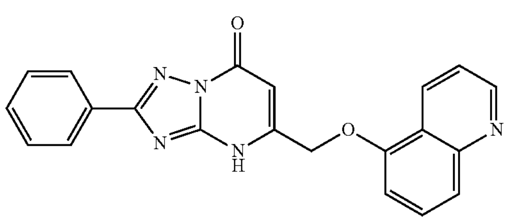 [SMILES: O=c1cc(COc2cccc3ncccc23)[nH]c2nc(-c3ccccc3)nn12] | 369.3761 | 370.3761 | 2.65 |
| 1-81 | 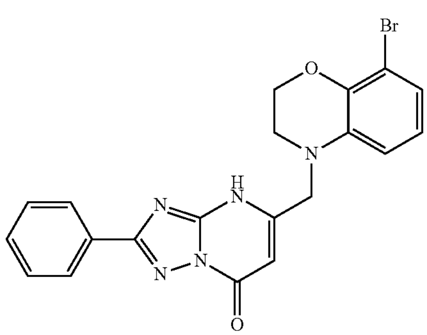 [SMILES: O=c1cc(CN2CCOc3c(Br)cccc32)[nH]c2nc(-c3ccccc3)nn12] | 438.2773 | 439.27734 | 4.48 |

| ID | Structure | EMW | MS m/z (M+ + H) | Retention Time (RT, min) |
|---|---|---|---|---|
| 1-82 | 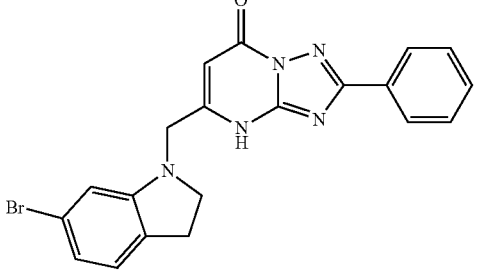 | 422.2779 | 423.27794 | 4.78 |
| 1-83 | 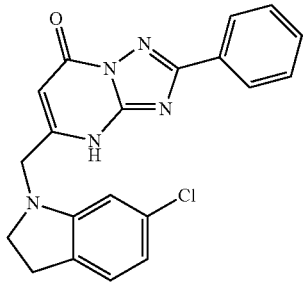 [SMILES: O=c1cc(CN2CCc3ccc(Cl)cc32)[nH]c2nc(-c3ccccc3)nn12] | 377.8269 | 378.82694 | 4.68 |
| 1-84 | 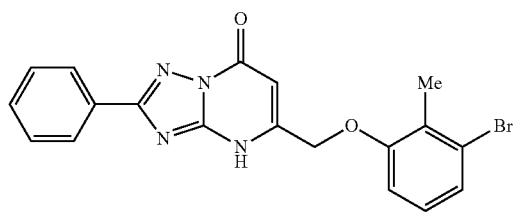 [SMILES: Cc1c(Br)cccc1OCc1cc(=O)n2nc(-c3ccccc3)nc2[nH]1] | 410.04 | 411.50 | 4.51 |
| 1-85 | 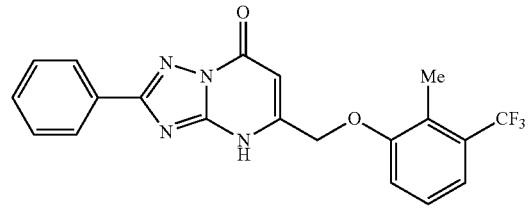 [SMILES: Cc1c(OCc2cc(=O)n3nc(-c4ccccc4)nc3[nH]2)cccc1C(F)(F)F] | 400.11 | 401.59 | 4.55 |
| 1-86 | 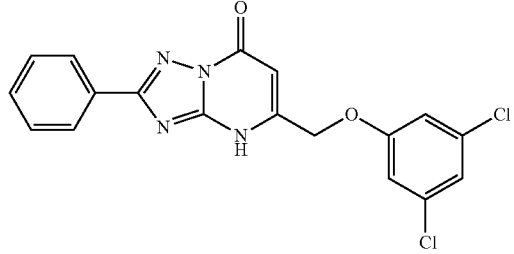 [SMILES: O=c1cc(COc2cc(Cl)cc(Cl)c2)[nH]c2nc(-c3ccccc3)nn12] | 386.03 | 387.52 | 4.56 |
| 1-87 | 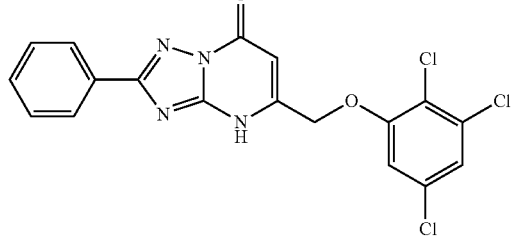 | 419.99 | 421.46 | 4.75 |

-continued

| ID | Structure | EMW | MS m/z (M⁺ + H) | Retention Time (RT, min) |
|---|---|---|---|---|
| 1-88 | 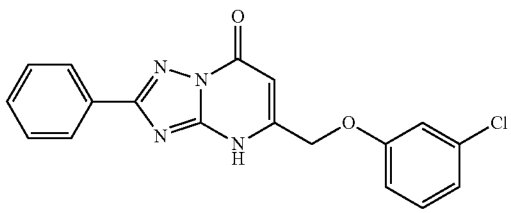 [SMILES: O=c1cc(COc2cccc(Cl)c2)[nH]c2nc(-c3ccccc3)nn12] | 352.07 | 353.56 | 4.07 |
| 1-89 | 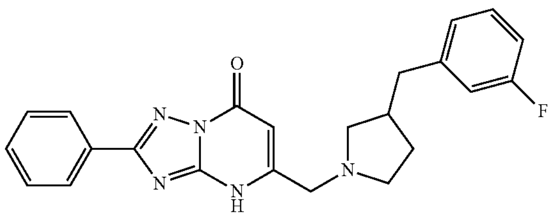 [SMILES: O=c1cc(CN2CCC(Cc3cccc(F)c3)C2)[nH]c2nc(-c3ccccc3)nn12] | 403.18 | 404.45 | 3.3 |
| 1-90 | 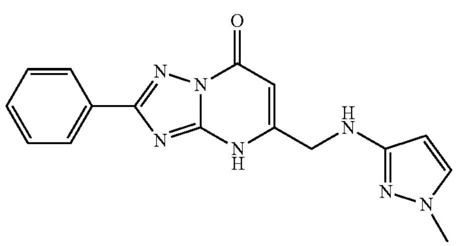 [SMILES: Cn1ccc(NCc2cc(=O)n3nc(-c4ccccc4)nc3[nH]2)n1] | 321.13 | 322.34 | 2.62 |
| 1-91 | 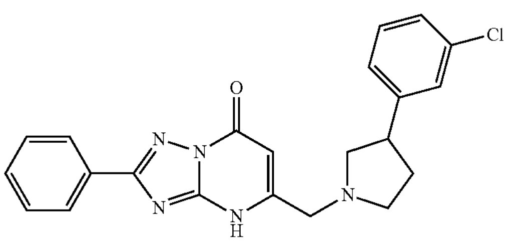 [SMILES: O=c1cc(CN2CCC(c3cccc(Cl)c3)C2)[nH]c2nc(-c3ccccc3)nn12] | 405.14 | 406.88 | 3.32 |
| 1-92 | 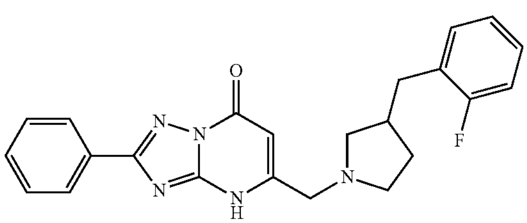 [SMILES: O=c1cc(CN2CCC(Cc3ccccc3F)C2)[nH]c2nc(-c3ccccc3)nn12] | 403.18 | 404.45 | 3 |
| 1-93 | 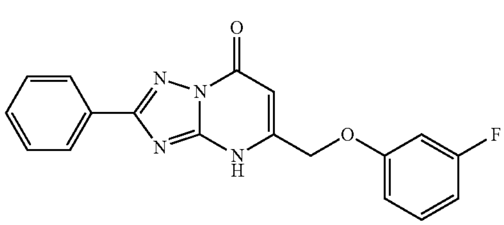 [SMILES: O=c1cc(COc2cccc(F)c2)[nH]c2nc(-c3ccccc3)nn12] | 336.10 | 337.32 | 4.04 |

-continued
| ID | Structure | EMW | MS m/z (M⁺ + H) | Retention Time (RT, min) |
|---|---|---|---|---|
| 1-94 | 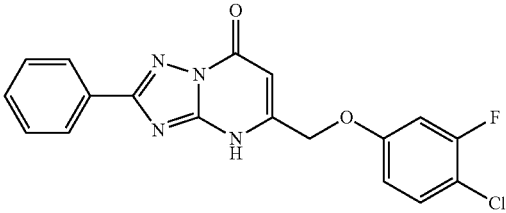 [SMILES: O=c1cc(COc2ccc(Cl)c(F)c2)[nH]c2nc(-c3ccccc3)nn12] | 370.06 | 371.76 | 4.42 |
| 1-95 | 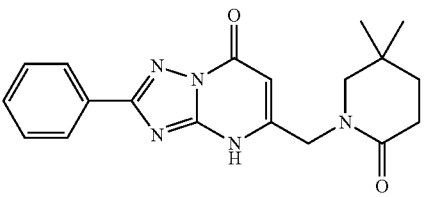 [SMILES: CC1(C)CCC(=O)N(Cc2cc(=O)n3nc(-c4ccccc4)nc3[nH]2)C1] | 351.17 | 352.40 | 3.45 |
| 1-96 | 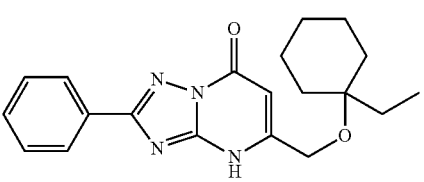 [SMILES: CCC1(OCc2cc(=O)n3nc(-c4ccccc4)nc3[nH]2)CCCCC1] | 352.19 | 353.43 | 4.95 |
| 1-97 | 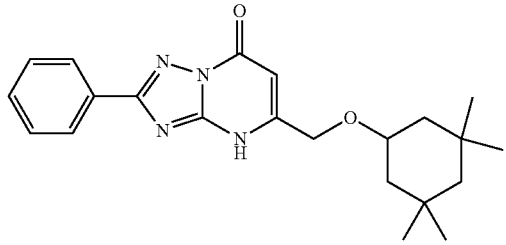 [SMILES: CC1(C)CC(OCc2cc(=O)n3nc(-c4ccccc4)nc3[nH]2)CC(C)(C)C1] | 380.22 | 381.48 | 5.38 |
| 1-98 | 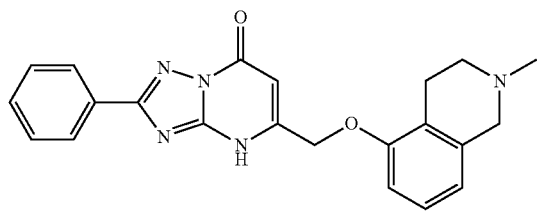 [SMILES: CN1CCc2c(cccc2OCc2cc(=O)n3nc(-c4ccccc4)nc3[nH]2)C1] | 387.17 | 388.43 | 2.66 |
| 1-99 | 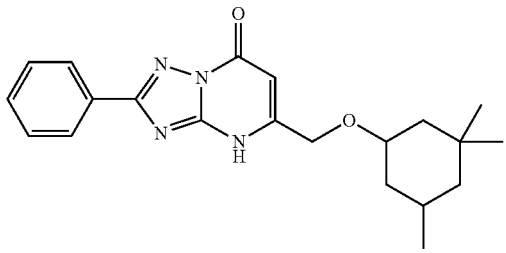 [SMILES: CC1CC(OCc2cc(=O)n3nc(-c4ccccc4)nc3[nH]2)CC(C)(C)C1] | 366.21 | 367.46 | 5.19 and 5.37 (cis + trans) |
| 1-101 | 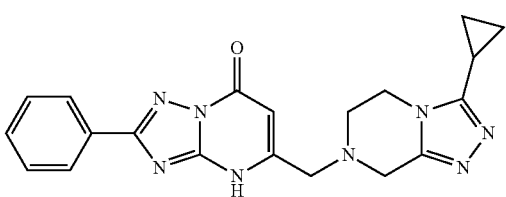 [SMILES: O=c1cc(CN2CCn3c(nnc3C3CC3)C2)[nH]c2nc(-c3ccccc3)nn12] | 388.18 | 389.43 | 2.49 |

-continued
| ID | Structure | EMW | MS m/z (M+ + H) | Retention Time (RT, min) |
|---|---|---|---|---|
| 1-102 | 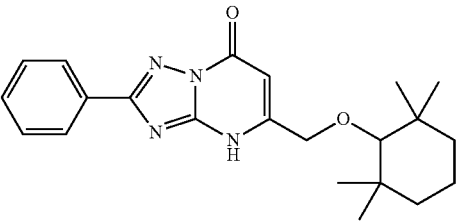 [SMILES: CC1(C)CCCC(C)(C)C1OCc1cc(=O)n2nc(-c3ccccc3)nc2[nH]1] | 380.22 | 381.48 | 5.52 |
| 1-103 | 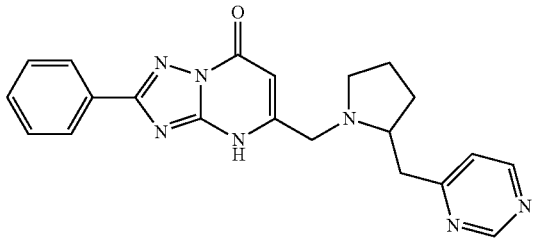 [SMILES: O=c1cc(CN2CCCC2Cc2ccncn2)[nH]c2nc(-c3ccccc3)nn12] | 387.18 | 388.44 | 2.25 |
| 1-104 | 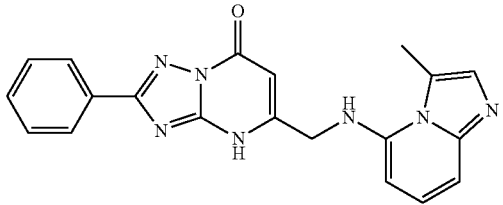 [SMILES: Cc1cnc2cccc(NCc3cc(=O)n4nc(-c5ccccc5)nc4[nH]3)n12] | 371.15 | 372.40 | 2.2 |
| 1-105 | 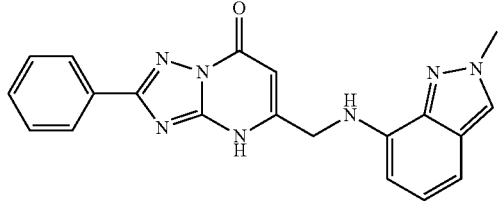 [SMILES: Cn1cc2cccc(NCc3cc(=O)n4nc(-c5ccccc5)nc4[nH]3)c2n1] | 371.15 | 372.40 | 3.58 |
| 1-106 | 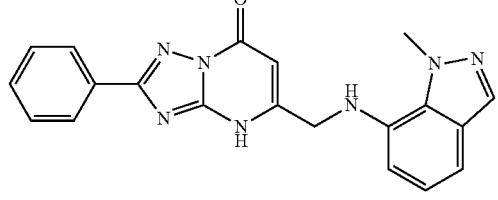 | 371.15 | 372.40 | 3.62 |
| 1-107 | 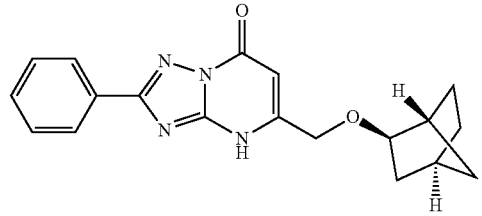 [SMILES: O=c1cc(CO[C@@H]2C[C@H]3CC[C@@H]2C3)[nH]c2nc(-c3ccccc3)nn12] | 336.16 | 337.39 | 4.41 |

-continued

| ID | Structure | EMW | MS m/z (M⁺ + H) | Retention Time (RT, min) |
|---|---|---|---|---|
| 1-108 | 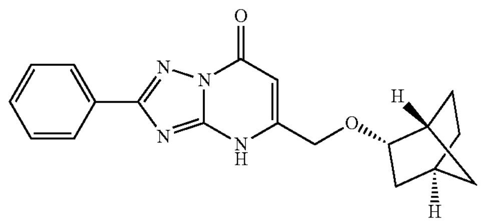 [SMILES: O=c1cc(CO[C@H]2C[C@H]3CC[C@@H]2C3)[nH]c2nc(-c3ccccc3)nn12] | 336.16 | 337.39 | 4.41 |
| 1-109 | 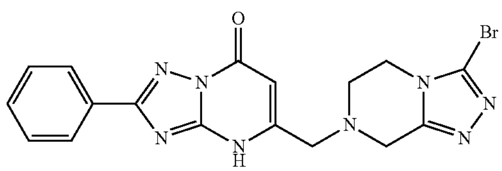 [SMILES: O=c1cc(CN2CCn3c(Br)nnc3C2)[nH]c2nc(-c3ccccc3)nn12] | 426.06 | 428.26 | 2.77 |
| 1-110 | 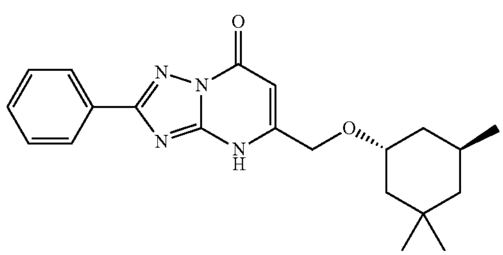 [SMILES: C[C@@H]1C[C@@H](OCc2cc(=O)n3nc(-c4ccccc4)nc3[nH]2)CC(C)(C)C1] | 366.21 | 367.46 | 5.3 |
| 1-111 | 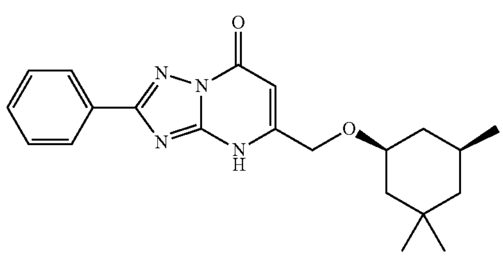 [SMILES: C[C@@H]1C[C@H](OCc2cc(=O)n3nc(-c4ccccc4)nc3[nH]2)CC(C)(C)C1] | 366.21 | 367.46 | 5.12 |
| 1-112 | 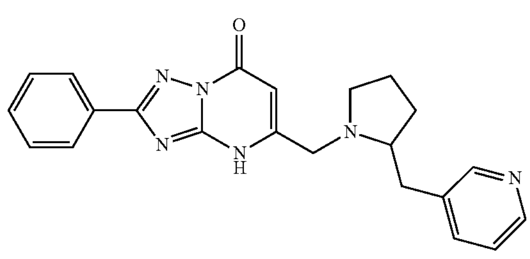 [SMILES: O=c1cc(CN2CCCC2Cc2cccnc2)[nH]c2nc(-c3ccccc3)nn12] | 386.19 | 387.45 | 1.88 |
| 1-113 | 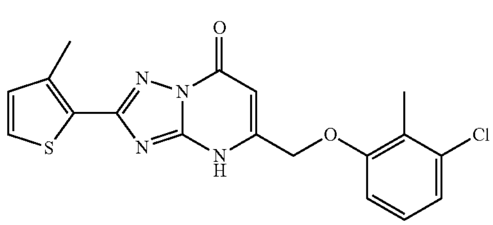 | 386.06 | 387.86 | 5.17 |

-continued

| ID | Structure | EMW | MS m/z (M+ + H) | Retention Time (RT, min) |
|---|---|---|---|---|
| 1-115 | 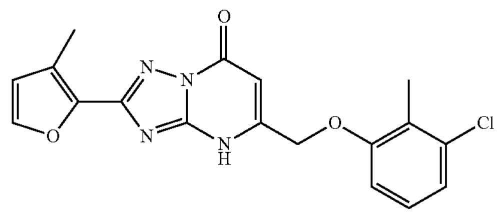 [SMILES: Cc1ccoc1-c1nc2[nH]c(COc3cccc(Cl)c3C)cc(=O)n2n1] | 370.08 | 371.79 | 2.64 |
| 1-118 | 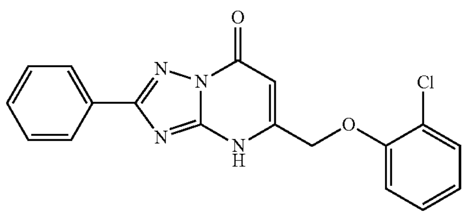 [SMILES: O=c1cc(COc2ccccc2Cl)[nH]c2nc(-c3ccccc3)nn12] | 352.07 | 353.77 | 4.36 |
| 1-131 | 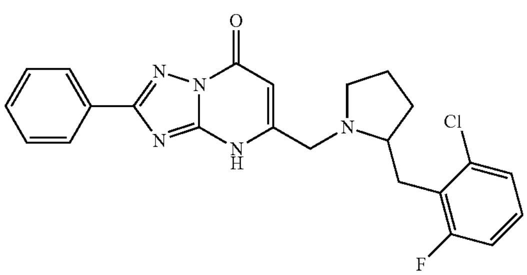 [SMILES: O=c1cc(CN2CCCC2Cc2c(F)cccc2Cl)[nH]c2nc(-c3ccccc3)nn12] | 437.14 | 438.90 | 3.11 |
| 1-134 | 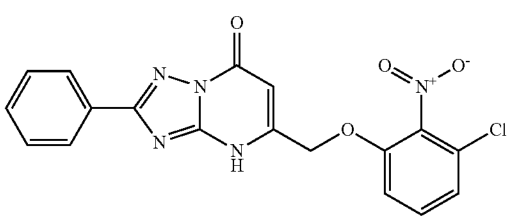 [SMILES: O=c1cc(COc2cccc(Cl)c2[N+](=O)[O-])[nH]c2nc(-c3ccccc3)nn12] | 398.07 | 398.77 | 4.07 |
| 1-135 | 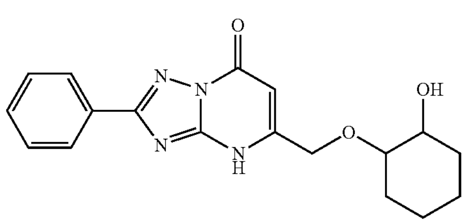 [SMILES: O=c1cc(COC2CCCCC2O)[nH]c2nc(-c3ccccc3)nn12] | 340.15 | 341.38 | 3.29 |
| 1-136 | 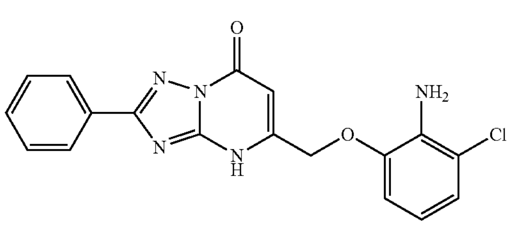 [SMILES: Nc1c(Cl)cccc1OCc1cc(=O)n2nc(-c3ccccc3)nc2[nH]1] | 367.08 | 368.79 | 3.7 |

-continued

| ID | Structure | EMW | MS m/z (M+ + H) | Retention Time (RT, min) |
| --- | --- | --- | --- | --- |
| 1-139 | 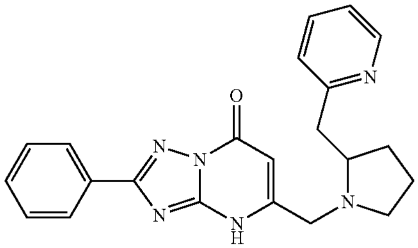 [SMILES: O=c1cc(CN2CCCC2Cc2ccccn2)[nH]c2nc(-c3ccccc3)nn12] | 386.19 | 387.45 | 2.13 |
| 1-141 | 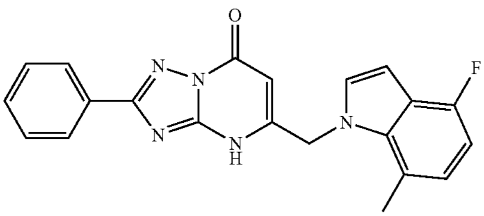 [SMILES: Cc1ccc(F)c2ccn(Cc3cc(=O)n4nc(-c5ccccc5)nc4[nH]3)c12] | 373.13 | 374.38 | 2.53 |
| 1-142 | 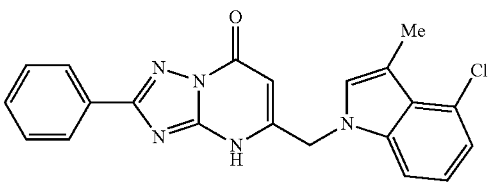 [SMILES: Cc1cn(Cc2cc(=O)n3nc(-c4ccccc4)nc3[nH]2)c2cccc(Cl)c12] | 389.10 | 390.57 | 4.60 |
| 1-143 | 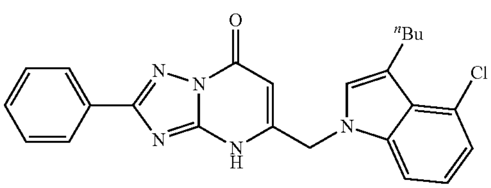 | 431.15 | 432.58 | 5.40 |
| 1-146 | 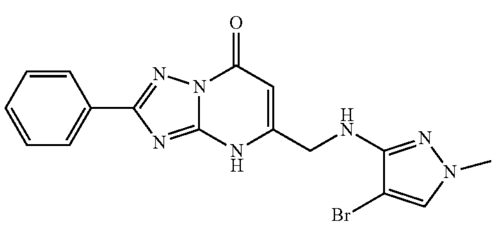 [SMILES: Cn1cc(Br)c(NCc2cc(=O)n3nc(-c4ccccc4)nc3[nH]2)n1] | 400.23 | 400.04 | 3.44 |
| 1-147 | 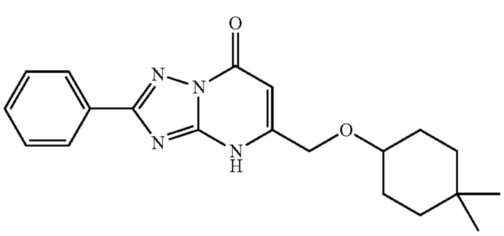 [SMILES: CC1(C)CCC(OCc2cc(=O)n3nc(-c4ccccc4)nc3[nH]2)CC1] | 352.43 | 353.19 | 5.06 |
| 1-148 | 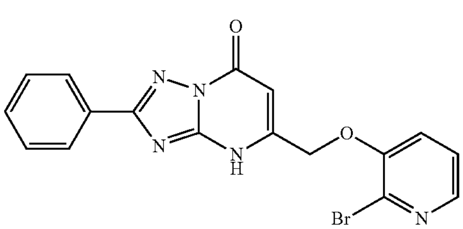 [SMILES: O=c1cc(COc2cccnc2Br)[nH]c2nc(-c3ccccc3)nn12] | 398.21 | 398.02 | 3.57 |

-continued

| ID | Structure | EMW | MS m/z (M⁺ + H) | Retention Time (RT, min) |
|---|---|---|---|---|
| 1-149 | 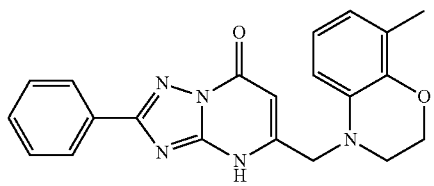 [SMILES: Cc1cccc2c1OCCN2Cc1cc(=O)n2nc(-c3ccccc3)nc2[nH]1] | 373.41 | 374.15 | 4.48 |
| 1-150 | 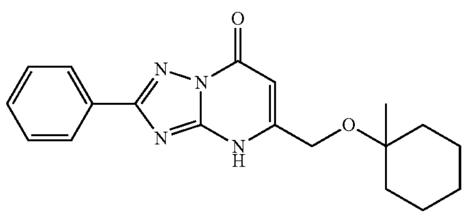 [SMILES: CC1(OCc2cc(=O)n3nc(-c4ccccc4)nc3[nH]2)CCCCC1] | 338.40 | 339.17 | 4.78 |
| 1-151 | 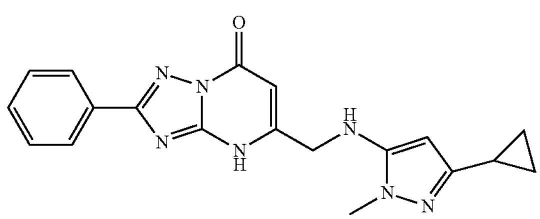 [SMILES: Cn1nc(C2CC2)cc1NCc1cc(=O)n2nc(-c3ccccc3)nc2[nH]1] | 361.40 | 362.17 | 2.80 |
| 1-152 | 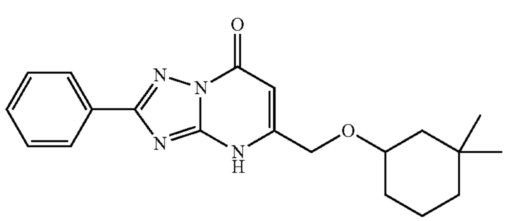 [SMILES: CC1(C)CCCC(OCc2cc(=O)n3nc(-c4ccccc4)nc3[nH]2)C1] | 352.43 | 353.19 | 5.02 |
| 1-155 | 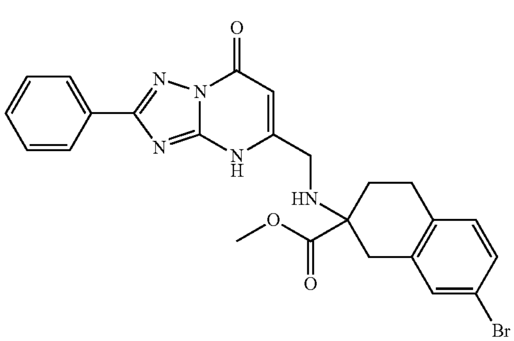 [SMILES: COC(=O)C1(NCc2cc(=O)n3nc(-c4ccccc4)nc3[nH]2)CCc2ccc(Br)cc2C1] | 507.09 | 508.56 | 4.31 |

Example 2

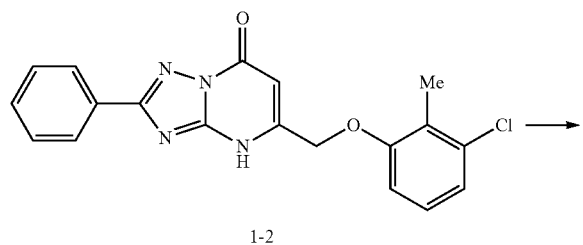

1-2

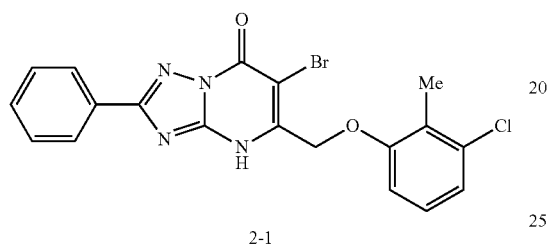

2-1

A reaction mixture of compound 1-2 (18.3 mg, 0.05 mmol) and N-bromosuccinimide (8.9 mg, 0.05 mmol) in ACN (0.5 mL) was stirred in microwave at 130° C. for 20 minutes. Purification using reverse phase HPLC gave compound 2-1 as a HCl salt after lyophilization. $^1$H NMR (400 MHz, CD$_3$OD) δ 8.24-8.16 (m, 2H), 8.14 (s, 2H), 7.50-7.42 (m, 3H), 7.09 (t, J=8.0 Hz, 1H), 6.95 (t, J=9.0 Hz, 2H), 5.23 (s, 2H), 2.32 (s, 3H).
The following compounds may be synthesized using this procedure:

Example 3

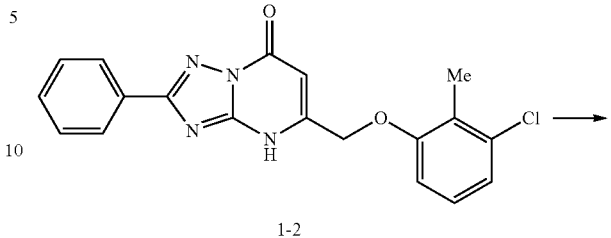

1-2

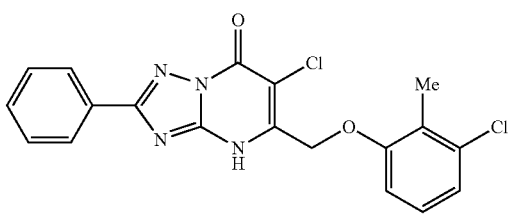

3-1

A reaction mixture of compound 1-1 (18.3 mg, 0.05 mmol) and N-chlorosuccinimide (6.7 mg, 0.05 mmol) in ACN (0.5 mL) was stirred in microwave at 130° C. for 20 minutes. Purification using reverse phase HPLC gave compound 3-1 as a HCl salt after lyophilization.

| ID | Structure | EMW | MS m/z (M$^+$ + H) | Retention Time (min) |
|---|---|---|---|---|
| 2-1 | 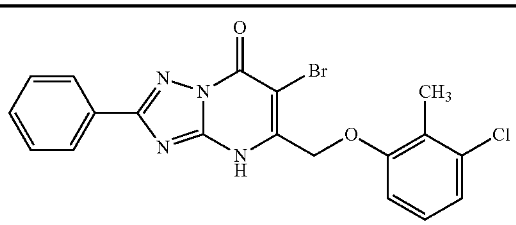 | 444.6971 | 445.18 | 5.38 |
| 2-2 | 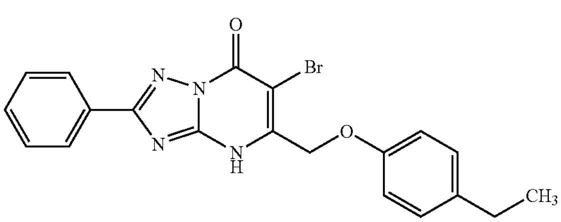 [SMILES: CCc1ccc(OCc2[nH]c3nc(-c4ccccc4)nn3c(=O)c2Br)cc1] | 424.2786 | 425.18 | 5.29 |

| ID | Structure | MW | MS m/z (M⁺ + H) | Retention Time (min) |
|---|---|---|---|---|
| 3-1 | 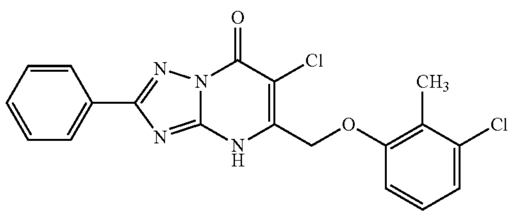 [SMILES: Cc1c(Cl)cccc1OCc1[nH]c2nc(-c3ccccc3)nn2c(=O)c1Cl] | 400.05 | 401.2 | 5.3 |

Example 4

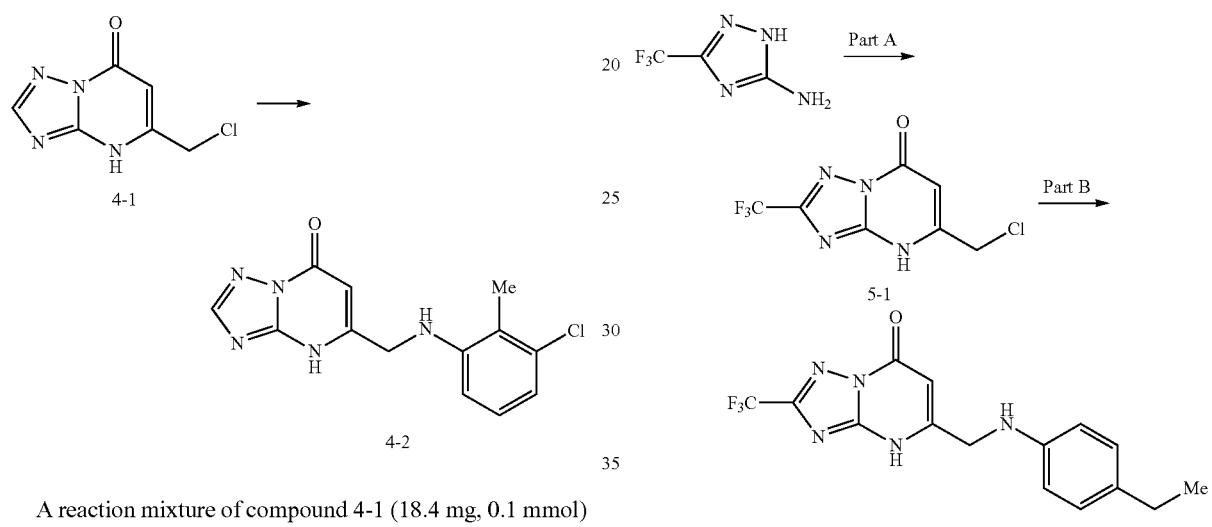

4-1

4-2

A reaction mixture of compound 4-1 (18.4 mg, 0.1 mmol) and 3-chloro-2-methylaniline (14.2 mg, 0.1 mmol) in DMA (0.5 mL) was stirred in microwave at 200° C. for 20 minutes. Purification using reverse phase HPLC gave compound 4-2 as a HCl salt after lyophilization.
The following compounds may be synthesized using this procedure:

Example 5

5-1

5-2

Part A:

A reaction mixture of 3-(trifluoromethyl)-1H-1,2,4-triazol-5-amine (76 mg, 0.5 mmol) and ethyl 4-chloro-3-oxobu-

| ID | Structure | MW | MS m/z (M⁺ + H) | Retention Time (min) |
|---|---|---|---|---|
| 4-2 | 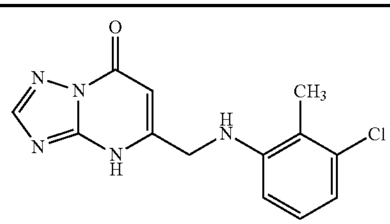 | 289.07 | 290.25 | 3.56 |
| 4-3 | | 269.13 | 270.29 | 3.35 | tanoate (68 μL, 0.5 mmol) in acetic acid (2 mL) was stirred at 180° C. for 20 minutes in microwave. The reaction mixture was concentrated and used for the next step without further purification.

Part B:

A reaction mixture of compound 5-1 (0.5 mmol), 4-ethylaniline (63 μL, 0.5 mmol) and DIEA (174 μL, 1 mmol) in DMA (2 mL) was stirred at 200° C. for 20 minutes in microwave. Purification using reverse phase HPLC gave compound 5-2 as a HCl salt after lyophilization.

The following compounds may be synthesized using this procedure:

| ID | Structure | MW | MS m/z (M⁺ + H) | Retention Time (min) |
|---|---|---|---|---|
| 5-2 | 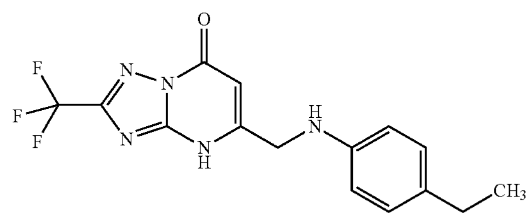 [SMILES: CCc1ccc(NCc2cc(=O)n3nc(C(F)(F)F)nc3[nH]2)cc1] | 337.12 | 338.16 | 4.61 |
| 5-3 | 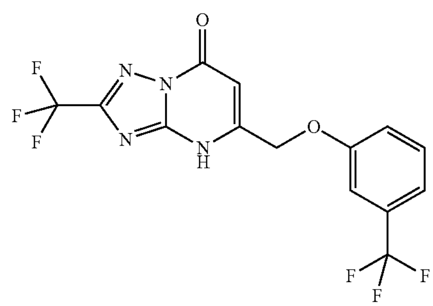 [SMILES: O=c1cc(COc2cccc(C(F)(F)F)c2)[nH]c2nc(C(F)(F)F)nn12] | 378.2359 | 379.23 | 4.79 |
| 5-4 | 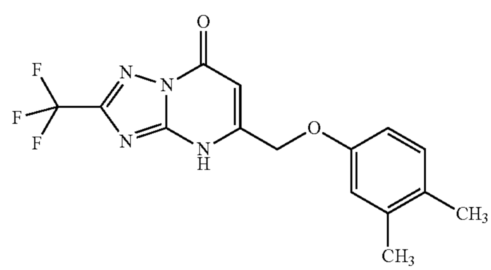 [SMILES: Cc1ccc(OCc2cc(=O)n3nc(C(F)(F)F)nc3[nH]2)cc1C] | 338.2917 | 339.32 | 4.73 |
| 5-5 | 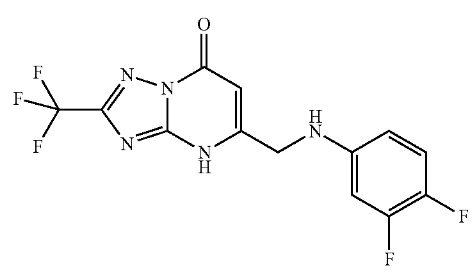 [SMILES: O=c1cc(CNc2ccc(F)c(F)c2)[nH]c2nc(C(F)(F)F)nn12] | 345.2336 | 346.25 | 4.12 |
| 5-6 | 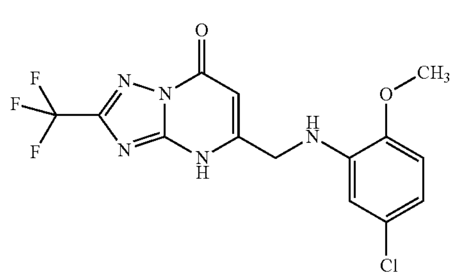 [SMILES: COc1ccc(Cl)cc1NCc1cc(=O)n2nc(C(F)(F)F)nc2[nH]1] | 373.7243 | 374.24 | 4.45 |

| ID | Structure | MW | MS m/z (M+ + H) | Retention Time (min) |
|---|---|---|---|---|
| 5-7 | 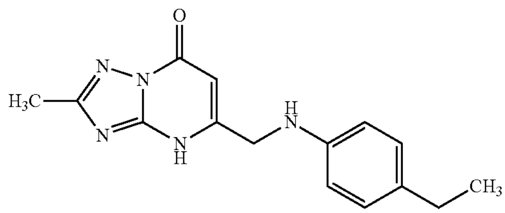 [SMILES: CCc1ccc(NCc2cc(=O)n3nc(C)nc3[nH]2)cc1] | 283.14 | 284.29 | 3.39 |
| 5-8 | 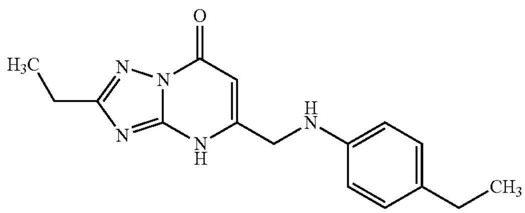 [SMILES: CCc1ccc(NCc2cc(=O)n3nc(CC)nc3[nH]2)cc1] | 297.16 | 298.28 | 3.68 |
| 5-9 | 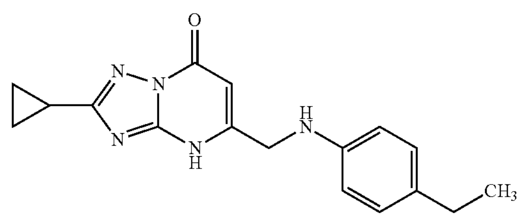 | 309.16 | 310.33 | 3.85 |

Example 6

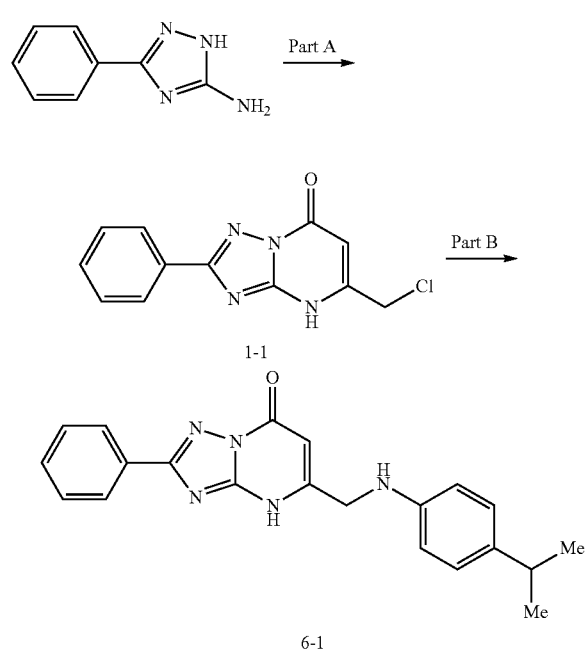

Part A:

To the solution of 3-phenyl-1H-1,2,4-triazol-5-amine (0.8 g, 5 mmol) in acetic acid (6 mL) was added ethyl 4-chloro-3-oxobutanoate (0.75 mL, 5.5 mmol). The reaction mixture was stirred for 24 hours at 80° C., and then cooled to room temperature. The reaction mixture was filtered. The precipitates were washed with ACN and dried to give compound 1-1 in a white powder (872 mg, 67% yield). $^1$H NMR (400 MHz, CD$_3$OD) δ 8.24-8.18 (m, 2H), 7.54-7.46 (m, 3H), 6.21 (s, 1H), 4.65 (s, 2H).

Part B:

A reaction mixture of compound 1-1 (26 mg, 0.1 mmol), 4-isopropylaniline (27 mg, 0.2 mmol) and DIEA (87 μL, 0.5 mmol) in DMA (2 mL) was stirred at 200° C. for 20 minutes in microwave. Purification using reverse phase HPLC gave compound 6-1 as an HCl salt after lyophilization.

The following compounds may be synthesized using this procedure:

| ID | Structure | MW | MS m/z (M+ + H) | Retention Time (min) |
|---|---|---|---|---|
| 6-1 | 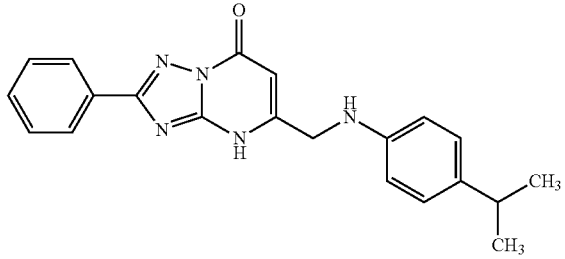 [SMILES: CC(C)c1ccc(NCc2cc(=O)n3nc(-c4ccccc4)nc3[nH]2)cc1] | 359.17 | 360.34 | 4.93 |
| 6-2 | 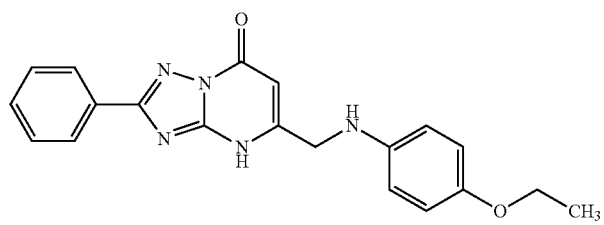 [SMILES: CCOc1ccc(NCc2cc(=O)n3nc(-c4ccccc4)nc3[nH]2)cc1] | 361.15 | 362.2 | 3.05 |
| 6-3 | 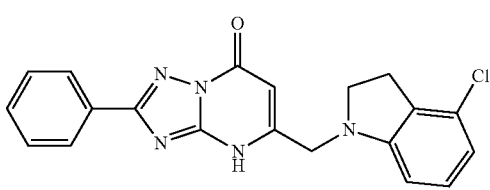 [SMILES: O=c1cc(CN2CCc3c(Cl)cccc32)[nH]c2nc(-c3ccccc3)nn12] | 377.1 | 378.22 | 4.87 |
| 6-4 | 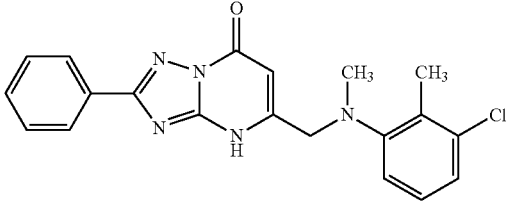 [SMILES: Cc1c(Cl)cccc1N(C)Cc1cc(=O)n2nc(-c3ccccc3)nc2[nH]1] | 379.12 | 380.29 | 4.97 |
| 6-5 | 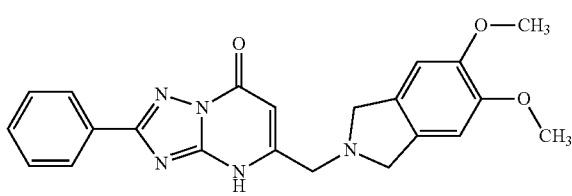 [SMILES: COc1cc2c(cc1OC)CN(Cc1cc(=O)n3nc(-c4ccccc4)nc3[nH]1)C2] | 403.16 | 404.33 | 2.52 |
Example 7
-continued
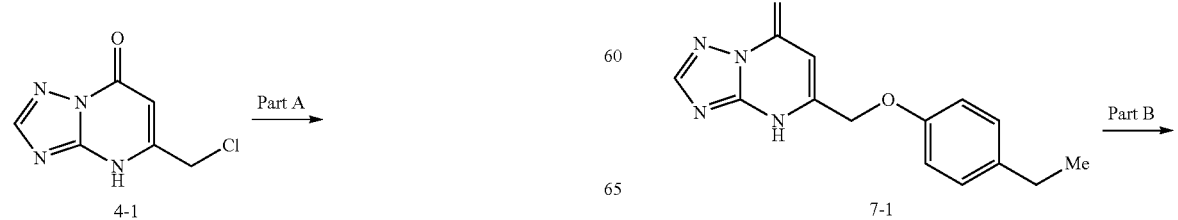

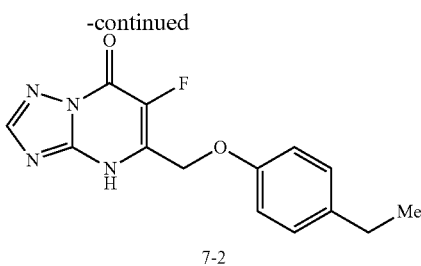

Part A:

A reaction mixture of 4-ethylphenol (61 mg, 0.5 mmol) and sodium hydride (60% in oil, 20 mg, 0.5 mmol) in DMA (1 mL) was stirred at room temperature for 15 minutes. To the resultant solution was added compound 4-1 (36.9 mg, 0.2 mmol). The reaction mixture was stirred in microwave at 210° C. for 30 minutes. Purification using reverse phase HPLC gave compound 7-1 as an HCl salt after lyophilization.

Part B:

A reaction mixture of compound 7-1 (16 mg, 0.06 mmol) and Selectfluor™ (21 mg, 0.06 mmol) in ACN (1 mL) was stirred at 100° C. for 10 minutes in microwave. Purification using reverse phase HPLC gave compound 7-2 as an HCl salt after lyophilization.

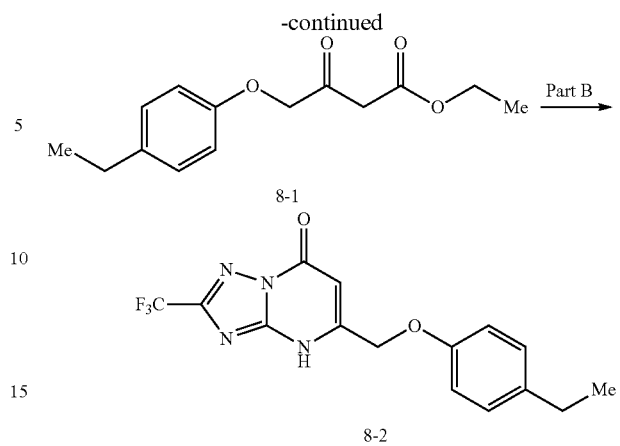

Part A:

To a mixture of potassium hydroxide (0.9 g, 16 mmol) in DMSO (16 mL) was added a solution of 4-ethylphenol (0.978 g, 8 mmol) in DMSO (1.6 mL) dropwise. The reaction mixture was stirred at room temperature for 30 minutes. Ethyl 4-chloro-3-oxobutanoate (1.09 mL, 8 mmol) was added. The reaction mixture was stirred at room temperature for over-

| ID | Structure | MW | MS m/z (M⁺ + H) | Retention Time (min) |
|---|---|---|---|---|
| 7-1 | 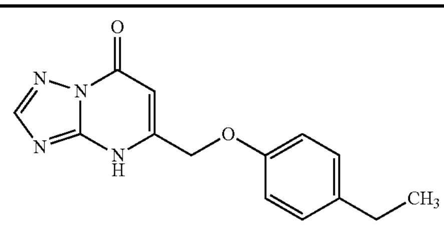 | 270.11 | 271.28 | 3.67 |
| 7-2 | 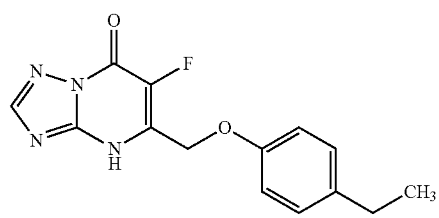 [SMILES: CCc1ccc(OCc2[nH]c3ncnn3c(=O)c2F)cc1] | 288.1 | 289.32 | 3.88 |

Example 8

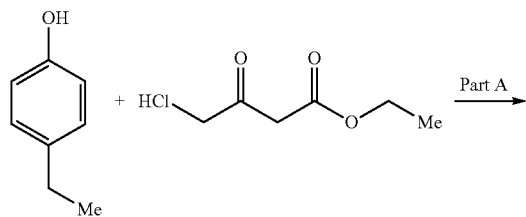

night. The reaction mixture was acidified with HCl aqueous solution (1 N). The organics were extracted with ethyl acetate. Chromatography on silica gel using 10% EtOAc in Hexane as the eluent gave compound 8-1 as a yellow oil (1.34 g, 67% yield). $^1$H NMR (400 MHz, CDCl$_3$) δ 7.09 (dd, J=8.4, 23.6 Hz, 2H), 6.78 (dd, J=8.4, 21.6 Hz, 2H), 4.62 (s, 1H), 4.26-4.14 (m, 2H), 3.63 (s, 1H), 2.64-2.54 (m, 2H), 1.32-1.16 (m, 6H).

Part B:

A reaction mixture of 3-(trifluoromethyl)-1H-1,2,4-triazol-5-amine (30 mg, 0.2 mmol) and compound 8-1 (50 mg, 0.2 mmol) in acetic acid (0.5 mL) was stirred at 180° C. for 20 minutes in microwave. Purification using reverse phase HPLC gave compound 8-2 as an HCl salt after lyophilization. The following compounds may be synthesized using this procedure:

| ID | Structure | MW | MS m/z (M+ + H) | Retention Time (min) |
|---|---|---|---|---|
| 8-2 | 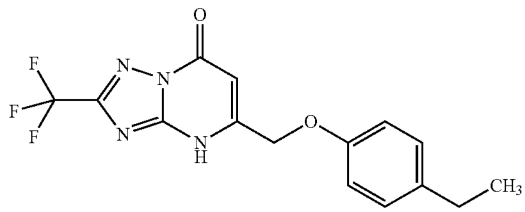 [SMILES: CCc1ccc(OCc2cc(=O)n3nc(C(F)(F)F)nc3[nH]2)cc1] | 338.1 | 339.23 | 4.86 |
| 8-3 | 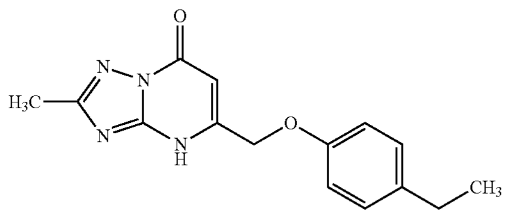 [SMILES: CCc1ccc(OCc2cc(=O)n3nc(C)nc3[nH]2)cc1] | 284.13 | 285.32 | 3.78 |
| 8-4 | 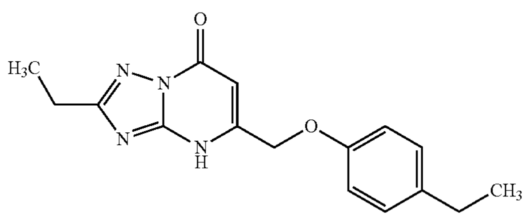 [SMILES: CCc1ccc(OCc2cc(=O)n3nc(CC)nc3[nH]2)cc1] | 298.14 | 299.35 | 4.05 |
| 8-5 | 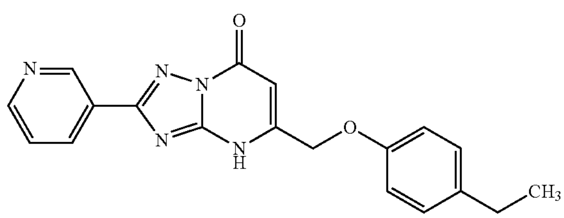 [SMILES: CCc1ccc(OCc2cc(=O)n3nc(-c4cccnc4)nc3[nH]2)cc1] | 347.14 | 348.28 | 3.56 |
| 8-6 | 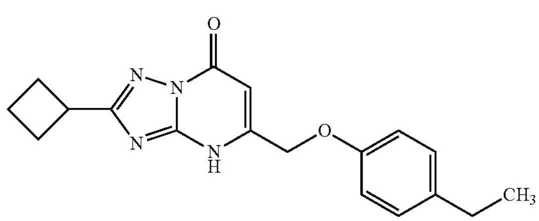 [SMILES: CCc1ccc(OCc2cc(=O)n3nc(C4CCC4)nc3[nH]2)cc1] | 324.16 | 325.31 | 4.46 |
| 8-7 | 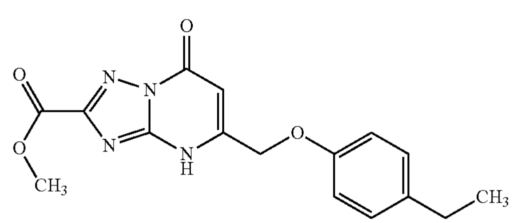 [SMILES: CCc1ccc(OCc2cc(=O)n3nc(C(=O)OC)nc3[nH]2)cc1] | 328.12 | 329.29 | 4.03 |
| 8-8 | 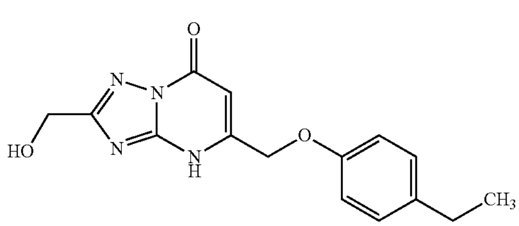 [SMILES: CCc1ccc(OCc2cc(=O)n3nc(CO)nc3[nH]2)cc1] | 300.12 | 301.32 | 3.46 |

-continued

| ID | Structure | MW | MS m/z (M+ + H) | Retention Time (min) |
|---|---|---|---|---|
| 8-9 | 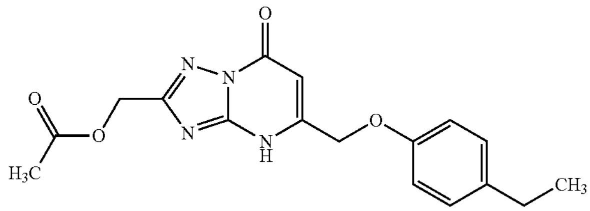 [SMILES: CCc1ccc(OCc2cc(=O)n3nc(COC(C)=O)nc3[nH]2)cc1] | 342.13 | 343.26 | 4.03 |
| 8-10 | 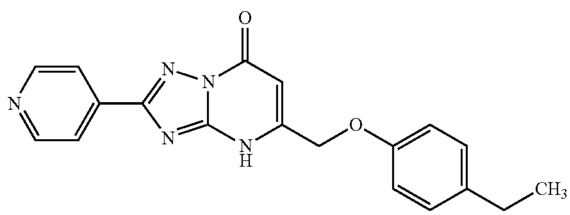 [SMILES: CCc1ccc(OCc2cc(=O)n3nc(-c4ccncc4)nc3[nH]2)cc1] | 347.14 | 348.35 | 3.47 |
| 8-11 | 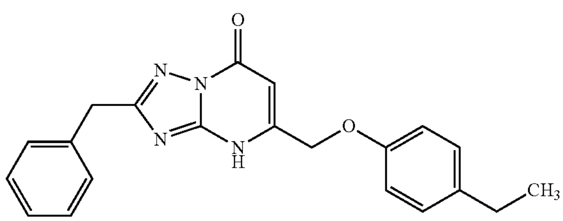 [SMILES: CCc1ccc(OCc2cc(=O)n3nc(Cc4ccccc4)nc3[nH]2)cc1] | 360.16 | 361.34 | 4.75 |
| 8-12 | 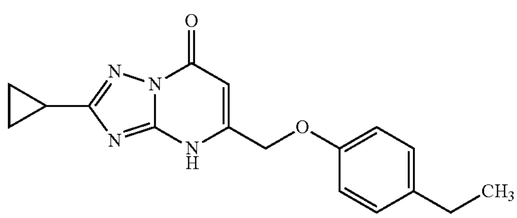 [SMILES: CCc1ccc(OCc2cc(=O)n3nc(C4CC4)nc3[nH]2)cc1] | 310.14 | 311.35 | 4.17 |
| 8-13 | 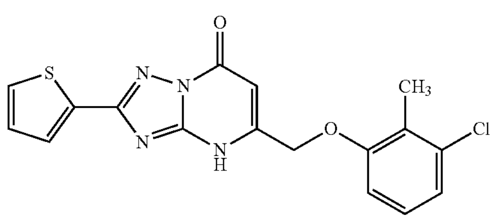 [SMILES: Cc1c(Cl)cccc1OCc1cc(=O)n2nc(-c3cccs3)nc2[nH]1] | 372.04 | 373.2 | 4.77 |
| 8-14 | 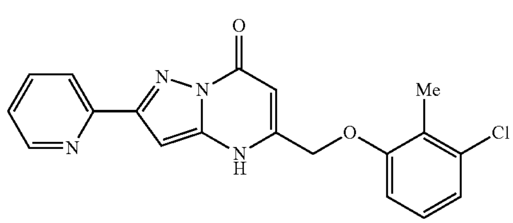 [SMILES: Cc1c(Cl)cccc1OCc1cc(=O)n2nc(-c3ccccn3)cc2[nH]1] | 366.09 | 367.61 | 3.57 |

Example 9

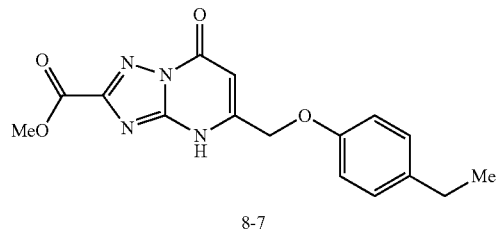

8-7

→

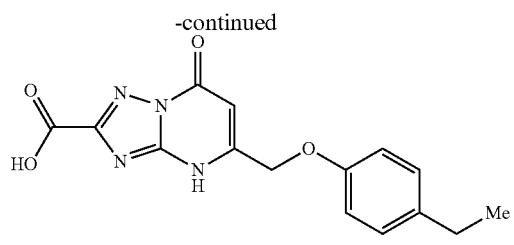

9-1

A reaction mixture of compound 8-7 (6 mg, 0.018 mmol) and lithium hydroxide monohydrate (1.6 mg, 0.036 mmol) in THF/water (2:1, 0.6 mL) was stirred at room temperature for 6 hours. Purification using reverse phase HPLC gave compound 9-1 after lyophilization.

| ID | Structure | MW | MS m/z (M⁺ + H) | Retention Time (min) |
|---|---|---|---|---|
| 9-1 | (see structure) | 314.1 | 315.26 | 3.7 |

Example 10

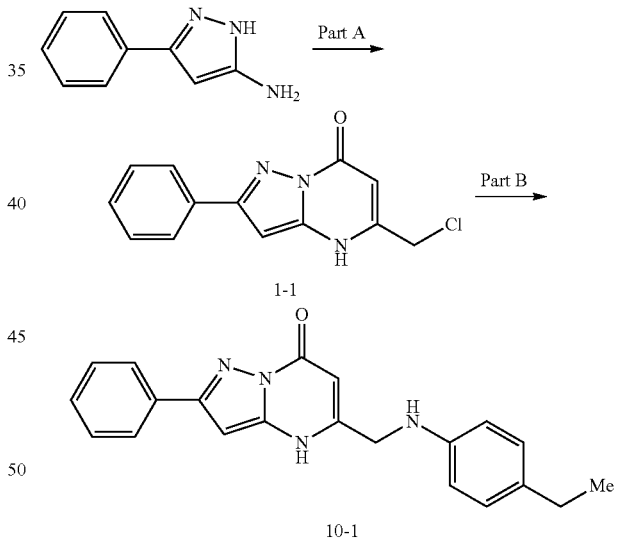

Part A:
A reaction mixture of 3-phenyl-1H-pyrazol-5-amine (159 mg, 1 mmol) and ethyl 4-chloro-3-oxobutanoate (136 µL, 1 mmol) in acetic acid (2 mL) was stirred at 180° C. for 20 minutes in microwave. The reaction mixture was concentrated and used for the next step without further purification.

Part B:
A reaction mixture of compound 1-1 (0.5 mmol), 4-ethylaniline (125 µL, 1 mmol) and DIEA (350 µL, 2 mmol) in DMA (2 mL) was stirred at 200° C. for 20 minutes in microwave. Purification using reverse phase HPLC gave compound 10-1 as an HCl salt after lyophilization.

The following compounds may be synthesized using this procedure:

| ID | Structure | MW | MS m/z (M⁺ + H) | Retention Time (min) |
|---|---|---|---|---|
| 10-1 | 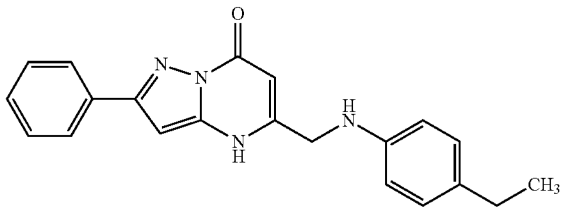 [SMILES: CCc1ccc(NCc2cc(=O)n3nc(-c4ccccc4)cc3[nH]2)cc1] | 344.16 | 345.28 | 4.66 |
| 10-2 | 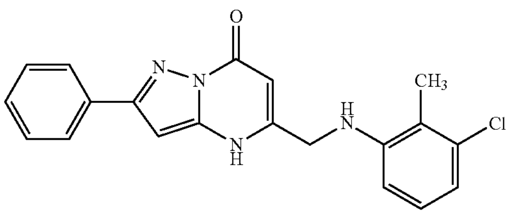 [SMILES: Cc1c(Cl)cccc1NCc1cc(=O)n2nc(-c3ccccc3)cc2[nH]1] | 364.11 | 365.3 | 4.76 |

Example 11

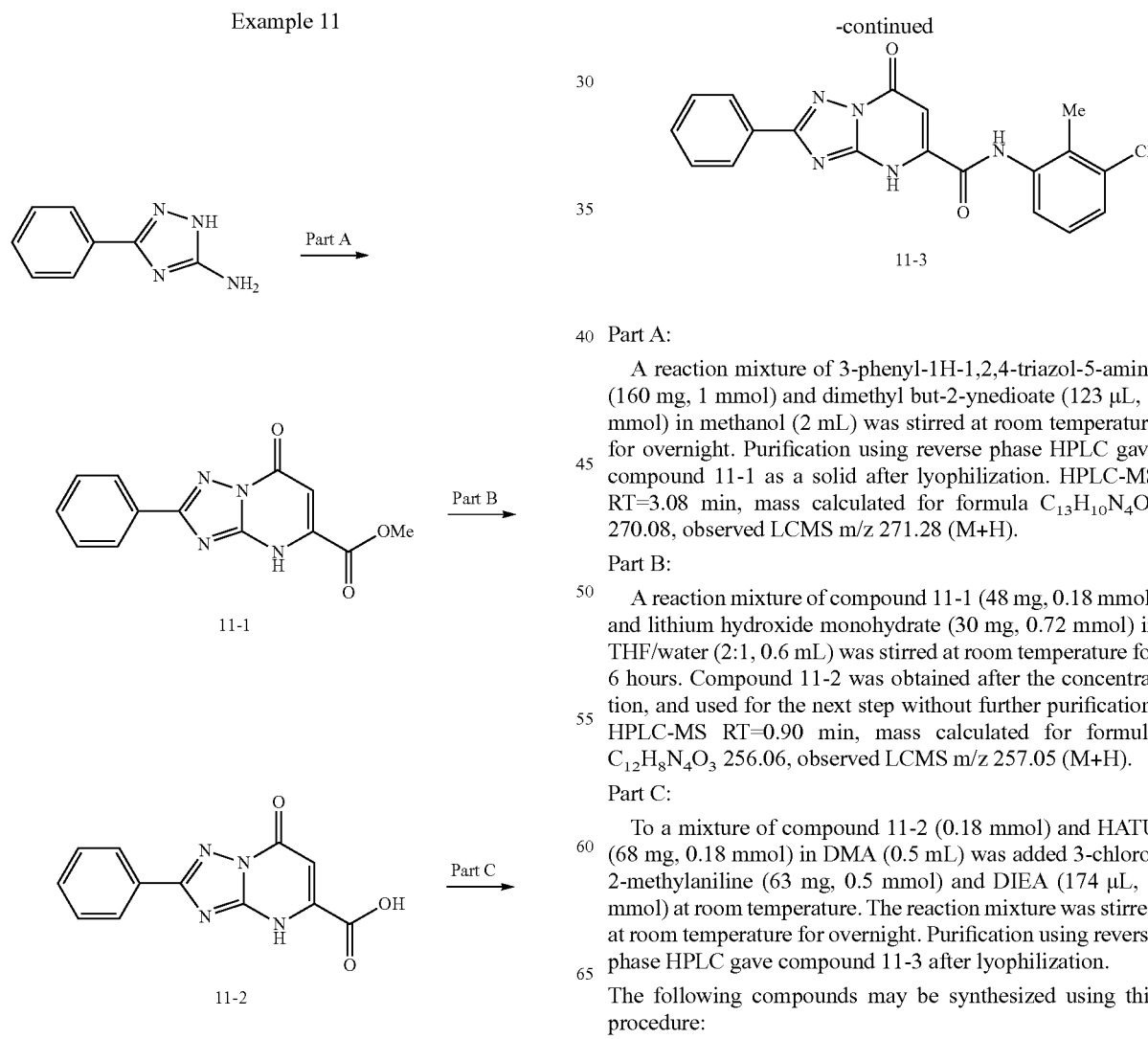

Part A:

A reaction mixture of 3-phenyl-1H-1,2,4-triazol-5-amine (160 mg, 1 mmol) and dimethyl but-2-ynedioate (123 µL, 1 mmol) in methanol (2 mL) was stirred at room temperature for overnight. Purification using reverse phase HPLC gave compound 11-1 as a solid after lyophilization. HPLC-MS RT=3.08 min, mass calculated for formula $C_{13}H_{10}N_4O_3$ 270.08, observed LCMS m/z 271.28 (M+H).

Part B:

A reaction mixture of compound 11-1 (48 mg, 0.18 mmol) and lithium hydroxide monohydrate (30 mg, 0.72 mmol) in THF/water (2:1, 0.6 mL) was stirred at room temperature for 6 hours. Compound 11-2 was obtained after the concentration, and used for the next step without further purification. HPLC-MS RT=0.90 min, mass calculated for formula $C_{12}H_8N_4O_3$ 256.06, observed LCMS m/z 257.05 (M+H).

Part C:

To a mixture of compound 11-2 (0.18 mmol) and HATU (68 mg, 0.18 mmol) in DMA (0.5 mL) was added 3-chloro-2-methylaniline (63 mg, 0.5 mmol) and DIEA (174 µL, 1 mmol) at room temperature. The reaction mixture was stirred at room temperature for overnight. Purification using reverse phase HPLC gave compound 11-3 after lyophilization.

The following compounds may be synthesized using this procedure:

| ID | Structure | MW | MS m/z (M+ + H) | Retention Time (min) |
|---|---|---|---|---|
| 11-3 | 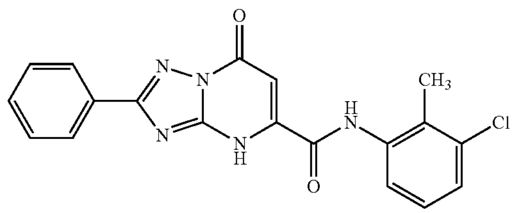 [SMILES: Cc1c(Cl)cccc1NC(=O)c1cc(=O)n2nc(-c3ccccc3)nc2[nH]1] | 379.08 | 380.28 | 4.32 |
| 11-4 | 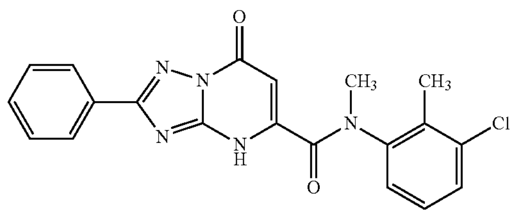 [SMILES: Cc1c(Cl)cccc1N(C)C(=O)c1cc(=O)n2nc(-c3ccccc3)nc2[nH]1] | 393.1 | 394.23 | 4.19 |

Example 12

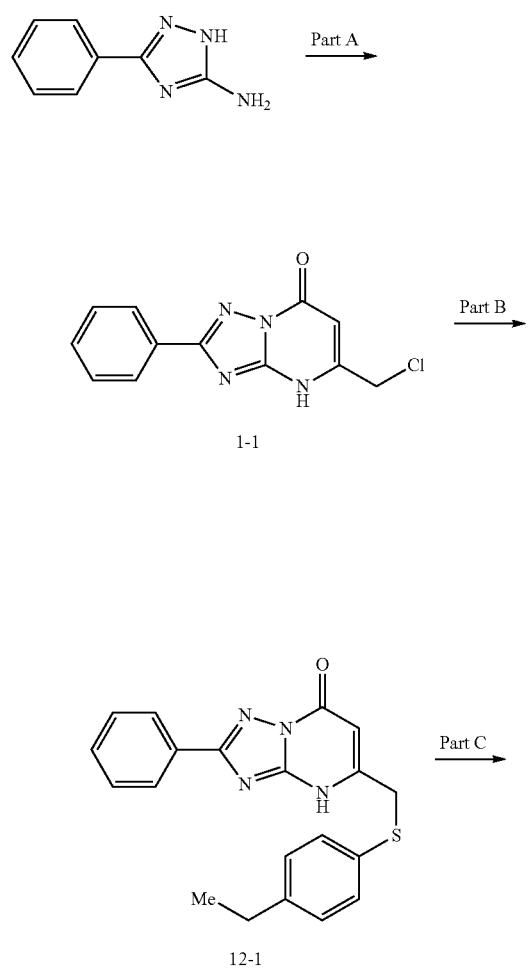

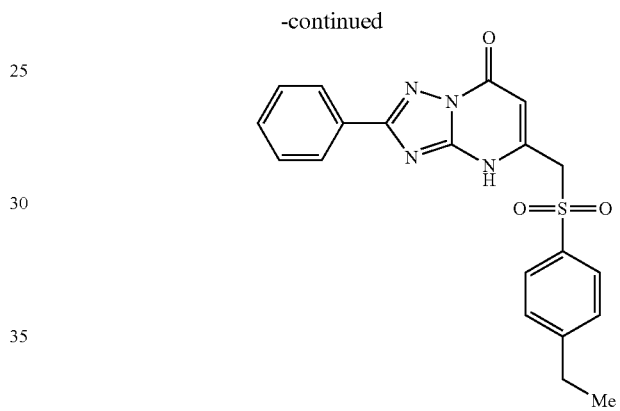

Part A:
  To the solution of 3-phenyl-1H-1,2,4-triazol-5-amine (0.8 g, 5 mmol) in acetic acid (6 mL) was added ethyl 4-chloro-3-oxobutanoate (0.75 mL, 5.5 mmol). The reaction mixture was stirred for 24 hours at 80° C., and then cooled to room temperature. The reaction mixture was filtered. The precipitates were washed with ACN and dried to give compound 1-1 in a white powder (872 mg, 67% yield). $^1$H NMR (400 MHz, CD$_3$OD) δ 8.24-8.18 (m, 2H), 7.54-7.46 (m, 3H), 6.21 (s, 1H), 4.65 (s, 2H).

Part B:
  A reaction mixture of compound 1-1 (52 mg, 0.2 mmol), 4-ethylbenzenethiol (69 mg, 0.5 mmol) and DIEA (87 μL, 0.5 mmol) in DMA (1 mL) was stirred at 180° C. for 20 minutes in microwave. Purification using reverse phase HPLC gave compound 12-1 after lyophilization. $^1$H NMR (400 MHz, CD$_3$OD) δ 8.22-8.15 (m, 2H), 7.52-7.46 (m, 3H), 7.35 (d, J=8.0 Hz, 2H), 7.17 (d, J=8.0 Hz, 2H), 5.67 (s, 1H), 4.03 (s, 2H), 2.61 (q, J=7.6 Hz, 2H), 1.18 (d, J=7.6 Hz, 3H).

Part C:
  A reaction mixture of compound 12-1 (7.2 mg, 0.02 mmol) and OXONE® (31 mg, 0.05 mmol) in a mixture of MeOH/water (1:1, 0.5 mL) was stirred at room temperature for overnight. Purification using reverse phase HPLC gave compound 12-2 after lyophilization.
  The following compounds may be synthesized using this procedure:

| ID | Structure | MW | MS m/z (M+ + H) | Retention Time (min) |
|---|---|---|---|---|
| 12-1 | 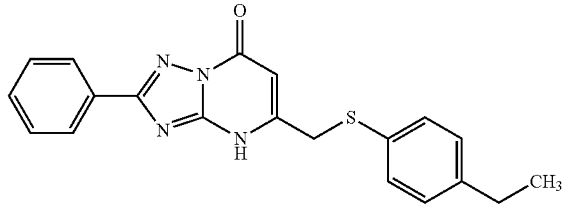 [SMILES: CCc1ccc(SCc2cc(=O)n3nc(-c4ccccc4)nc3[nH]2)cc1] | 362.12 | 363.25 | 5.01 |
| 12-2 | 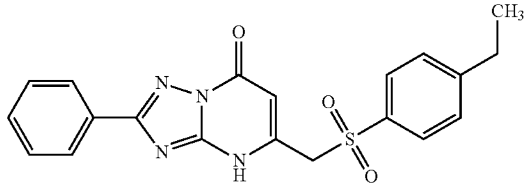 [SMILES: CCc1ccc(S(=O)(=O)Cc2cc(=O)n3nc(-c4ccccc4)nc3[nH]2)cc1] | 394.11 | 395.22 | 4.17 |

Example 13

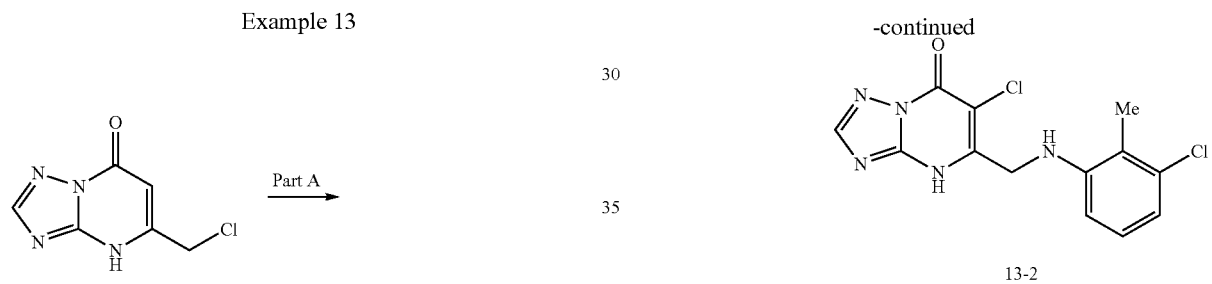

Part A:
A reaction mixture of 5-(chloromethyl)-[1,2,4]triazolo[1,5-a]pyrimidin-7(4H)-one (37 mg, 0.2 mmol) and N-bromosuccinimide (36 mg, 0.2 mmol) in ACN (2 mL) was stirred at room temperature for overnight. Compound 13-1 was obtained after the concentration, and used for the next step without further purification.

Part B:
A reaction mixture of compound 13-1 (26 mg, 0.1 mmol), 3-chloro-2-methylaniline (25 μL, 0.2 mmol) and DIEA (35 μL, 0.2 mmol) in DMA (0.5 mL) was stirred at 180° C. for 20 minutes in microwave. Purification using reverse phase HPLC gave compound 13-2 after lyophilization.

| ID | Structure | MW | MS m/z (M+ + H) | Retention Time (min) |
|---|---|---|---|---|
| 13-2 | 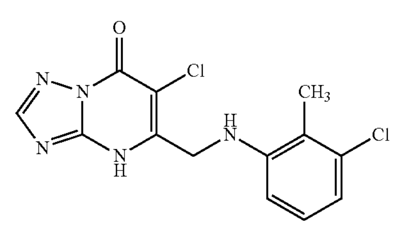 [SMILES: Cc1c(Cl)cccc1NCc1[nH]c2ncnn2c(=O)c1Cl] | 323.03 | 324.21 | 4.17 |

Example 14

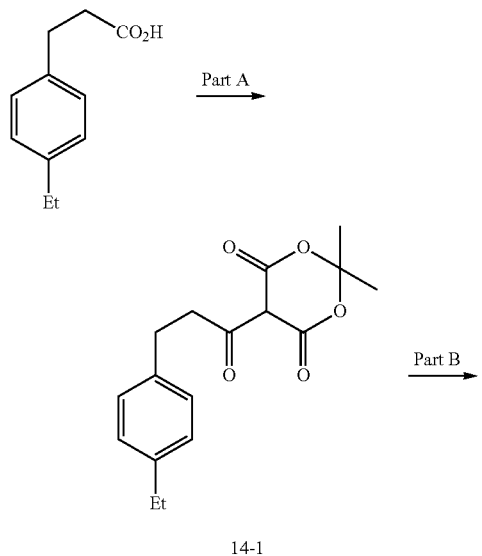

14-1

Part A:

A solution of 3-(4-ethylphenyl)propanoic acid (890 mg, 5 mmol), Meldrum's acid (720 mg, 5 mmol), DMAP (610 mg, 5 mmol) and DCC (5 mL, 1.0 M in DCM, 5 mmol) in DCM (10 mL) was stirred at room temperature for overnight. The mixture was filtered. The filtrate was concentrated. The residue was dissolved in EtOAc. The solution was washed with HCl aqueous solution (1 N) and brine. Compound 14-1 was obtained after the concentration, and used for the next step without further purification. (*J. Org. Chem.* 2005, 70, 5331)

Part B:

Compound 14-1 obtained from part A was dissolved in ethanol. The solution was heated at reflux for 3 hours. Compound 14-2 was obtained after the concentration, and used for the next step without further purification. HPLC-MS RT=2.13 min, mass calculated for formula $C_{15}H_{20}O_3$ 248.14, observed LCMS m/z 249.25 (M+H).

Part C:

A reaction mixture of compound 14-2 (50 mg, 0.2 mmol) and 3-phenyl-1H-1,2,4-triazol-5-amine (32 mg, 0.2 mmol) in AcOH (1 mL) was stirred at 160° C. for 20 minutes in microwave. Purification using reverse phase HPLC gave compound 14-3 after lyophilization.

| ID | Structure | MW | MS m/z (M⁺ + H) | Retention Time (min) |
|---|---|---|---|---|
| 14-3 | 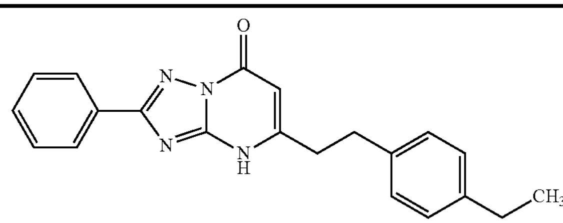 | 344.16 | 345.36 | 4.87 |

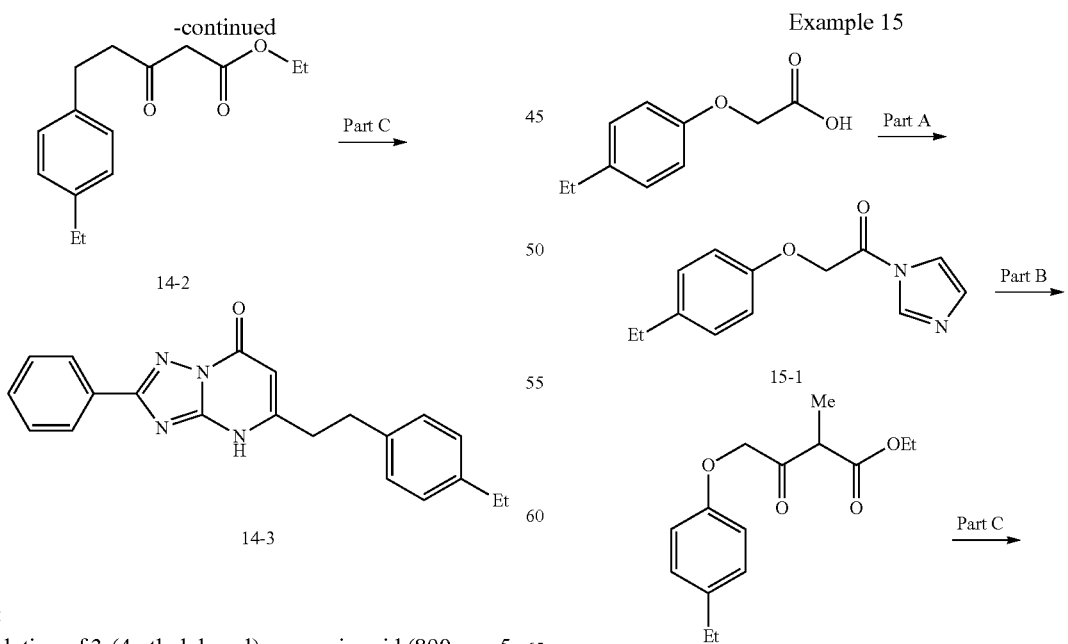

-continued

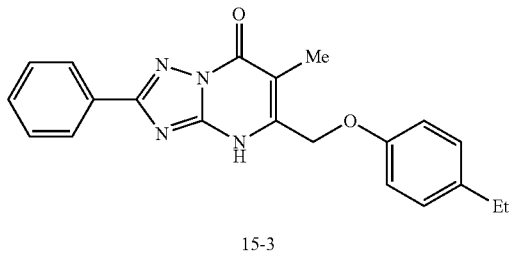

15-3

Part A:
Compound 5-1 was obtained by mixing 2-(4-ethylphenoxy)acetic acid (0.54 g, 3 mmol) and CDI (568 mg, 3.5 mmol) in ACN (5 mL) and stirring at room temperature for 30 minutes.

Part B:
To the solution of diethyl 2-methylmalonate (852 µL, 5 mmol) in ethanol (5 mL) was added a solution of potassium hydroxide (280 mg, 5 mmol) in ethanol (5 mL) dropwise at room temperature. The reaction mixture was stirred at room temperature for overnight. The solvent was removed. The residue was suspended in ACN (10 mL). To the suspension was added magnesium chloride (524 mg, 5.5 mmol) and triethylamine (976 µL, 7 mmol). The reaction mixture in ACN was stirred at room temperature for 2 hours. Then the solution of compound 15-1 in ACN obtained from part A was added. The mixture was stirred at room temperature for overnight, and then heated to reflux for 2 hours. The mixture was allowed to cool to room temperature, and acidified using HCl aqueous solution (1 N). The mixture was extracted with EtOAc twice. The combined organic layers were concentrated to afford compound 15-2 in use for the next step without further purification. HPLC-MS RT=2.42 min, mass calculated for formula $C_{15}H_{20}O_4$ 264.14, observed LCMS m/z 265.15 (M+H).

Part C:
A reaction mixture of compound 15-2 (79 mg, 0.3 mmol) and 3-phenyl-1H-1,2,4-triazol-5-amine (48 mg, 0.3 mmol) in AcOH (1 mL) was stirred at 160° C. for 20 minutes in microwave. Purification using reverse phase HPLC gave compound 15-3 after lyophilization.

Example 16

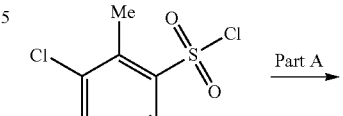

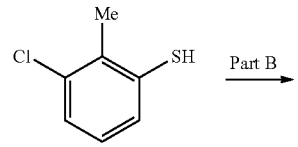

16-1

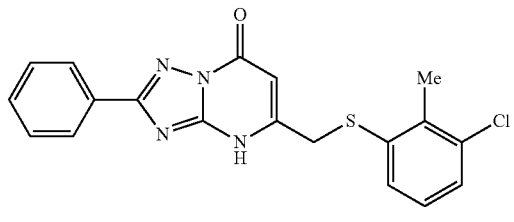

16-2

Part A:
A reaction mixture of 3-chloro-2-methylbenzene-1-sulfonyl chloride (0.9 g, 4 mmol) and triphenylphosphine (4.19 g, 16 mmol) in dioxane/water (4:1, 20 mL) was stirred at 100° C. for 2 hours. The mixture was diluted with water. The organic components were extracted with EtOAc twice. The combined EtOAc layers were concentrated. The residue was purified using chromatography. Compound 16-1 was eluted with 10% DCM in Hexane. Solvent evaporation afforded compound 16-1 as clear oil. $^1$H NMR (400 MHz, CD$_3$OD) δ 7.17 (d, J=8.4 Hz, 2H), 6.97 (t, J=8.4 Hz, 1H), 3.43 (s, 1H), 2.40 (s, 3H).

Part B:
A reaction mixture of compound 16-1 (16 mg, 0.1 mmol), 5-(chloromethyl)-2-phenyl-[1,2,4]triazolo[1,5-a]pyrimidin-7(4H)-one (26 mg, 0.1 mmol) and DIEA (87 µL, 0.5 mmol) in DMA (1 mL) was stirred at 150° C. for 20 minutes in microwave. Purification using reverse phase HPLC gave compound 16-2 after lyophilization.

| ID | Structure | MW | MS m/z (M$^+$ + H) | Retention Time (min) |
|---|---|---|---|---|
| 15-3 | 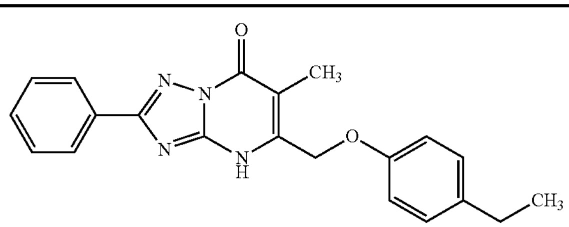 | 360.16 | 361.31 | 5.15 |

| ID | Structure | MW | MS m/z (M+ + H) | Retention Time (min) |
|---|---|---|---|---|
| 16-2 | 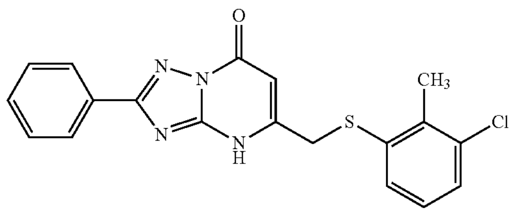 [SMILES: Cc1c(Cl)cccc1SCc1cc(=O)n2nc(-c3ccccc3)nc2[nH]1] | 382.07 | 383.23 | 4.88 |

Example 17

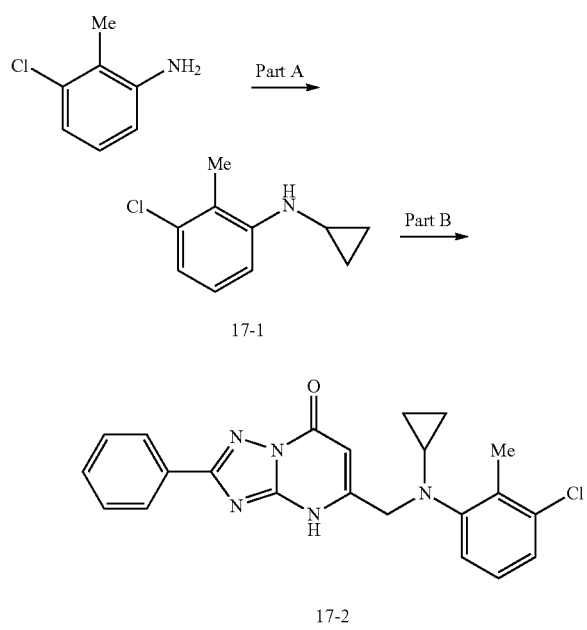

Part A:

A suspension of copper(II) acetate (908 mg, 5 mmol) and 2,2'-bipyridine (780 mg, 5 mmol) in DCE (35 mL) was heated to 70° C. and stirred at this temperature for 30 minutes. The mixture in warm DCE was added to the suspension of cyclopropyl boronic acid (860 mg, 10 mmol), 3-chloro-2-methylaniline (625 µL, 5 mmol) and sodium carbonate (1.06 g, 10 mmol) in DCE (15 mL). The reaction mixture was stirred at 70° C. for 6 hours. The mixture was filtered. The filtrate was concentrated. The residue was mixed with aqueous ammonia solution. The organic components were extracted with EtOAc. The combined EtOAc layers were concentrated. The residue was purified by chromatography. Elution with 10% EtOAc in Hexane gave compound 17-1 as a light yellow oil (334 mg, 37% yield). $^1$H NMR (400 MHz, CDCl$_3$) δ 7.05 (t, J=8.0 Hz, 1H), 6.96 (d, J=8.4 Hz, 1H), 6.80 (d, J=7.2 Hz, 1H), 4.11 (br s, 1H), 2.48-2.38 (m, 1H), 2.16 (s, 3H), 0.81-0.74 (m, 2H), 0.60-0.50 (m, 2H).

Part B:

A reaction mixture of compound 17-1 (27 mg, 0.15 mmol), 5-(chloromethyl)-2-phenyl-[1,2,4]triazolo[1,5-a]pyrimidin-7(4H)-one (26 mg, 0.1 mmol) and DIEA (35 µL, 0.2 mmol) in DMA (0.5 mL) was stirred at 220° C. for 20 minutes in microwave. Purification using reverse phase HPLC gave compound 17-2 after lyophilization.

The following compounds may be synthesized using this procedure:

| ID | Structure | MW | MS m/z (M+ + H) | Retention Time (min) |
|---|---|---|---|---|
| 17-2 | 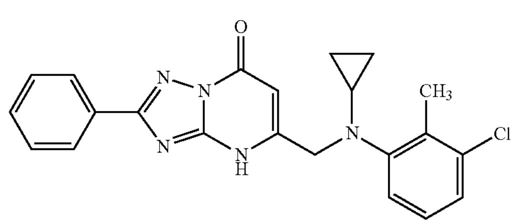 [SMILES: Cc1c(Cl)cccc1N(Cc1cc(=O)n2nc(-c3ccccc3)nc2[nH]1)C1CC1] | 405.14 | 406.32 | 5.58 |
| 17-3 | 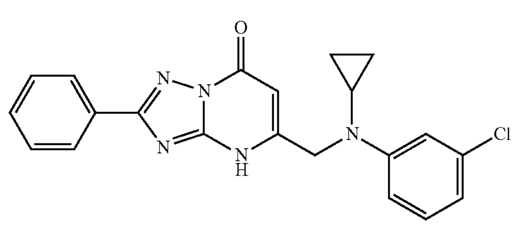 [SMILES: O=c1cc(CN(c2cccc(Cl)c2)C2CC2)[nH]c2nc(-c3ccccc3)nn12] | 391.12 | 392.32 | 5.01 |

Example 18

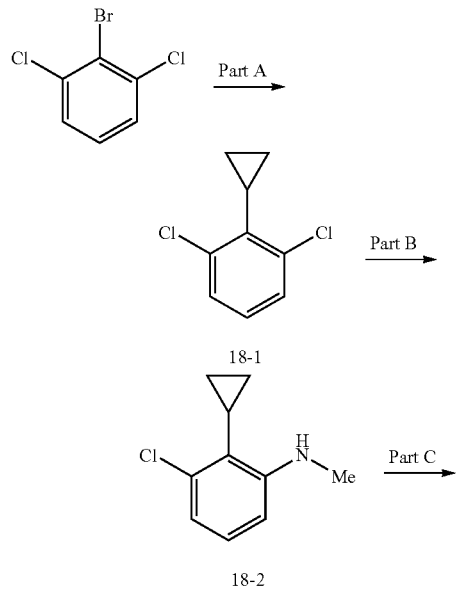

Part A:

A reaction mixture of 2-bromo-1,3-dichlorobenzene (1.13 g, 5 mmol), cyclopropyl boronic acid (0.86 g, 10 mmol), tetrakis(triphenylphosphine)palladium (0.35 g, 0.3 mmol) and tripotassium phosphate (2.12 g, 10 mmol) in dioxane (6 mL) was stirred at 110° C. for overnight. The reaction mixture was filtered. The filtrate was concentrated. The residue was purified by chromatography. Elution with 10% DCM in hexane gave compound 18-1 as a light yellow oil (0.85 g, 91% yield). $^1$H NMR (400 MHz, CDCl$_3$) δ 7.26 (d, J=8.4 Hz, 2H), 7.07 (dt, J=0.8, 8.8 Hz, 1H), 1.82-1.72 (m, 1H), 1.18-1.11 (m, 2H), 0.81-0.74 (m, 2H).

Part B:

A reaction mixture of compound 18-1 (187 mg, 1 mmol), methylamine hydrochloride (68 mg, 1 mmol), tris(dibenzylideneacetone)dipalladium (18.3 mg, 0.02 mmol), X-Phos (38 mg, 0.08 mmol) and cesium carbonate (652 mg, 2 mmol) in THF (3 mL) was stirred at 70° C. for overnight. The reaction mixture was filtered. The filtrate was concentrated. The residue was purified by chromatography. Elution with 10% EtOAc in hexane gave compound 18-2 (1 mg, 0.6% yield). $^1$H NMR (400 MHz, CDCl$_3$) δ 7.06 (t, J=8.0 Hz, 1H), 6.72 (d, J=7.2 Hz, 1H), 6.52 (d, J=8.0 Hz, 1H), 2.91 (s, 3H), 1.54-1.44 (m, 1H), 1.13-1.04 (m, 2H), 0.69-0.61 (m, 2H).

Part C:

A reaction mixture of compound 18-2 (1 mg, 5.5 µmol), 5-(chloromethyl)-2-phenyl-[1,2,4]triazolo[1,5-a]pyrimidin-7(4H)-one (2.9 mg, 11 µmol) and DIEA (1.9 µL, 11 µmol) in DMA (0.2 mL) was stirred at 220° C. for 20 minutes in microwave. Purification using reverse phase HPLC gave compound 18-3 after lyophilization.

| ID | Structure | MW | MS m/z (M⁺ + H) | Retention Time (min) |
|---|---|---|---|---|
| 18-3 | 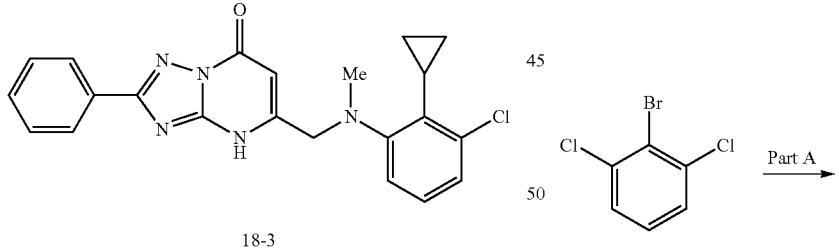 | 405.14 | 406.29 | 5.35 |

Example 19

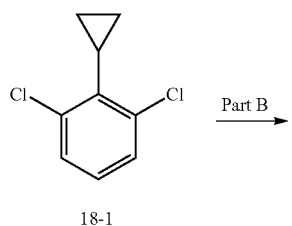

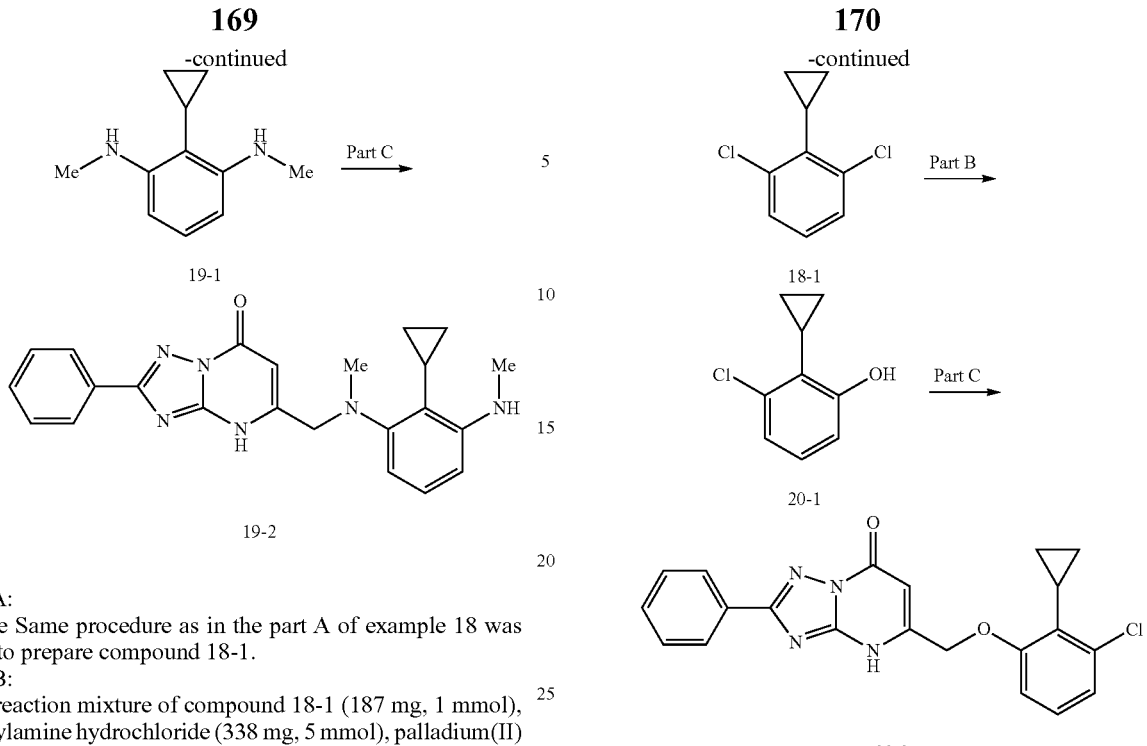

Part A:
The Same procedure as in the part A of example 18 was used to prepare compound 18-1.

Part B:
A reaction mixture of compound 18-1 (187 mg, 1 mmol), methylamine hydrochloride (338 mg, 5 mmol), palladium(II) acetate (11.2 mg, 0.05 mmol), X-Phos (38 mg, 0.08 mmol) and sodium tert-butoxide (480 mg, 5 mmol) in THF (3 mL) was stirred at 65° C. for overnight. The reaction mixture was filtered through celite. The filtrate was concentrated. The residue was purified by chromatography. Elution with 10% EtOAc in hexane gave compound 19-1 (70 mg, 40% yield). $^1$H NMR (400 MHz, CDCl$_3$) δ 7.11 (t, J=8.4 Hz, 1H), 6.11 (d, J=8.4 Hz, 2H), 4.39 (br s, 2H), 2.89 (s, 6H), 1.32-1.22 (m, 1H), 1.06-1.00 (m, 2H), 0.57-0.51 (m, 2H).

Part C:
A reaction mixture of compound 19-1 (17.6 mg, 0.1 mmol), 5-(chloromethyl)-2-phenyl-[1,2,4]triazolo[1,5-a]pyrimidin-7(4H)-one (13 mg, 0.05 mmol) and DIEA (17 µL, 0.1 mmol) in DMA (0.2 mL) was stirred at 220° C. for 20 minutes in microwave. Purification using reverse phase HPLC gave compound 19-2 after lyophilization.

Part A:
The Same procedure as in the part A of example 18 was used to prepare compound 18-1.

Part B:
A reaction mixture of compound 18-1 (187 mg, 1 mmol), potassium hydroxide (62 mg, 1.1 mmol), tris(dibenzylideneacetone)dipalladium (28 mg, 0.03 mmol) and tert-butyl X-Phos (43 mg, 0.1 mmol) in dioxane/water (1:1, 1 mL) was stirred at 100° C. for 2 hours. The reaction mixture was mixed with aqueous ammonium chloride solution. The organic components were extracted with EtOAc. The combined EtOAc layers were washed with brine, and then concentrated. The residue was purified by chromatography. Elution with 10%

| ID | Structure | MW | MS m/z (M⁺ + H) | Retention Time (min) |
|---|---|---|---|---|
| 19-2 | 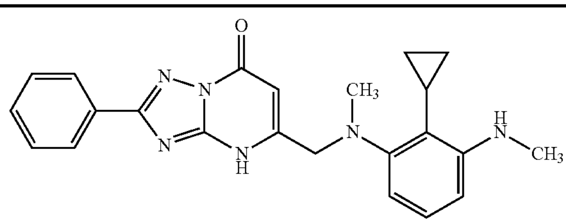 | 400.2 | 401.37 | 3.57 |

Example 20

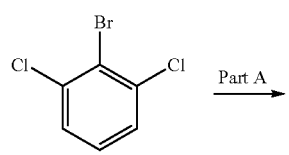

EtOAc in hexane gave compound 20-1 (120 mg, 71% yield) as yellow oil. $^1$H NMR (400 MHz, CDCl$_3$) δ 7.07 (dt, J=0.8, 8.4 Hz, 1H), 6.92 (dd, J=0.8, 8.4 Hz, 1H), 6.79 (dd, J=1.2, 8.4 Hz, 1H), 5.96 (br s, 1H), 1.68-1.60 (m, 1H), 1.19-1.13 (m, 2H), 0.75-0.70 (m, 2H).

Part C:
A reaction mixture of compound 20-1 (17 mg, 0.1 mmol) and sodium hydride (60% in oil, 6 mg, 0.15 mmol) in DMA (0.4 mL) was stirred at room temperature for 15 minutes. To the resultant clear solution was added compound 1-1 (26 mg, 0.1 mmol). The reaction mixture was stirred in microwave at 210° C. for 30 minutes. Purification using reverse phase HPLC gave compound 20-2 after lyophilization, or chromatography on silica gel with 10% Methanol in DCM.

| ID | Structure | MW | MS m/z (M⁺ + H) | Retention Time (min) |
|---|---|---|---|---|
| 20-2 | 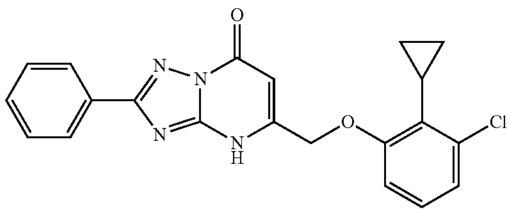 [SMILES: O=c1cc(COc2cccc(Cl)c2C2CC2)[nH]c2nc(-c3ccccc3)nn12] | 392.1 | 393.28 | 5.17 |

Part A:
A solution of sec-butyllithium in cyclohexane (1.4 M, 4.3 mL, 6 mmol) in THF (10 mL) was cooled to −75° C. in a dry ice/methanol bath. 1,3-Dichlorobenzene (685 μL, 6 mmol) was added. The reaction mixture was stirred at −75° C. for 45 minutes. Diethyl sulfate (945 μL, 7.2 mmol) was added. The reaction mixture was allowed to warm up to room temperature, and stirred for overnight. The mixture was quenched with aqueous ammonium chloride solution. The organic components were extracted with EtOAc. The combined EtOAc layers were washed with brine, and then concentrated. The residue was purified by chromatography. Elution with 10% EtOAc in hexane gave compound 21-1 (715 mg, 68% yield) as clear oil. ¹H NMR (400 MHz, CDCl₃) δ 7.26 (d, J=8.0 Hz, 2H), 7.04 (d, J=8.0 Hz, 1H), 2.95 (q, J=7.6 Hz, 2H), 1.18 (t, J=7.6 Hz, 3H).

Part B:
A reaction mixture of compound 21-1 (175 mg, 1 mmol), potassium hydroxide (62 mg, 1.1 mmol), tris(dibenzylideneacetone)dipalladium (28 mg, 0.03 mmol) and tert-butyl X-Phos (43 mg, 0.1 mmol) in dioxane/water (1:1, 1 mL) was stirred at 100° C. for 2 hours. The reaction mixture was mixed with aqueous ammonium chloride solution. The organic components were extracted with EtOAc. The combined EtOAc layers were washed with brine, and then concentrated. The residue was purified by chromatography. Elution with 10% EtOAc in hexane gave compound 21-2 (102 mg, 65% yield) as clear oil. ¹H NMR (400 MHz, CDCl₃) δ 7.02-6.92 (m, 2H), 6.67 (dd, J=2.0, 7.6 Hz, 1H), 4.78 (br s, 1H), 2.80 (q, J=7.2 Hz, 2H), 1.17 (t, J=7.2 Hz, 3H).

Part C:
A reaction mixture of compound 21-2 (24 mg, 0.15 mmol) and sodium hydride (60% in oil, 6 mg, 0.15 mmol) in DMA (0.4 mL) was stirred at room temperature for 15 minutes. To the resultant clear solution was added 5-(chloromethyl)-2-phenyl-[1,2,4]triazolo[1,5-a]pyrimidin-7(4H)-one (26 mg, 0.1 mmol). The reaction mixture was stirred in microwave at 210° C. for 30 minutes. Purification using reverse phase HPLC gave compound 21-3 after lyophilization.

Example 21

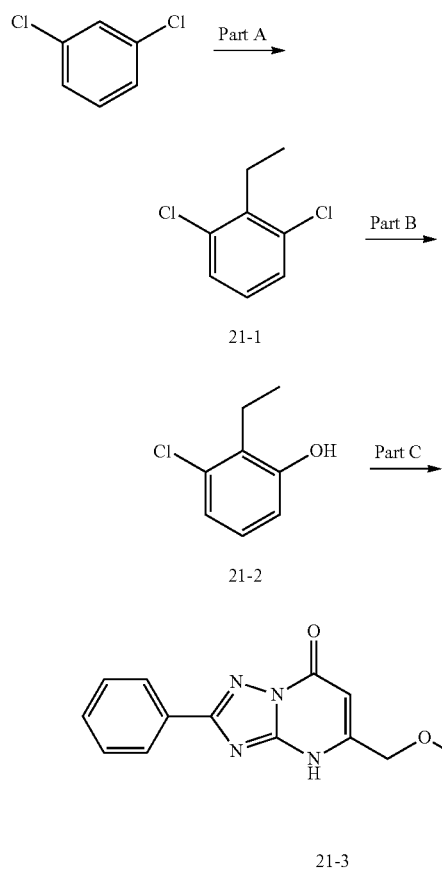

| ID | Structure | MW | MS m/z (M⁺ + H) | Retention Time (min) |
|---|---|---|---|---|
| 21-3 | 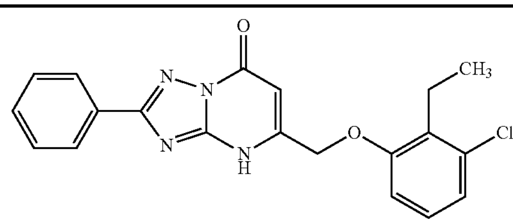 | 380.1 | 381.28 | 5.18 |

Example 22

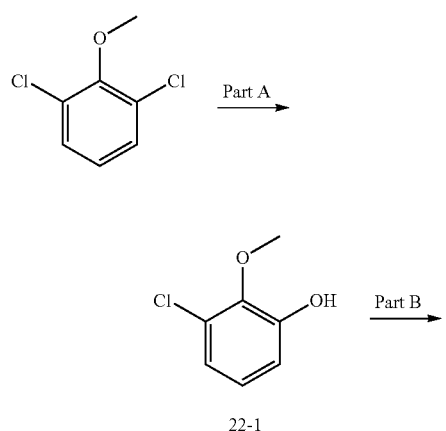

22-1

1-55

Part A:
A reaction mixture of 1,3-dichloro-2-methoxybenzene (885 mg, 5 mmol), potassium hydroxide (280 mg, 5 mmol), tris(dibenzylideneacetone)dipalladium (115 mg, 0.125 mmol) and tert-butyl X-Phos (159 mg, 0.375 mmol) in dioxane/water (1:1, 5 mL) was stirred at 100° C. for 2 hours. The reaction mixture was mixed with aqueous hydrochloride solution (1 N). The organic components were extracted with EtOAc. The combined EtOAc layers were washed with brine, and then concentrated. The residue was purified by chromatography. Elution with 10% EtOAc in hexane gave 3-chloro-2-methoxyphenol (22-1, 489 mg, 62% yield) as yellow oil. $^1$H NMR (400 MHz, CDCl$_3$) δ 6.98-6.84 (m, 3H), 5.73 (br s, 1H), 3.93 (s, 3H).

Part B:
The Same procedure as in the part C of example 21 was used to prepare compound 1-55.
The following compound may be synthesized using this procedure:

Example 23

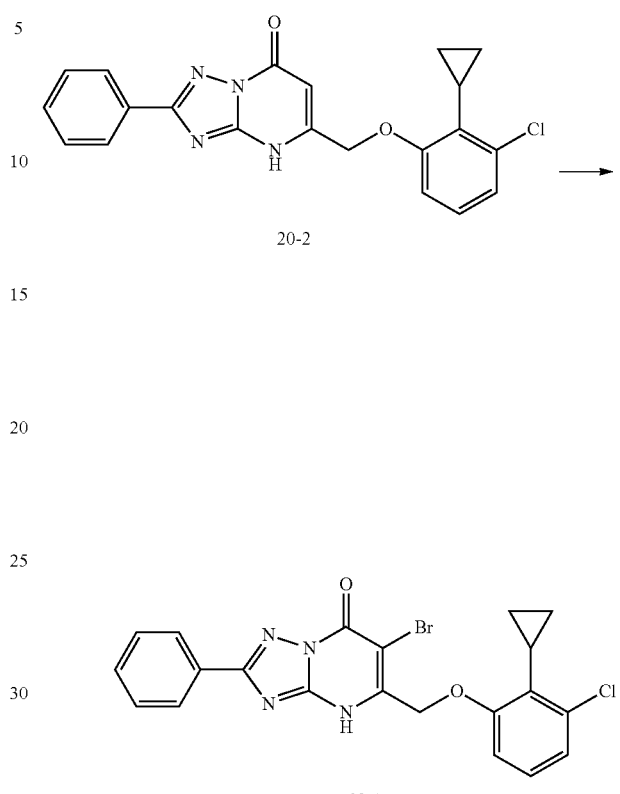

20-2

23-1

A reaction mixture of compound 20-2 (19.6 mg, 0.05 mmol) and N-bromosuccinimide (8.9 mg, 0.05 mmol) in acetic acid (0.5 mL) was stirred at room temperature for 30 minutes. The reaction mixture was concentrated. Purification using reverse phase HPLC gave compound 23-1 as an HCl salt after lyophilization.

| ID | Structure | EMW | MS m/z (M$^+$ + H) | Retention Time (min) |
|---|---|---|---|---|
| 22-2 | 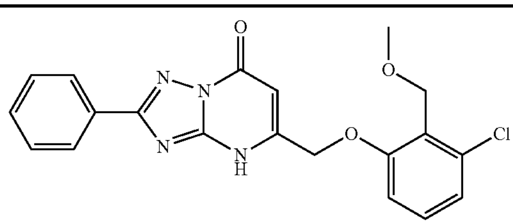 | 396.10 | 397.57 | 4.30 |

| ID | Structure | MW | MS m/z (M⁺ + H) | Retention Time (min) |
|---|---|---|---|---|
| 23-1 | 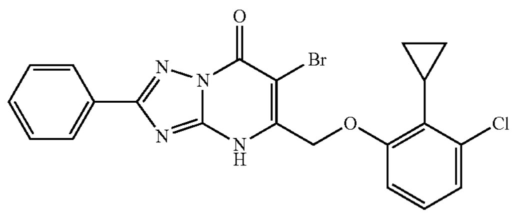 [SMILES: O=c1c(Br)c(COc2cccc(Cl)c2C2CC2)[nH]c2nc(-c3ccccc3)nn12] | 470.01 | 471.06 | 5.57 |

Example 24

Method A

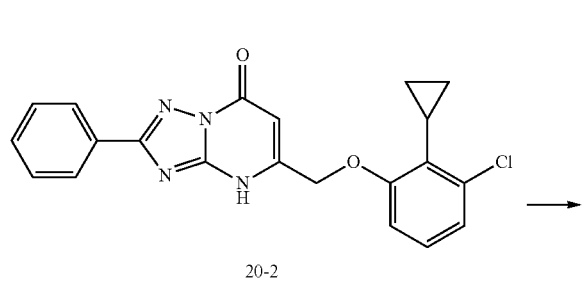

20-2

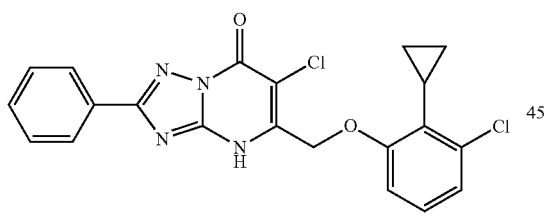

24-1

Method B

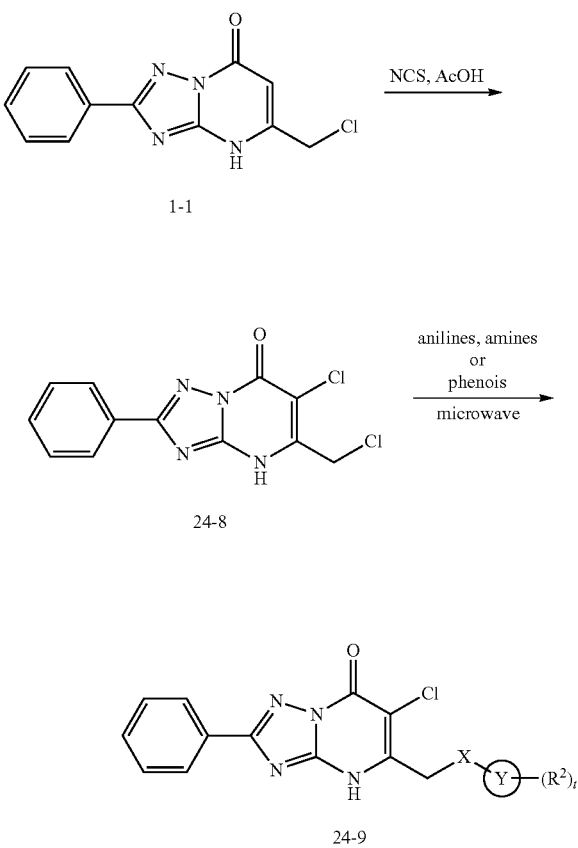

A reaction mixture of compound 20-2 (19.6 mg, 0.05 mmol) and N-chlorosuccinimide (6.7 mg, 0.05 mmol) in acetic acid (0.5 mL) was stirred at room temperature overnight. The reaction mixture was concentrated. Purification using reverse phase HPLC gave compound 24-1 as an HCl salt after lyophilization.

Alternatively, analogs 24-9 can be synthesized through compound 24-8 by the following procedure. To a round bottom flask was added compound 1-1 (500 mg, 1.91 mmol) and acetic acid (10 mL). The resulting mixture was stirred at room temperature for 48 h until SM had disappeared. The product was dried and the crude material was purified by chromatography on silica gel 10% EtOAc/Hex, RF=0.2 to afford compound 24-8 400 mg, yield 71%.

| ID | Structure | MW | MS m/z (M+ + H) | Retention Time (min) |
|---|---|---|---|---|
| 24-1 | 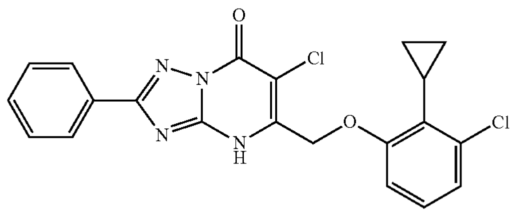 [SMILES: O=c1c(Cl)c(COc2cccc(Cl)c2C2CC2)[nH]c2nc(-c3ccccc3)nn12] | 426.07 | 427.16 | 5.51 |
| 24-2 | 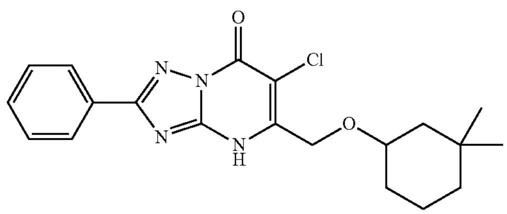 [SMILES: CC1(C)CCCC(OCc2[nH]c3nc(-c4ccccc4)nn3c(=O)c2Cl)C1] | 386.15 | 387.15 | 5.44 |
| 24-3 | 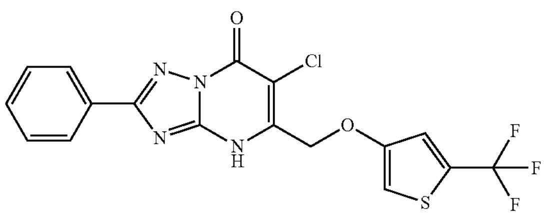 [SMILES: O=c1c(Cl)c(COc2csc(C(F)(F)F)c2)[nH]c2nc(-c3ccccc3)nn12] | 426.02 | 427.02 | 4.83 |
| 24-4 | 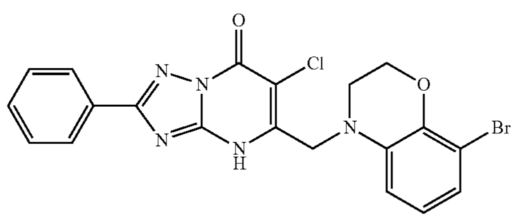 [SMILES: O=c1c(Cl)c(CN2CCOc3c(Br)cccc32)[nH]c2nc(-c3ccccc3)nn12] | 471.01 | 472.01 | 5.47 |
| 24-5 | 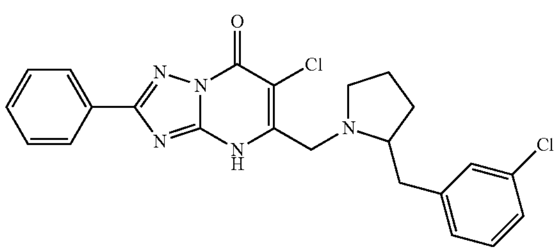 [SMILES: O=c1c(Cl)c(CN2CCCC2Cc2cccc(Cl)c2)[nH]c2nc(-c3ccccc3)nn12] | 453.11 | 454.11 | 5.31 |
| 24-6 | 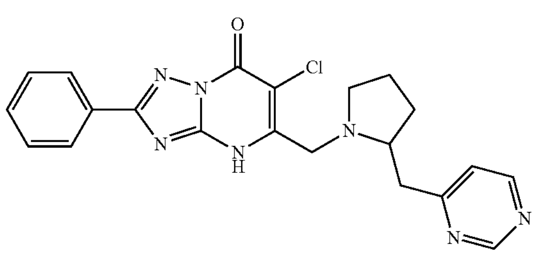 [SMILES: O=c1c(Cl)c(CN2CCCC2Cc2ccncn2)[nH]c2nc(-c3ccccc3)nn12] | 421.14 | 422.14 | 2.2 |
| 24-7 | 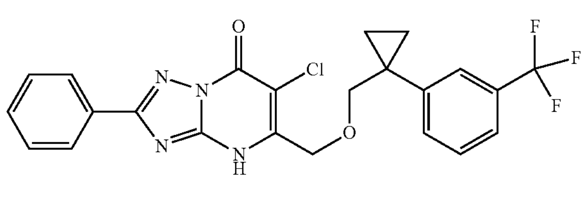 [SMILES: O=c1c(Cl)c(COCC2(c3cccc(C(F)(F)F)c3)CC2)[nH]c2nc(-c3ccccc3)nn12] | 474.11 | 475.11 | 4.64 |

-continued

| ID | Structure | MW | MS m/z (M+ + H) | Retention Time (min) |
|---|---|---|---|---|
| 24-8 | 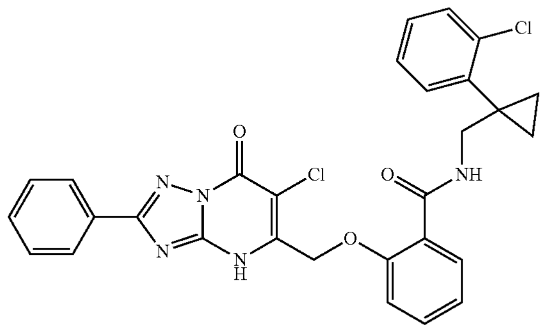 [SMILES: O=C(NCC1(c2ccccc2Cl)CC1)c1ccccc1OCc1[nH]c2nc(-c3ccccc3)nn2c(=O)c1Cl] | 559.1181 | 561.43 | 3.87 |
| 24-9 | 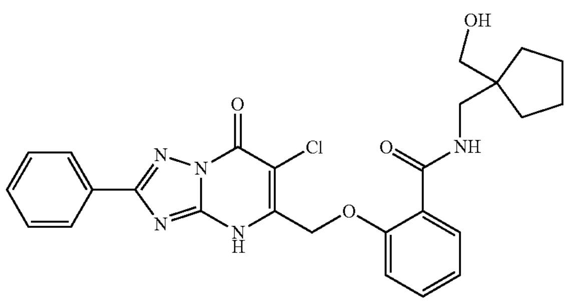 [SMILES: O=C(NCC1(CO)CCCC1)c1ccccc1OCc1[nH]c2nc(-c3ccccc3)nn2c(=O)c1Cl] | 507.1676 | 508.97 | 4.05 |
| 24-10 | 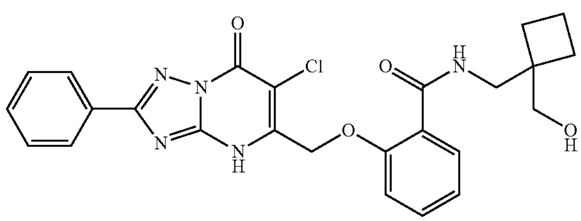 [SMILES: O=C(NCC1(CO)CCC1)c1ccccc1OCc1[nH]c2nc(-c3ccccc3)nn2c(=O)c1Cl] | 493.1519 | 494.94 | 3.87 |
| 24-11 | 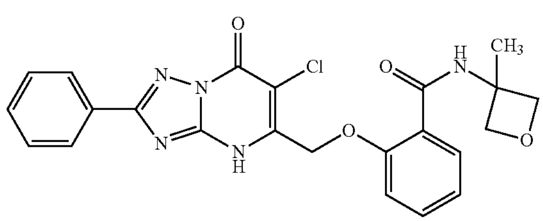 [SMILES: CC1(NC(=O)c2ccccc2OCc2[nH]c3nc(-c4ccccc4)nn3c(=O)c2Cl)COC1] | 465.1206 | 466.89 | 3.62 |
| 24-12 | 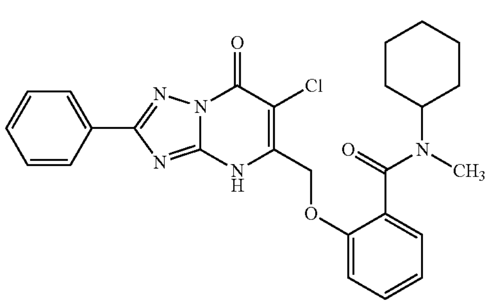 [SMILES: CN(C(=O)c1ccccc1OCc1[nH]c2nc(-c3ccccc3)nn2c(=O)c1Cl)C1CCCCC1] | 491.1727 | 492.97 | 4.79 |

| ID | Structure | MW | MS m/z (M⁺ + H) | Retention Time (min) |
|---|---|---|---|---|
| 24-13 | 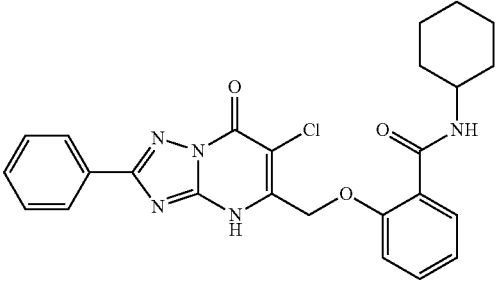 [SMILES: O=C(NC1CCCCC1)c1ccccc1OCc1[nH]c2nc(-c3ccccc3)nn2c(=O)c1Cl] | 477.157 | 478.94 | 4.47 |
| 24-14 | 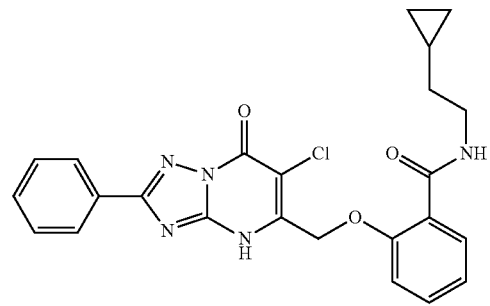 | 463.1414 | 464.92 | 4.51 |
| 24-15 | 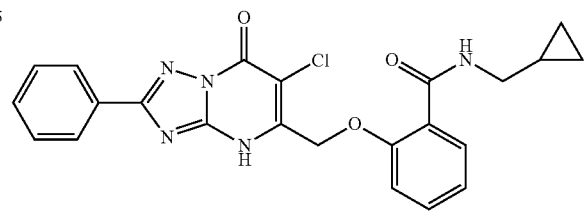 | 449.1257 | 450.89 | 3.99 |
| 24-16 | 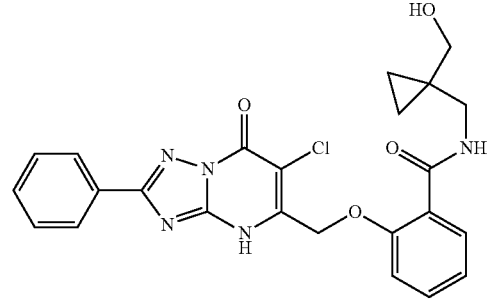 [SMILES: O=C(NCC1(CO)CC1)c1ccccc1OCc1[nH]c2nc(-c3ccccc3)nn2c(=O)c1Cl] | 479.1363 | 480.92 | 4.29 |
| 24-17 | 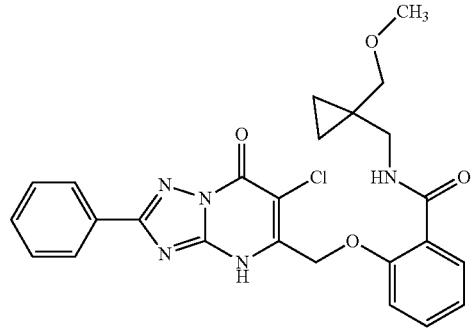 [SMILES: COCC1(CNC(=O)c2ccccc2OCc2[nH]c3nc(-c4ccccc4)nn3c(=O)c2Cl)CC1] | 493.1519 | 494.94 | 4.08 |

| ID | Structure | MW | MS m/z (M+ + H) | Retention Time (min) |
|---|---|---|---|---|
| 24-18 | 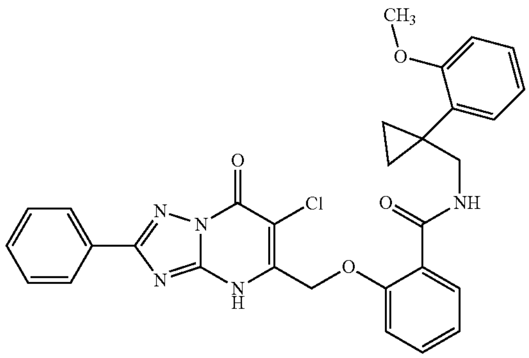 [SMILES: COc1ccccc1C1(CNC(=O)c2ccccc2OCc2[nH]c3nc(-c4ccccc4)nn3c(=O)c2Cl)CC1] | 555.1676 | 557.01 | 4.5 |

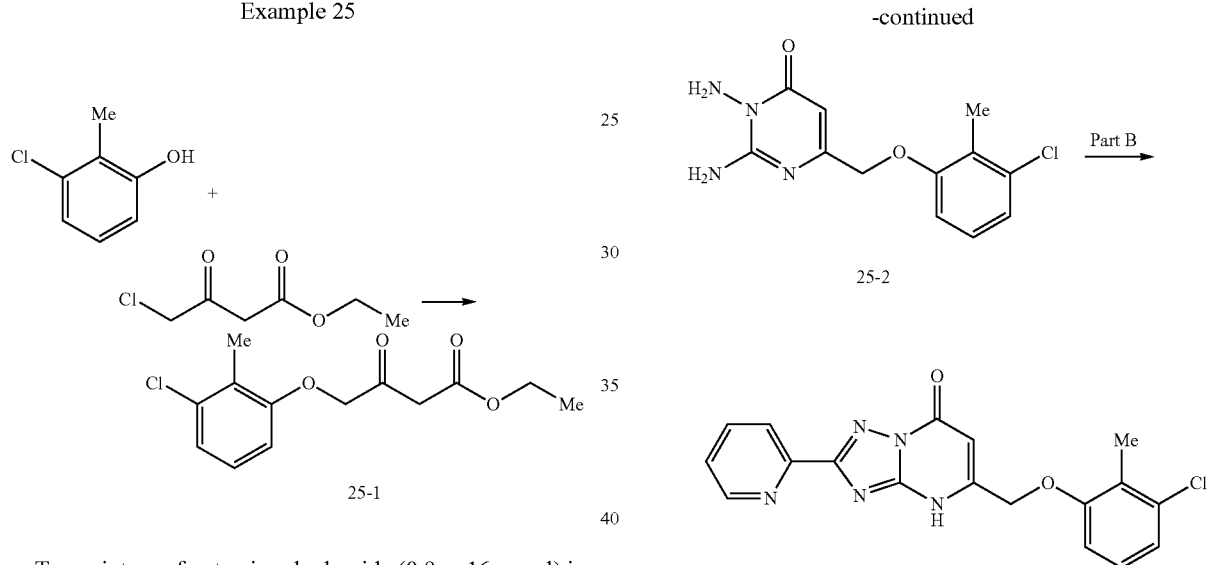

Example 25

To a mixture of potassium hydroxide (0.9 g, 16 mmol) in DMSO (16 mL) was added 3-chloro-2-methylphenol (1.14 g, 8 mmol). The reaction mixture was stirred at room temperature for 30 minutes. Ethyl 4-chloro-3-oxobutanoate (1.09 mL, 8 mmol) was added. The reaction mixture was stirred at room temperature for overnight. The reaction mixture was acidified with HCl aqueous solution (1 N). The organics were extracted with ethyl acetate. Chromatography on silica gel using 10% EtOAc in Hexane as the eluent gave the desired product (25-1) as a clear oil (1.57 g, 73% yield).

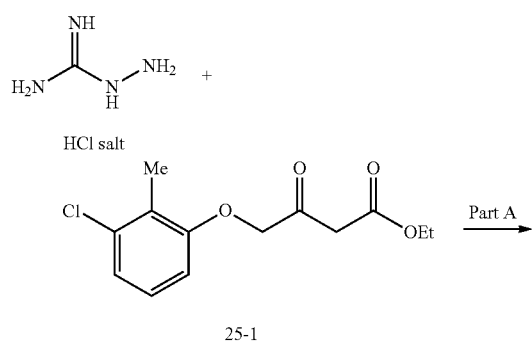

Part A:

A reaction mixture of aminoguanidine hydrochloride (55 mg, 0.5 mmol), ethyl 4-(3-chloro-2-methylphenoxy)-3-oxobutanoate (25-1, 135 mg, 0.5 mmol) and DIEA (174 μL, 1 mmol) in DMA (1.5 mL) was stirred at 180° C. for 20 minutes in microwave. The resultant solution of compound 25-2 in DMA was used for the next step without further purification. HPLC-MS RT=1.30 min, mass calculated for formula $C_{15}H_{20}O_4$ 280.07, observed LCMS m/z 281.20 (M+H).

Part B:

To the solution of compound 25-2 in DMA (28 mg, 0.1 mmol, 0.3 mL) obtained from last step was added picolinoyl chloride hydrochloride (35.6 mg, 0.2 mmol). The reaction mixture was stirred at 220° C. for 30 minutes in microwave. Purification using reverse phase HPLC gave compound 25-3.

The following compounds may be synthesized using this procedure:

| ID | Structure | MW | MS m/z (M⁺ + H) | Retention Time (min) |
|---|---|---|---|---|
| 25-3 | 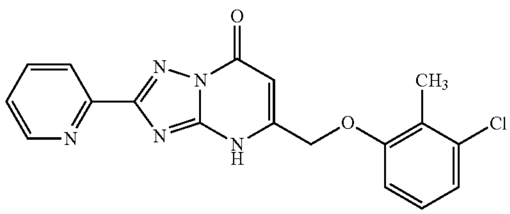 | 367.08 | 368.22 | 3.98 |
| 25-4 | 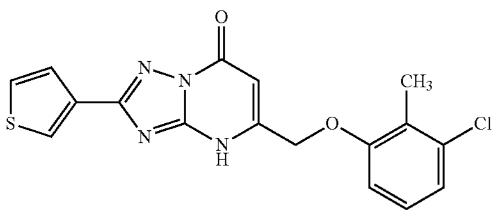 [SMILES: Cc1c(Cl)cccc1OCc1cc(=O)n2nc(-c3ccsc3)nc2[nH]1] | 372.05 | 373.18 | 4.68 |
| 25-5 | 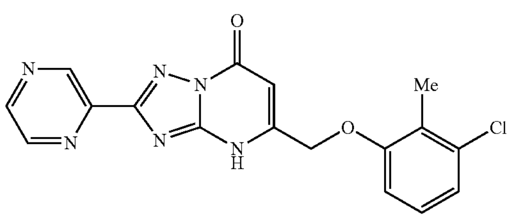 [SMILES: Cc1c(Cl)cccc1OCc1cc(=O)n2nc(-c3cnccn3)nc2[nH]1] | 368.08 | 369.20 | 3.89 |
| 25-6 | 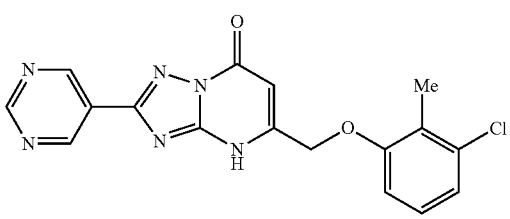 [SMILES: Cc1c(Cl)cccc1OCc1cc(=O)n2nc(-c3cncnc3)nc2[nH]1] | 368.08 | 369.59 | 3.83 |
| 25-7 | 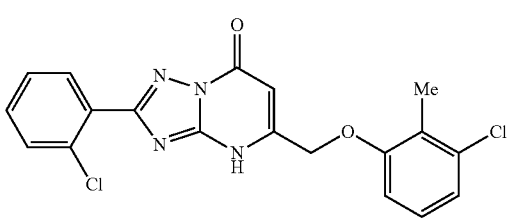 [SMILES: Cc1c(Cl)cccc1OCc1cc(=O)n2nc(-c3ccccc3Cl)nc2[nH]1] | 400.05 | 401.14 | 4.91 |
| 25-8 | 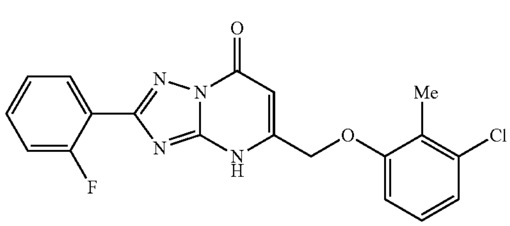 [SMILES: Cc1c(Cl)cccc1OCc1cc(=O)n2nc(-c3ccccc3F)nc2[nH]1] | 384.08 | 385.12 | 4.84 |

Example 26

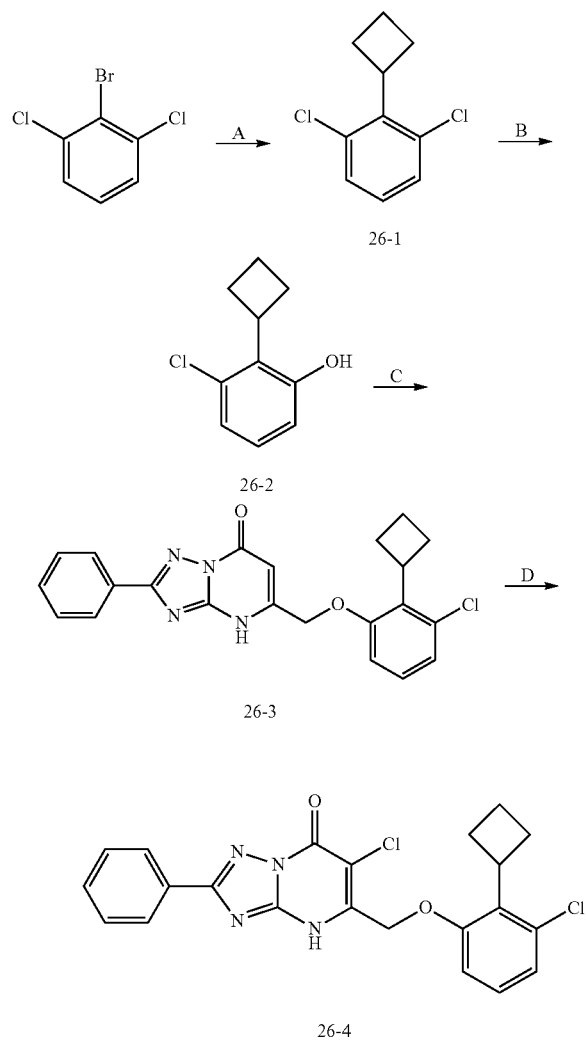

Step A:

A reaction mixture of 2-bromo-1,3-dichlorobenzene (452 mg, 2 mmol), palladium acetate (22.4 mg, 0.1 mmol), S-Phos (61.5 mg, 0.15 mmol) and cyclobutylzinc bromide in THF solution (0.5 M, 4 mL) was stirred at 65° C. under an atmosphere of argon for overnight. The reaction mixture was diluted with EtOAc, and concentrated. The residue was purified by chromatography. Elution with 10% DCM in hexane gave compound 26-1 as clear oil (0.31 g, 77% yield). $^1$H NMR (400 MHz, CDCl$_3$) δ 7.24 (d, J=8.0 Hz, 2H), 7.01 (t, J=8.0 Hz, 1H), 4.25 (quintet, J=9.5 Hz, 1H), 2.86-2.74 (m, 2H), 2.42-2.30 (m, 2H), 2.05-1.90 (m, 2H).

Step B:

A reaction mixture of compound 26-1 (300 mg, 1.5 mmol), potassium hydroxide (92.4 mg, 1.65 mmol), tris(dibenzylideneacetone)dipalladium (34.3 mg, 0.0375 mmol) and tert-butyl X-Phos (51 mg, 0.12 mmol) in dioxane/water (1:1, 2 mL) was stirred at 100° C. under an atmosphere of argon for 3 hours. The reaction mixture was mixed with aqueous ammonium chloride solution. The organic components were extracted with EtOAc. The combined EtOAc layers were washed with brine, and then concentrated. The residue was purified by chromatography. Elution with 10% EtOAc in hexane gave compound 26-2 (120 mg, 44% yield) as colorless solid. $^1$H NMR (400 MHz, CDCl$_3$) δ 6.95 (t, J=8.0 Hz, 1H), 6.90 (dd, J=1.6, 8.0 Hz, 1H), 6.62 (dd, J=1.6, 8.0 Hz, 1H), 4.89 (br s, 1H), 4.05-3.94 (m, 1H), 2.72-2.60 (m, 2H), 2.42-2.32 (m, 2H), 2.07-1.95 (m, 1H), 1.95-1.85 (m, 1H).

Step C:

A reaction mixture of compound 1-1 (52 mg, 0.2 mmol), compound 26-2 (36.5 mg, 0.2 mmol) and K$_2$CO$_3$ (69 mg, 0.5 mmol) in DMA (0.5 mL) was stirred in microwave at 150° C. for 15 minutes. Purification using reverse phase HPLC gave compound 26-3 after lyophilization.

Step D:

A reaction mixture of compound 26-3 (101.8 mg, 0.25 mmol) and N-chlorosuccinimide (33.5 mg, 0.25 mmol) in DMF (1.5 mL) was stirred at room temperature for overnight. The reaction mixture was concentrated. The residue was dissolved in DMSO/ACN, and recrystallization gave compound 26-4.

The following compounds were synthesized using the procedure:

| ID | Structure | EMW | MS m/z (M$^+$ + H) | Retention Time (min) |
|---|---|---|---|---|
| 26-3 | 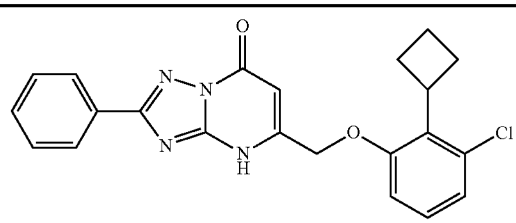 | 406.12 | 407.62 | 5.00 |
| 26-4 | 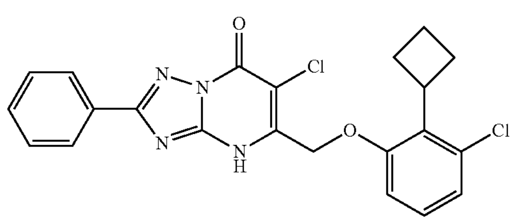 [SMILES: O=c1c(Cl)c(COc2cccc(Cl)c2C2CCC2)[nH]c2nc(-c3ccccc3)nn12] | 440.08 | 441.52 | 5.26 |

Example 28

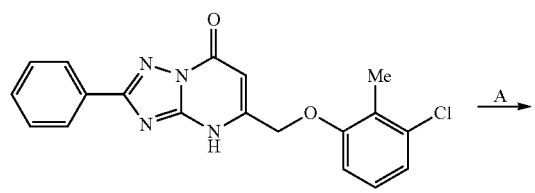

1-2

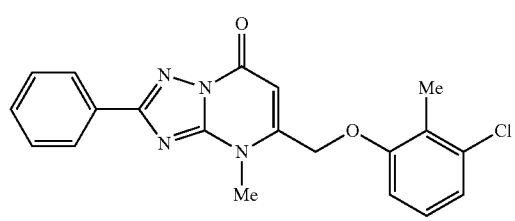 [SMILES: Cc1c(Cl)cccc1OCc1cc(=O)n2nc(-c3ccccc3)nc2n1C]

Step A:

A reaction mixture of compound 1-2 (18.3 mg, 0.05 mmol), $Cs_2CO_3$ and iodomethane (12.5 μL, 0.2 mmol) in DMA was stirred at room temperature. The product was purified using reverse phase HPLC.

The following compound was synthesized using the procedure:

| ID | Structure | EMW | MS m/z (M⁺ + H) | Retention Time (min) |
|---|---|---|---|---|
| 28-1 | (structure shown) | 380.10 | 381.10 | 5.21 |

-continued

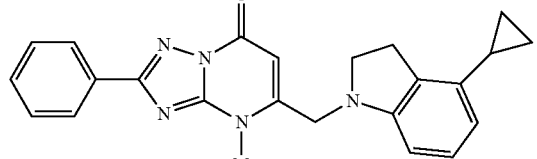

Step A:

A reaction mixture of 4-bromo-2,3-dihydro-1H-indole HCl salt (469 mg, 2 mmol), cyclopropylboronic acid (258 mg, 3 mmol), palladium acetate (22.4 mg, 0.1 mmol), S-Phos (65.6 mg, 0.16 mmol) and potassium phosphate (1.06 g, 5 mmol) in dioxane was stirred at 80° C. for overnight. The reaction mixture was filtered, and concentrated. Column chromatography using an eluent of 15% EtOAc in Hexane gave product 29-1.

Step B:

A reaction mixture of compound 29-1 (15.9 mg, 0.1 mmol), compound 1-1 (26 mg, 0.1 mmol) and sodium hydride (12 mg, 0.3 mmol, 60% dispersion in mineral oil) in DMA was stirred in microwave. The product was purified using reverse phase HPLC.

The following compound was synthesized using the procedure:

Example 29

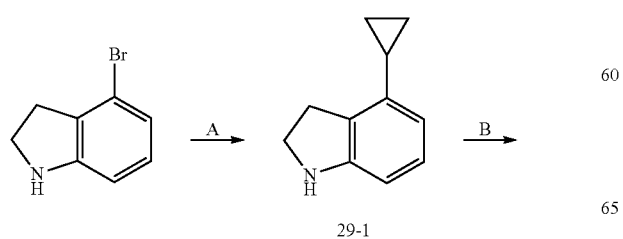

29-1

| ID | Structure | EMW | MS m/z (M⁺ + H) | Retention Time (min) |
|---|---|---|---|---|
| 29-1 | 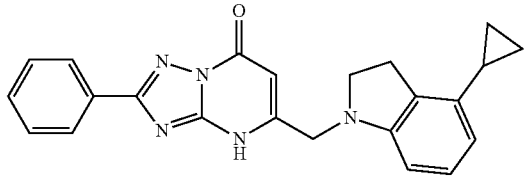 [SMILES: O=c1cc(CN2CCc3c(C4CC4)cccc32)[nH]c2nc(-c3ccccc3)nn12] | 383.17 | 384.65 | 4.63 |

Example 30

Example 31

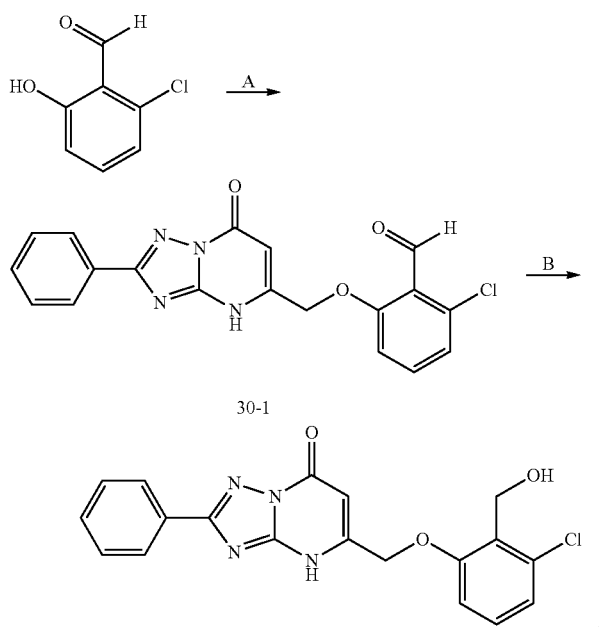

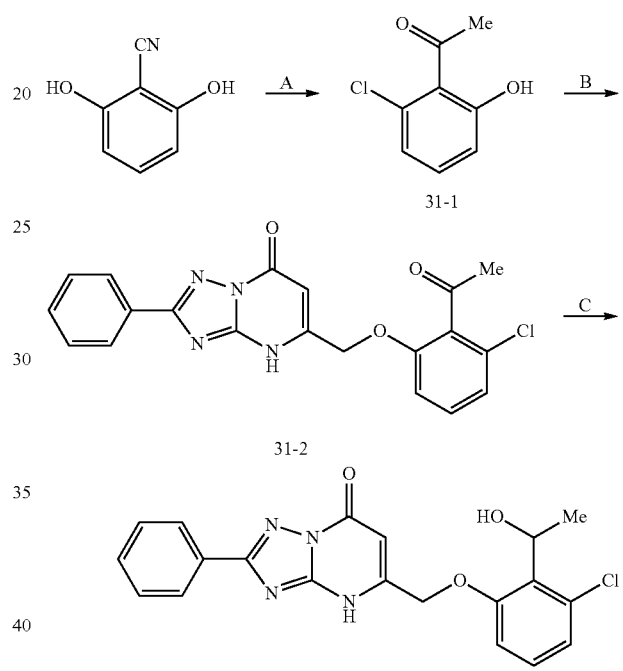

Step A:
A reaction mixture of 2-chloro-6-hydroxybenzaldehyde (31.3 mg, 0.2 mmol), compound 1-1 (26 mg, 0.1 mmol) and potassium carbonate (55 mg, 0.4 mmol) in DMA was stirred in microwave at 150° C. for 15 minutes. Compound 30-1 was purified using reverse phase HPLC.

Step B:
A reaction mixture of compound 30-1 and sodium borohydride in methanol was stirred at room temperature. The product was purified using reverse phase HPLC.

The following compound was synthesized using the procedure:

Step A:
To a solution of 2-chloro-6-hydroxybenzonitrile (614 mg, 4 mmol) in THF (10 mL) was added methylmagnesium bromide solution in toluene|THF (3/1, 1.4 M, 6.4 mL, 9 mmol). (Caution: Gas evolution!) The reaction mixture was stirred at room temperature under a flow of argon until gas evolution stopped. The reaction mixture was sealed in the tube, and heated to 65° C. for stirring overnight. The reaction mixture was quenched with water, and acidified with aqueous HCl solution. The organic mixture containing product was

| ID | Structure | EMW | MS m/z (M⁺ + H) | Retention Time (min) |
|---|---|---|---|---|
| 30-2 | 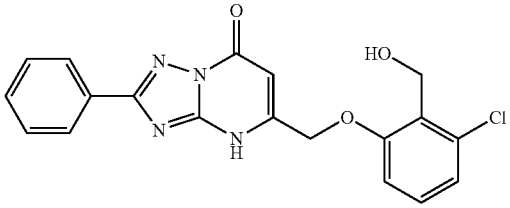 [SMILES: O=c1cc(COc2cccc(Cl)c2CO)[nH]c2nc(-c3ccccc3)nn12] | 382.08 | 383.55 | 3.61 | extracted with DCM. Column chromatography with an eluent of DCM/Hexane (1/1) gave product 31-1 (100 mg, 15% yield).

Step B:

A reaction mixture of compound 31-1 (17 mg, 0.1 mmol), compound 1-1 (26 mg, 0.1 mmol) and sodium hydride (12 mg, 0.3 mmol, 60% dispersion in mineral oil) in DMA was stirred in microwave. The product 31-2 was purified using reverse phase HPLC.

Step C:

A reaction mixture of compound 31-2 and sodium borohydride in methanol was stirred at room temperature. The product was purified using reverse phase HPLC.

The following compounds were synthesized using the procedure:

| ID | Structure | EMW | MS m/z (M⁺ + H) | Retention Time (min) |
|---|---|---|---|---|
| 31-2 | 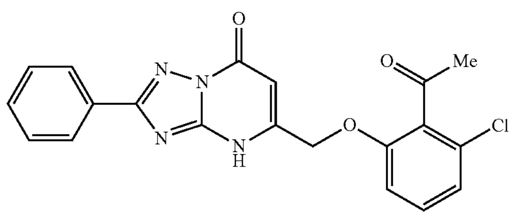 [SMILES: CC(=O)c1c(Cl)cccc1OCc1cc(=O)n2nc(-c3ccccc3)nc2[nH]1] | 394.08 | 395.53 | 3.55 |
| 31-3 | 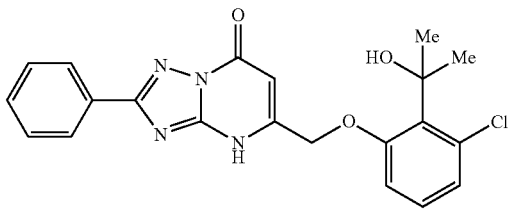 [SMILES: CC(C)(O)c1c(Cl)cccc1OCc1cc(=O)n2nc(-c3ccccc3)nc2[nH]1] | 396.10 | 397.56 | 3.58 |

Example 32

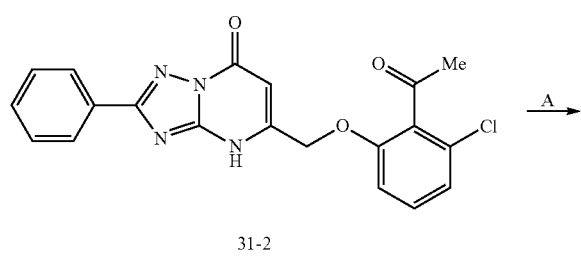

31-2

Step A:

To a solution of 2-chloro-6-hydroxybenzonitrile (614 mg, 4 mmol) in THF (10 mL) was added methylmagnesium bromide solution in toluene/THF (3/1, 1.4 M, 6.4 mL, 9 mmol). (Caution: Gas evolution!) The reaction mixture was stirred at room temperature under a flow of argon until gas evolution stopped. The reaction mixture was sealed in the tube, and heated to 65° C. for stirring overnight. The reaction mixture was quenched with water, and acidified with aqueous HCl solution. The organic mixture containing product was extracted with DCM. Column chromatography with an eluent of DCM/Hexane (1/1) gave product 31-1 (100 mg, 15% yield).

Step B:

A reaction mixture of compound 31-2 and methylmagnesium chloride solution in THF (3 M) was stirred at room temperature. The product was purified using reverse phase HPLC.

The following compound was synthesized using the procedure:

| ID | Structure | EMW | MS m/z (M⁺ + H) | Retention Time (min) |
|---|---|---|---|---|
| 32-1 | 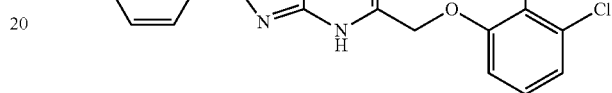 | 410.11 | 411.52 | 3.86 |

Example 33

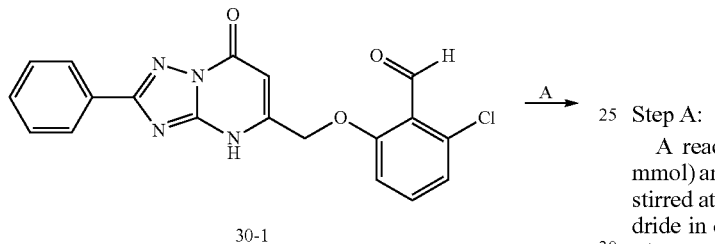

30-1

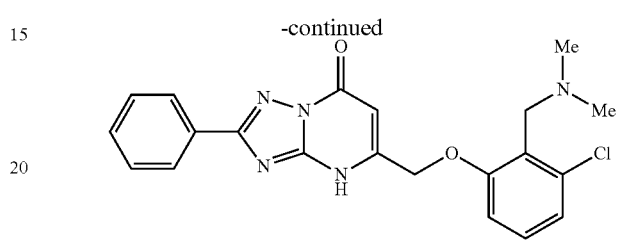

Step A:

A reaction mixture of compound 30-1 (4.5 mg, 0.0118 mmol) and dimethylamine in THF solution (2 M, 0.5 mL) was stirred at room temperature for 1 hour. Then sodium borohydride in excess was added, followed by methanol (0.2 mL). The reaction mixture was stirred at room temperature for 1 hour. The product was purified using reverse phase HPLC.

The following compounds were synthesized using the procedure:

| ID | Structure | EMW | MS m/z (M⁺ + H) | Retention Time (min) |
|---|---|---|---|---|
| 33-1 | 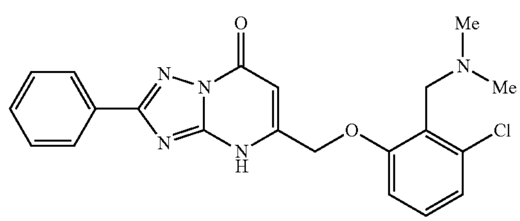 [SMILES: CN(C)Cc1c(Cl)cccc1OCc1cc(=O)n2nc(-c3ccccc3)nc2[nH]1] | 409.13 | 410.59 | 2.79 |
| 33-2 | 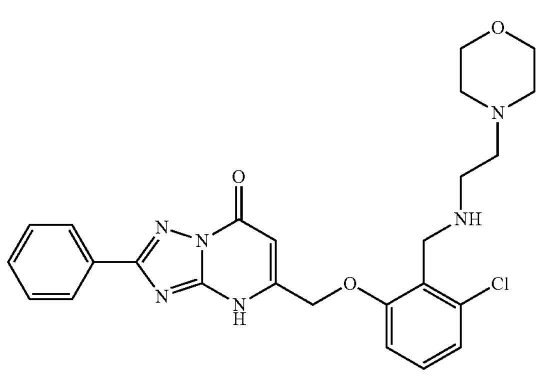 [SMILES: O=c1cc(COc2cccc(Cl)c2CNCCN2CCOCC2)[nH]c2nc(-c3ccccc3)nn12] | 494.18 | 495.64 | 2.46 |

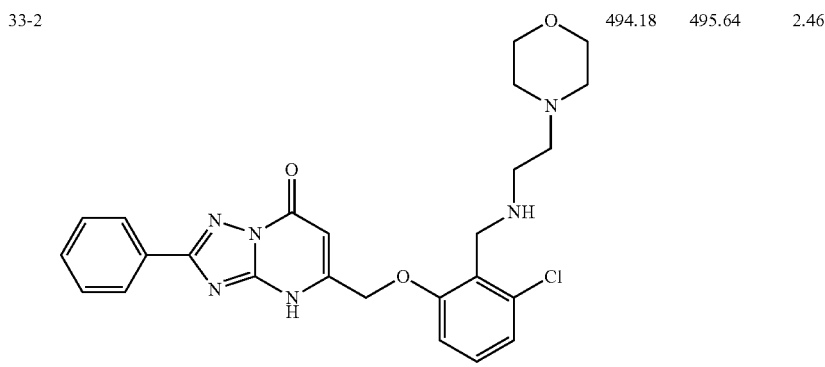

| ID | Structure | EMW | MS m/z (M⁺ + H) | Retention Time (min) |
|---|---|---|---|---|
| 33-3 | 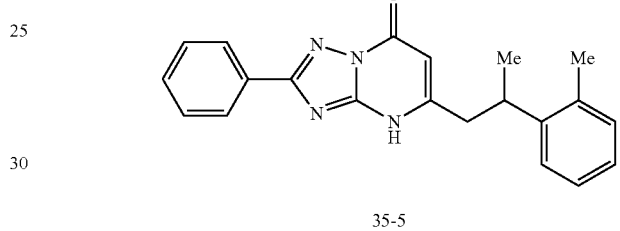 | 507.22 | 508.65 | 2.43 |

Example 35

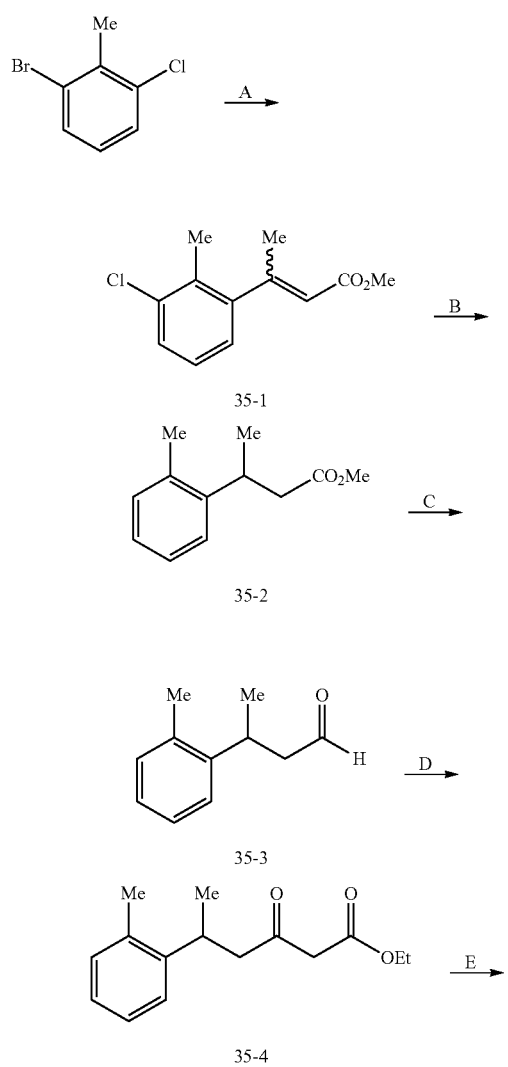

Step A:

A reaction mixture of 1-bromo-3-chloro-2-methylbenzene (1.03 g, 5 mmol), methyl but-2-enoate (583 μL, 5.5 mmol), Pd$_2$(DBA)$_3$ (137.4 mg, 0.15 mmol), tri-t-butylphosphonium tetrafluoroborate (87 mg, 0.3 mmol) and N,N-dicyclohexylmethylamine (1.27 mL, 6 mmol) in dioxane (5 mL) was stirred at room temperature under an atmosphere of argon for overnight. Some precipitates formed. The reaction mixture was filtered, and concentrated. Column chromatography with an eluent of 10% EtOAc in Hexane gave compound 35-1 as yellow oil.

Step B:

A reaction mixture of compound 35-1 and palladium on carbon (5%, 1 g) in methanol was stirred under an atmosphere of H$_2$ at room temperature for overnight. The mixture was filtered. The filtrate gave compound 35-2 (600 mg, 62% yield over step A and B) after concentration.

Step C:

To the solution of compound 35-2 (600 mg, 2.65 mmol) in DCM was added a solution of DIBALH (2.65 mL, 2.65 mmol, 1 M in hexanes) at −78° C. The reaction mixture was stirred at −78° C. for an hour. Then, the reaction mixture was quenched with EtOAc. An aqueous solution of potassium sodium tartrate was added to the mixture, and the resultant mixture was stirred vigorously for an hour. The organic layer was separated, and the aqueous layer was extracted with EtOAc. The combined organic extracts were concentrated under reduced pressure. The residue was purified by silica gel column chromatography to give compound 35-3.

Step D:

To a suspension of tin(II) chloride (19 mg, 0.1 mmol) in DCM (2 mL) was added ethyl diazoacetate (135 μL, 1.1 mmol). Then a solution of compound 35-3 (200 mg, 1 mmol)

in DCM (2 mL) was added dropwise under argon over 15 minutes. After gas evolution had stopped in 45 minutes or so, an additional amount of tin(II) chloride was added. The reaction mixture was stirred for overnight at room temperature, and filtered through celite. The filtrate was concentrated. The residue was purified by column chromatography (10% EtOAc in Hexane) to give compound 35-4 (200 mg, 81% yield).

Step E:

A reaction mixture of compound 35-4 (28.3 mg, 0.1 mmol) and 3-phenyl-1H-1,2,4-triazol-5-amine (16 mg, 0.1 mmol) in ethanol was stirred at 80° C. for overnight. The product was purified using reverse phase HPLC.

The following compound was synthesized using the procedure:

-continued

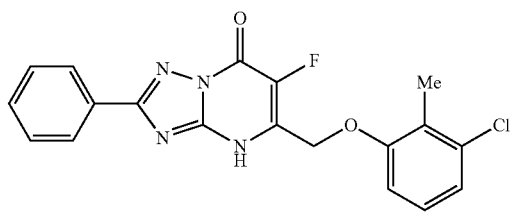

| ID | Structure | EMW | MS m/z (M$^+$ + H) | Retention Time (min) |
|---|---|---|---|---|
| 35-5 | 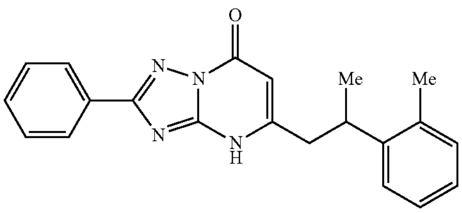 [SMILES: Cc1ccccc1C(C)Cc1cc(=O)n2nc(-c3ccccc3)nc2[nH]1] | 344.16 | 345.1 | 4.65 |

A reaction mixture of compound 1-2 (10 mg, 0.027 mmol), Selectfluor® (10 mg, 0.027 mmol) and lithium hydroxide monohydrate (1.1 mg, 0.027 mmol) in ACN was stirred in microwave at 180° C. for 30 minutes. The product was purified using reverse phase HPLC.

| ID | Structure | EMW | MS m/z (M$^+$ + H) | Retention Time (min) |
|---|---|---|---|---|
| 36-1 | 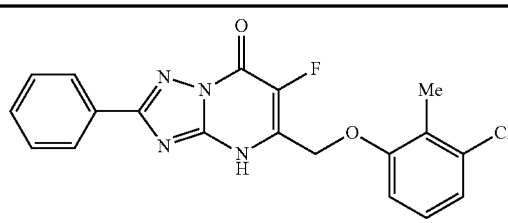 | 384.08 | 385.2 | 3.50 |

Example 36

Example 37

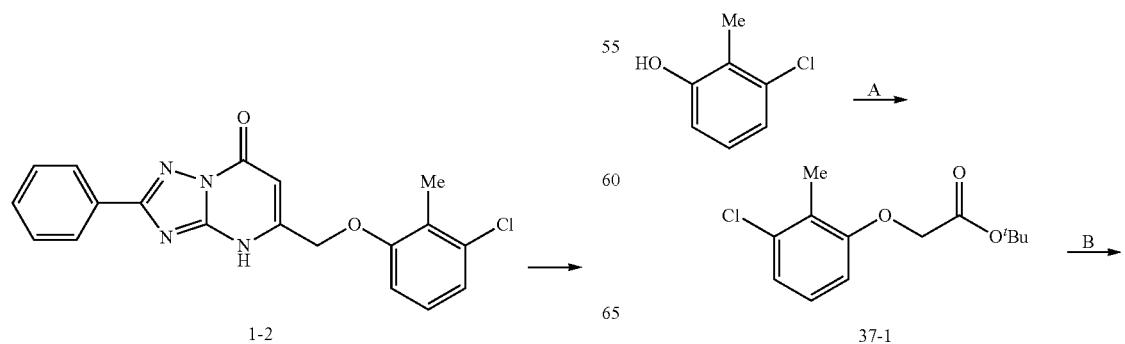

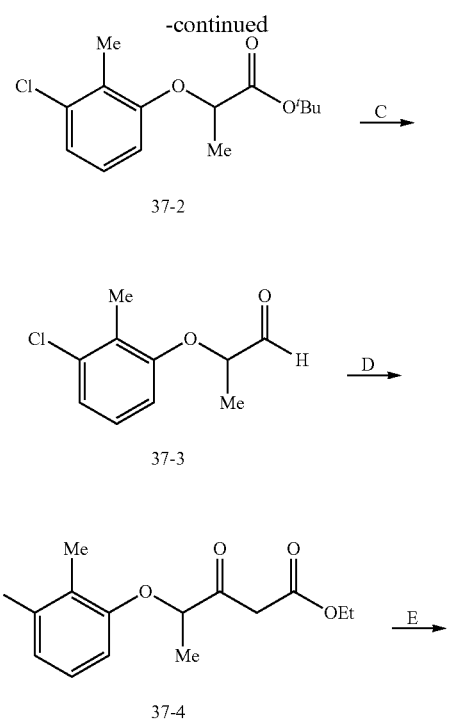

37-2

37-3

37-4

Step A:
A reaction mixture of 3-chloro-2-methylphenol (1.14 g, 8 mmol), tert-butyl 2-bromoacetate (1.5 mL, 10 mmol) and potassium hydroxide (448 mg, 8 mmol) in DMSO (10 mL) was stirred at room temperature for overnight. The mixture was quenched with aqueous HCl solution. The product was extracted using EtOAc. The organic layer was separated and concentrated. The residue was purified by silica gel column chromatography (10% EtOAc in Hexane) to give compound 37-1 (2 g, 97% yield) as clear oil.

Step B:
To a solution of LDA (2.5 mL, 4.5 mmol, 1.8 M) in THF (10 mL) at −40° C. was added a solution of compound 37-1 (770 mg, 3 mmol) in THF (10 mL) slowly. The mixture was warmed up to −15° C. and stirred at this temperature for 20 minutes. Methyl iodide (0.93 mL, 15 mmol) was added. The reaction mixture was allowed to warm up to room temperature and stirred for overnight. The mixture was quenched with aqueous ammonium chloride solution. The product was extracted using EtOAc. The combined EtOAc layers were concentrated. The residue was purified by silica gel column chromatography (10% EtOAc in Hexane) to give compound 37-2 (0.5 g, 62% yield).

Step C:
To the solution of compound 37-2 (0.5 g, 1.8 mmol) in DCM (30 mL) was added a solution of DIBALH (2 mL, 2 mmol, 1 M in hexanes) at −78° C. The reaction mixture was warmed to −60° C. and stirred at this temperature for an hour. Then, the reaction mixture was quenched with EtOAc. An aqueous solution of potassium sodium tartrate was added to the mixture, and the resultant mixture was stirred vigorously for an hour. The organic layer was separated, and the aqueous layer was extracted with EtOAc. The combined organic extracts were concentrated under reduced pressure. The residue was purified by silica gel column chromatography to give compound 37-3 (180 mg, 50% yield).

Step D:
To a suspension of tin(II) chloride (19 mg, 0.1 mmol) in DCM (2 mL) was added ethyl diazoacetate (135 μL, 1.1 mmol). Then a solution of compound 37-3 (180 mg, 0.9 mmol) in DCM (2 mL) was added dropwise under argon over 10 minutes. After gas evolution had stopped in 45 minutes or so, an additional amount of tin(II) chloride was added. The reaction mixture was stirred for overnight at room temperature, and filtered through celite. The filtrate was concentrated. The residue was purified by silica gel column chromatography (10% EtOAc in Hexane) to give compound 37-4 (200 mg, 78% yield).

Step E:
A reaction mixture of compound 37-4 (28.4 mg, 0.1 mmol) and 3-phenyl-1H-1,2,4-triazol-5-amine (16 mg, 0.1 mmol) in ethanol was stirred at 80° C. for overnight. The product was purified using reverse phase HPLC. The two pure enantiomers (37-6 and 37-7) were chirally separated from 37-5 by chiral cell column (20 micron, 50×500 mm, 100% MeOH with 0.1% TFA as mobile phase at 80 mL/min).
The following compounds were synthesized using the procedure:

| ID | Structure | EMW | MS m/z (M⁺ + H) | Retention Time (min) |
|---|---|---|---|---|
| 37-5 | 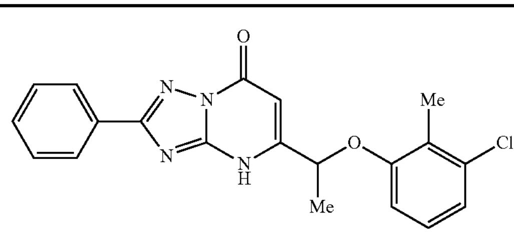 | 380.10 | 381.19 | 4.82 |

-continued

| ID | Structure | EMW | MS m/z (M⁺ + H) | Retention Time (min) |
|---|---|---|---|---|
| 37-6 | 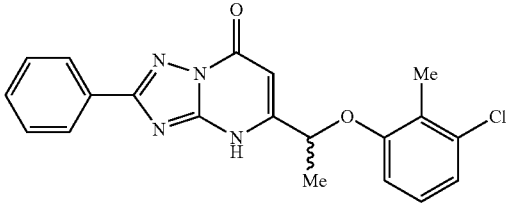 [SMILES: Cc1c(Cl)cccc1OC(C)c1cc(=O)n2nc(-c3ccccc3)nc2[nH]1] | 380.10 | 381.19 | 11.48 (ent-1) |
| 37-7 | 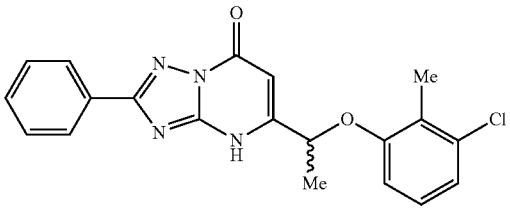 [SMILES: Cc1c(Cl)cccc1OC(C)c1cc(=O)n2nc(-c3ccccc3)nc2[nH]1] | 380.10 | 381.19 | 16.29 (ent-2) |

Example 38

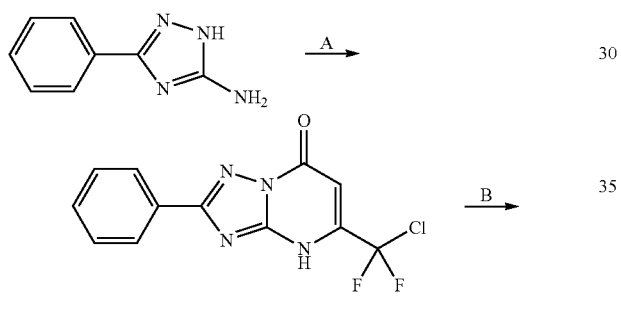

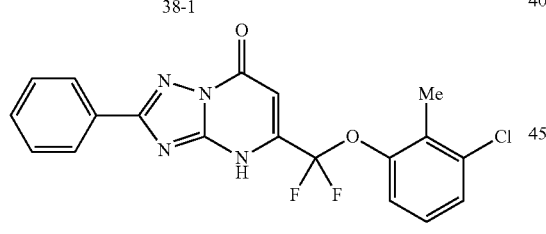

Step A:

To the solution of 3-phenyl-1H-1,2,4-triazol-5-amine (32 mg, 0.2 mmol) in DMA (0.5 mL) was added ethyl 4-chloro-4,4-difluoro-3-oxobutanoate (40 mg, 0.2 mmol). The reaction mixture was stirred in microwave at 180° C. for 20 minutes, and then cooled to room temperature. The product, compound 38-1, was purified by reverse phase HPLC.

Step B:

A reaction mixture of 3-chloro-2-methylphenol (42.8 mg, 0.3 mmol) and sodium hydride (60% dispersion in mineral oil, 20 mg, 0.5 mmol) in DMA was stirred at room temperature for 15 minutes. To the resultant clear solution was added compound 38-1 (0.1 mmol). The reaction mixture was stirred in microwave at 210° C. for 30 minutes. The product was purified by reverse phase HPLC.

| ID | Structure | EMW | MS m/z (M⁺ + H) | Retention Time (min) |
|---|---|---|---|---|
| 38-2 | 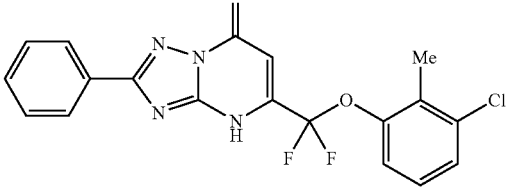 | 402.07 | 403.50 | 4.69 |

Example 39

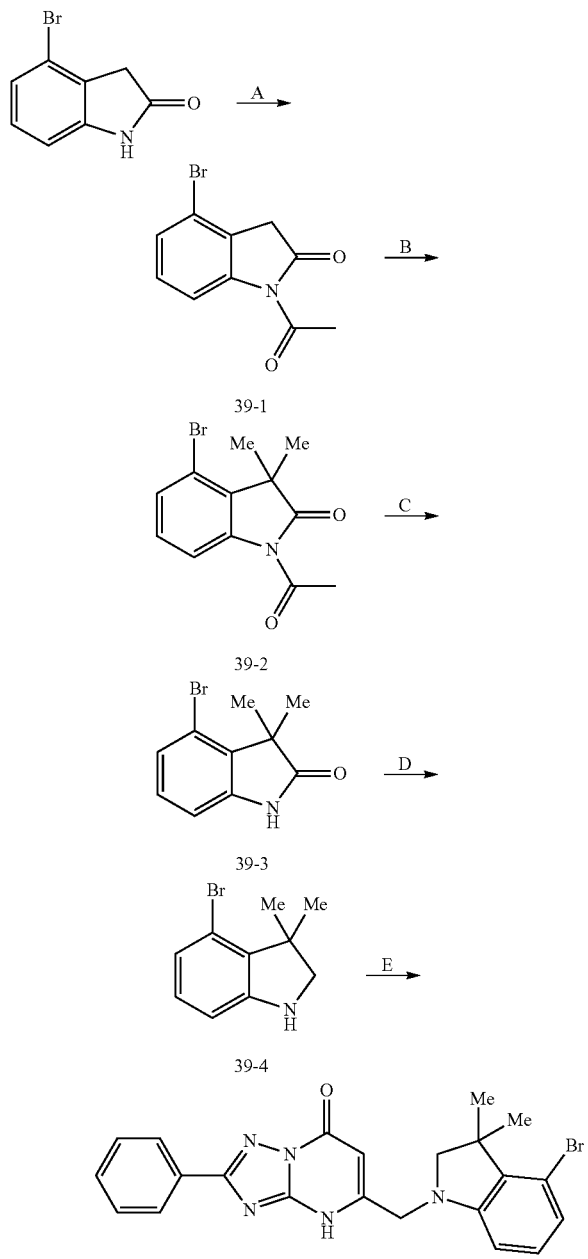

Step A:

A solution of 4-bromoindolin-2-one (1.7 g, 8 mmol) and acetic anhydride (2 mL) in xylenes (20 mL) was heated at reflux for overnight. The mixture was concentrated. The residue was dissolved in EtOAc. The EtOAc layer was washed with aqueous NaHCO$_3$ solution, and then concentrated. The residue was purified by silica gel column chromatography (10% EtOAc in Hexanes) to give compound 39-1 (0.87 g, 43% yield) as white solid.

Step B:

To a suspension of NaH (180 mg, 4.5 mmol, 60% dispersion in mineral oil) in THF (5 mL) was added compound 39-1 (506 mg, 2 mmol) portionwise. The reaction mixture was stirred at room temperature for 20 minutes. Methyl iodide (311 µL, 5 mmol) was added dropwise. The reaction mixture was stirred at room temperature for overnight, and then quenched with aqueous NH$_4$Cl solution. The product was extracted from the aqueous layer using EtOAc three times. The combined EtOAc layers were concentrated. The residue was purified by silica gel column chromatography (10% EtOAc in Hexanes) to give compound 39-2 (344.6 mg, 61% yield).

Step C:

To the solution of compound 39-2 (344 mg, 1.2 mmol) in ethanol (5 mL) at room temperature was added NaOH aqueous solution (2 mL, 3 M). The reaction mixture was stirred at room temperature for 2 hours, and then acidified with NH$_4$Cl aqueous solution. The product was extracted three times from the aqueous layer using EtOAc. The combined EtOAc layers were concentrated to give compound 39-3 (330 mg).

Step D:

To the solution of compound 39-3 (180 mg, 0.75 mmol) in toluene (5 mL) at 85° C. was added a solution of Vitride® (350 mg, 70 wt. % in toluene) dropwise over the course of 15 minutes. After the addition was finished, heating was continued for 15 minutes at 85° C., and then cooled to room temperature. The reaction mixture was quenched with NaOH aqueous solution. The product was extracted three times from the aqueous layer using EtOAc. The combined EtOAc layers were concentrated to give compound 39-4.

Step E:

A reaction mixture of compound 1-1 (26 mg, 0.1 mmol), compound 39-4 (34 mg, 0.15 mmol) and DIEA (35 µL, 0.2 mmol) in DMA (2 mL) was stirred at 200° C. for 20 minutes in microwave. The product was purified by reverse phase HPLC.

| ID | Structure | EMW | MS m/z (M$^+$ + H) | Retention Time (min) |
|---|---|---|---|---|
| 39-5 | 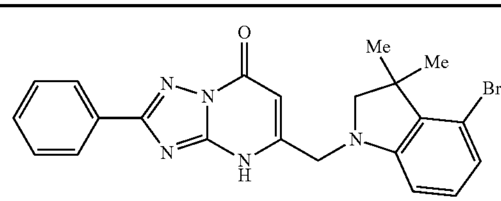 | 449.09 | 450.32 | 5.36 |

Example 40

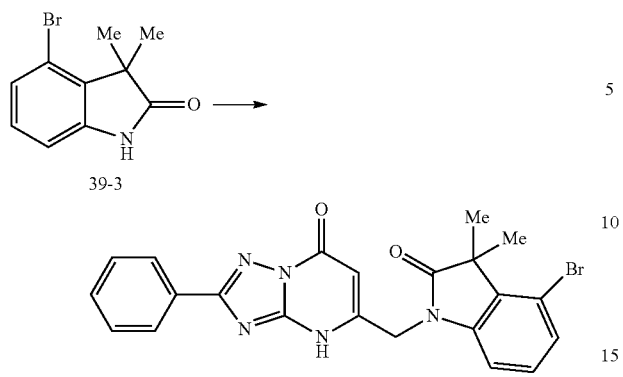

A reaction mixture of compound 39-3 (24 mg, 0.1 mmol) and sodium hydride (60% dispersion in mineral oil, 6 mg, 0.15 mmol) in DMA (0.5 mL) was stirred at room temperature for 15 minutes. To the resultant clear solution was added compound 1-1 (13 mg, 0.05 mmol). The reaction mixture was stirred in microwave at 220° C. for 30 minutes. The product was purified by reverse phase HPLC.

| ID | Structure | EMW | MS m/z (M$^+$ + H) | Retention Time (min) |
|---|---|---|---|---|
| 40-1 | 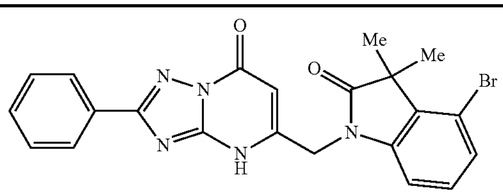 | 463.06 | 464.10 | 4.65 |

Example 41

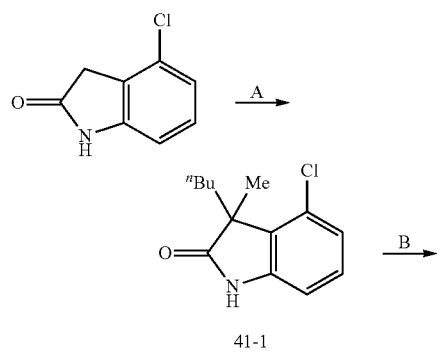

-continued

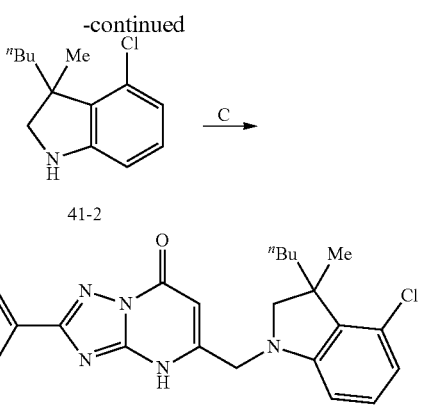

Step A:
To the solution of 4-chloroindolin-2-one (838 mg, 5 mmol) and TMEDA (1.5 mL, 10 mmol) in THF (15 mL) at −78° C. was added n-BuLi solution (6.25 mL, 10 mmol, 1.6 M in Hexanes) dropwise. The reaction mixture was stirred at −78° C. for 1 hour. Methyl iodide (312 μL, 5 mmol) was added. The reaction mixture was allowed to warm up to room temperature and stirred for one hour. The mixture was quenched with aqueous NH$_4$Cl solution. The product was extracted three times from the aqueous layer using EtOAc. The combined EtOAc layers were concentrated. The residue was purified by silica gel column chromatography to give compound 41-1.

Step B:

Using the procedure in STEP D of example 39, compound 41-2 was prepared.

Step C:

Using the procedure in example 40, the final product was prepared.

| ID | Structure | EMW | MS m/z (M$^+$ + H) | Retention Time (min) |
|---|---|---|---|---|
| 41-3 | 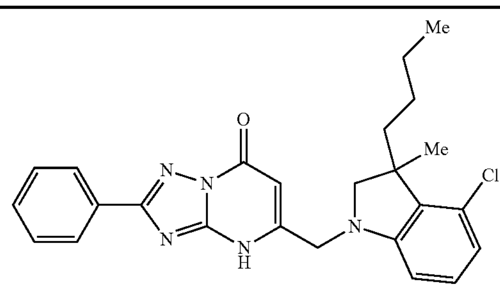 | 447.18 | 448.62 | 5.66 |

Example 42

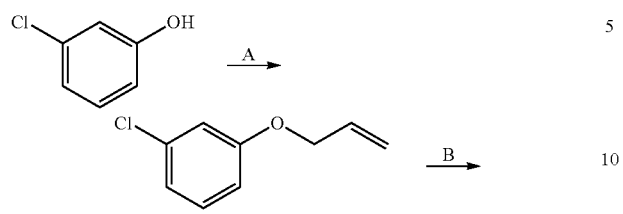

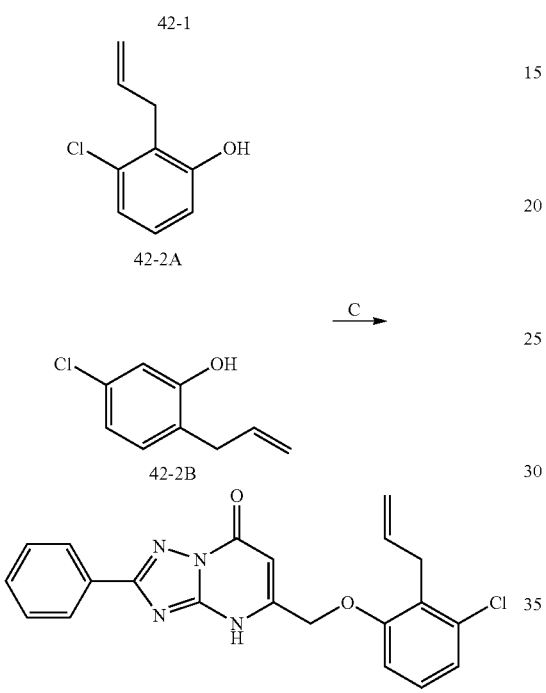

Step A:

A reaction mixture of 3-chlorophenol (900 mg, 7 mmol), allyl bromide (1.18 mL, 14 mmol) and potassium carbonate (1.94 g, 14 mmol) in acetonitrile was stirred at 80° C. for overnight. The reaction mixture was filtered. The filtrate was concentrated to give compound 42-1 as colorless oil (1.14 g, 97% yield).

Step B:

To a solution of compound 42-1 (1 g, 6 mmol) in anhydrous 1,2-dichloroethane (12 mL) was added a solution of tin(IV) chloride (7 mL, 1 M in heptane). The reaction mixture was stirred at room temperature. The reaction mixture was quenched with water in cold. The product was extracted with methylenechloride. Column chromatography with 10% EtOAc in Hexane gave compound 42-2A and 42-2B respectively. $^1$H NMR (400 MHz, CDCl$_3$) of compound 42-2A: δ 7.08-7.02 (m, 1H), 6.99 (dd, J=1.2, 8.4 Hz, 1H), 6.75-6.70 (m, 1H), 6.04-5.92 (m, 1H), 5.15-5.08 (m, 2H), 4.99 (br s, 1H), 3.60 (dt, J=1.6, 6.0 Hz, 2H). $^1$H NMR (400 MHz, CDCl$_3$) of compound 42-2B: δ 7.02 (d, J=8.0 Hz, 1H), 6.89-6.81 (m, 2H), 6.04-5.92 (m, 1H), 5.20-5.12 (m, 2H), 5.01 (br s, 1H), 3.37 (dt, J=1.6, 6.0 Hz, 2H).

Step C:

A reaction mixture of compound 42-2 (16.8 mg, 0.1 mmol), compound 1-1 (13 mg, 0.05 mmol) and K$_2$CO$_3$ (55 mg, 0.4 mmol) in DMA was stirred at 150° C. for 15 minutes. The product was purified by reverse phase HPLC.

The following compounds were synthesized using the procedure:

| ID | Structure | EMW | MS m/z (M$^+$ + H) | Retention Time (min) |
|---|---|---|---|---|
| 42-3 | 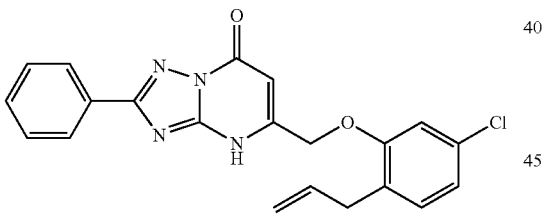 | 392.10 | 393.58 | 4.75 |

| ID | Structure | EMW | MS m/z (M+ + H) | Retention Time (min) |
|---|---|---|---|---|
| 42-4 | 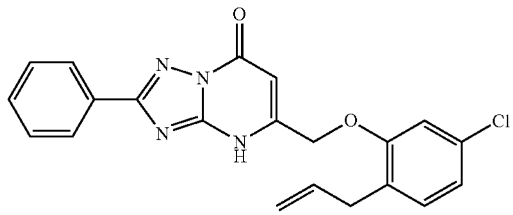 [SMILES: C=CCc1ccc(Cl)cc1OCc1cc(=O)n2nc(-c3ccccc3)nc2[nH]1] | 392.10 | 393.59 | 4.69 |

Example 43

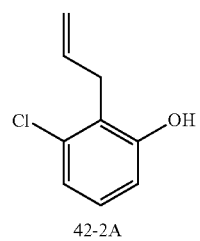

42-2A

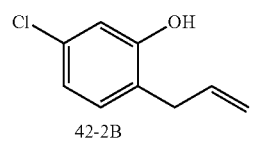

42-2B

A →

43-1A

B →

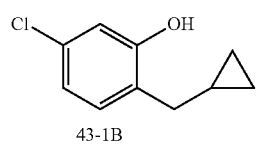

43-1B

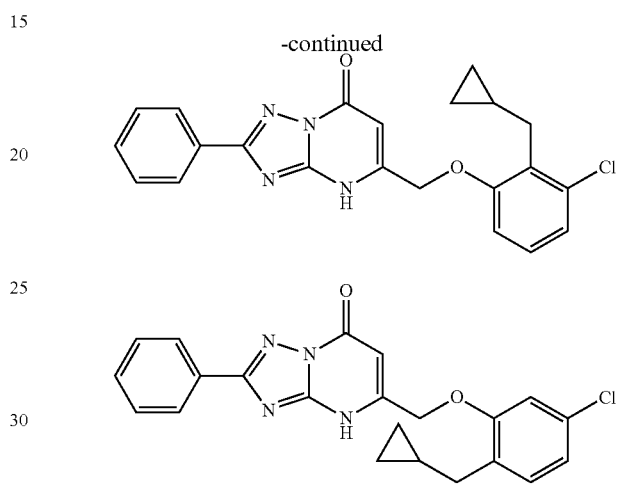

Step A:

To a solution of diethyl zinc (0.72 mL, 0.72 mmol, 1 M in hexanes) in DCM (2 mL) at 0° C. was added trifluoroacetic acid (55 μL, 0.72 mmol) dropwise. The mixture was stirred at 0° C. for 20 minutes. Diiodomethane (193 mg, 0.72 mmol) was added. The mixture was stirred at 0° C. for 20 minutes. A solution of compound 42-2 (60 mg, 0.36 mmol) in DCM (1 mL) was added. The reaction mixture was warmed to room temperature and stirred for one hour. The mixture was quenched with aqueous HCl solution. The product was extracted with EtOAc. Column chromatography on silica gel with 10% EtOAc in hexane gave compound 43-1.

Step B:

A reaction mixture of compound 43-1, compound 1-1 (13 mg, 0.05 mmol) and $K_2CO_3$ (69 mg, 0.5 mmol) in DMA was stirred at 150° C. for 15 minutes. The product was purified by reverse phase HPLC.

The following compounds were synthesized using the procedure:

| ID | Structure | EMW | MS m/z (M+ + H) | Retention Time (min) |
|---|---|---|---|---|
| 43-2 | 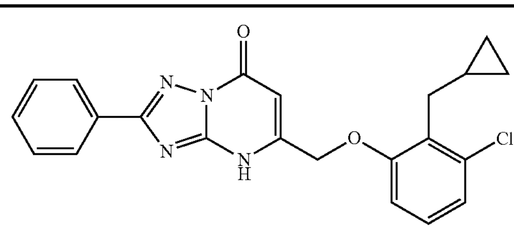 | 406.12 | 407.62 | 4.91 |

| ID | Structure | EMW | MS m/z (M+ + H) | Retention Time (min) |
|---|---|---|---|---|
| 43-3 | 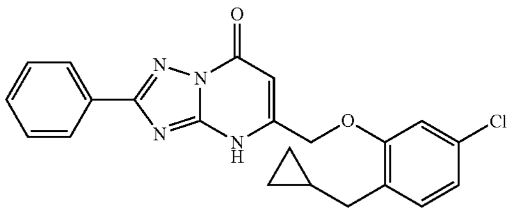 [SMILES: O=c1cc(COc2cc(Cl)ccc2CC2CC2)[nH]c2nc(-c3ccccc3)nn12] | 406.12 | 407.61 | 4.93 |

Example 44

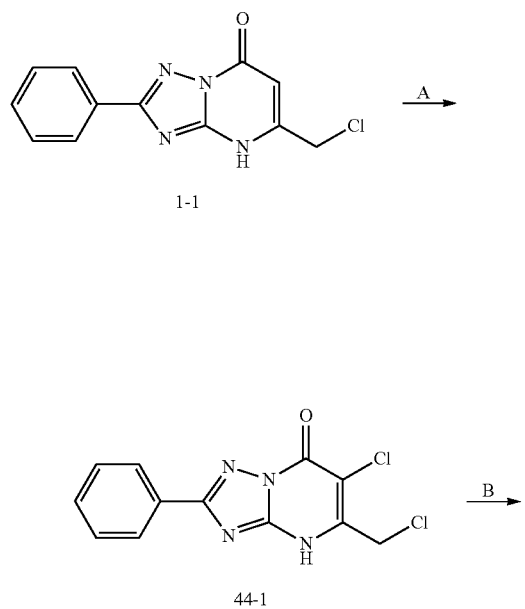

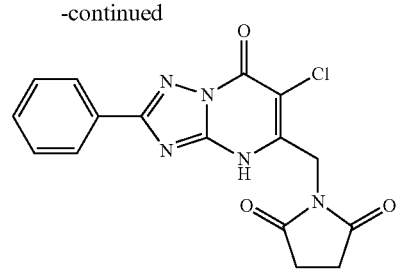

Step A:

A reaction mixture of compound 1-1 (26 mg, 0.1 mmol) and N-chlorosuccinimide (13.4 mg, 0.1 mmol) in acetic acid (1 mL) was stirred at room temperature for overnight. The reaction mixture was concentrated. The residue was used in the next step without further purification.

Step B:

To the solution of the residue from last step in DMA (0.5 mL) was added sodium hydride (8 mg, 0.2 mmol, 60% dispersion in mineral oil). The reaction mixture was stirred in microwave at 230° C. for 40 minutes. The product was purified by reverse phase HPLC.

The following compound was synthesized using the procedure:

| ID | Structure | EMW | MS m/z (M+ + H) | Retention Time (min) |
|---|---|---|---|---|
| 44-2 | 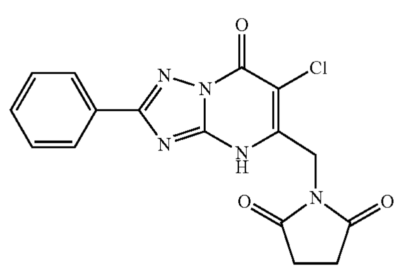 [SMILES: O=C1CCC(=O)N1Cc1[nH]c2nc(-c3ccccc3)nn2c(=O)c1Cl] | 357.06 | 358.19 | 2.88 |

Example 45

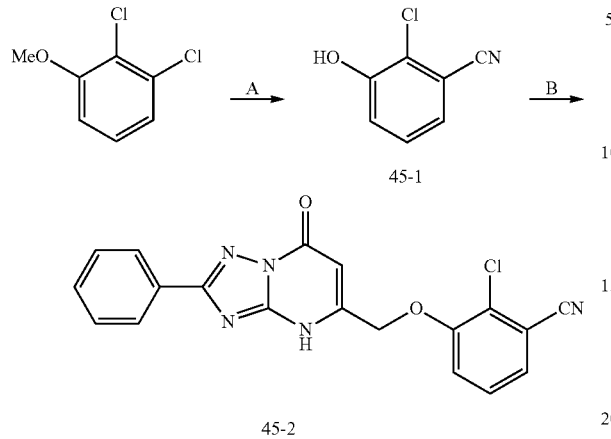

Step A:
To a solution of 2-chloro-3-methoxybenzonitrile (1.34 g, 8 mmol) in DCM (20 mL) at −78° C. was added boron tribromide solution (40 mL, 40 mmol, 1 M in DCM). The reaction mixture was allowed to warm up to room temperature and stirred for overnight. The mixture was concentrated. The residue was quenched with water (CAUTION: exothermic!) The product was extracted with EtOAc. The combined EtOAc layer was concentrated to give compound 45-1.

Step B:
A reaction mixture of compound 1-1 (13 mg, 0.05 mmol), compound 45-1 (15.3 mg, 0.1 mmol) and sodium hydride (6 mg, 0.15 mmol, 60% dispersion in mineral oil) in DMA (0.5 mL) was stirred in microwave at 210° C. for 20 minutes. The product was purified by reverse phase HPLC.

The following compound was synthesized using the procedure:

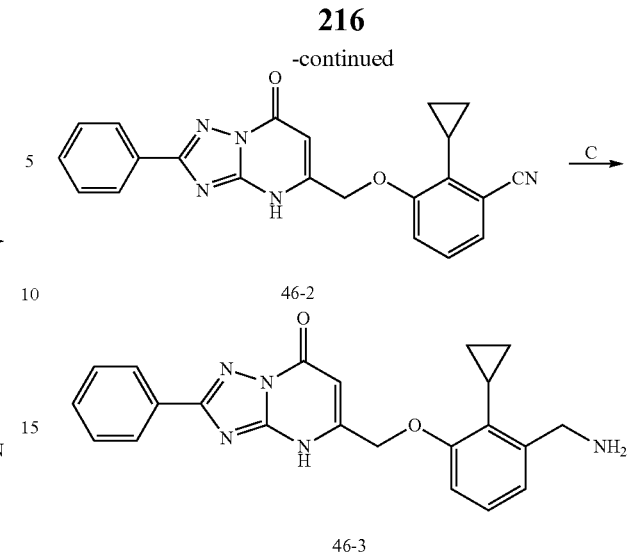

Step A:
A reaction mixture of compound 45-1 (460 mg, 3 mmol), cyclopropyl boronic acid (430 mg, 5 mmol), palladium acetate (40.3 mg, 0.18 mmol), S-Phos (102.6 mg, 0.25 mmol) and potassium phosphate (1.06 g, 5 mmol) in dioxane was stirred at 100° C. for overnight. The reaction mixture was quenched with aqueous HCl solution (1 M). Aqueous NaHCO₃ solution was added to adjust the pH value of the solution to 7. The organic product was extracted with EtOAc. The combined EtOAc layer was concentrated. The residue was purified by silica gel column chromatography with 10% EtOAc in hexane. Compound 46-1 (25 mg) was obtained as white solid.

Step B:
A reaction mixture of compound 1-1 (26 mg, 0.1 mmol), compound 46-1 (24 mg, 0.15 mmol) and sodium hydride (6 mg, 0.15 mmol, 60% dispersion in mineral oil) in DMA (0.5 mL) was stirred in microwave at 215° C. for 30 minutes. The product was purified by reverse phase HPLC.

Step C:
The solution of compound 46-2 in methanol was passing through a Raney-Nickel cartridge in H-tube with the flow rate of 0.4 mL/min, the temperature of 40° C. and the pressure of 40 bar. The product solution in methanol was concentrated. The product (46-3) was purified by reverse phase HPLC.

The following compound was synthesized using the procedure:

| ID | Structure | EMW | MS m/z (M⁺ + H) | Retention Time (min) |
|---|---|---|---|---|
| 45-2 | 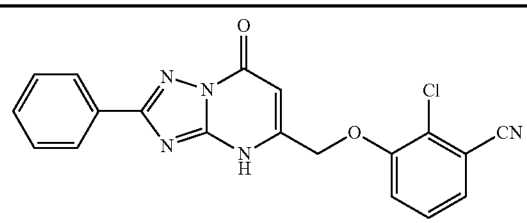 | 377.07 | 378.23 | 4.09 |

Example 46

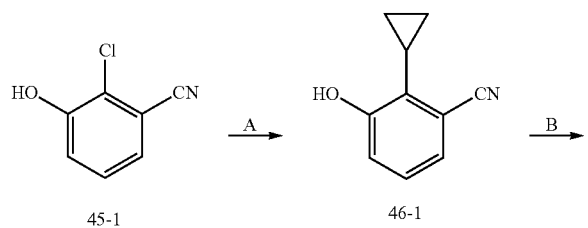

| ID | Structure | EMW | MS m/z (M⁺ + H) | Retention Time (min) |
|---|---|---|---|---|
| 46-2 | 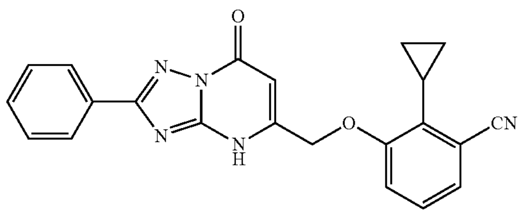 [SMILES: N#Cc1cccc(OCc2cc(=O)n3nc(-c4ccccc4)nc3[nH]2)c1C1CC1] | 383.14 | 384.25 | 4.35 |
| 46-3 | 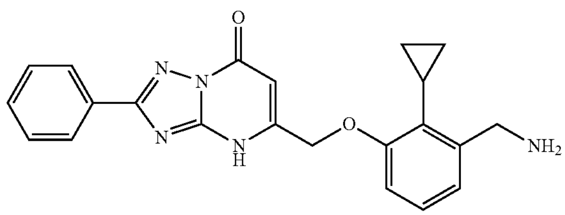 [SMILES: NCc1cccc(OCc2cc(=O)n3nc(-c4ccccc4)nc3[nH]2)c1C1CC1] | 387.17 | 388.19 | 2.94 |

Example 47

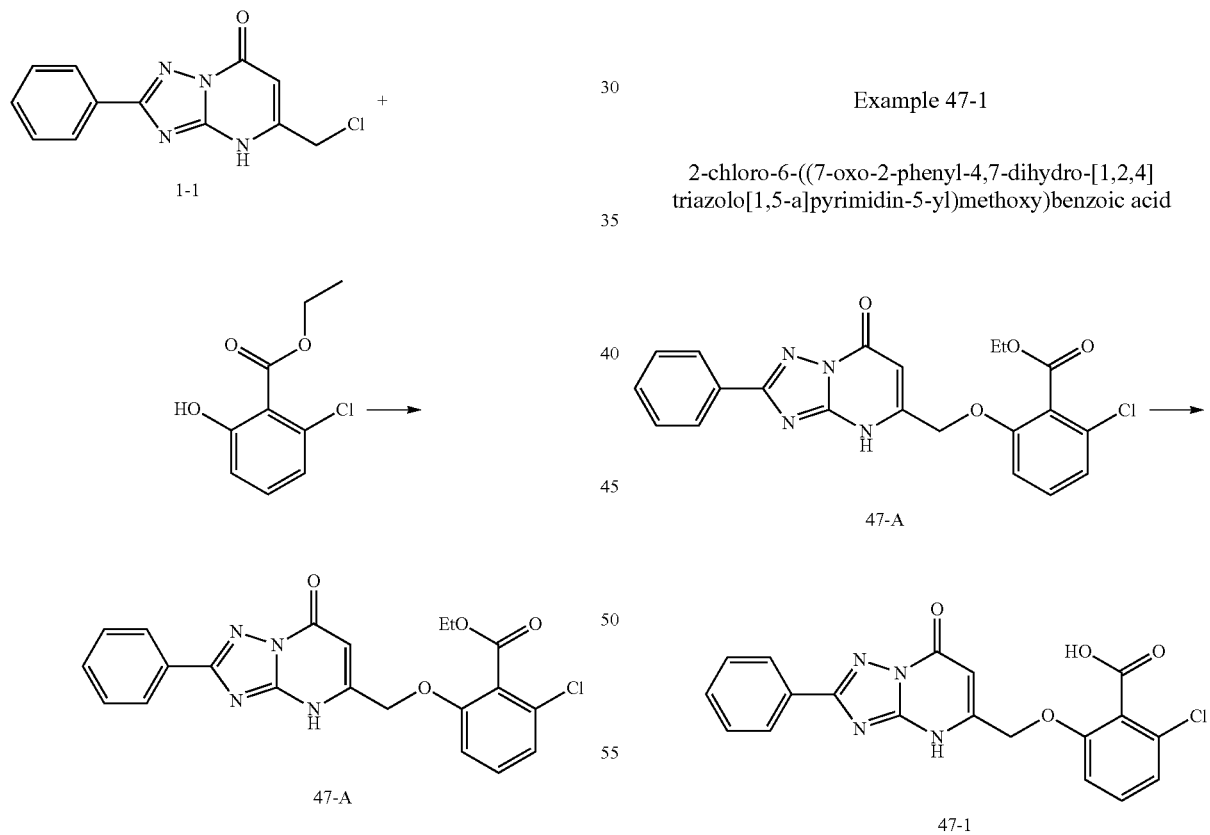

Compound 1-1 (6.42 g, 24.6 mmol) was dissolved in DMA (35 mL) and then ethyl-2-chloro-6 hydroxybenzoate (1.1 equiv, 27.0 mmol, 5.44 g), and $K_2CO_3$ (3.0 equiv, 73.8 mmol, 10.2 g) were added and allowed to stir at 90° C. for 18 h. At the end of the reaction the solution was extracted with an ethyl acetate and sodium bicarbonate wash. The solid product crashed out and was filtered through a glass filter funnel with a medium pore-sized frit, and then placed under high vacuum.

Compound 47-A: HPLC-MS (5 min) RT=1.787 min, mass calculated for formula $C_{21}H_{17}ClN_4O_4$ 424.09, observed LCMS m/z 425.20 (M+H).

Example 47-1

2-chloro-6-((7-oxo-2-phenyl-4,7-dihydro-[1,2,4]triazolo[1,5-a]pyrimidin-5-yl)methoxy)benzoic acid Compound 47-A was then dissolved in ethanol and 2 M KOH in water (3.0 equiv.) was added. The mixture stirred at 100° C. for 5 h. After cooling to room temperature, 1 N HCl was added until the solution reached a pH of 3. An aqueous work up with water and DCM resulted in solid product crashing out. The solid was filtered through a glass filter funnel with a medium pore-sized frit, and then placed under high vacuum. HPLC-MS (5 min) RT=3.176 min, mass calculated for formula $C_{19}H_{13}ClN_4O_4$ 396.06, observed LCMS m/z 397.55 (M+H).

Example 47-2

2-chloro-N-(1-methyl-1H-pyrazol-5-yl)-6-((7-oxo-2-phenyl-4,7-dihydro-[1,2,4]triazolo[1,5-a]pyrimidin-5-yl)methoxy)benzamide

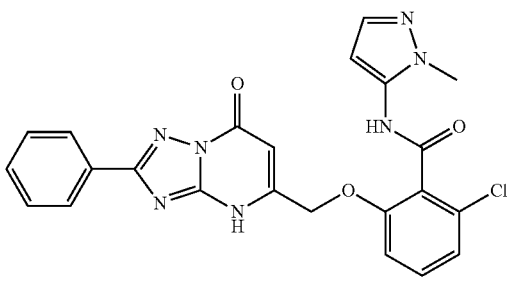

47-2

Compound 47-1 (0.05 mmol, 20 mg) and HATU (1.5 equiv, 0.075 mmol, 28.5 mg) were dissolved in DMF and stirred at room temperature for 5 min. Then, 1-methyl-1H-pyrazol-5-ylamine (1.2 equiv, 0.06 mmol, 5.87 mg) was added and allowed to stir at room temperature for 18 h. The reaction solvent was evaporated in vacuo, then dissolved in DMSO/acetonitrile (3:1), filtered through 0.45 μM filter cartridge and purified using reverse phase HPLC to provide product. HPLC-MS (10 min) RT=3.269 min, mass calculated for formula $C_{23}H_{18}ClN_7O_3$ 475.12, observed LCMS m/z 476.58 (M+H).

Example 47-3

2-chloro-N-(cyclopropylmethyl)-6-(7-oxo-2-phenyl-4,7-dihydro-[1,2,4]triazolo[1,5-a]pyrimidin-5-yl)methoxy)benzamide

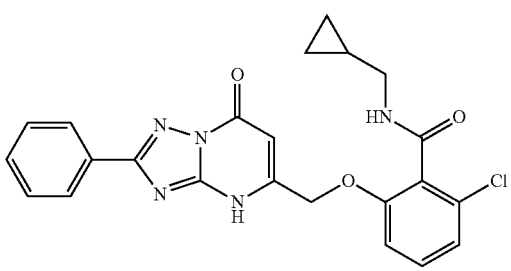

47-3

Compound 47-3 was synthesized according to 47-2 but stirred at 60° C. using compound 47-1 and cyclopropylmethanamine. HPLC-MS (10 min) RT=3.818 min, mass calculated for formula $C_{23}H_{20}ClN_5O_3$ 449.13, observed LCMS m/z 450.57 (M+H).

Example 47-4

2-chloro-N-((1-(4-chlorophenyl)cyclopropyl)methyl)-6-((7-oxo-2-phenyl-4,7-dihydro-[1,2,4]triazolo[1,5-a]pyrimidin-5-yl)methoxy)benzamide

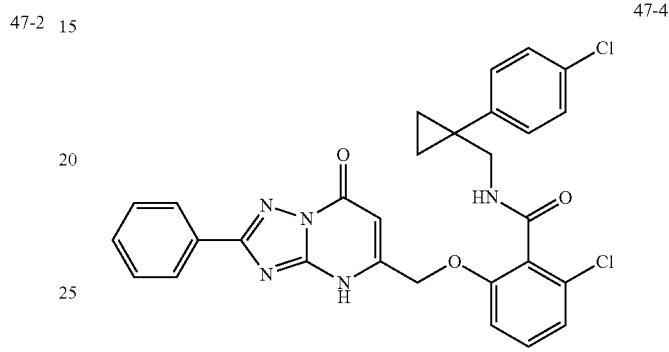

47-4

Compound 47-1, DIEA (3.0 equiv., 1.5 mmol, 261 μL), and HATU (1.5 equiv, 0.75 mmol, 287 mg) were dissolved in DMA (3 mL) and stirred at 40° C. for 5 min. Then, (1-(4-chlorophenyl)cyclopropyl)methanamine (1.1 equiv, 0.55 mmol, 120 mg) was added and allowed to stir at 40° C. for 18 h. The reaction solvent was evaporated in vacuo, then dissolved in DMSO/acetonitrile (3:1), filtered through 0.45 uM filter cartridge and purified using reverse phase HPLC to provide product. HPLC-MS (10 min) RT=5.773 min, mass calculated for formula $C_{29}H_{23}Cl_2N_5O_3S$ 559.12, observed LCMS m/z 559.87 (M+H).

Example 47-5

2-chloro-N-(cyclobutylmethyl)-6-((7-oxo-2-phenyl-4,7-dihydro-[1,2,4]triazolo[1,5-a]pyrimidin-5-yl)methoxy)benzamide 47-5

Compound 47-5 was synthesized according to 47-2 using 47-1 and cyclobutylmethanamine. HPLC-MS (10 min)

RT=4.168 min, mass calculated for formula $C_{24}H_{22}ClN_5O_3$ 463.14, observed LCMS m/z 464.57 (M+H).

Example 47-6

4-[2-chloro-6-[(4,7-dihydro-7-oxo-2-phenyl[1,2,4]triazolo[1,5-a]pyrimidin-5-yl)methoxy]benzoyl]thiomorpholine, 1,1-dioxide

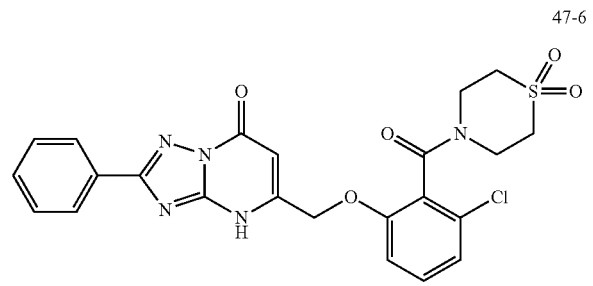 [SMILES: O=C(c1c(Cl)cccc1OCc1cc(=O)n2nc(-c3ccccc3)nc2[nH]1)N1CCS(=O)(=O)CC1]

47-6

Compound 47-1 (0.05 mmol, 20 mg), DIEA (2.0 equiv., 0.10 mmol, 17.5 μL), and HATU (1.5 equiv, 0.075 mmol, 28.5 mg) were dissolved in DMF and stirred at room temperature for 5 min. Then, thiomorpholine 1,1-dioxide (1.2 equiv, 0.075 mmol, 8.1 mg) was added and allowed to stir at room temperature for 18 h. The reaction solvent was evaporated in vacuo, then dissolved in DMSO/acetonitrile (3:1), filtered through 0.45 μM filter cartridge and purified using reverse phase HPLC to provide product. HPLC-MS (10 min) RT=3.164 min, mass calculated for formula $C_{23}H_{20}ClN_5O_5S$ 513.09, observed LCMS m/z 514.55 (M+H).

Example 47-7

2-chloro-N-(1,3-dimethyl-1H-pyrazol-5-yl)-6-((7-oxo-2-phenyl-4,7-dihydro-[1,2,4]triazolo[1,5-a]pyrimidin-5-yl)methoxy)benzamide

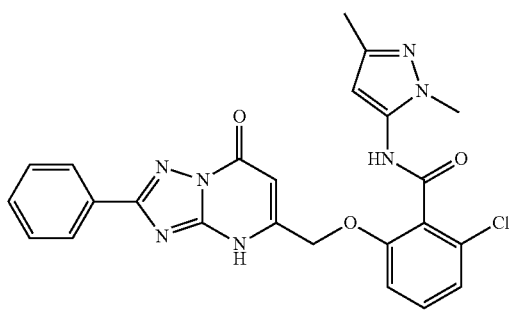

47-7

Compound 47-7 was synthesized according to 47-6 using 47-1 and 1,3-dimethyl-1H-pyrazol-5-amine. HPLC-MS (10 min) RT=3.328 min, mass calculated for formula $C_{24}H_{20}ClN_7O_3$ 489.13, observed LCMS m/z 490.59 (M+H).

Example 47-8

2-chloro-N-(5-methylisoxazol-3-yl)-6-((7-oxo-2-phenyl-4,7-dihydro-[1,2,4]triazolo[1,5-a]pyrimidin-5-yl)methoxy)benzamide

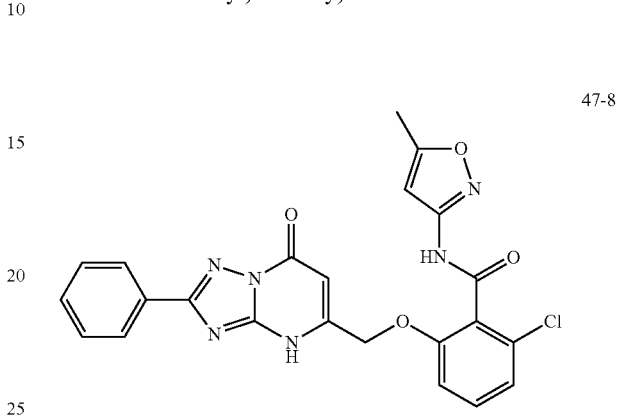

47-8

Compound 47-1 (0.05 mmol, 20 mg), DIEA (2.0 equiv., 0.10 mmol, 17.4 μL), and HATU (1.5 equiv, 0.075 mmol, 28.5 mg) were dissolved in NMP and stirred at room temperature for 5 min. Then, 5-methylisoxazol-3-amine (1.2 equiv, 0.06 mmol, 5.9 mg) was added and allowed to stir at 85° C. for 18 h. The reaction solvent was evaporated in vacuo, then dissolved in DMSO/acetonitrile (3:1), filtered through 0.45 uM filter cartridge and purified using reverse phase HPLC to provide product. HPLC-MS (10 min) RT=3.654 min, mass calculated for formula $C_{23}H_{17}ClN_6O_4$ 476.10, observed LCMS m/z 477.53 (M+H).

Example 47-9

(S)-5-((3-chloro-2-(2-(methoxymethyl)pyrrolidine-1-carbonyl)phenoxy)methyl)-2-phenyl-[1,2,4]triazolo[1,5-a]pyrimidin-7(4H)-one

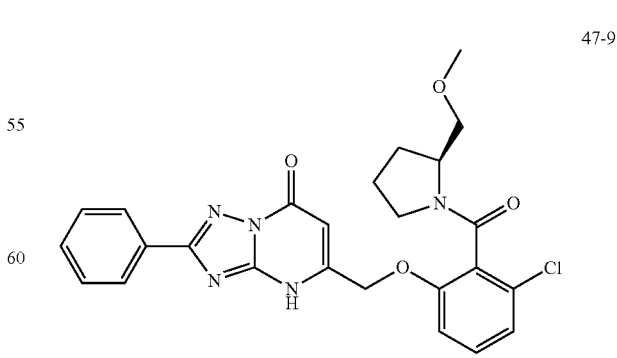

47-9

Compound 47-9 was synthesized according to 47-6 using 47-1 and (S)-2-(methoxymethyl)pyrrolidine. HPLC-MS (10 min) RT=4.063 min, mass calculated for formula $C_{25}H_{24}ClN_5O_4$ 493.15, observed LCMS m/z 494.62 (M+H).

Example 47-10

((R)-5-((3-chloro-2-(2-(methoxymethyl)pyrrolidine-1-carbonyl)phenoxy)methyl)-2-phenyl-[1,2,4]triazolo[1,5-a]pyrimidin-7(4H)-one

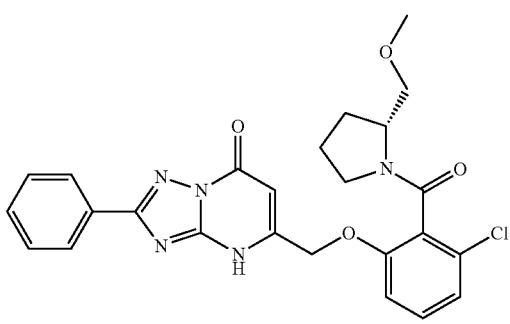

47-10

Compound 47-10 was synthesized according to 47-6 using 47-1 and (R)-2-(methoxymethyl)pyrrolidine. HPLC-MS RT=4.086 min, mass calculated for formula $C_{25}H_{24}ClN_5O_4$ 493.15, observed LCMS m/z 494.62 (M+H).

Example 47-11

2-chloro-N-(3-cyclopropyl-1-methyl-1H-pyrazol-5-yl)-64(7-oxo-2-phenyl-4,7-dihydro-[1,2,4]triazolo[1,5-a]pyrimidin-5-yl)methoxy)benzamide

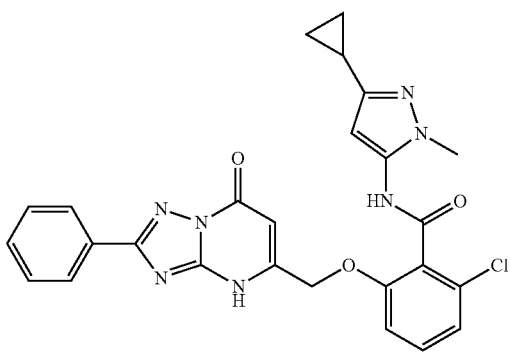

47-11

Compound 47-11 was synthesized according to 47-6 using 47-1 and 3-cyclopropyl-1-methyl-1H-pyrazol-5-amine.

HPLC-MS RT=3.666 min, mass calculated for formula $C_{26}H_{22}ClN_7O_3$ 515.15, observed LCMS m/z 516.59 (M+H).

Example 47-12

2-chloro-N-(1-(hydroxymethyl)cyclopropyl)-6-((7-oxo-2-phenyl-4,7-dihydro-[1,2,4]triazolo[1,5-a]pyrimidin-5-yl)methoxy)benzamide

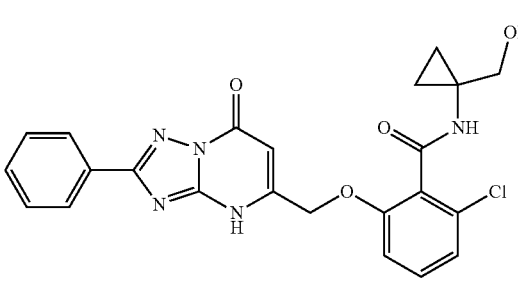

47-12

Compound 47-12 was synthesized according to 47-6 using 47-1 and (1-aminocyclopropyl)methanol. HPLC-MS RT=3.059 min, mass calculated for formula $C_{23}H_{20}ClN_5O_4$ 465.12, observed LCMS m/z 466.58 (M+H).

Example 47-13

2-chloro-N-((1-hydroxycyclohexyl)methyl)-6-((7-oxo-2-phenyl-4,7-dihydro-[1,2,4]triazolo[1,5-a]pyrimidin-5-yl)methoxy)benzamide

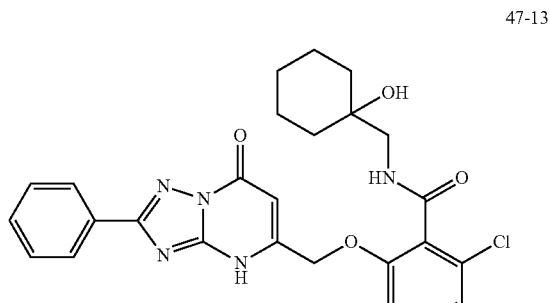

47-13

Compound 47-13 was synthesized according to 47-6 using 47-1 and 1-(aminomethyl)cyclohexanol. HPLC-MS RT=3.748 min, mass calculated for formula $C_{26}H_{26}ClN_5O_4$ 507.17, observed LCMS m/z 508.63 (M+H).

RT=3.491 min, mass calculated for formula $C_{25}H_{24}ClN_5O_4$ 493.15, observed LCMS m/z 494.64 (M+H).

Example 47-14

2-chloro-N-(1-(hydroxymethyl)cyclohexyl)-6-(7-oxo-2-phenyl-4,7-dihydro-[1,2,4]triazolo[1,5-a]pyrimidin-5-yl)methoxy)benzamide

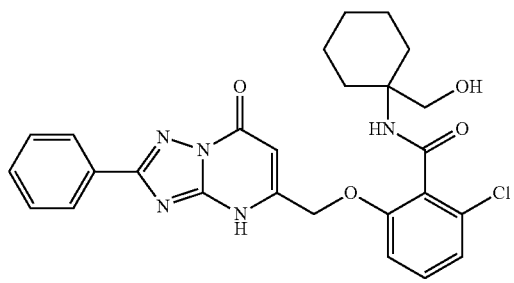

47-14

Compound 47-14 was synthesized according to 47-6 using 47-1 and (1-aminocyclohexyl)methanol. HPLC-MS RT=3.748 min, mass calculated for formula $C_{26}H_{26}ClN_5O_4$ 507.17, observed LCMS m/z 508.63 (M+H).

Example 47-16

2-chloro-N-(1-(2-methoxyphenyl)cyclopropyl)-6-(7-oxo-2-phenyl-4,7-dihydro-[1,2,4]triazolo[1,5-a]pyrimidin-5-yl)methoxy)benzamide

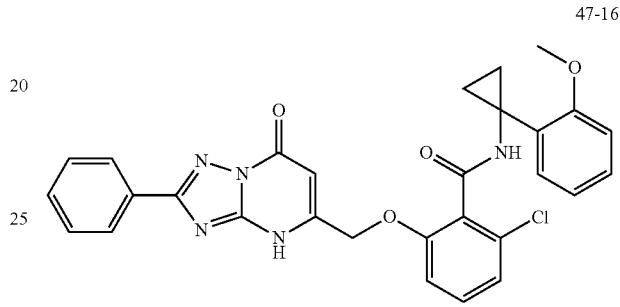

47-16

Compound 47-16 was synthesized according to 47-6 using 47-1 and 1-(2-methoxyphenyl)cyclopropanamine. HPLC-MS RT=4.343 min, mass calculated for formula $C_{29}H_{24}ClN_5O_4$ 541.15, observed LCMS m/z 542.62 (M+H).

Example 47-15

2-chloro-N-((1-hydroxycyclopentyl)methyl)-6-((7-oxo-2-phenyl-4,7-dihydro-[1,2,4]triazolo[1,5-a]pyrimidin-5-yl)methoxy)benzamide

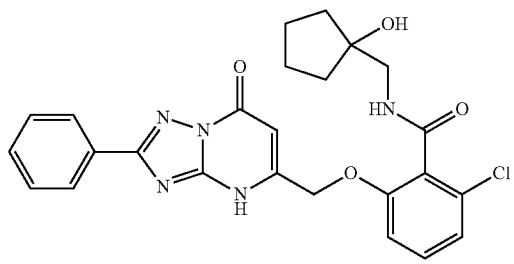

47-15

Compound 47-15 was synthesized according to 47-6 using 47-1 and 1-(aminomethyl)cyclopentanol. HPLC-MS

Example 47-17

2-chloro-N-(1-(hydroxymethyl)cyclopentyl)-6-((7-oxo-2-phenyl-4,7-dihydro-[1,2,4]triazolo[1,5-a]pyrimidin-5-yl)methoxy)benzamide

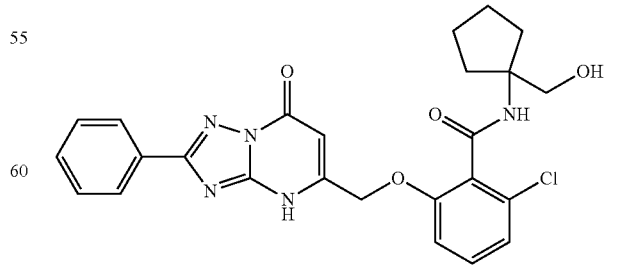

47-17

Compound 47-17 was synthesized according to 47-6 using 47-1 and (1-aminocyclopentyl)methanol. HPLC-MS RT=3.748 min, mass calculated for formula $C_{25}H_{24}ClN_5O_4$ 493.15, observed LCMS m/z 494.59 (M+H).

HPLC-MS RT=3.748 min, mass calculated for formula $C_{25}H_{24}ClN_5O_4$ 493.15, observed LCMS m/z 494.64 (M+H).

Example 47-18

2-chloro-N-((1-(hydroxymethyl)cyclopropyl)methyl)-6-((7-oxo-2-phenyl-4,7-dihydro-[1,2,4]triazolo[1,5-a]pyrimidin-5-yl)methoxy)benzamide

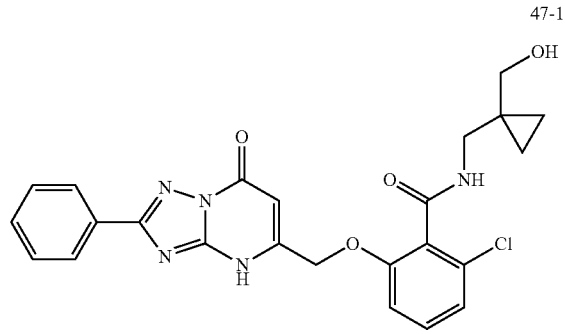

47-18

Compound 47-18 was synthesized according to 47-6 using 47-1 and (1-(aminomethyl)cyclopropyl)methanol. HPLC-MS RT=3.188 min, mass calculated for formula $C_{24}H_{22}ClN_5O_4$ 479.14, observed LCMS m/z 480.53 (M+H).

Example 47-19

2-chloro-N-((1-(methoxymethyl)cyclopropyl)methyl)-6-((7-oxo-2-phenyl-4,7-dihydro-[1,2,4]triazolo[1,5-a]pyrimidin-5-yl)methoxy)benzamide

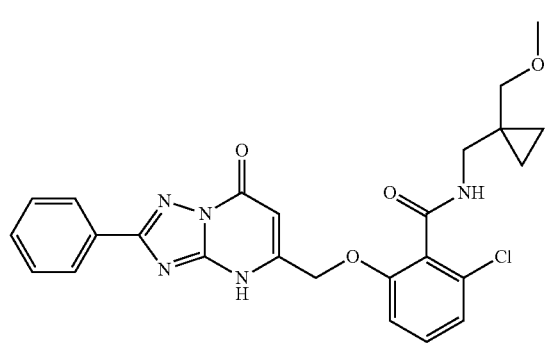

47-19

Compound 47-19 was synthesized according to 47-6 using 47-1 and (1-(methoxymethyl)cyclopropyl)methanamine.

Example 47-20

2-chloro-N-((1-(hydroxymethyl)cyclopentyl)methyl)-6-((7-oxo-2-phenyl-4,7-dihydro-[1,2,4]triazolo[1,5-a]pyrimidin-5-yl)methoxy)benzamide

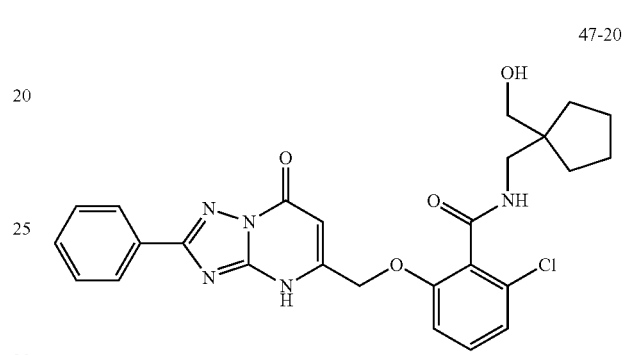

47-20

Compound 47-20 was synthesized according to 47-6 using 47-1 and (1-(aminomethyl)cyclopentyl)methanol. HPLC-MS RT=3.713 min, mass calculated for formula $C_{26}H_{26}ClN_5O_4$ 507.17, observed LCMS m/z 508.63 (M+H).

Example 47-21

2-chloro-N-(4-(hydroxymethyl)tetrahydro-2H-pyran-4-yl)-6-((7-oxo-2-phenyl-4,7-dihydro-[1,2,4]triazolo[1,5-a]pyrimidin-5-yl)methoxy)benzamide

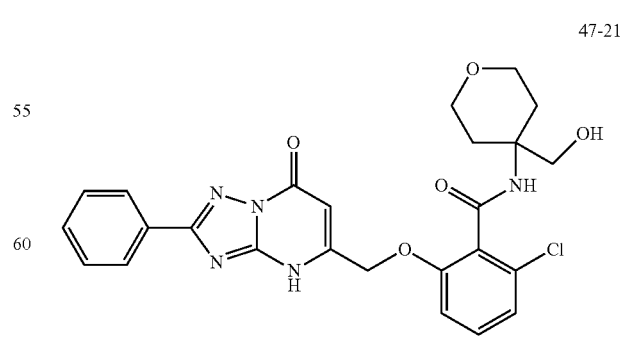

47-21

Compound 47-21 was synthesized according to 47-6 using 47-1 and (4-aminotetrahydro-2H-pyran-4-yl)methanol.

HPLC-MS RT=3.024 min, mass calculated for formula $C_{25}H_{24}ClN_5O_5$ 509.15, observed LCMS m/z 510.62 (M+H).

Example 47-22

2-chloro-N-(2-methyl-2-morpholinopropyl)-6-((7-oxo-2-phenyl-4,7-dihydro-[1,2,4]triazolo[1,5-a]pyrimidin-5-yl)methoxy)benzamide

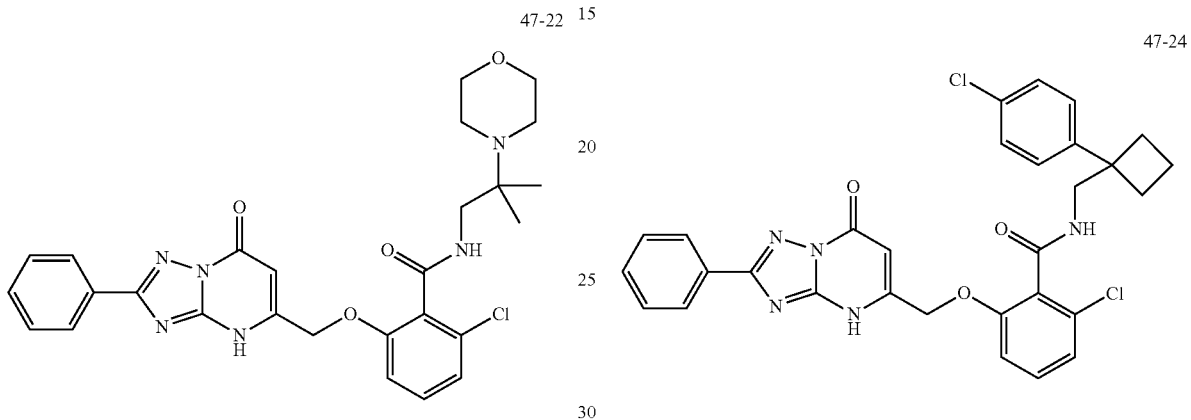

47-22

Compound 47-22 was synthesized according to 47-6 using 47-1 and 2-methyl-2-morpholinopropan-1-amine. HPLC-MS RT=2.721 min, mass calculated for formula $C_{27}H_{29}ClN_6O_4$ 536.19, observed LCMS m/z 537.68 (M+H).

Example 47-23

2-chloro-N-((1-(2-methoxyphenyl)cyclobutyl)methyl)-64(7-oxo-2-phenyl-4,7-dihydro-[1,2,4]triazolo[1,5-a]pyrimidin-5-yl)methoxy)benzamide 47-23

Compound 47-23 was synthesized according to 47-6 using 47-1 and (1-(2-methoxyphenyl)cyclobutyl)methanamine.

HPLC-MS RT=4.891 min, mass calculated for formula $C_{31}H_{28}ClN_5O_4$ 569.18, observed LCMS m/z 570.62 (M+H).

Example 47-24

2-chloro-N-((1-(4-chlorophenyl)cyclobutyl)methyl)-6-((7-oxo-2-phenyl-4,7-dihydro-[1,2,4]triazolo[1,5-a]pyrimidin-5-yl)methoxy)benzamide 47-24

Compound 47-24 was synthesized according to 47-6 using 47-1 and (1-(4-chlorophenyl)cyclobutyl)methanamine. HPLC-MS RT=5.019 min, mass calculated for formula $C_{30}H_{25}Cl_2N_5O_3$ 573.13, observed LCMS m/z 574.57 (M+H).

Example 47-25

2-chloro-N-((4-hydroxytetrahydro-2H-pyran-4-yl)methyl)-6-((7-oxo-2-phenyl-4,7-dihydro-[1,2,4]triazolo[1,5-a]pyrimidin-5-yl)methoxy)benzamide

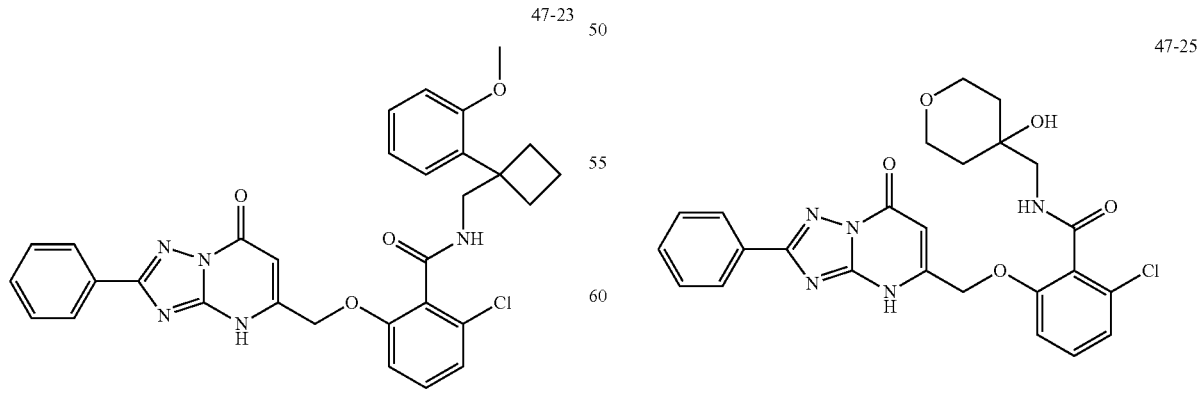

47-25

Compound 47-25 was synthesized according to 47-6 using 47-1 and 4-(aminomethyl)tetrahydro-2H-pyran-4-ol. HPLC- MS RT=2.954 min, mass calculated for formula $C_{25}H_{24}ClN_5O_5$ 509.15, observed LCMS m/z 510.62 (M+H).

Example 47-26

2-chloro-N-((4-(hydroxymethyl)tetrahydro-2H-pyran-4-yl)methyl)-6-((7-oxo-2-phenyl-4,7-dihydro-[1,2,4]triazolo[1,5-a]pyrimidin-5-yl)methoxy)benzamide

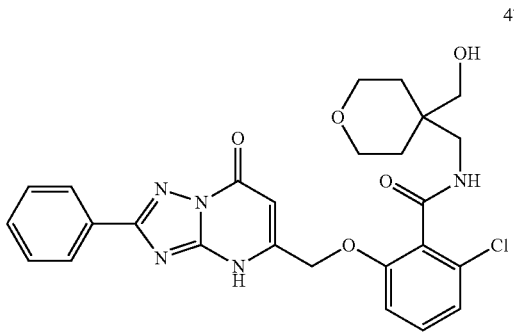

47-26

Compound 47-26 was synthesized according to 47-6 using 47-1 and (4-(aminomethyl)tetrahydro-2H-pyran-4-yl)methanol. HPLC-MS RT=3.071 min, mass calculated for formula $C_{26}H_{26}ClN_5O_5$ 523.16, observed LCMS m/z 524.62 (M+H).

Example 47-27

N-(3-tert-butyl-1-(4-chlorophenyl)-1H-pyrazol-5-yl)-2-chloro-6-((7-oxo-2-phenyl-4,7-dihydro-[1,2,4]triazolo[1,5-a]pyrimidin-5-yl)methoxy)benzamide 47-27

Compound 47-27 was synthesized according to 47-6 using 47-1 and 3-tert-butyl-1-(4-chlorophenyl)-1H-pyrazol-5-amine. HPLC-MS RT=4.996 min, mass calculated for formula $C_{32}H_{27}Cl_2N_7O_3$ 627.16, observed LCMS m/z 628.67 (M+H).

Example 47-28

2-chloro-N-((3-methyloxetan-3-yl)methyl)-6-((7-oxo-2-phenyl-4,7-dihydro-[1,2,4]triazolo[1,5-a]pyrimidin-5-yl)methoxy)benzamide

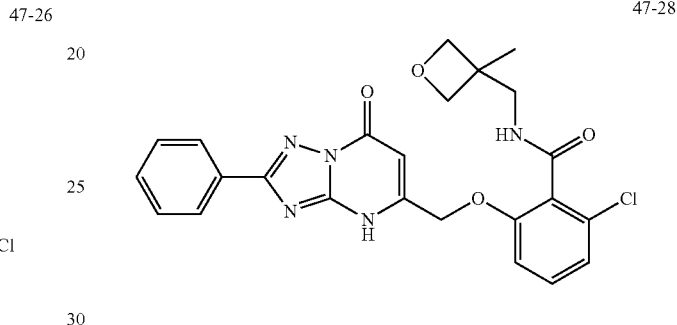

47-28

Compound 47-28 was synthesized according to 47-6 using 47-1 and (3-methyloxetan-3-yl)methanamine. HPLC-MS RT=2.756 min, mass calculated for formula $C_{24}H_{22}ClN_5O_4$ 479.14, observed LCMS m/z 480.59 (M+H).

Example 47-29

2-chloro-N-((1-(2-chlorophenyl)cyclopropyl)methyl)-6-((7-oxo-2-phenyl-4,7-dihydro-[1,2,4]triazolo[1,5-a]pyrimidin-5-yl)methoxy)benzamide

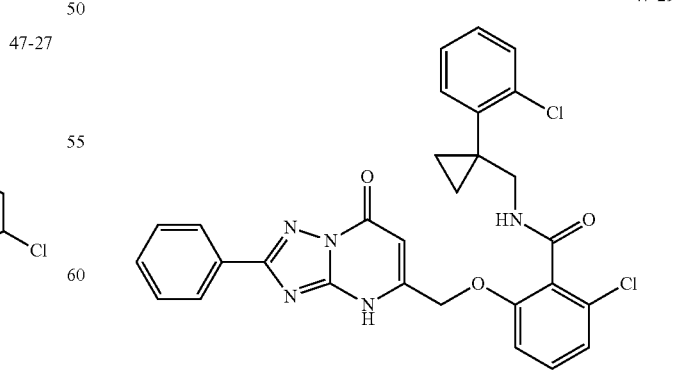

47-29

Compound 47-29 was synthesized according to 47-6 using 47-1 and (1-(2-chlorophenyl)cyclopropyl)methanamine.

HPLC-MS RT=4.774 min, mass calculated for formula $C_{29}H_{23}Cl_2N_5O_3$ 559.12, observed LCMS m/z 560.59 (M+H).

Example 47-30

2-chloro-N-((1-(hydroxymethyl)cyclobutyl)methyl)-6-((7-oxo-2-phenyl-4,7-dihydro-[1,2,4]triazolo[1,5-a]pyrimidin-5-yl)methoxy)benzamide

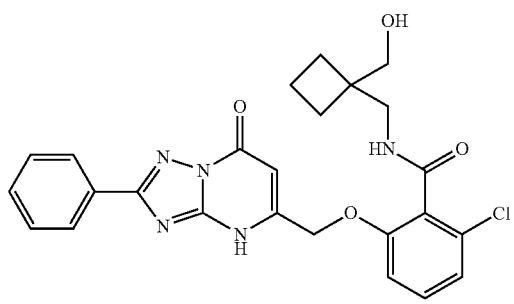

47-30

Compound 47-30 was synthesized according to 47-6 using 47-1 and (1-(aminomethyl)cyclobutyl)methanol. HPLC-MS RT=3.456 min, mass calculated for formula $C_{25}H_{24}ClN_5O_4$ 493.15, observed LCMS m/z 494.60 (M+H).

Example 47-32

2-chloro-N-(3-cyclopropyl-1H-pyrazol-5-yl)-6-((7-oxo-2-phenyl-4,7-dihydro-[1,2,4]triazolo[1,5-a]pyrimidin-5-yl)methoxy)benzamide

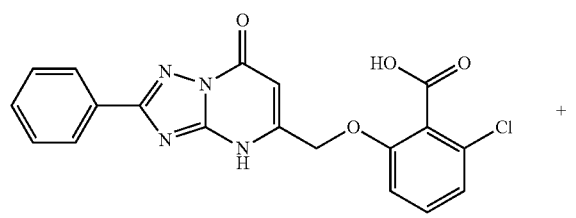

47-1

+

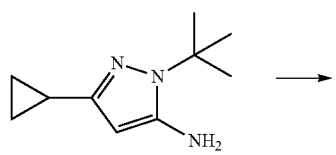

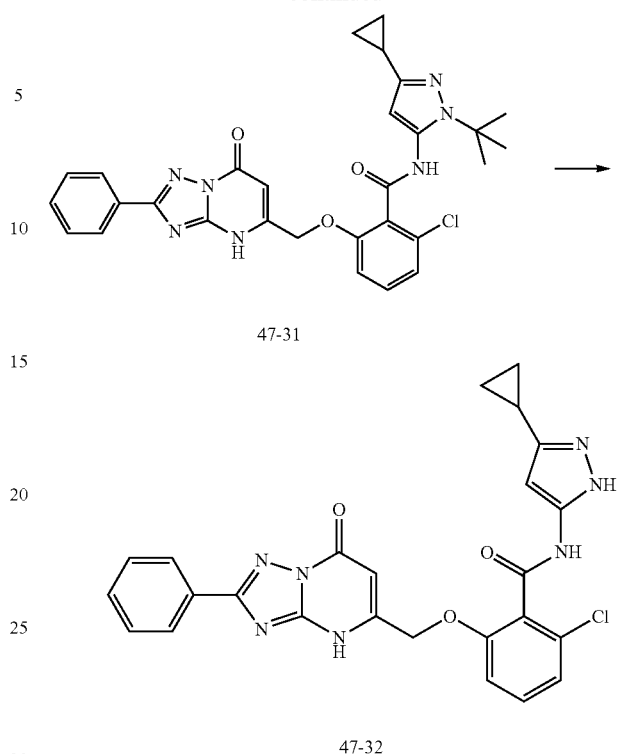

Step A: Synthesis of 1-tert-butyl-3-cyclopropyl-1H-pyrazol-5-amine 1-tert-Butyl-3-cyclopropyl-1H-pyrazol-5-amine was prepared by reacting 3-cyclopropyl-3-oxopropanenitrile (5.0 mmol, 545 mg) and tert-butylhydrazine (3.5 mmol, 440 mg) in ethanol under reflux conditions for 6 h. Solvent was removed in vacuo. $^1$H NMR (400 MHz) CDCl$_3$: 5.36 (s, 1H), 3.61 (s, 1H), 2.51-2.45 (m, 1H), 1.75 (s, 9H, t-Bu), 1.107-1.104 (m, 2H), 0.73-0.72 (m, 2H).

Step B: Synthesis of compound 47-31

1-tert-Butyl-3-cyclopropyl-1H-pyrazol-5-amine was reacted with 47-1 according to 47-6 (except the solvent was NMP at 80° C. for 18 h). Solvent was evaporated and in vacuo, then dissolved in DMSO/acetonitrile (3:1), filtered through 0.45 uM filter cartridge and purified using reverse phase HPLC to provide compound 47-31. HPLC-MS RT=4.121 min, mass calculated for formula $C_{29}H_{28}ClN_7O_3$ 557.19, observed LCMS m/z 558.01 (M+H).

Step C: Synthesis compound 47-32

Compound 47-31 was then stirred with formic acid at 90° C. for 4 h. Solvent was evaporated in vacuo, then dissolved in DMSO/acetonitrile (3:1), and purified using reverse phase HPLC to provide compound 47-32. HPLC-MS RT=4.30 min, mass calculated for formula $C_{25}H_{20}ClN_7O_3$ 501.13, observed LCMS m/z 501.88 (M+H). $^1$H NMR (400 MHz) DMSO-d$_6$: 11.06 (s, 1H), 8.15-8.12 (m, 2H), 7.59-7.54 m, 3H), 7.42 (t, J=8.4, 1H), 7.19 (d, J=8.0, 1H), 7.14 (d, J=8.8, 1H), 6.27 (s, 1H), 6.07 (s, 3H), 5.23 (s, 3H), 1.93-1.88 (m, 1H), 0.97-0.93 (m, 2H), 0.76-0.72 (m, 2H).

Example 47-33

2-chloro-N-(3-methyl-1H-pyrazol-5-yl)-64(7-oxo-2-phenyl-4,7-dihydro-[1,2,4]triazolo[1,5-a]pyrimidin-5-yl)methoxy)benzamide

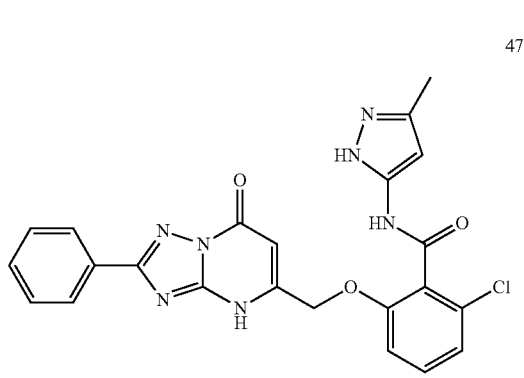

47-33

Compound 47-33 was synthesized according to 47-32 using 47-1 and 1-tert-butyl-3-methyl-1H-pyrazol-5-amine. HPLC-MS RT=4.05 min, mass calculated for formula $C_{23}H_{18}ClN_7O_3$ 475.12, observed LCMS m/z 475.99 (M+H). $^1$H NMR (400 MHz) DMSO-$d_6$: 12.0 (b, NH), 10.8 (2, 1H), 8.10-8.08 (m, 2H), 7.53-7.48 (m, 3H), 7.37-7.33 (m, 1H), 7.12 (d, J=8.4, 1H), 7.06 (d, J=8.4, 1H), 6.38 (s, 1H), 5.97 (s, 1H), 5.15 (s, 2H—CH$_2$), 2.19 (s, 3H, methyl).

Example 47-34

2-chloro-N-((3-(hydroxymethyl)oxetan-3-yl)methyl)-6-((7-oxo-2-phenyl-4,7-dihydro-[1,2,4]triazolo[1,5-a]pyrimidin-5-yl)methoxy)benzamide 47-34

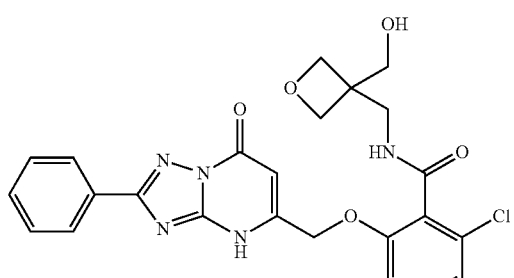

Compound 47-34 was synthesized according to 47-4 using 47-1 and (3-(aminomethyl)oxetan-3-yl)methanol. HPLC-MS RT=2.709 min, mass calculated for formula $C_{24}H_{22}ClN_5O_5$ 495.13, observed LCMS m/z 495.85 (M+H).

Example 47-35

2-chloro-N-((3-(hydroxymethyl)oxetan-3-yl)methyl)-6-((7-oxo-2-phenyl-4,7-dihydro-[1,2,4]triazolo[1,5-a]pyrimidin-5-yl)methoxy)benzamide

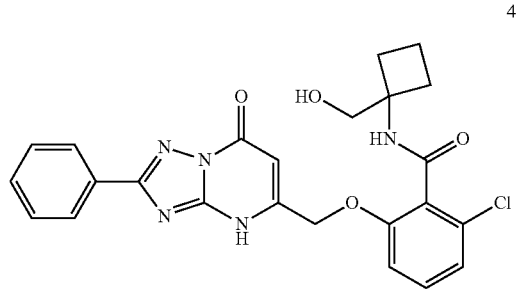

47-35

Compound 47-35 was synthesized according to 47-4 using 47-1 and (1-aminocyclobutyl)methanol. HPLC-MS RT=4.051 min, mass calculated for formula $C_{24}H_{22}ClN_5O_4$ 479.14, observed LCMS m/z 479.88 (M+H).

Example 47-36

2-chloro-N-(1-cyclobutylethyl)-6-(7-oxo-2-phenyl-4,7-dihydro-[1,2,4]triazolo[1,5-a]pyrimidin-5-yl)methoxy)benzamide

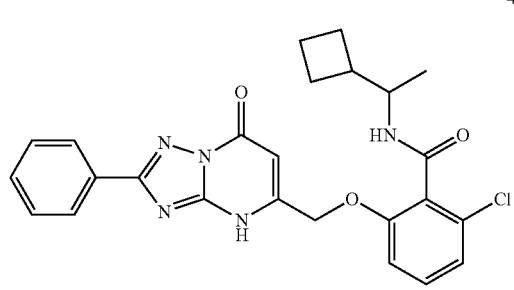

47-36

Compound 47-36 was synthesized according to 47-4 using 47-1 and 1-cyclobutylethanamine. HPLC-MS RT=5.124 min, mass calculated for formula 477.16, observed LCMS m/z 477.87 (M+H).

Example 47-37

2-chloro-N-((1-(3-chlorophenyl)cyclobutyl)methyl)-6-((7-oxo-2-phenyl-4,7-dihydro-[1,2,4]triazolo[1,5-a]pyrimidin-5-yl)methoxy)benzamide

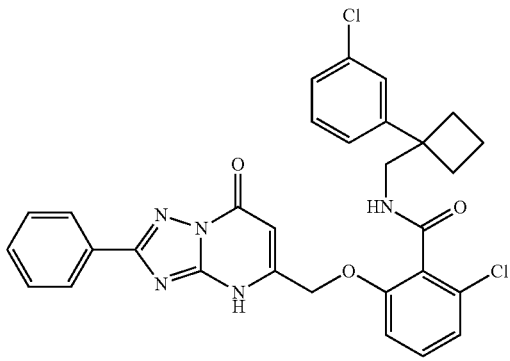

47-37

Compound 47-37 was synthesized according to 47-4 using 47-1 and (1-(3-chlorophenyl)cyclobutyl)methanamine. HPLC-MS RT=5.918 min, mass calculated for formula 573.13, observed LCMS m/z 573.89 (M+H).

Example 47-38

2-chloro-N-((1-(3-methoxyphenyl)cyclobutyl)methyl)-6-((7-oxo-2-phenyl-4,7-dihydro-[1,2,4]triazolo[1,5-a]pyrimidin-5-yl)methoxy)benzamide

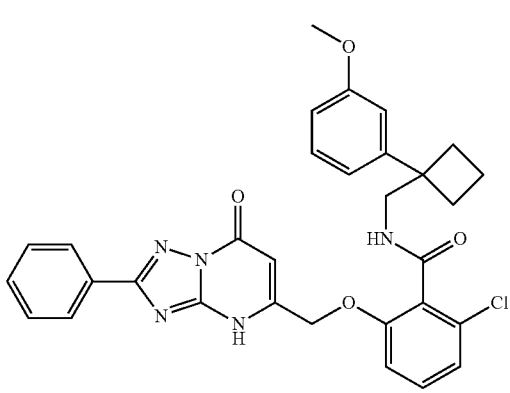

47-38

Compound 47-38 was synthesized according to 47-4 using 47-1 and (1-(3-methoxyphenyl)cyclobutyl)methanamine. HPLC-MS RT=5.603 min, mass calculated for formula $C_{31}H_{28}ClN_5O_4$ 569.18, observed LCMS m/z 569.98 (M+H).

Example 47-39

(R)-5-((3-chloro-2-(2-(2-hydroxyethyl)piperidine-1-carbonyl)phenoxy)methyl)-2-phenyl-[1,2,4]triazolo[1,5-a]pyrimidin-7(4H)-one

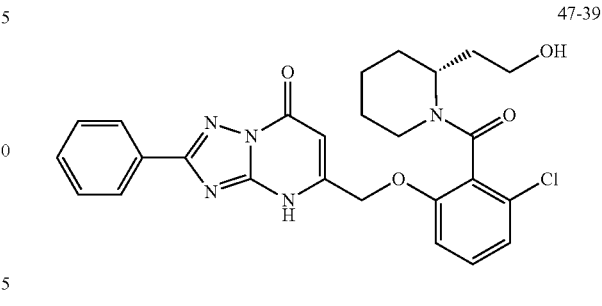

47-39

Compound 47-39 was synthesized according to 47-4 using 47-1 and (R)-2-(piperidin-2-yl)ethanol. HPLC-MS RT=5.603 min, mass calculated for formula $C_{31}H_{28}ClN_5O_4$ 569.18, observed LCMS m/z 569.98 (M+H). $^1$H NMR (400 MHz) DMSO: 8.07-8.04 (m, 2H), 7.49-7.47 (m, 3H), 7.36-7.32 (m, 1H), 7.12-7.08 (m, 2H), 6.00 (s, 1H), 5.03 (d, J=8, 2H), 3.30-3.02 (m, 5H), 1.52-1.44 (m, 8H).

Example 47-40

2-chloro-N-(1-methyl-1H-pyrazol-3-yl)-6-(7-oxo-2-phenyl-4,7-dihydro-[1,2,4]triazolo[1,5-a]pyrimidin-5-yl)methoxy)benzamide

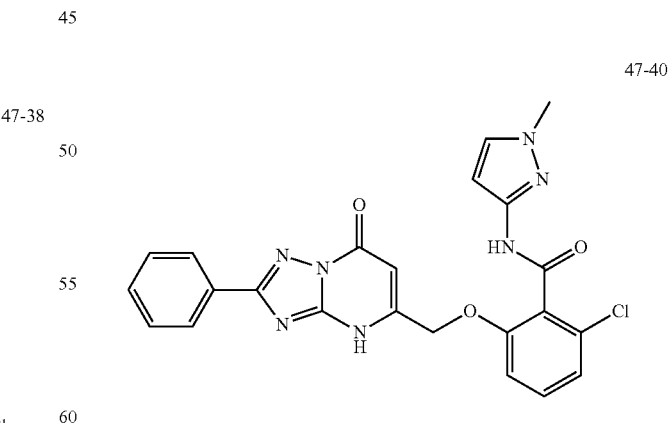

47-40

Compound 47-40 was synthesized according to 47-2 using 47-1 and 1-methyl-1H-pyrazol-3-amine. HPLC-MS RT=3.363 min, mass calculated for formula $C_{23}H_{18}ClN_7O_3$ 475.12, observed LCMS m/z 476.53 (M+H).

The following compounds may be synthesized using this procedure:

| ID | Structure | EMW | MS m/z (M⁺ + H) | Retention Time (min) |
|---|---|---|---|---|
| 47-46 | 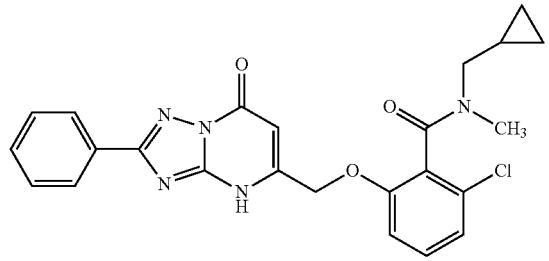 | 463.1414 | 464.92 | 4.15 |
| 47-47 | 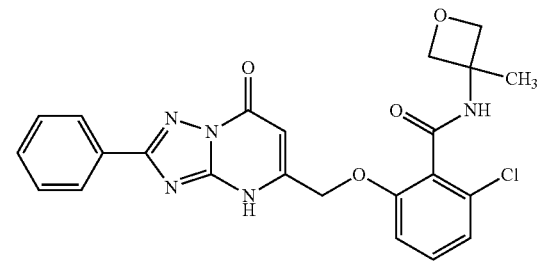 | 465.1206 | 466.89 | 3.24 |
| 47-48 | 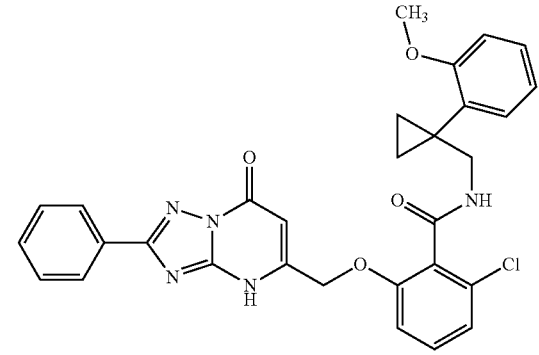 [SMILES: COc1ccccc1C1(CNC(=O)c2c(Cl)cccc2OCc2cc(=O)n3nc(-c4ccccc4)nc3[nH]2)CC1] | 555.1676 | 557.01 | 4.52 |
| 47-49 | 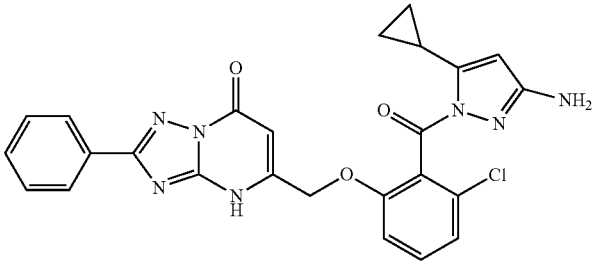 | 501.1319 | 502.92 | 3.64 |
| 47-50 | 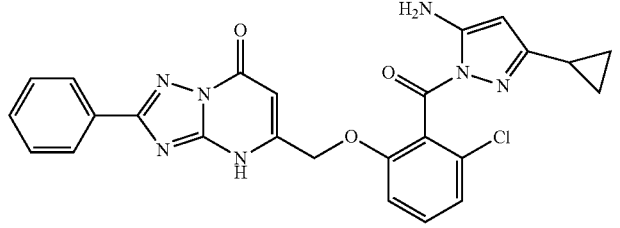 | 501.1319 | 502.92 | 4.03 |

| ID | Structure | EMW | MS m/z (M⁺ + H) | Retention Time (min) |
|---|---|---|---|---|
| 47-51 | 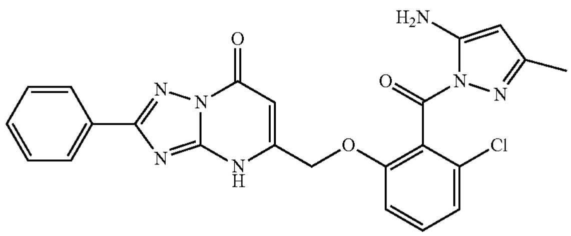 | 475.1162 | 476.89 | 3.28 |
| 47-52 | 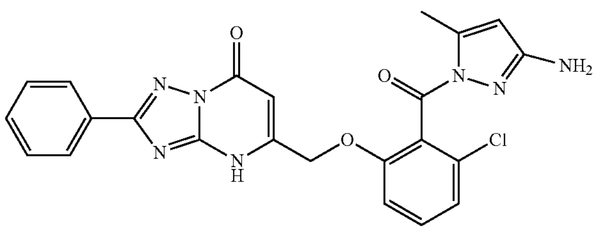 | 475.1162 | 476.89 | 3.71 |
| 47-53 | 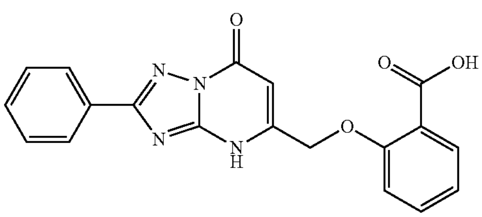 | 362.1016 | 363.34 | 3.26 |
| 47-54 | 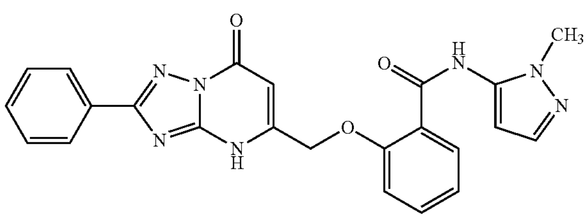 | 441.1552 | 442.44 | 3.22 |
| 47-55 | 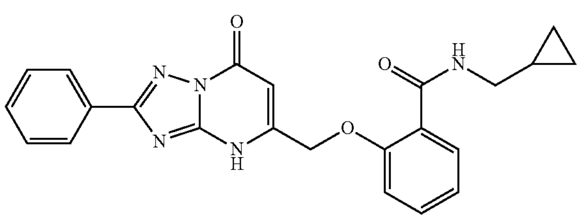 | 415.1646 | 416.45 | 3.75 |
| 47-56 | 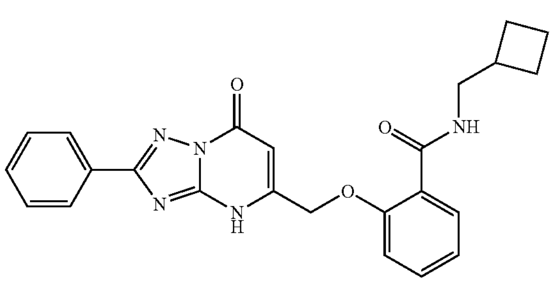 | 429.1803 | 430.47 | 4.04 |

-continued

| ID | Structure | EMW | MS m/z (M⁺ + H) | Retention Time (min) |
|---|---|---|---|---|
| 47-57 | 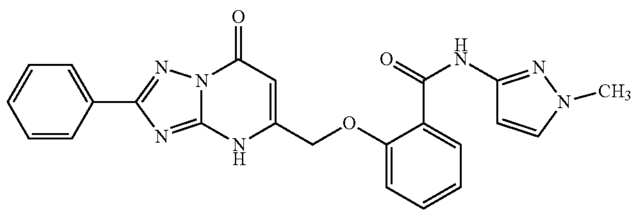 | 441.1552 | 442.44 | 3.42 |
| 47-58 | 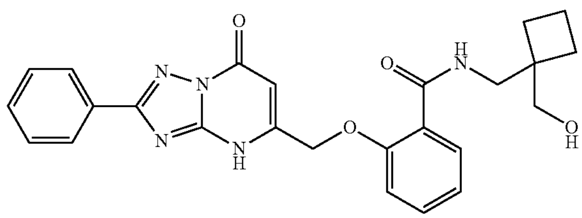 | 459.1909 | 460.50 | 3.44 |
| 47-59 | 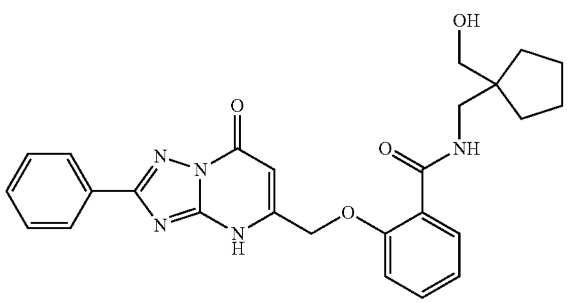 | 473.2065 | 474.52 | 3.62 |
| 47-60 | 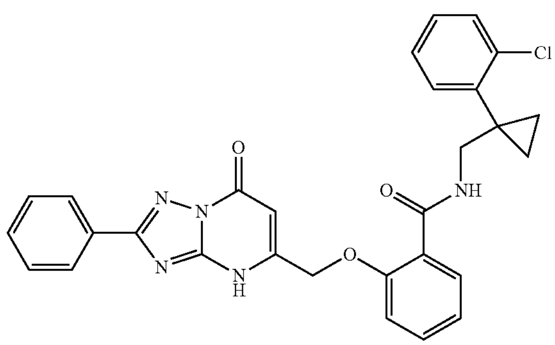 | 525.157 | 526.99 | 4.52 |
| 47-61 | 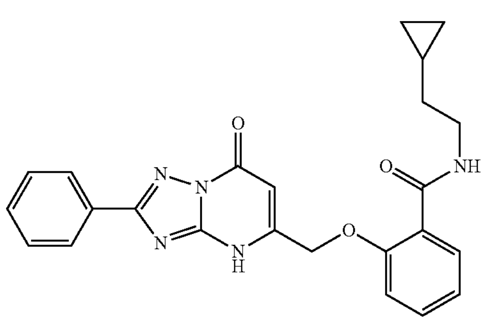 | 429.1803 | 430.47 | 3.82 |

-continued
| ID | Structure | EMW | MS m/z (M+ + H) | Retention Time (min) |
|---|---|---|---|---|
| 47-62 | 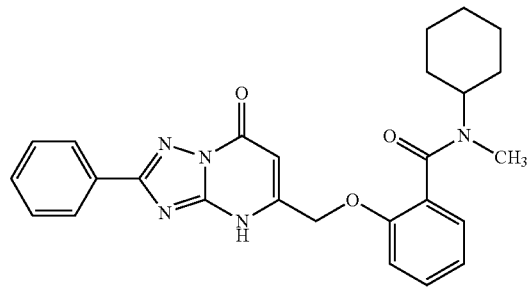 | 457.2116 | 458.52 | 4.34 |
| 47-63 | 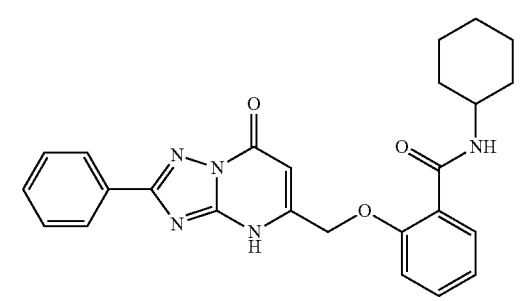 | 443.196 | 444.50 | 3.99 |
| 47-64 | 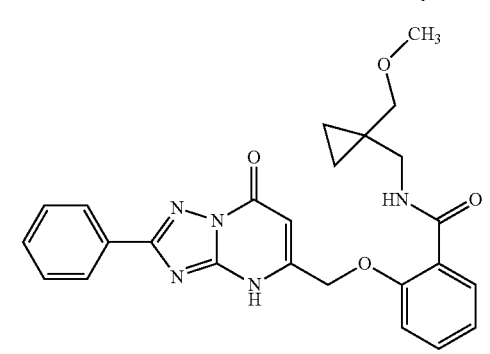 | 459.1909 | 460.50 | 3.55 |
| 47-65 | 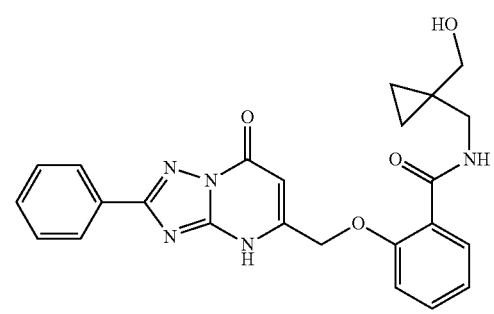 | 445.1752 | 446.47 | 3.1 |
Example 48
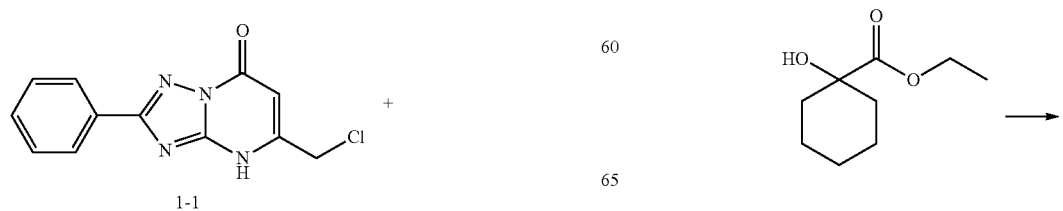
-continued

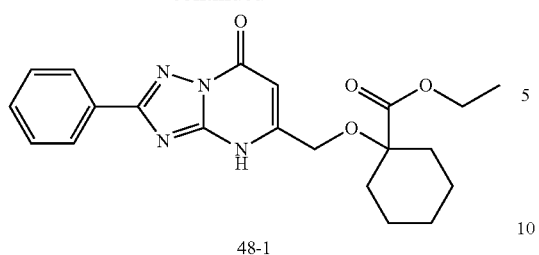

48-1

To the solution of ethyl 1-hydroxycyclohexanecarboxylate (660.66 mg, 3.8361 mmol) in DMF (10 mL) in a Biotage microwave vial was added sodium hydride (60% in paraffin oil, 368.23 mg, 15.344 mmol). The reaction mixture was stirred at RT for few minutes compound 1-1 (1 g, 3.836 mmol) was added. The resulting mixture was purged under nitrogen then heated in microwave on 300 watts, 200° C. for 20 min. The compound 48-1 was dried and the crude material was purified by chromatography on silica gel 30% EtOAc/Hex to afford 0.5 g of 48-1 (yield 33%).

Example 48-2

1-((7-oxo-2-phenyl-4,7-dihydro-[1,2,4]triazolo[1,5-a]pyrimidin-5-yl)methoxy)cyclohexanecarboxylic acid

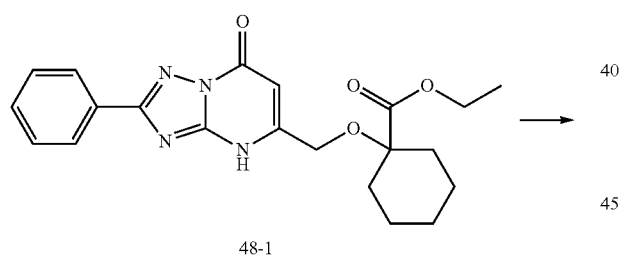

Compound 48-1 (1 equiv.) was dissolved up into ethanol (5 mL) and 2 M KOH, the resulting mixture was stirred for 1 h. at room temperature. Acetic acid was used to adjust the pH to 5. Ethyl acetate was used to extract the product from the aqueous layer. The organic layer was concentrated and the residue was crystallized to afford compound 48-2 (300 mg, 64% yield).

Example 48-4

4-[[1-[(4,7-dihydro-7-oxo-2-phenyl[1,2,4]triazolo[1,5-a]pyrimidin-5-yl)methoxy]cyclohexyl]carbonyl]thiomorpholine, 1,1-dioxide

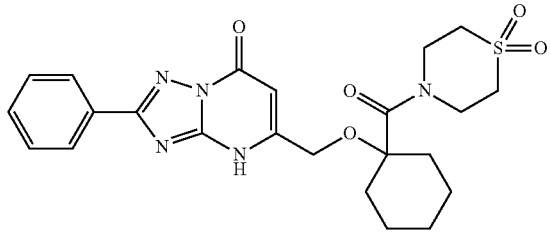

Compound 48-4 was synthesized according to 47-6 using 48-2 and thiomorpholine 1,1-dioxide. HPLC-MS RT=3.503 min, mass calculated for formula $C_{23}H_{27}N_5O_5S$ 485.17, observed LCMS m/z 486.60 (M+H).

Example 48-5

(S)-5-((1-(2-(methoxymethyl)pyrrolidine-1-carbonyl)cyclohexyloxy)methyl)-2-phenyl-[1,2,4]triazolo[1,5-a]pyrimidin-7(4H)-one

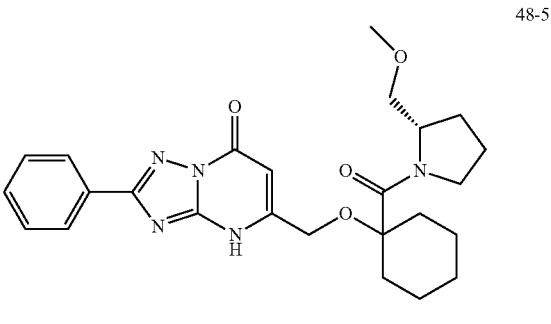 [SMILES: COC[C@@H]1CCCN1C(=O)C1(OCc2cc(=O)n3nc(-c4ccccc4)nc3[nH]2)CCCCC1]

Compound 48-5 was synthesized according to 47-6 using 48-2 and (S)-2-(methoxymethyl)pyrrolidine. HPLC-MS RT=4.214 min, mass calculated for formula $C_{25}H_{31}N_5O_4$ 465.24, observed LCMS m/z 466.69 (M+H).

Example 48-6

(R)-5-((1-(2-(methoxymethyl)pyrrolidine-1-carbonyl)cyclohexyloxy)methyl)-2-phenyl-[1,2,4]triazolo[1,5-a]pyrimidin-7(4H)-one

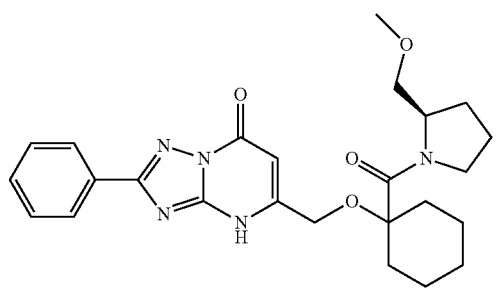

48-6

Compound 48-6 was synthesized according to 47-6 using 48-2 and (R)-2-(methoxymethyl)pyrrolidine. HPLC-MS RT=4.227 min, mass calculated for formula $C_{25}H_{31}N_5O_4$ 465.24, observed LCMS m/z 466.70 (M+H).

Example 48-7

5-((1-((1S,2S,5R)-2-(hydroxymethyl)-3-azabicyclo[3.1.0]hexane-3-carbonyl)cyclohexyloxy)methyl)-2-phenyl-[1,2,4]triazolo[1,5-a]pyrimidin-7(4H)-one

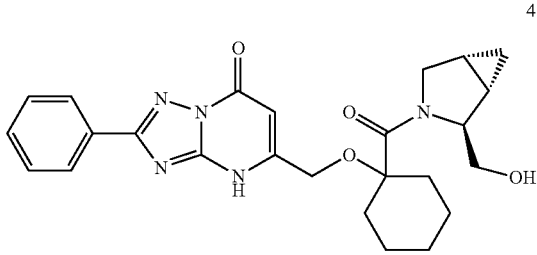

48-7

Compound 48-7 was synthesized according to 47-6 using 48-2 and (1S,2S,5R)-3-azabicyclo[3.1.0]hexan-2-ylmethanol. HPLC-MS RT=3.223 min, mass calculated for formula $C_{25}H_{29}N_5O_4$ 463.22, observed LCMS m/z 464.69 (M+H).

Example 48-8

N-(1-(2-chlorophenyl)cyclopropyl)-1-(7-oxo-2-phenyl-4,7-dihydro-[1,2,4]triazolo[1,5-a]pyrimidin-5-yl)methoxy)cyclohexanecarboxamide

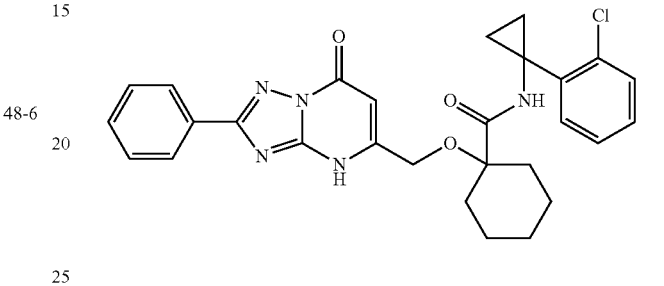

48-8

Compound 48-8 was synthesized according to 47-6 using 48-2 and 1-(2-chlorophenyl)cyclopropanamine hydrochloride. HPLC-MS RT=4.69 min, mass calculated for formula $C_{28}H_{28}ClN_5O_3$ 517.19, observed LCMS m/z 518.1.

Example 48-9

N-(1-(3-chlorophenyl)cyclopropyl)-1-((7-oxo-2-phenyl-4,7-dihydro-[1,2,4]triazolo[1,5-a]pyrimidin-5-yl)methoxy)cyclohexanecarboxamide


48-9

Compound 48-9 was synthesized according to 47-6 using 48-2 and 1-(3-chlorophenyl)cyclopropanamine hydrochloride. HPLC-MS RT=5.70 min, mass calculated for formula $C_{28}H_{28}ClN_5O_3$ 517.19, observed LCMS m/z 518.1.

Example 48-10

N-(1-(3-chloro-2-fluorophenyl)cyclopropyl)-1-(7-oxo-2-phenyl-4,7-dihydro-[1,2,4]triazolo[1,5-a]pyrimidin-5-yl)methoxy)cyclohexanecarboxamide

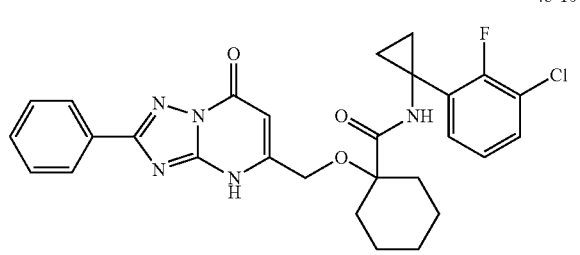

48-10

Compound 48-10 was synthesized according to 47-6 using 48-2 and 1-(3-chloro-2-fluorophenyl)cyclopropanamine. HPLC-MS RT=4.76 min, mass calculated for formula $C_{28}H_{27}ClFN_5O_3$ 535.18, observed LCMS m/z 536.

Example 48-11

N-(1-(hydroxymethyl)cyclobutyl)methyl)-1-((7-oxo-2-phenyl-4,7-dihydro-[1,2,4]triazolo[1,5-a]pyrimidin-5-yl)methoxy)cyclohexanecarboxamide

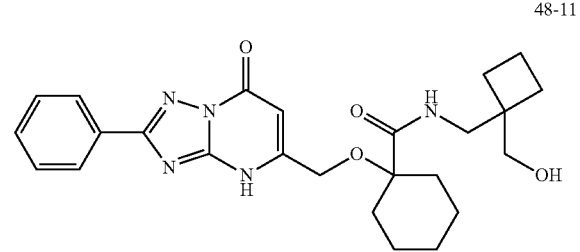 [SMILES: O=C(NCC1(CO)CCC1)C1(OCc2cc(=O)n3nc(-c4ccccc4)nc3[nH]2)CCCCC1]

48-11

Compound 48-11 was synthesized according to 47-6 using 48-2 and (1-(aminomethyl)cyclobutyl)methanol. HPLC-MS RT=3.88 min, mass calculated for formula $C_{25}H_{31}N_5O_4$ 465.24, observed LCMS m/z 466.

Example 48-12

N-((1-(2-methoxyphenyl)cyclopropyl)methyl)-1-((7-oxo-2-phenyl-4,7-dihydro-[1,2,4]triazolo[1,5-a]pyrimidin-5-yl)methoxy)cyclohexanecarboxamide

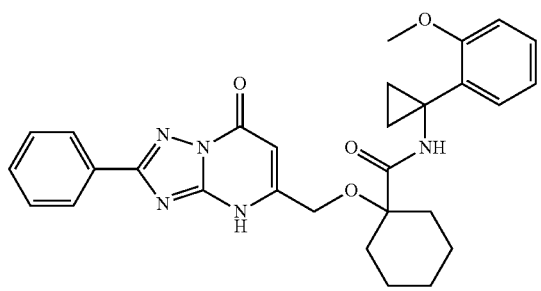

48-12

Compound 48-12 was synthesized according to 47-6 using 48-2 and (1-(2-methoxyphenyl)cyclopropyl)methanamine. HPLC-MS RT=3.44 min, mass calculated for formula $C_{30}H_{33}N_5O_4$ 527.25, observed LCMS m/z 528.

Example 48-13

N-(1-(2-methoxyphenyl)cyclopropyl)-1-((7-oxo-2-phenyl-4,7-dihydro-[1,2,4]triazolo[1,5-a]pyrimidin-5-yl)methoxy)cyclohexanecarboxamide

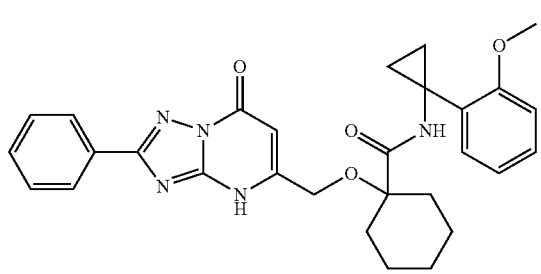

48-13

Compound 48-13 was synthesized according to 47-6 using 48-2 and 1-(2-methoxyphenyl)cyclopropanamine hydrochloride. HPLC-MS RT=5.06 min, mass calculated for formula $C_{29}H_{31}N_5O_4$ 513.24, observed LCMS m/z 514.

Example 48-14

N-((1-(2-chlorophenyl)cyclopropyl)methyl)-1-((7-oxo-2-phenyl-4,7-dihydro-[1,2,4]triazolo[1,5-a]pyrimidin-5-yl)methoxy)cyclohexanecarboxamide

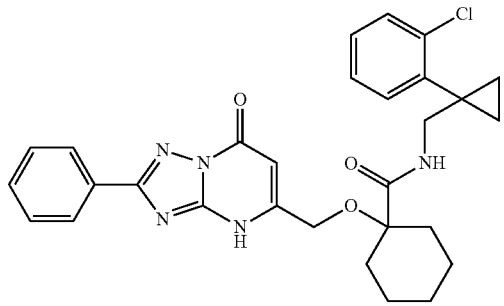

48-14

Compound 48-14 was synthesized according to 47-6 using 48-2 and [1-(2-chloro-phenyl)-cyclopropyl]-methylamine hydrochloride. HPLC-MS RT=4.88 min, mass calculated for formula $C_{29}H_{30}ClN_5O_3$ 531.20, observed LCMS m/z 532.

Example 48-15

N-((1-(hydroxymethyl)cyclopentyl)methyl)-1-((7-oxo-2-phenyl-4,7-dihydro-[1,2,4]triazolo[1,5-a]pyrimidin-5-yl)methoxy)cyclohexanecarboxamide

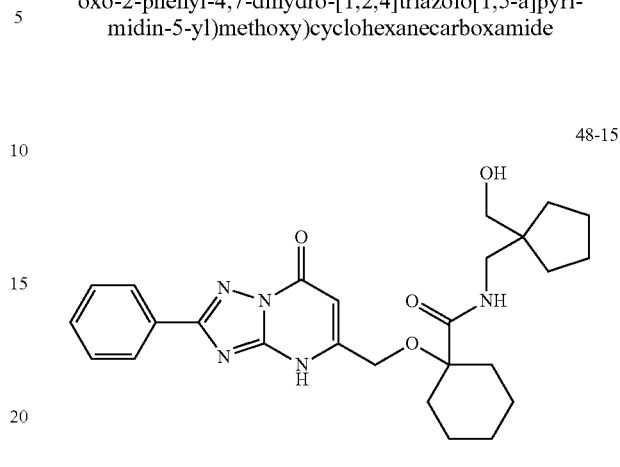

48-15

Compound 48-15 was synthesized according to 47-6 using 48-2 and (1-(aminomethyl)cyclopentyl)methanol. HPLC-MS RT=5.00 min, mass calculated for formula $C_{26}H_{33}N_5O_4$ 479.25, observed LCMS m/z 480.

The following compounds were synthesized using the procedure:

| ID | Structure | EMW | MS m/z (M⁺ + H) | Retention Time (min) |
|---|---|---|---|---|
| 48-16 | 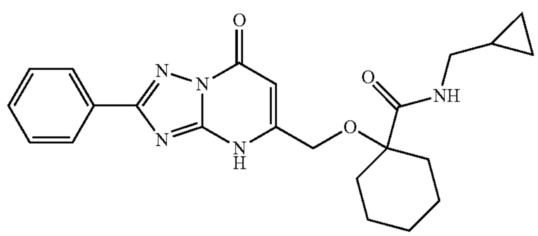 | 421.2116 | 422.49 | 4.59 |
| 48-17 | 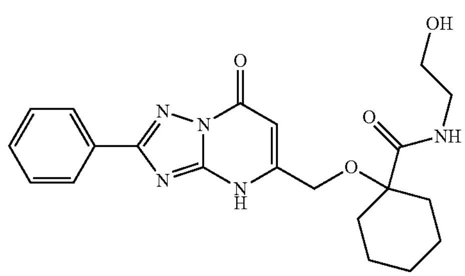 | 411.1909 | 412.45 | 3.64 |
| 48-18 | 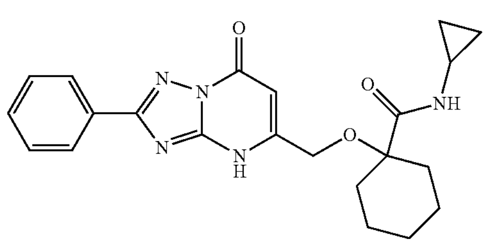 [SMILES: O=C(NC1CC1)C1(OCc2cc(=O)n3nc(-c4ccccc4)nc3[nH]2)CCCCC1] | 407.196 | 408.47 | 3.9 |

-continued

| ID | Structure | EMW | MS m/z (M⁺ + H) | Retention Time (min) |
|---|---|---|---|---|
| 48-19 | 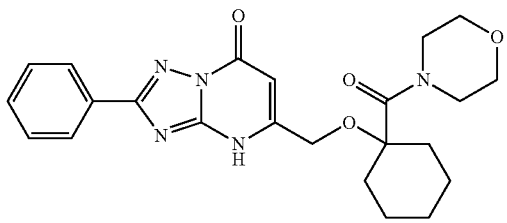 [SMILES: O=C(N1CCOCC1)C1(OCc2cc(=O)n3nc(-c4ccccc4)nc3[nH]2)CCCCC1] | 437.2065 | 438.49 | 3.76 |
| 48-20 | 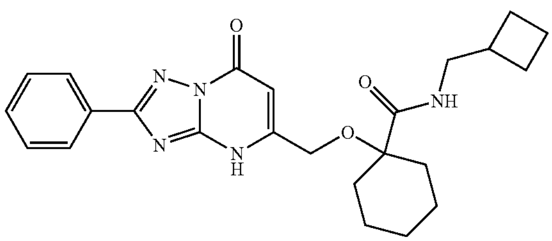 [SMILES: O=C(NCC1CCC1)C1(OCc2cc(=O)n3nc(-c4ccccc4)nc3[nH]2)CCCCC1] | 435.2273 | 436.52 | 4.52 |
| 48-21 | 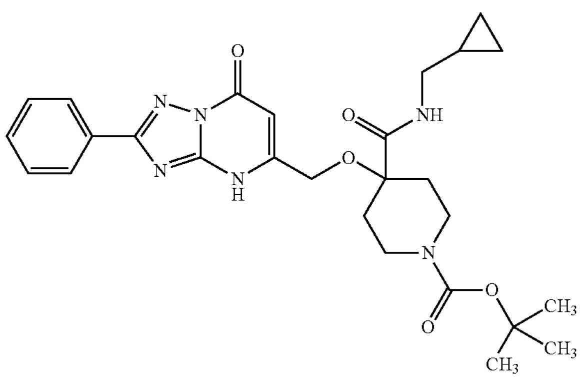 [SMILES: CC(C)(C)OC(=O)N1CCC(OCc2cc(=O)n3nc(-c4ccccc4)nc3[nH]2)(C(=O)NCC2CC2)CC1] | 522.2593 | 523.60 | 4.37 |
| 48-22 | 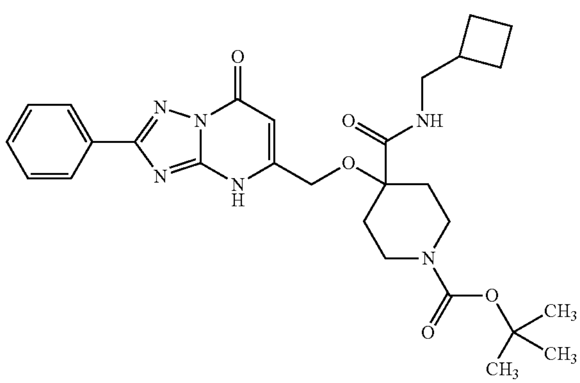 [SMILES: CC(C)(C)OC(=O)N1CCC(OCc2cc(=O)n3nc(-c4ccccc4)nc3[nH]2)(C(=O)NCC2CCC2)CC1] | 536.275 | 537.62 | 3.34 |
| 48-23 | 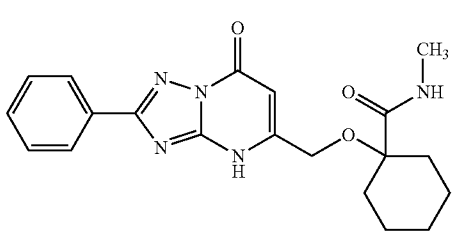 [SMILES: CNC(=O)C1(OCc2cc(=O)n3nc(-c4ccccc4)nc3[nH]2)CCCCC1] | 381.1803 | 382.43 | 3.57 |

-continued
| ID | Structure | EMW | MS m/z (M+ + H) | Retention Time (min) |
|---|---|---|---|---|
| 48-24 | 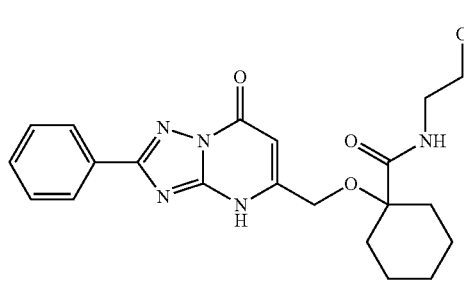 | 425.2065 | 426.48 | 3.73 |
| 48-25 | 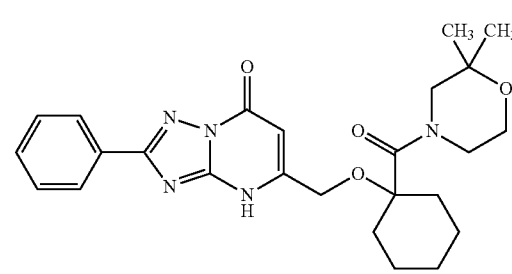 | 465.2378 | 466.55 | 4.05 |
| 48-26 | 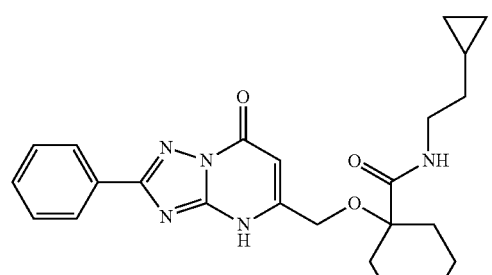 | 435.2273 | 436.52 | 4.4 |
| 48-27 | 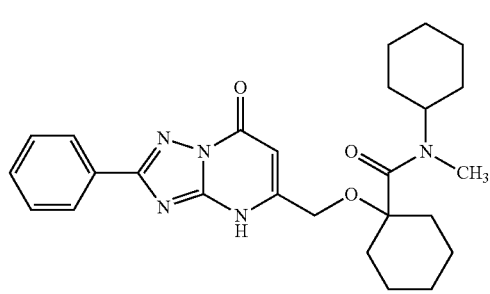 [SMILES: CN(C(=O)C1(OCc2cc(=O)n3nc(-c4ccccc4)nc3[nH]2)CCCCC1)C1CCCCC1] | 463.2586 | 464.57 | 4.69 |
| 48-28 | 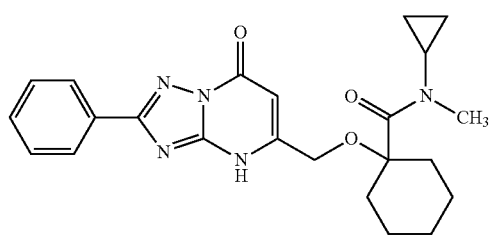 [SMILES: CN(C(=O)C1(OCc2cc(=O)n3nc(-c4ccccc4)nc3[nH]2)CCCCC1)C1CC1] | 421.2116 | 422.49 | 4.07 |

-continued

| ID | Structure | EMW | MS m/z (M⁺ + H) | Retention Time (min) |
|---|---|---|---|---|
| 48-29 | 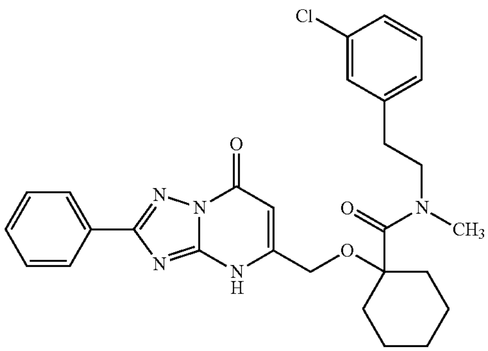 [SMILES: CN(CCc1cccc(Cl)c1)C(=O)C1(OCc2cc(=O)n3nc(-c4ccccc4)nc3[nH]2)CCCCC1] | 519.204 | 521.02 | 5.02 |
| 48-30 | 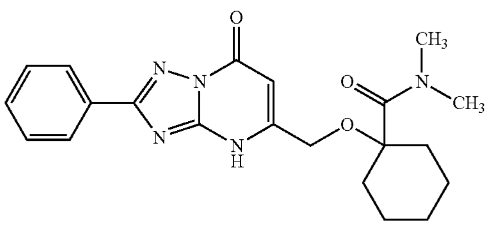 [SMILES: CN(C)C(=O)C1(OCc2cc(=O)n3nc(-c4ccccc4)nc3[nH]2)CCCCC1] | 395.196 | 396.46 | 3.79 |
| 48-31 | 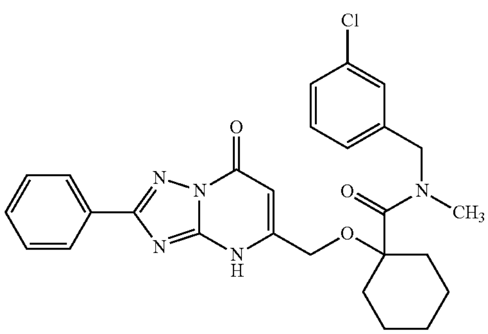 [SMILES: CN(Cc1cccc(Cl)c1)C(=O)C1(OCc2cc(=O)n3nc(-c4ccccc4)nc3[nH]2)CCCCC1] | 505.1883 | 507.00 | 4.82 |
| 48-32 | 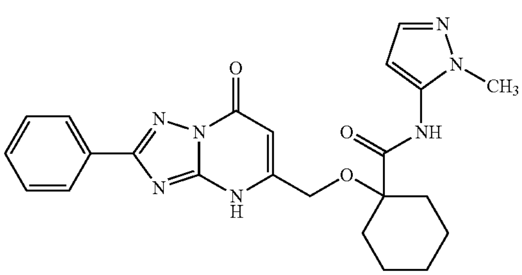 [SMILES: Cn1nccc1NC(=O)C1(OCc2cc(=O)n3nc(-c4ccccc4)nc3[nH]2)CCCCC1] | 447.2022 | 448.49 | 3.62 |
| 48-33 | 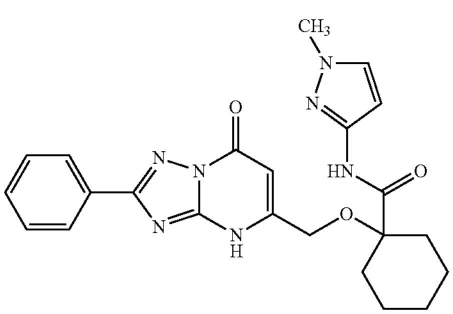 [SMILES: Cn1ccc(NC(=O)C2(OCc3cc(=O)n4nc(-c5ccccc5)nc4[nH]3)CCCCC2)n1] | 447.2022 | 448.49 | 4.88 |

-continued
| ID | Structure | EMW | MS m/z (M⁺ + H) | Retention Time (min) |
|---|---|---|---|---|
| 48-34 | 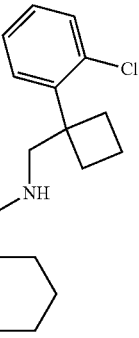 | 545.2197 | 547.06 | 3.75 |
| 48-35 | 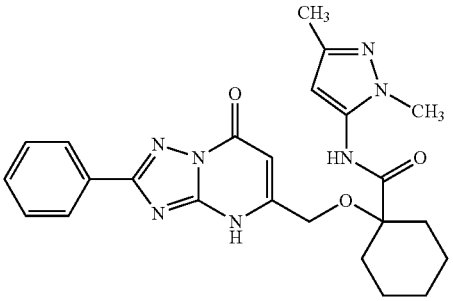 [SMILES: Cc1cc(NC(=O)C2(OCc3cc(=O)n4nc(-c5ccccc5)nc4[nH]3)CCCCC2)n(C)n1] | 461.2178 | 462.52 | 3.7 |
| 48-36 | 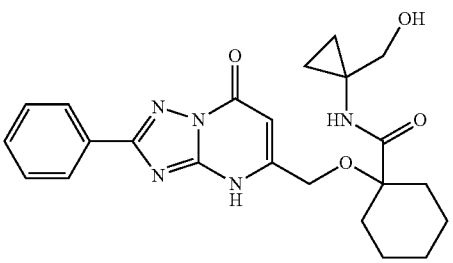 [SMILES: O=C(NC1(CO)CC1)C1(OCc2cc(=O)n3nc(-c4ccccc4)nc3[nH]2)CCCCC1] | 437.2065 | 438.49 | 3.88 |
| 48-37 | 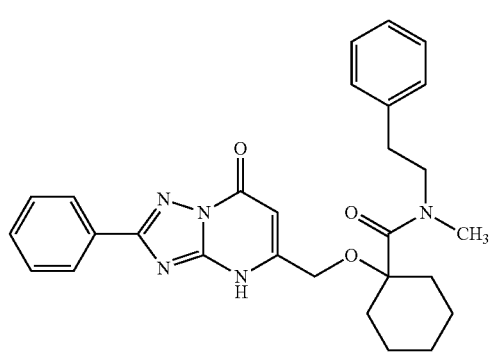 [SMILES: CN(CCc1ccccc1)C(=O)C1(OCc2cc(=O)n3nc(-c4ccccc4)nc3[nH]2)CCCCC1] | 485.2429 | 486.58 | 3.51 |
| 48-38 | 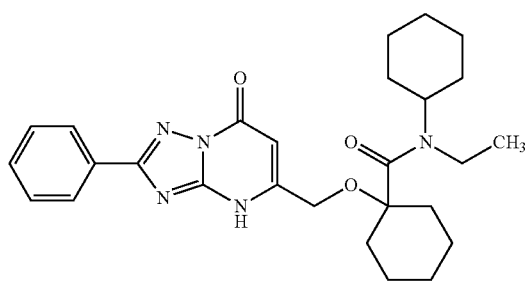 [SMILES: CCN(C(=O)C1(OCc2cc(=O)n3nc(-c4ccccc4)nc3[nH]2)CCCCC1)C1CCCCC1] | 477.2743 | 478.60 | 4.72 |

-continued
| ID | Structure | EMW | MS m/z (M⁺ + H) | Retention Time (min) |
|---|---|---|---|---|
| 48-39 | 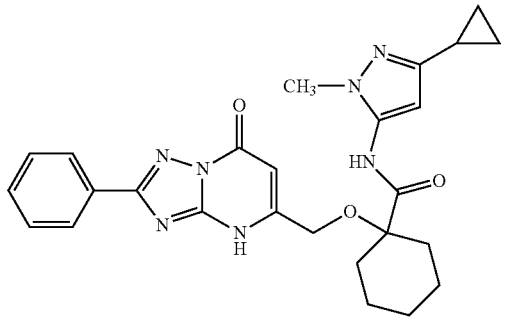 [SMILES: Cn1nc(C2CC2)cc1NC(=O)C1(OCc2cc(=O)n3nc(-c4ccccc4)nc3[nH]2)CCCCC1] | 487.2335 | 488.55 | 3.98 |
| 48-40 | 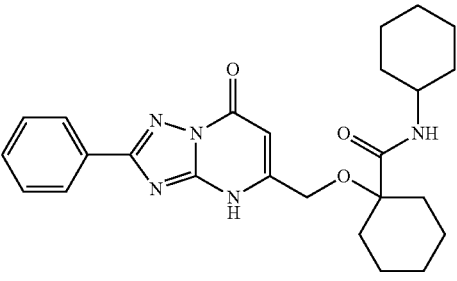 [SMILES: O=C(NC1CCCCC1)C1(OCc2cc(=O)n3nc(-c4ccccc4)nc3[nH]2)CCCCC1] | 449.2429 | 450.55 | 4.61 |
| 48-41 | 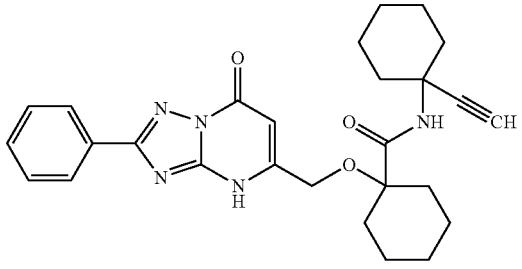 [SMILES: C#CC1(NC(=O)C2(OCc3cc(=O)n4nc(-c5ccccc5)nc4[nH]3)CCCCC2)CCCCC1] | 473.2429 | 474.57 | 4.65 |
| 48-42 | 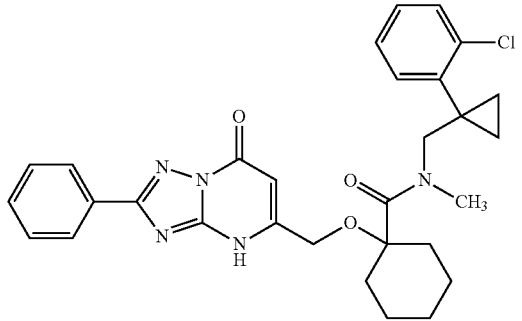 [SMILES: CN(CC1(c2ccccc2Cl)CC1)C(=O)C1(OCc2cc(=O)n3nc(-c4ccccc4)nc3[nH]2)CCCCC1] | 545.2197 | 547.06 | 5.2 |
| 48-43 | 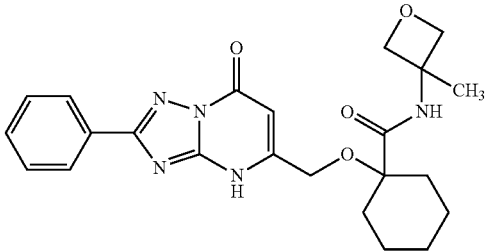 [SMILES: CC1(NC(=O)C2(OCc3cc(=O)n4nc(-c5ccccc5)nc4[nH]3)CCCCC2)COC1] | 437.2065 | 438.49 | 3 |

| ID | Structure | EMW | MS m/z (M⁺ + H) | Retention Time (min) |
|---|---|---|---|---|
| 48-44 | 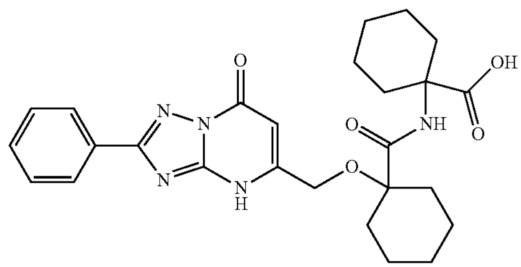 [SMILES: O=C(O)C1(NC(=O)C2(OCc3cc(=O)n4nc(-c5ccccc5)nc4[nH]3)CCCCC2)CCCCC1] | 493.2327 | 494.56 | 4.14 |
| 48-45 | 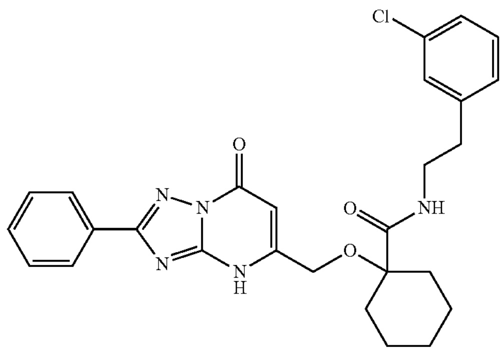 [SMILES: O=C(NCCc1cccc(Cl)c1)C1(OCc2cc(=O)n3nc(-c4ccccc4)nc3[nH]2)CCCCC1] | 505.1883 | 507.00 | 4.69 |
| 48-46 | 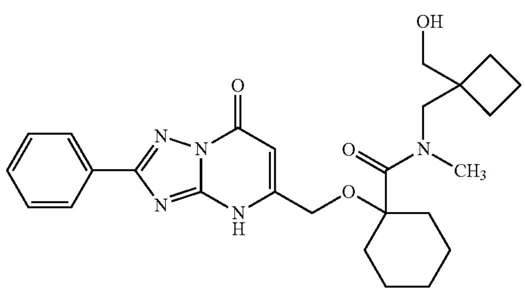 [SMILES: CN(CC1(CO)CCC1)C(=O)C1(OCc2cc(=O)n3nc(-c4ccccc4)nc3[nH]2)CCCCC1] | 479.2535 | 480.57 | 5 |
| 48-47 | 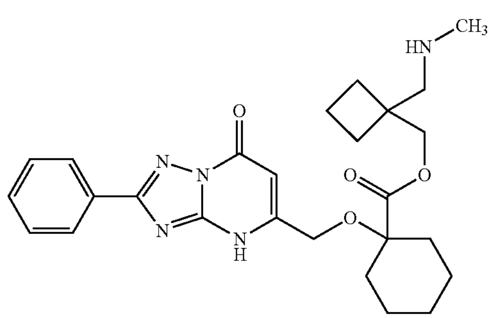 [SMILES: CNCC1(COC(=O)C2(OCc3cc(=O)n4nc(-c5ccccc5)nc4[nH]3)CCCCC2)CCC1] | 479.2535 | 480.57 | 5.1 |
| 48-48 | 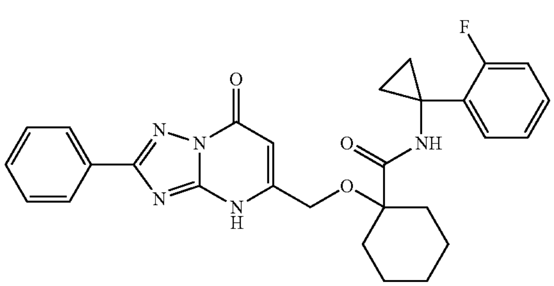 [SMILES: O=C(NC1(c2ccccc2F)CC1)C1(OCc2cc(=O)n3nc(-c4ccccc4)nc3[nH]2)CCCCC1] | 501.2178 | 502.55 | 5.47 |

-continued

| ID | Structure | EMW | MS m/z (M+ + H) | Retention Time (min) |
|---|---|---|---|---|
| 48-49 | 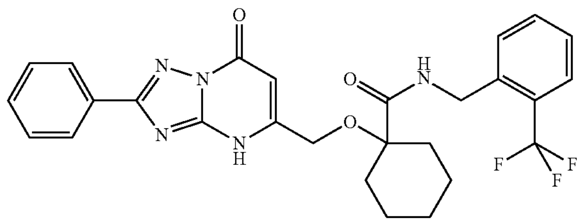 [SMILES: O=C(NCc1ccccc1C(F)(F)F)C1(OCc2cc(=O)n3nc(-c4ccccc4)nc3[nH]2)CCCCC1] | 525.199 | 526.52 | 4.73 |
| 48-50 | 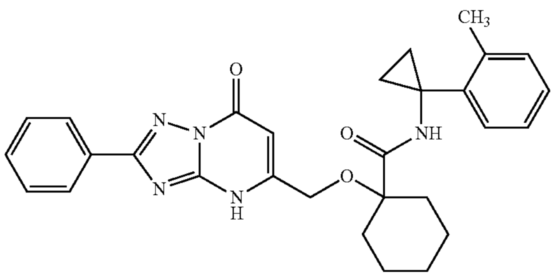 | 497.2429 | 498.59 | 5.69 |
| 48-51 | 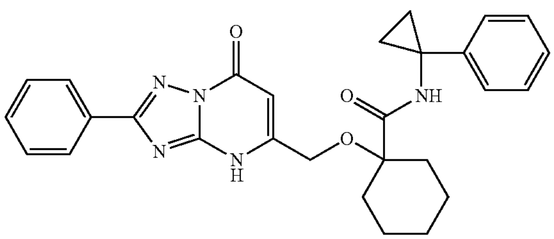 [SMILES: O=C(NC1(c2ccccc2)CC1)C1(OCc2cc(=O)n3nc(-c4ccccc4)nc3[nH]2)CCCCC1] | 483.2273 | 484.56 | 4.51 |
| 48-52 | 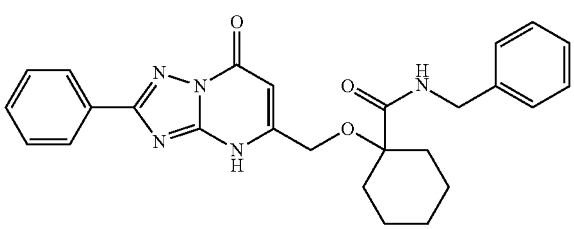 [SMILES: O=C(NCc1ccccc1)C1(OCc2cc(=O)n3nc(-c4ccccc4)nc3[nH]2)CCCCC1] | 457.2116 | 458.52 | 4.29 |
| 48-53 | 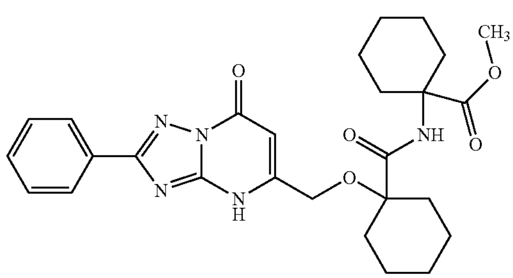 [SMILES: COC(=O)C1(NC(=O)C2(OCc3cc(=O)n4nc(-c5ccccc5)nc4[nH]3)CCCCC2)CCCCC1] | 507.2484 | 508.58 | 4.78 |
| 48-54 | 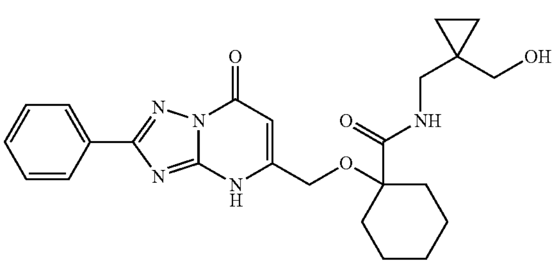 [SMILES: O=C(NCC1(CO)CC1)C1(OCc2cc(=O)n3nc(-c4ccccc4)nc3[nH]2)CCCCC1] | 451.2222 | 452.52 | 4.05 |

-continued
| ID | Structure | EMW | MS m/z (M+ + H) | Retention Time (min) |
|---|---|---|---|---|
| 48-55 | 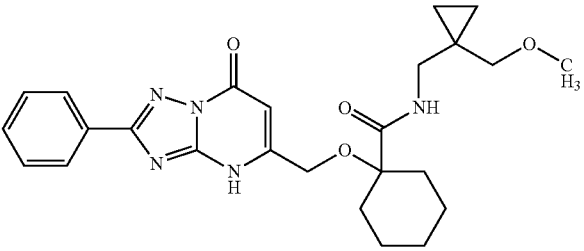 [SMILES: COCC1(CNC(=O)C2(OCc3cc(=O)n4nc(-c5ccccc5)nc4[nH]3)CCCCC2)CC1] | 465.2378 | 466.55 | 3.44 |
| 48-56 | 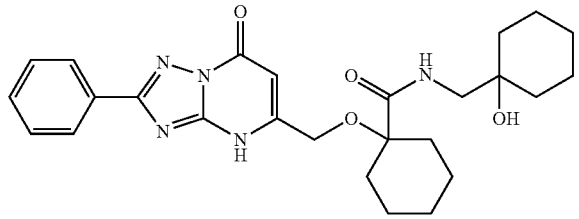 [SMILES: O=C(NCC1(O)CCCCC1)C1(OCc2cc(=O)n3nc(-c4ccccc4)nc3[nH]2)CCCCC1] | 479.2535 | 480.57 | 4.12 |
| 48-57 | 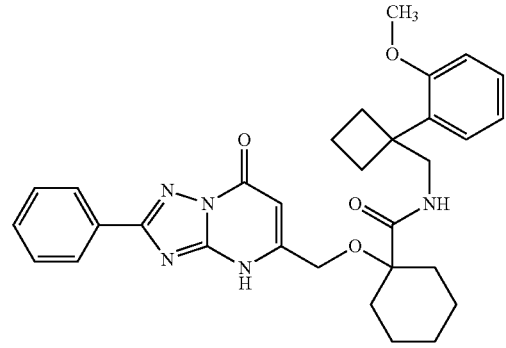 [SMILES: COc1ccccc1C1(CNC(=O)C2(OCc3cc(=O)n4nc(-c5ccccc5)nc4[nH]3)CCCCC2)CCC1] | 541.2692 | 542.64 | 5.11 |
| 48-58 | 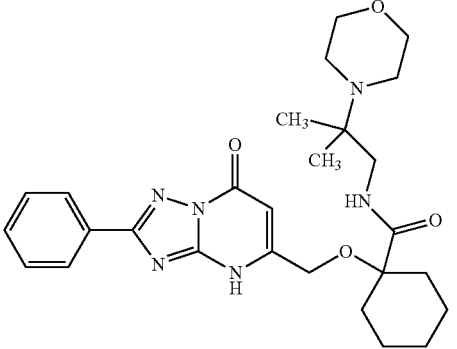 [SMILES: CC(C)(CNC(=O)C1(OCc2cc(=O)n3nc(-c4ccccc4)nc3[nH]2)CCCCC1)N1CCOCC1] | 508.2801 | 509.61 | 3.14 |
| 48-59 | 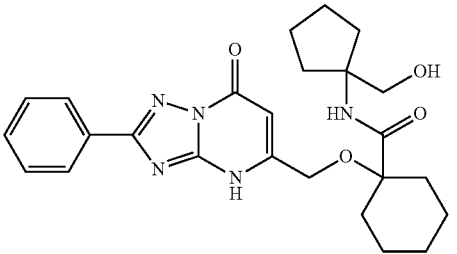 [SMILES: O=C(NC1(CO)CCCC1)C1(OCc2cc(=O)n3nc(-c4ccccc4)nc3[nH]2)CCCCC1] | 465.2378 | 466.55 | 4.02 |

-continued
| ID | Structure | EMW | MS m/z (M⁺ + H) | Retention Time (min) |
|---|---|---|---|---|
| 48-60 | 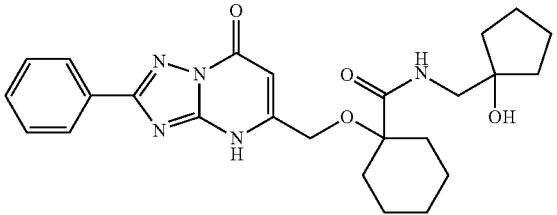 [SMILES: O=C(NCC1(O)CCCC1)C1(OCc2cc(=O)n3nc(-c4ccccc4)nc3[nH]2)CCCCC1] | 465.2378 | 466.55 | 4.61 |
| 48-61 | 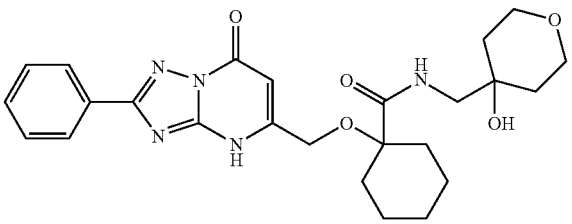 [SMILES: O=C(NCC1(O)CCOCC1)C1(OCc2cc(=O)n3nc(-c4ccccc4)nc3[nH]2)CCCCC1] | 481.2327 | 482.54 | 3.42 |
| 48-62 | 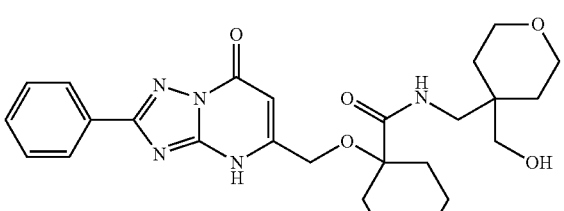 | 495.2484 | 496.57 | 3.57 |
| 48-63 | 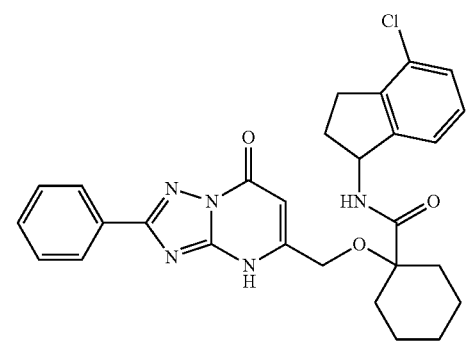 [SMILES: O=C(NC1CCc2c(Cl)cccc21)C1(OCc2cc(=O)n3nc(-c4ccccc4)nc3[nH]2)CCCCC1] | 517.1883 | 519.01 | 4.86 |
| 48-64 | 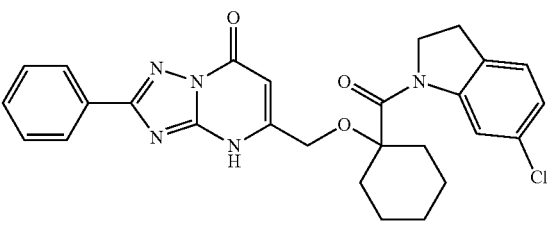 [SMILES: O=C(N1CCc2ccc(Cl)cc21)C1(OCc2cc(=O)n3nc(-c4ccccc4)nc3[nH]2)CCCCC1] | 503.1727 | 504.98 | 4.98 |
| 48-65 | 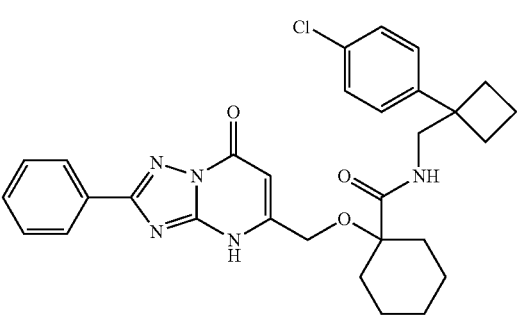 [SMILES: O=C(NCC1(c2ccc(Cl)cc2)CCC1)C1(OCc2cc(=O)n3nc(-c4ccccc4)nc3[nH]2)CCCCC1] | 545.2197 | 547.06 | 5.14 |

| ID | Structure | EMW | MS m/z (M+ + H) | Retention Time (min) |
|---|---|---|---|---|
| 48-66 | 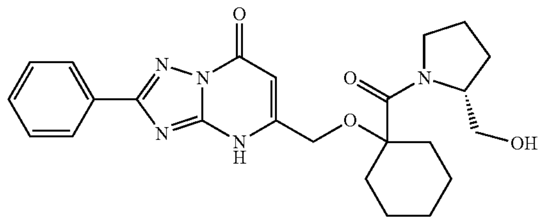 [SMILES: O=C(N1CCC[C@@H]1CO)C1(OCc2cc(=O)n3nc(-c4ccccc4)nc3[nH]2)CCCCC1] | 451.2222 | 452.52 | 3.71 |
| 48-67 | 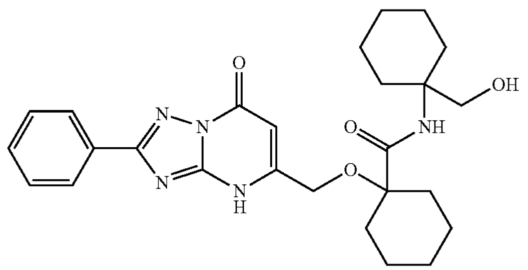 [SMILES: O=C(NC1(CO)CCCCC1)C1(OCc2cc(=O)n3nc(-c4ccccc4)nc3[nH]2)CCCCC1] | 479.2535 | 480.57 | 4.26 |
| 48-68 | 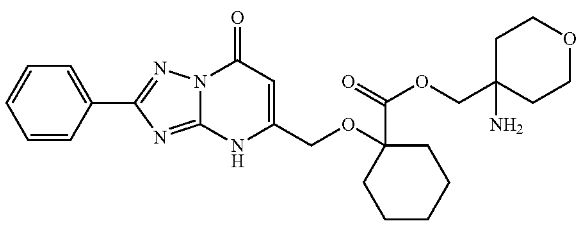 [SMILES: NC1(COC(=O)C2(OCc3cc(=O)n4nc(-c5ccccc5)nc4[nH]3)CCCCC2)CCOCC1] | 481.2327 | 482.54 | 3.05 |
| 48-69 | 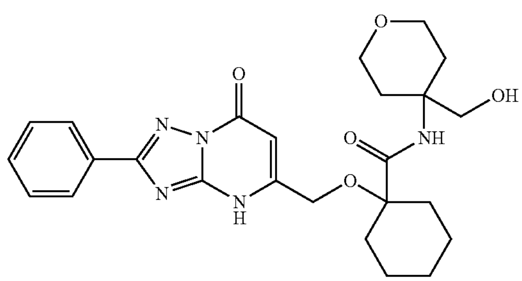 [SMILES: O=C(NC1(CO)CCOCC1)C1(OCc2cc(=O)n3nc(-c4ccccc4)nc3[nH]2)CCCCC1] | 481.2327 | 482.54 | 3.5 |
| 48-70 | 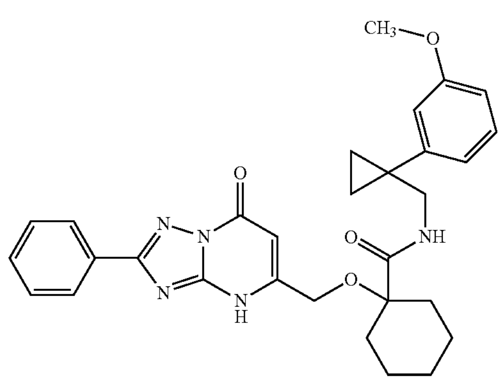 [SMILES: COc1cccc(C2(CNC(=O)C3(OCc4cc(=O)n5nc(-c6ccccc6)nc5[nH]4)CCCCC3)CC2)c1] | 527.2535 | 528.61 | 4.54 |

-continued
| ID | Structure | EMW | MS m/z (M⁺ + H) | Retention Time (min) |
|---|---|---|---|---|
| 48-71 | 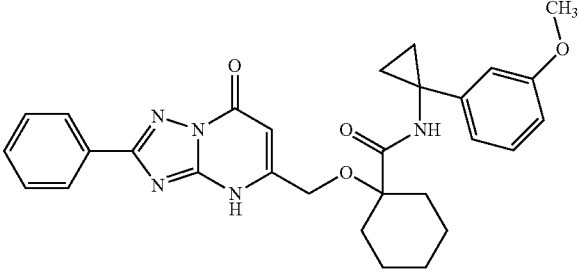 [SMILES: COc1cccc(C2(NC(=O)C3(OCc4cc(=O)n5nc(-c6ccccc6)nc5[nH]4)CCCCC3)CC2)c1] | 513.2378 | 514.59 | 4.42 |
| 48-72 | 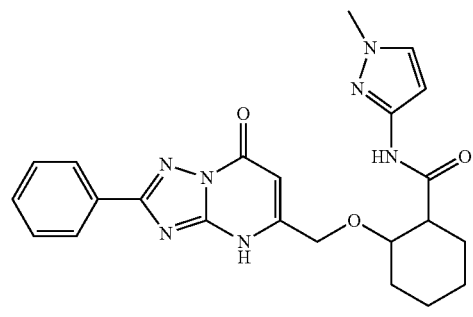 [SMILES: Cn1ccc(NC(=O)C2CCCCC2OCc2cc(=O)n3nc(-c4ccccc4)nc3[nH]2)n1] | 447.2022 | 448.49 | 3.33 |
| 48-73 | 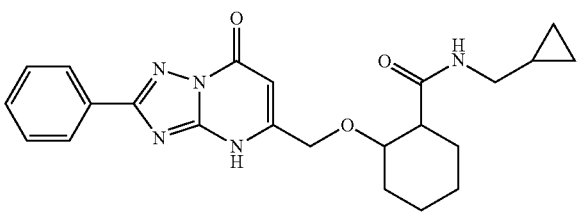 [SMILES: O=C(NCC1CC1)C1CCCCC1OCc1cc(=O)n2nc(-c3ccccc3)nc2[nH]1] | 421.2116 | 422.49 | 3.77 |
| 48-74 | 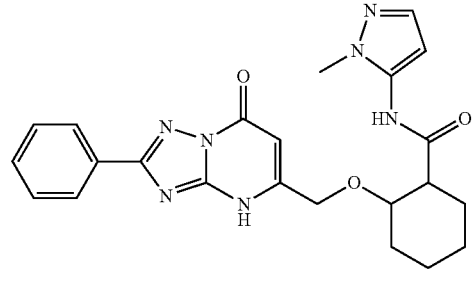 [SMILES: Cn1nccc1NC(=O)C1CCCCC1OCc1cc(=O)n2nc(-c3ccccc3)nc2[nH]1] | 447.2022 | 448.49 | 3.24 |
| 48-75 | 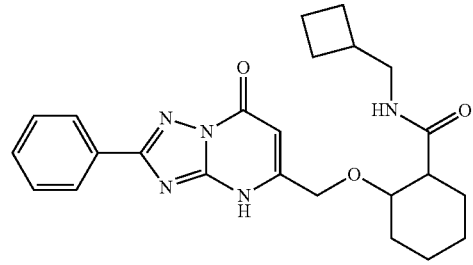 [SMILES: O=C(NCC1CCC1)C1CCCCC1OCc1cc(=O)n2nc(-c3ccccc3)nc2[nH]1] | 435.2273 | 436.52 | 4.14 |

-continued
| ID | Structure | EMW | MS m/z (M⁺ + H) | Retention Time (min) |
|---|---|---|---|---|
| 48-76 | 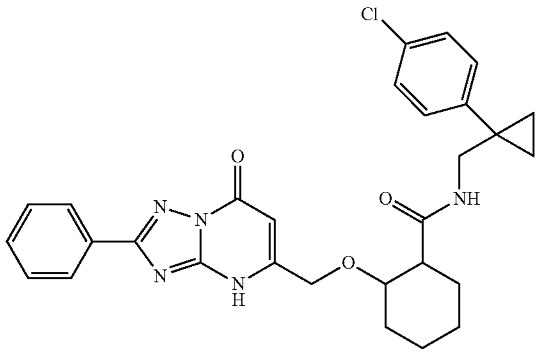 [SMILES: O=C(NCC1(c2ccc(Cl)cc2)CC1)C1CCCCC1OCc1cc(=O)n2nc(-c3ccccc3)nc2[nH]1] | 531.204 | 532.23 | 5.99 |
| 48-77 | 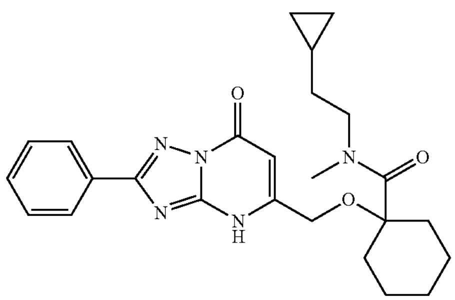 [SMILES: CN(CCC1CC1)C(=O)C1(OCc2cc(=O)n3nc(-c4ccccc4)nc3[nH]2)CCCCC1] | 449.2427 | 450.55 | 4.59 |
| 48-78 | 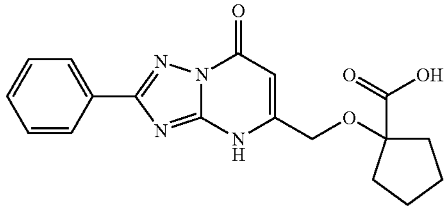 [SMILES: O=C(O)C1(OCc2cc(=O)n3nc(-c4ccccc4)nc3[nH]2)CCCC1] | 354.1328 | 3551329 | 3.63 |
Example 49
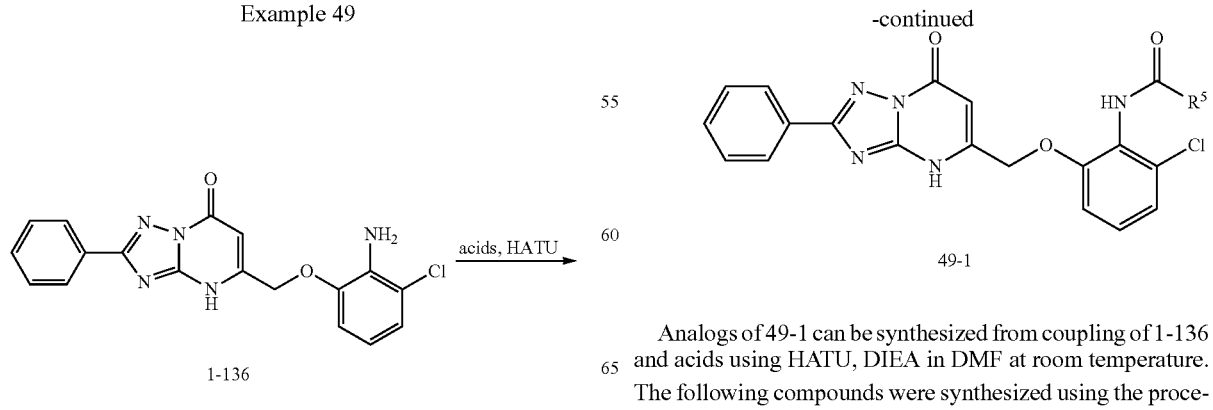
Analogs of 49-1 can be synthesized from coupling of 1-136 and acids using HATU, DIEA in DMF at room temperature. The following compounds were synthesized using the procedure:

| ID | Structure | EMW | MS m/z (M⁺ + H) | Retention Time (min) |
|---|---|---|---|---|
| 49-2 | 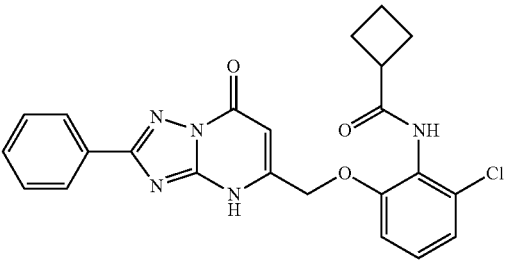 [SMILES: O=C(Nc1c(Cl)cccc1OCc1cc(=O)n2nc(-c3ccccc3)nc2[nH]1)C1CCC1] | 449.1257 | 450.89 | 4.06 |
| 49-3 | 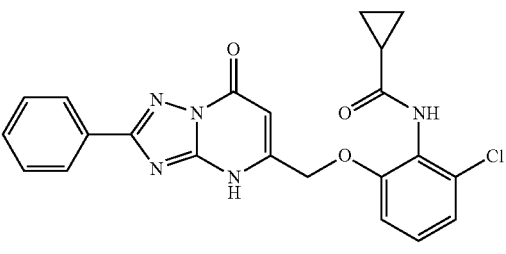 [SMILES: O=C(Nc1c(Cl)cccc1OCc1cc(=O)n2nc(-c3ccccc3)nc2[nH]1)C1CC1] | 435.11 | 436.86 | 3.78 |
| 49-4 | 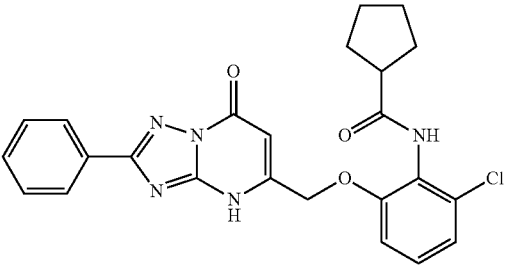 [SMILES: O=C(Nc1c(Cl)cccc1OCc1cc(=O)n2nc(-c3ccccc3)nc2[nH]1)C1CCCC1] | 463.1414 | 464.92 | 4.32 |
| 49-5 | 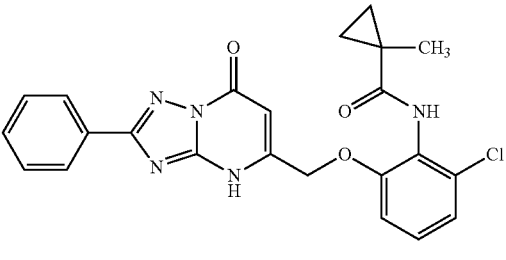 [SMILES: CC1(C(=O)Nc2c(Cl)cccc2OCc2cc(=O)n3nc(-c4ccccc4)nc3[nH]2)CC1] | 449.1257 | 450.89 | 4.11 |
| 49-6 | 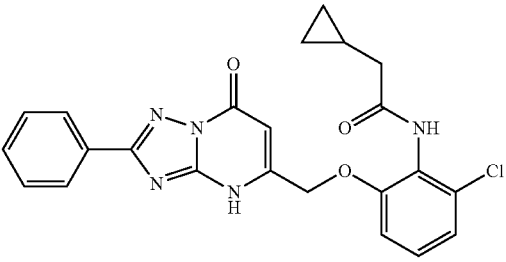 [SMILES: O=C(CC1CC1)Nc1c(Cl)cccc1OCc1cc(=O)n2nc(-c3ccccc3)nc2[nH]1] | 449.1257 | 450.89 | 3.99 |

Example 50
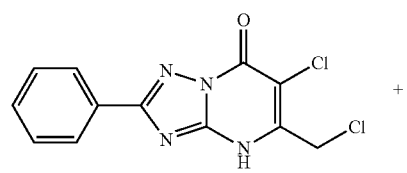
24-8
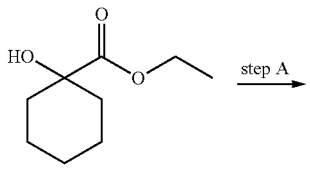
step A →
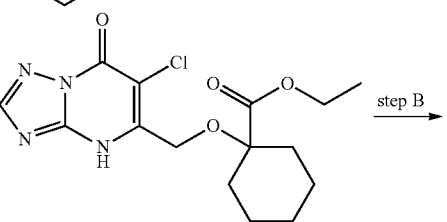
50-1
step B →
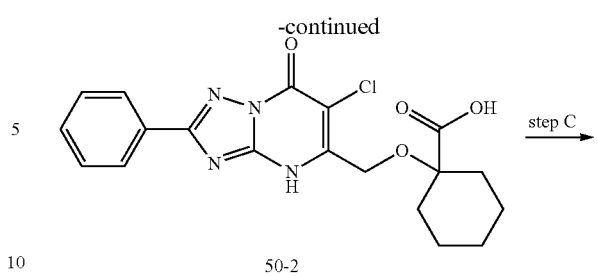
50-2
step C →
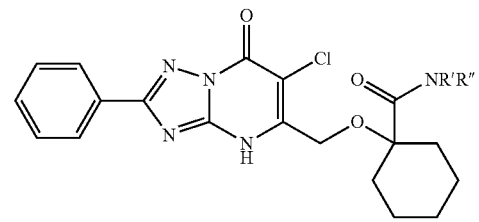
50-3
Analogs of 50-3 were synthesized according to compounds 48-1 (step A), 48-2 (step B) and 47-6 (step C).
The following compounds were synthesized using the procedure:
| ID | Structure | EMW | MS m/z (M⁺ + H) | Retention Time (min) |
|---|---|---|---|---|
| 50-4 | 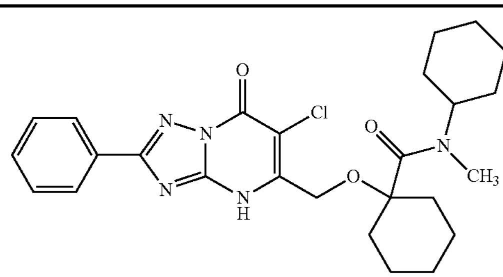 | 497.2197 | 499.02 | 5.1 |
| 50-5 | 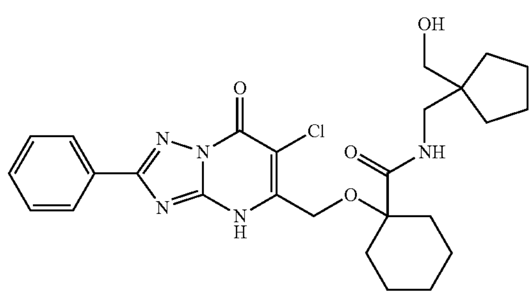 [SMILES: O=C(NCC1(CO)CCCC1)C1(OCc2[nH]c3nc(-c4ccccc4)nn3c(=O)c2Cl)CCCCC1] | 513.2146 | 515.02 | 4.51 |
| 50-6 | 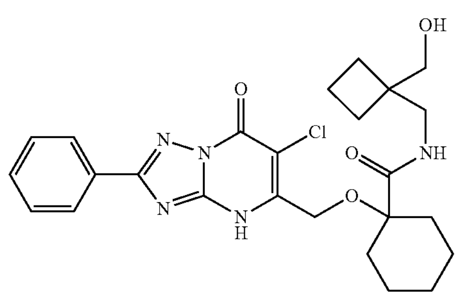 [SMILES: O=C(NCC1(CO)CCC1)C1(OCc2[nH]c3nc(-c4ccccc4)nn3c(=O)c2Cl)CCCCC1] | 499.1989 | 500.99 | 4.29 |

Example 51

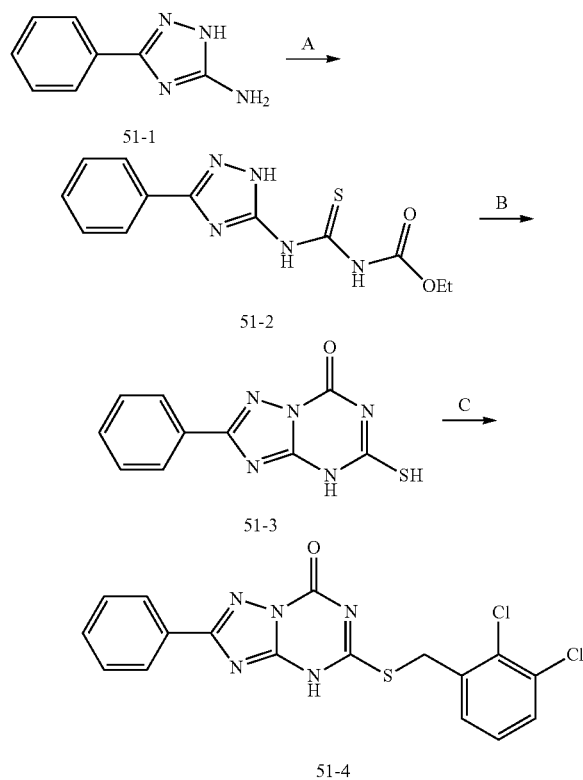

Example 52

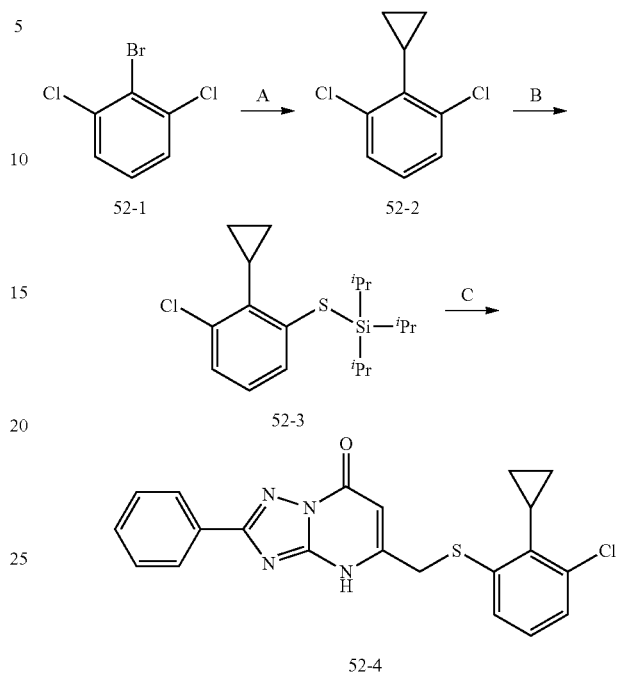

Step A:
A reaction mixture of 3-phenyl-1H-1,2,4-triazol-5-amine (32 mg, 0.2 mmol) and ethoxycarbonyl isothiocyanate (23.6 µL, 0.2 mmol) in DMF/acetone mixture (1/1, 0.5 mL) was stirred at 90° C. for overnight. The mixture was concentrated. The product 51-2 was purified by reversed phase HPLC.

Step B:
A reaction mixture of compound 1-2 (11.6 mg, 0.04 mmol) and sodium carbonate (21.2 mg, 0.2 mmol) in water (0.5 mL) was stirred in microwave at 100° C. for 20 minutes. The mixture was concentrated. The product 51-3 was purified by reversed phase HPLC.

Step C:
A reaction mixture of compound 1-3 (4.9 mg, 0.02 mmol), 1-(bromomethyl)-2,3-dichlorobenzene (7.2 mg, 0.03 mmol) and potassium carbonate (6.9 mg, 0.05 mmol) in DMA was stirred at room temperature for 1 hour. The product 51-4 was purified by reversed phase HPLC.

Step A:
A reaction mixture of 2-bromo-1,3-dichlorobenzene (1.13 g, 5 mmol), cyclopropyl boronic acid (0.86 g, 10 mmol), tetrakis(triphenylphosphine)palladium (0.35 g, 0.3 mmol) and tripotassium phosphate (2.12 g, 10 mmol) in dioxane (6 mL) was stirred at 110° C. under an atmosphere of argon for overnight. The reaction mixture was filtered. The filtrate was concentrated. The residue was purified by chromatography. Elution with 10% DCM in hexane gave compound 52-2 as light yellow oil (0.85 g, 91% yield). $^1$H NMR (400 MHz, CDCl$_3$) δ 7.26 (d, J=8.4 Hz, 2H), 7.07 (dt, J=0.8, 8.8 Hz, 1H), 1.82-1.72 (m, 1H), 1.18-1.11 (m, 2H), 0.81-0.74 (m, 2H).

Step B:
A reaction mixture of compound 52-2 (748 mg, 4 mmol), triisopropylsilanethiol (945 µL, 4.4 mmol), 1,1'-bis(di-isopropylphosphino)ferrocene palladium dichloride (83.7 mg, 0.2 mmol) and sodium tert-butoxide (423 mg, 4.4 mmol) in toluene (8 mL) was stirred at 100° C. under an atmosphere of argon for overnight. The reaction mixture was filtered. The filtrate was concentrated. The residue was purified by chromatography. Elution with 10% DCM in hexane gave compound 52-3 as clear oil (1.33 g, 98% yield).

| ID | Structure | EMW | MS m/z (M$^+$ + H) | Retention Time (min) |
|---|---|---|---|---|
| 51-4 | 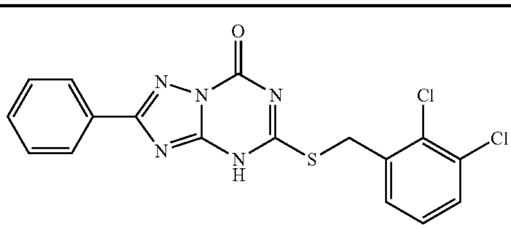 | 403.01 | 403.81 | 5.67 |

285

Step C:

A reaction mixture of compound 52-3 (34 mg, 0.1 mmol), 5-(chloromethyl)-2-phenyl-[1,2,4]triazolo[1,5-a]pyrimidin-7(4H)-one (26 mg, 0.1 mmol) and tetrabutylammonium fluoride (0.2 mmol, 0.2 mL, 1 M in THF) in DMA (0.3 mmol) was stirred at room temperature for overnight. The product 52-4 was purified by reversed phase HPLC.

286

-continued

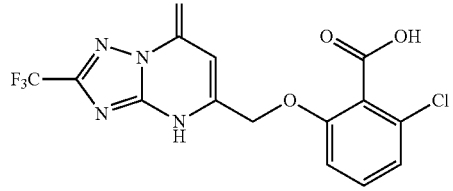

53-3

| ID | Structure | EMW | MS m/z (M⁺ + H) | Retention Time (min) |
|---|---|---|---|---|
| 52-4 | 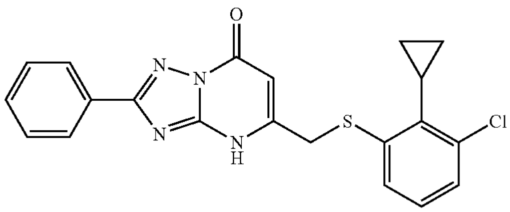 [SMILES: O=c1cc(CSc2cccc(Cl)c2C2CC2)[nH]c2nc(-c3ccccc3)nn12] | 408.08 | 409.08 | 5.46 |
| 52-5 | 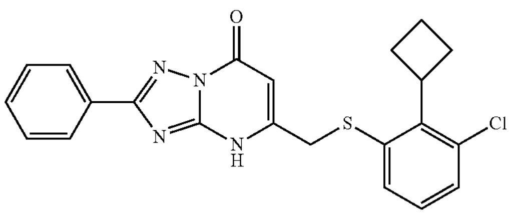 | 422.10 | 423.10 | 5.84 |

Example 53

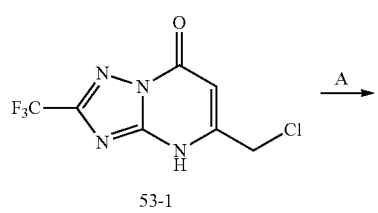

53-1

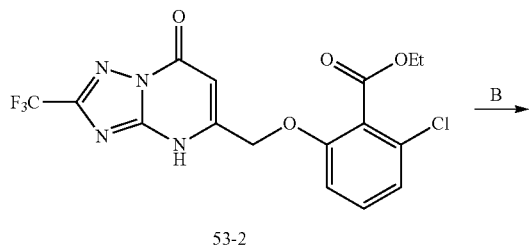

53-2

Step A:

A reaction mixture of compound 38-1 (25 mg, 0.1 mmol), ethyl 2-chloro-6-hydroxybenzoate (30 mg, 0.15 mmol) and potassium carbonate (69 mg, 0.5 mmol) in DMA was stirred in microwave at 150° C. for 15 minutes. The reaction mixture was filtered. The filtrate containing compound 53-2 was used for the next step.

Step B:

To the filtrate from last step was added lithium hydroxide monohydrate (12.6 mg, 0.3 mmol) in water. The reaction mixture was stirred in microwave at 180° C. for 15 minutes. The reaction mixture was concentrated. The residue was purified by reverse phase HPLC to give compounds 53-2 and 53-3.

| ID | Structure | EMW | MS m/z (M⁺ + H) | Retention Time (min) |
|---|---|---|---|---|
| 53-2 | 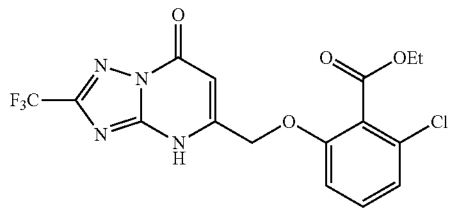 | 416.05 | 417.86 | 3.99 |
| 53-3 | 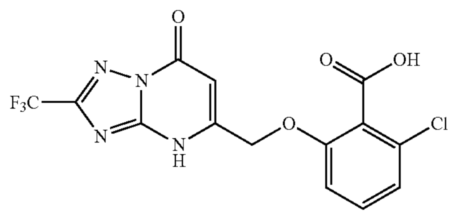 | 388.02 | 389.79 | 2.84 |

Example 54

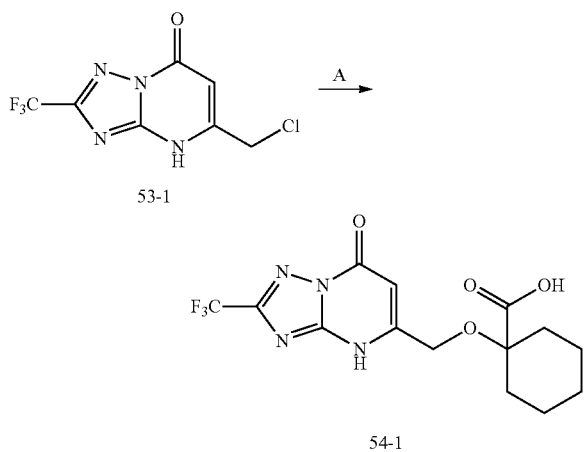

Step A:

A reaction mixture of compound 53-1 (25 mg, 0.1 mmol), ethyl 1-hydroxycyclohexanecarboxylate (25.8 mg, 0.15 mmol) and sodium hydride (16 mg, 0.4 mmol, 60% dispersion in mineral oil) in DMA was stirred in microwave at 180° C. for 15 minutes. The reaction mixture was filtered. The filtrate was purified by reverse phase HPLC to give compound 54-1.

Assay

Useful assays to determine the FABP inhibitory activity of the inventive compounds are described below:

MCP-1 Assay in THP-1 Macrophage

1. Cell culture: Culture THP-1 cells at $1 \times 10^5$ cells/ml in 35 mL T75 tissue culture flask at 37° C., 5% $CO_2$, change medium every 2-3 days. THP-1 Medium: RPMI-1640 (ATCC) with 10% FBS, 1% Penicillin/streptomycin.

2. Cell differentiation: Seed $4 \times 10^5$ cells/ml in 100 µL differentiation medium per well in poly-D-lysine-coated 384-well plate. Differentiate cells for 24 hrs. Differentiation medium: THP-1 medium with 40 nM PMA (Cat. #8139-1 MG, Sigma). Poly-D-Lysine coated 384-well plate: CELLCOAT Poly-D-Lysine, Ref #781946, Greiner Bio-One.

3. Cell treatment: After 24 hrs differentiation, remove differentiation medium, then change medium to 100 µL/well Optimum medium (Cat#31985, Invitrogen) containing 1% lipoprotein-deficient serum (Cat S5519, Sigma) with and without compounds. Treat cells for 24 hrs with:

a. Optimum 1% LPDS medium as control,
   b. 6 concentrations dose starting at 25 mM of 2-(2'-(5-ethyl-3,4-diphenyl-1H-pyrazol-1-yl)biphenyl-3-yloxy)acetic acid (*Bioorg. Med. Chem. Lett.,* 2007, 17, 3511) as a positive control.
   c. 6 concentrations dose starting at 25 mM of the present FABP4 compounds.

hMCP-1 assay: after compounds treatment for 24 hrs, transfer 10 µL samples from each well to MSD hMCP-1 plate (Cat# K21AYB-2, MDS), measure hMCP-1 concentration following protocol as manufacturer suggested.

| ID | Structure | EMW | MS m/z (M⁺ + H) | Retention Time (min) |
|---|---|---|---|---|
| 54-1 | 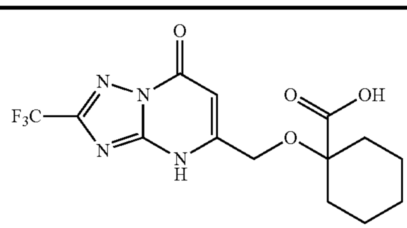 | 360.10 | 361.86 | 3.07 |

TdF (Temperature Dependence Fluorescence) Assay for FABP3 and FABP4

The SAR (Structure Activity Relationship) for FABP3 and FABP4 ligands covered by this invention was interrogated using the TdF (Temperature Dependence Fluorescence) assay or best known as thermal shift assay (M. W. Pantoliano et al, *J. Biomol. Screen* 6 (2001) 429-440). The TdF assay was mainly conducted in the 96-well based CHROMO-4 real time fluorescence plate reader (BioRad). The Sypro Orange (Sigma-Aldrich), environmentally sensitive fluorescence dye, was used to monitor the protein folding-unfolding transition. Protein-ligand binding was gauged by the change (or shift) in the unfolding transition temperature ($\Delta T_m$) acquired at protein alone with respect to protein in the presence of ligand of interest.

The compound of interest was first prepared in DMSO stock (typical concentration: 10 mM). Sample of 20 µL was then added into the 96-well PCR plate, where it consisted of 3 µM protein (FABP4 or FABP3) and 15, 50 or 100 µM compound (depending on compound's solubility) in buffer (25 mM HEPES, 150 mM NaCl, pH=7.5 and 1 mM DTT) incorporated with Sypro Orange dye (5× final concentration). Final percentage of DMSO resided in the sample was 2%. The sample plate was heated from 30° C. to 90° C. with thermal ramping rate of 1° C./min. The fluorescence signals were acquired with excitation and emission wavelengths centered at 490 and 560 nm respectively. The instrument thermal stability was ±0.2° C. The melting temperatures ($T_m$) for FABP4 and FABP3 proteins under aforementioned conditions occurred at 61.0±0.2° C. and 64.8±0.2° C. respectively.

Theoretical basis for TdF-based ligand binding affinity constant

The derivation of TdF-based ligand binding affinity constant ($K_d$) followed closely those previously formulated by Brandts and Lin, *Biochemistry* 29 (1990) 6927-6940. In brief, the binding constant of the ligand at the $T_m$ is expressed as below:

$$K_L(T_m) = \frac{\{\exp\{-(\Delta H_u(T_0)/R)(1/T_m - 1/T_0) + (\Delta C p_u/R)[\ln(T_m/T_0) + (T_0/T_m) - 1]\} - 1\}}{[L_{Tm}]}$$

where $T_o$ is the midpoint of unfolding for unliganded protein and $T_m$ is the midpoint of unfolding in presence of ligand. $[L_{Tm}]$ is free ligand at $T_m$. The $\Delta H_u$ and $\Delta Cp_u$ are the enthalpy of unfolding and heat capacity change of unfolding for the protein respectively. The $\Delta C_{Pu}$ is proportional to the size of protein and is an approximate quantity in the above equation (empirically, $\Delta Cp_u$=(MW of protein/115)*14 cal/mol*K). Following algorithm derived by Mayhood et al, (*Analytical Biochemistry* 345 (2005) 187-197), the $T_0$ and $\Delta H_u$ can be determined separately from nonlinear regression fitting the temperature dependent protein alone curve to the following equation:

$$F(T) = \frac{(Y_n + m_n(T)) + (Y_u + m_u(T))\exp\left\{-\left(\frac{\Delta H_u}{RT}\right)\left(1 - \frac{T}{T_0}\right)\right\}}{1 + \exp\left\{-\left(\frac{\Delta H_u}{RT}\right)\left(1 - \frac{T}{T_0}\right)\right\}}$$

Where F(T) is the observed fluorescence intensity at any temperature T, $Y_n$ and $Y_u$ are the predicted fluorescence intensities for fully folded and unfolded protein, respectively; $m_n$ and $m_u$ are slope correction for changes in $Y_r$ and $Y_u$ with respect to changes in temperature (analogously replace $T_0$ with $T_m$ in the above equation for liganded protein to yield $T_m$). The nonlinear regression fitting in general readily reaches convergence by properly constraining the initial values for the fitting parameters (e.g. the initial "guess" for the $\Delta H_u$ was constrained to 120 kcal/mol; initial $Y_n$ and $m_n$ were set to 1 and zero to best represent the melting curve along the low temperature region; negative slope of −0.5 was initially chosen for $m_u$; initial $T_m$ was also constrained to 50° C.).

Finally, the ligand binding affinity constant at any temperature T (i.e. 25° C.) can be thermodynamically connected to the preceding $K_L(T_m)$ via $$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

(see Brandts et al and Mayhood et al, shown above) where $\Delta H_L$ (T) is the van't Hoff enthalpy of ligand binding at temperature T and $\Delta Cp_L$ is the heat capacity upon ligand binding. For simplicity, the $\Delta Cp_L$ and $\Delta H_L$ (T) were set to zero and −7 kcal/mol respectively. (The $\Delta Cp_L$ accounts for minimal portion of total protein-ligand binding energetics and is therefore set to zero (For example, see Hossein Naghibi et al, *Proc. Natl. Acad. Sci.* 92, 5597-5599 (1995), where $\Delta Cp_L$ was estimated to ~2% of $\Delta H_L$ at 25° C. obtained from calorimetric study of binding RNase A and 2'-CMP)).

TdCD (Temperature-dependent Circular Dichroism) Assay for FABP3/4/5

JASCO 810 spectropolarimeter was used to measure Circular Dichroism (CD) spectra and temperature-dependent protein unfolding profiles. The instrument is equipped with a 6-cell piezoelectric temperature controller. Ellipticity was monitored at 226 nm as a function of temperature with a 1 mm path length cell. The scan rate was 1° C./min with a 4 s response time and 30 s equilibration between measurements.

Stock protein FABP5 (3.5 mgs/mL), FABP4 (1.8 mgs/mL) and FABP3 (3 mgs/mL) were diluted to 10-15 µM with 25 mM HEPES pH 7.5, 150 mM NaCl, 1 mM DTT. 10 mM stocks of individual compounds were made in 100% DMSO. The compounds were tested at 50 µM and 25 µM concentrations. DMSO was added to protein-alone (apo) samples to 1% to compensate for DMSO amounts in protein+ligand samples. Data were analyzed using Jasco software and the midpoints of the protein unfolding transitions ($T_m$), and the ligand binding constants ($K_L$) were calculated as previously described (See, for example, Mayhood et al, *Analytical Biochemistry* 345 (2005) 187-197; Smith et al, *Biochemistry* 46 (2007) 1358-1367; Brandts et al, *Biochemistry* 29 (1990) 6927-6940; and Matulis et al, *Biochemistry* 44 (2005) 5258-5266).

Briefly, the $T_o$ (midpoint of unfolding for the unliganded protein) was calculated from best fit of the unfolding data to the equation below:

$$Y_{obs} = \frac{(Y_n + m_n(T)) + (Y_u + m_u(T))\exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}{1 + \exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}$$

Where, $Y_{obs}$ is the observed ellipticity value at any temperature T, $Y_n$ and $Y_u$ are the predicted ellipticity values for fully folded and unfolded species, respectively, $m_n$ and $m_u$ are slope correction for changes in $Y_n$ and $Y_u$ with respect to changes in temperature. $T_0$ is the midpoint temperature at which the unliganded protein unfolds and $\Delta H_u$ and $\Delta Cp_u$ are the heat of unfolding and heat capacity of unfolding, respectively for the unliganded species.

In presence of ligand, the midpoint temperature ($T_m$) defines where the equilibrium concentrations of unfolded and folded species are equal. Incorporation of the unliganded free energy of binding and subsequent thermodynamic substitution yielded the binding constant of the ligand at the $T_m$ value of unfolding:

$$K_L(T_m) = \frac{\{\exp\{-(\Delta H_u(T_0)/R)(1/T_m - 1/T_0) + (\Delta Cp_u/R)[\ln(T_m/T_0) + (T_0/T_m) - 1]\} - 1\}}{[L_{Tm}]}$$

where, $T_0$ is the midpoint of unfolding for unliganded protein and $T_m$ is the midpoint of unfolding in presence of ligand. $[L_{Tm}]$ is free ligand at $T_m$.

Based on estimates for enthalpy of binding, $\Delta H_L$ (estimated to be −7 kcal/mol) and ligand binding heat capacity $\Delta Cp_L$ (set to be zero), the ligand binding association constant ($K_L$) at temperature T=20° C. were calculated as below. Based on reasonable boundary change of the estimated ligand binding $\Delta H_L$, a 50% uncertainty was uniformly assigned to the calculated TdCD $K_d$ ($1/K_L$) values at T=20° C.

$$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

The Kd values obtained for FABP and FABP5 inhibition by some representative compounds of the present invention are shown below in the Table.

| Example ID | FABP4 TdF Kd (μM) | FABP5 TdCD Kd (μM) |
|---|---|---|
| 1-2 | B | D |
| 1-3 | B | |
| 1-5 | B | D |
| 1-6 | B | |
| 1-7 | C | |
| 1-8 | C | |
| 1-9 | B | |
| 1-10 | B | |
| 1-11 | B | |
| 1-12 | C | |
| 1-13 | B | |
| 1-14 | C | |
| 1-15 | C | |
| 1-16 | B | |
| 1-17 | B | E |
| 1-18 | B | |
| 1-19 | C | |
| 1-20 | C | |
| 1-21 | B | |
| 1-22 | C | |
| 1-23 | C | |
| 1-24 | B | |
| 1-25 | C | |
| 1-26 | C | |
| 1-27 | B | |
| 1-28 | C | |
| 1-29 | C | |
| 1-30 | C | |
| 1-31 | B | |
| 1-32 | B | |
| 1-33 | B | |
| 1-34 | C | |
| 1-35 | B | |
| 1-36 | C | |
| 1-37 | C | |
| 1-38 | C | |
| 1-39 | B | |
| 1-40 | C | |
| 1-41 | C | |
| 1-42 | C | |
| 1-43 | C | |
| 1-44 | C | |
| 1-45 | C | |
| 1-46 | C | |
| 1-47 | C | |
| 1-48 | C | |
| 1-49 | C | |
| 1-51 | C | |
| 1-52 | B | |
| 1-54 | C | |
| 1-55 | B | |
| 1-56 | C | |
| 1-57 | B | |
| 1-58 | B | |
| 1-59 | C | |
| 1-60 | B | |
| 1-61 | C | |
| 1-62 | B | |
| 1-63 | B | |
| 1-64 | C | |
| 1-65 | C | |
| 1-66 | B | |
| 1-67 | B | |
| 1-68 | B | |
| 1-69 | B | |
| 1-70 | B | |
| 1-71 | C | |
| 1-72 | C | |
| 1-73 | B | |
| 1-74 | C | |
| 1-75 | C | |
| 1-76 | C | |
| 1-77 | C | |
| 1-78 | C | |
| 1-79 | C | |
| 1-80 | B | |
| 1-81 | B | |
| 1-82 | B | |
| 1-83 | B | |
| 1-84 | B | |
| 1-85 | B | |
| 1-86 | B | |
| 1-87 | B | |
| 1-88 | B | |
| 1-89 | C | |
| 1-90 | C | |
| 1-91 | C | |
| 1-92 | C | |
| 1-93 | B | |
| 1-94 | B | |
| 1-95 | C | |
| 1-96 | C | |
| 1-97 | B | |
| 1-98 | C | |
| 1-99 | B | |
| 1-101 | C | |
| 1-102 | C | |
| 1-103 | C | |
| 1-104 | C | |
| 1-105 | C | |
| 1-106 | C | |
| 1-107 | B | |
| 1-108 | B | |
| 1-109 | C | |

Table of Kd data

| Example ID | FABP4 TdF Kd (μM) | FABP5 TdCD Kd (μM) |
|---|---|---|
| 1-110 | B | |
| 1-111 | B | |
| 1-112 | C | |
| 1-113 | C | |
| 1-115 | C | |
| 1-118 | B | |
| 1-131 | B | |
| 1-134 | B | |
| 1-135 | C | |
| 1-136 | B | |
| 1-139 | C | |
| 1-141 | C | |
| 1-142 | B | |
| 1-143 | B | |
| 1-146 | C | |
| 1-147 | B | |
| 1-148 | C | |
| 1-149 | B | |
| 1-150 | B | |
| 1-151 | C | |
| 1-152 | B | D |
| 1-155 | C | |
| 2-1 | B | |
| 2-2 | C | |
| 3-1 | B | |
| 4-2 | C | |
| 4-3 | C | |
| 5-2 | C | |
| 5-3 | C | |
| 5-4 | C | |
| 5-5 | C | |
| 5-6 | C | |
| 5-7 | C | |
| 5-8 | C | |
| 5-9 | C | |
| 6-1 | C | |
| 6-2 | C | |
| 6-3 | B | E |
| 6-4 | B | E |
| 6-5 | C | |
| 7-1 | C | |
| 7-2 | C | |
| 8-2 | C | |
| 8-3 | C | |
| 8-4 | C | |
| 8-5 | C | |
| 8-6 | C | |
| 8-7 | C | |
| 8-8 | C | |
| 8-9 | C | |
| 8-10 | C | |
| 8-11 | C | |
| 8-12 | C | |
| 8-13 | B | |
| 8-14 | C | |
| 9-1 | C | |
| 10-1 | C | |
| 10-2 | C | |
| 11-3 | C | |
| 11-4 | C | |
| 12-1 | B | |
| 12-2 | C | |
| 13-2 | C | |
| 14-3 | C | |
| 15-3 | C | |
| 16-2 | B | |
| 17-2 | C | |
| 17-3 | B | |
| 18-3 | B | |
| 19-2 | B | |
| 20-2 | B | D |
| 21-3 | B | |
| 22-2 | B | |
| 23-1 | B | |
| 24-1 | B | D |
| 24-2 | B | |
| 24-3 | B | |
| 24-4 | B | |
| 24-5 | C | |
| 24-6 | C | |
| 24-7 | B | |
| 24-8 | B | |
| 24-9 | B | |
| 24-10 | C | |
| 24-11 | C | |
| 24-12 | B | |
| 24-13 | B | |
| 24-14 | B | |
| 24-15 | B | |
| 24-16 | B | |
| 24-17 | B | |
| 24-18 | A | |
| 25-3 | B | |
| 25-4 | B | |
| 25-5 | C | |
| 25-6 | C | |
| 25-7 | C | |
| 25-8 | C | |
| 26-3 | B | D |
| 26-4 | B | |
| 28-1 | C | |
| 29-1 | C | |
| 30-2 | B | |
| 31-2 | B | |
| 33-1 | C | |
| 33-2 | C | |
| 33-3 | C | |
| 35-5 | B | |
| 36-1 | B | |
| 37-5 | B | |
| 37-6 | B | |
| 37-7 | B | |
| 39-5 | B | |
| 41-3 | B | |
| 42-3 | B | |
| 42-4 | B | |
| 43-2 | B | |
| 43-3 | B | |
| 45-2 | B | |
| 46-2 | B | |
| 46-3 | C | |
| 47-1 | B | |
| 47-2 | B | |
| 47-3 | B | |
| 47-4 | A | |
| 47-5 | B | |
| 47-6 | C | |
| 47-7 | B | |
| 47-8 | B | |
| 47-9 | B | |
| 47-10 | B | |
| 47-11 | B | |
| 47-12 | B | |
| 47-13 | B | |
| 47-14 | B | |
| 47-15 | B | |
| 47-17 | B | |
| 47-18 | B | |
| 47-19 | B | |
| 47-20 | B | |
| 47-21 | B | |
| 47-22 | B | |
| 47-23 | B | |
| 47-24 | A | |
| 47-25 | B | |
| 47-26 | B | |

Table of Kd data

| Example ID | FABP4 TdF Kd (μM) | FABP5 TdCD Kd (μM) |
|---|---|---|
| 47-27 | A | |
| 47-28 | A | |
| 47-29 | A | |
| 47-30 | B | |
| 47-32 | B | |
| 47-34 | B | |
| 47-35 | B | |
| 47-36 | B | |
| 47-37 | A | |
| 47-38 | A | |
| 47-40 | B | |
| 47-46 | C | |
| 47-47 | B | |
| 47-48 | B | |
| 47-49 | B | |
| 47-50 | A | |
| 47-51 | A | |
| 47-52 | B | |
| 47-53 | C | |
| 47-54 | B | |
| 47-55 | B | |
| 47-56 | B | |
| 47-57 | C | |
| 47-58 | B | |
| 47-59 | B | |
| 47-60 | B | |
| 47-61 | B | |
| 47-62 | B | |
| 47-63 | B | |
| 47-64 | B | |
| 47-65 | B | |
| 48-2 | C | |
| 48-4 | C | |
| 48-5 | C | |
| 48-6 | B | |
| 48-7 | B | |
| 48-8 | A | |
| 48-9 | A | |
| 48-10 | A | |
| 48-11 | A | |
| 48-12 | A | |
| 48-13 | A | |
| 48-14 | B | |
| 48-15 | A | |
| 48-16 | B | |
| 48-17 | B | |
| 48-18 | C | |
| 48-19 | C | |
| 48-20 | B | |
| 48-21 | C | |
| 48-22 | C | |
| 48-23 | C | |
| 48-24 | B | |
| 48-25 | B | |
| 48-26 | B | |
| 48-27 | B | |
| 48-28 | B | |
| 48-29 | B | |
| 48-30 | C | |
| 48-31 | B | |
| 48-32 | B | |
| 48-33 | B | |
| 48-34 | B | |
| 48-35 | C | |
| 48-36 | B | |
| 48-37 | B | |
| 48-38 | B | |
| 48-39 | B | |
| 48-40 | B | |
| 48-41 | B | |
| 48-42 | B | |
| 48-43 | C | |
| 48-44 | B | |
| 48-45 | B | |
| 48-46 | B | |
| 48-47 | C | |
| 48-48 | B | |
| 48-49 | B | |
| 48-50 | B | |
| 48-51 | B | |
| 48-52 | B | |
| 48-53 | B | |
| 48-54 | B | |
| 48-55 | B | |
| 48-56 | B | |
| 48-57 | B | |
| 48-58 | B | |
| 48-59 | B | |
| 48-60 | B | |
| 48-61 | B | |
| 48-62 | B | |
| 48-63 | B | |
| 48-64 | B | |
| 48-65 | A | |
| 48-66 | C | |
| 48-67 | B | |
| 48-68 | C | |
| 48-69 | C | |
| 48-70 | B | |
| 48-71 | B | |
| 48-76 | B | |
| 48-77 | B | |
| 48-78 | C | |
| 49-2 | B | |
| 49-3 | B | |
| 49-4 | B | |
| 49-5 | B | |
| 49-6 | B | |
| 50-4 | B | |
| 50-5 | A | |
| 50-6 | B | |
| 51-4 | C | |
| 52-4 | A | |
| 52-5 | A | |
| 53-3 | C | |
| 54-1 | C | |

Affinity range: A ≤ 0.001 uM, 0.5 ≤ B < 0.001 μM, C > 0.5 μM, D ≤ 0.5 μM, E > 0.5 μM.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound, or a pharmaceutically acceptable salt of said compound, the compound being represented by the general formula I:

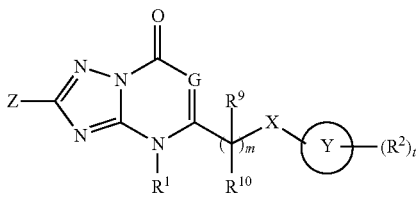

wherein:
Y is a ring as described below;
X is
   C(R⁷R⁸), or O;
G is C(R⁶);
Ring Y is aryl, heteroaryl, heterocyclyl or cycloalkyl, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and CF₃;
R¹ is H, alkyl, -alkyl-OR⁴, haloalkyl, haloalkoxy or -alkyl-CN;
m is 1-2;
t is 0-4;
each R² is independently selected from the group consisting of halo, CN, —OR⁵, alkyl, haloalkyl, haloalkoxy, aryl, heteroaryl, heterocyclyl, cycloalkyl, —NH₂, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—NH₂, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)₂, —C(O)N(aryl)₂, —C(O)N(heteroaryl)₂, —C(O)N(heterocyclyl)₂, —C(O)—N(cycloalkyl)₂, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—NH₂, —C(O)R⁵, and —C(O)OR⁵, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R⁵, CN and CF₃;
Z is H, —OR⁵, —C(O)OR⁵, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —OR⁵, alkyl, haloalkyl, haloalkoxy, aryl, heteroaryl, heterocyclyl, cycloalkyl, —C(O)—NH₂, —C(O)N(H)(CH₃), —NH—C(O)—NH₂, —C(O)R⁵, and —C(O)OR⁵;
R⁴ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF₃;
R⁵ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)R⁴, CN and CF₃;
R⁶ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF₃;
R⁷ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF₃;
R⁸ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and CF₃;
R⁹ is H, halo, alkyl, cycloalkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and CF₃; and
R¹⁰ is H, halo, alkyl, cycloalkyl, aryl or heteroaryl, —C(O)OH, —C(O)—NH₂, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)₂, —C(O)N(aryl)₂, —C(O)N(heteroaryl)₂, —C(O)N(heterocyclyl)₂, —C(O)—N(cycloalkyl)₂, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—NH₂, —C(O)R⁵, and —C(O)OR⁵, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)R⁵, CN and CF₃;
or alternatively, R⁹ and R¹⁰ can together form =O or R⁹ and R¹⁰ can be joined to form a spirocyclyl group.

2. The compound of claim 1, wherein R¹ is H, alkyl, -alkyl-OR⁴, -alkyl-halo, haloalkyl, haloalkoxy or -alkyl-CN.

3. The compound of claim 1, wherein t is 0 or 1.

4. The compound of claim 1, wherein R² is halo.

5. The compound of claim 1, wherein R² is CN.

6. The compound of claim 1, wherein Z is phenyl, wherein said phenyl may be unsubstituted or optionally independently substituted with one or more substituents which can be the same or different, each substituents being independently selected from the group consisting of halo, CN, —OR⁵, alkyl, haloalkyl, haloalkoxy, aryl, heteroaryl, heterocyclyl, cycloalkyl, —C(O)—NH₂, —NH—C(O)—NH₂, and —C(O)OR⁵.

7. The compound of claim 1, wherein Z is thiophenyl, wherein said thiophenyl may be unsubstituted or optionally independently substituted with one or more substituents which can be the same or different, each substituents being independently selected from the group consisting of halo, CN, —OR$^5$, alkyl, haloalkyl, haloalkoxy, aryl, heteroaryl, heterocyclyl, cycloalkyl, —C(O)—NH$_2$, —NH—C(O)—NH$_2$, and —C(O)OR$^5$.
8. A compound, or a pharmaceutically acceptable salt of said compound, wherein the compound is:
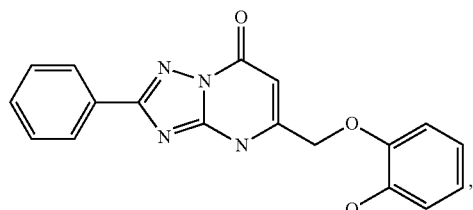
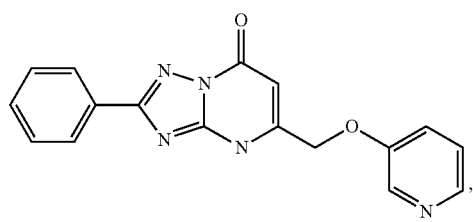
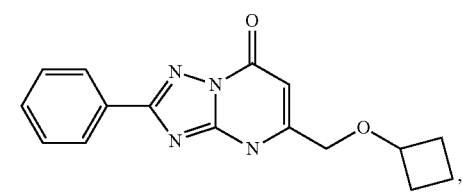
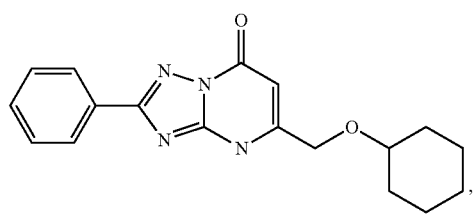
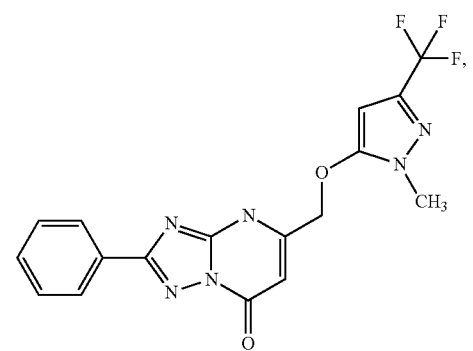
-continued
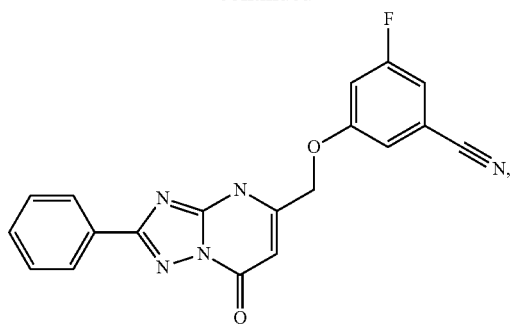
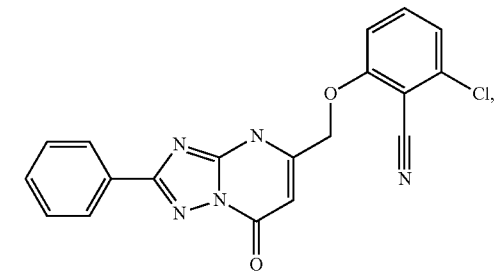
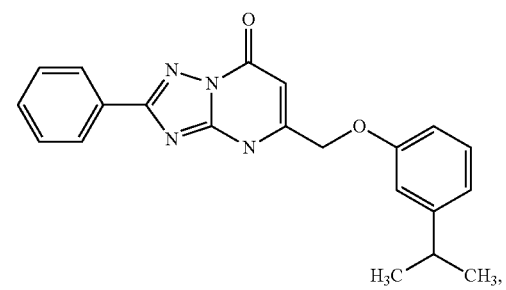
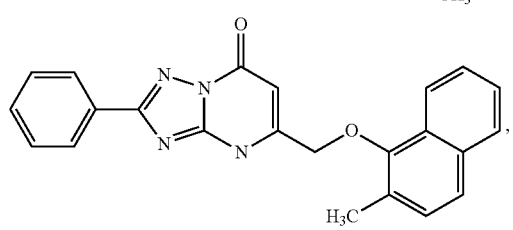
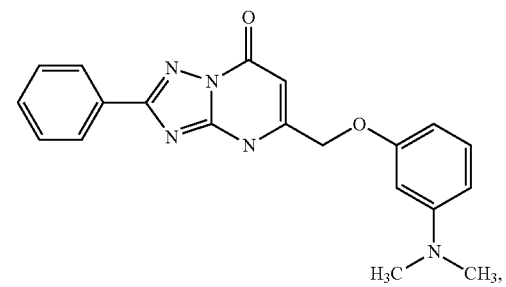

301
-continued
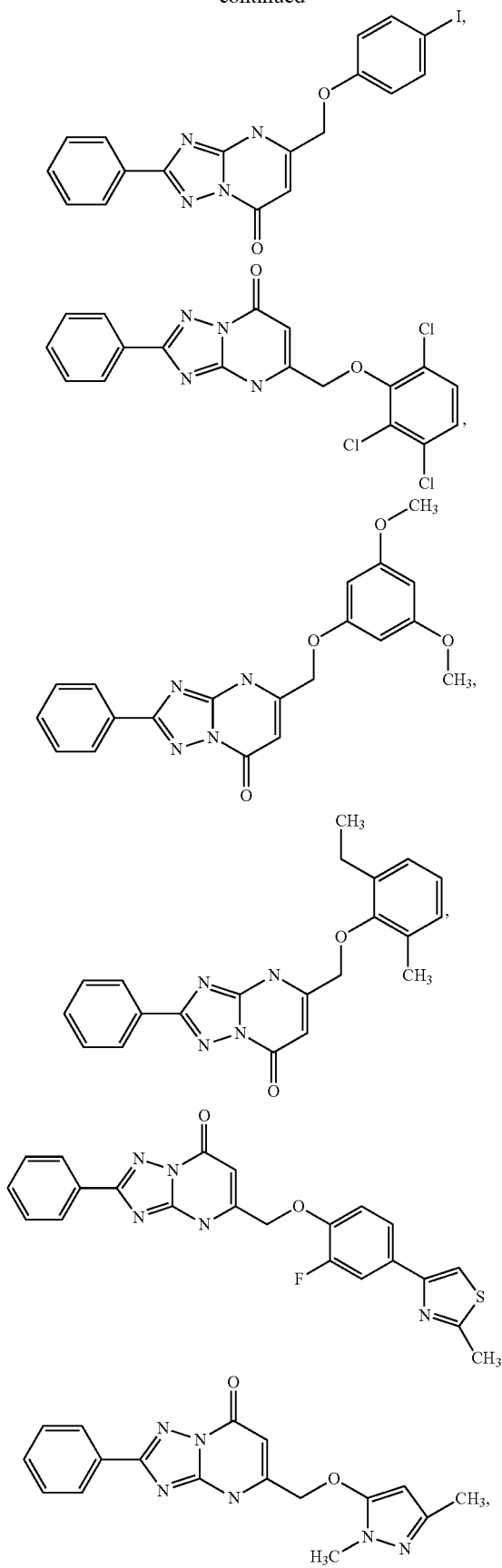
302
-continued
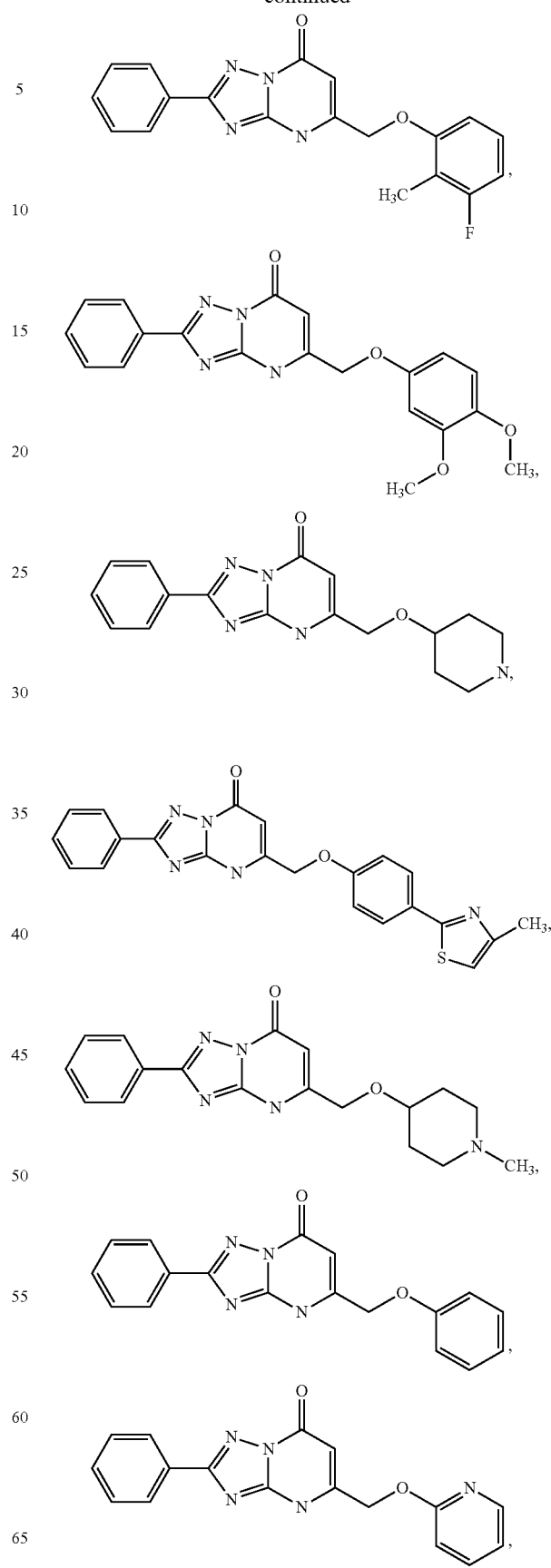

303
-continued
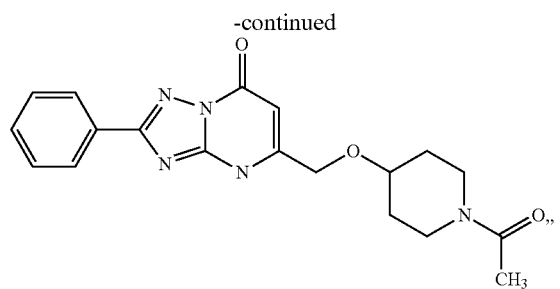
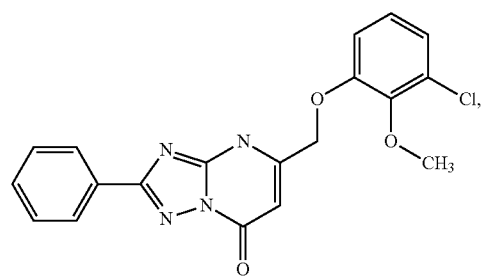 [SMILES: COc1c(Cl)cccc1OCc1cc(=O)n2nc(-c3ccccc3)nc2[nH]1]
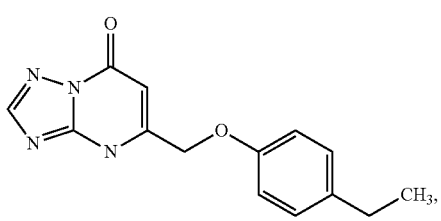
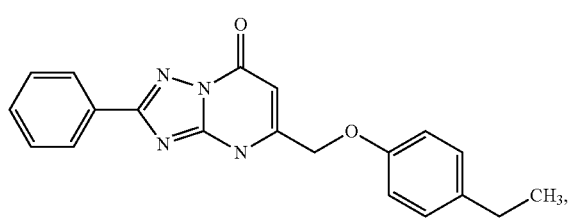
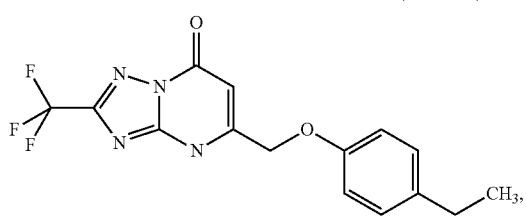
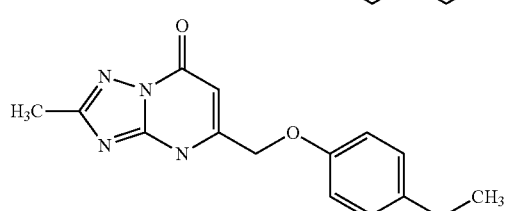
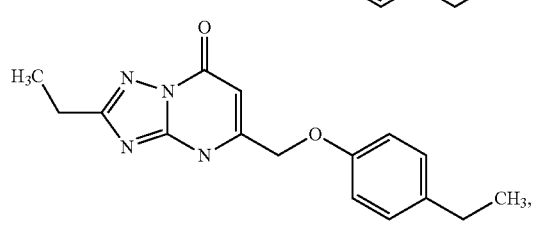
304
-continued
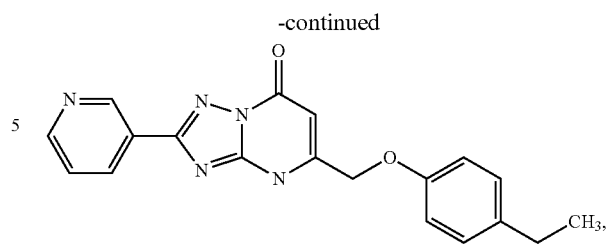
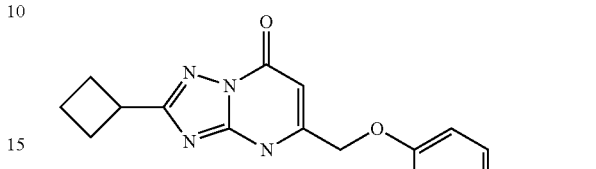
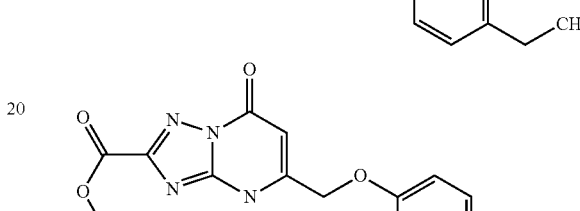
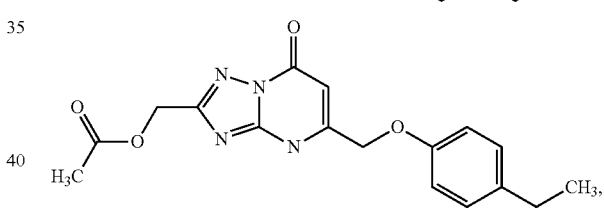
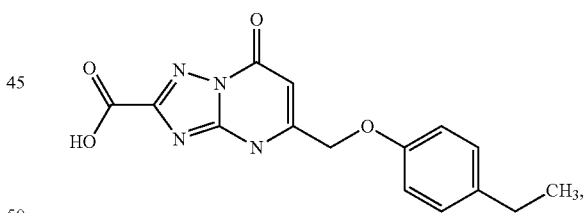
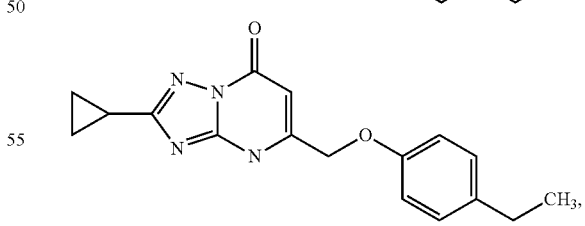
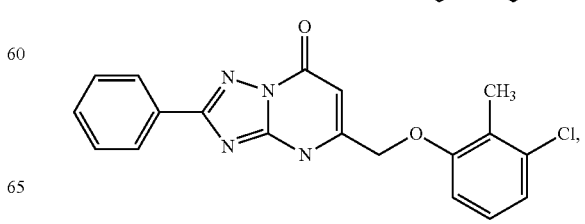

305
-continued
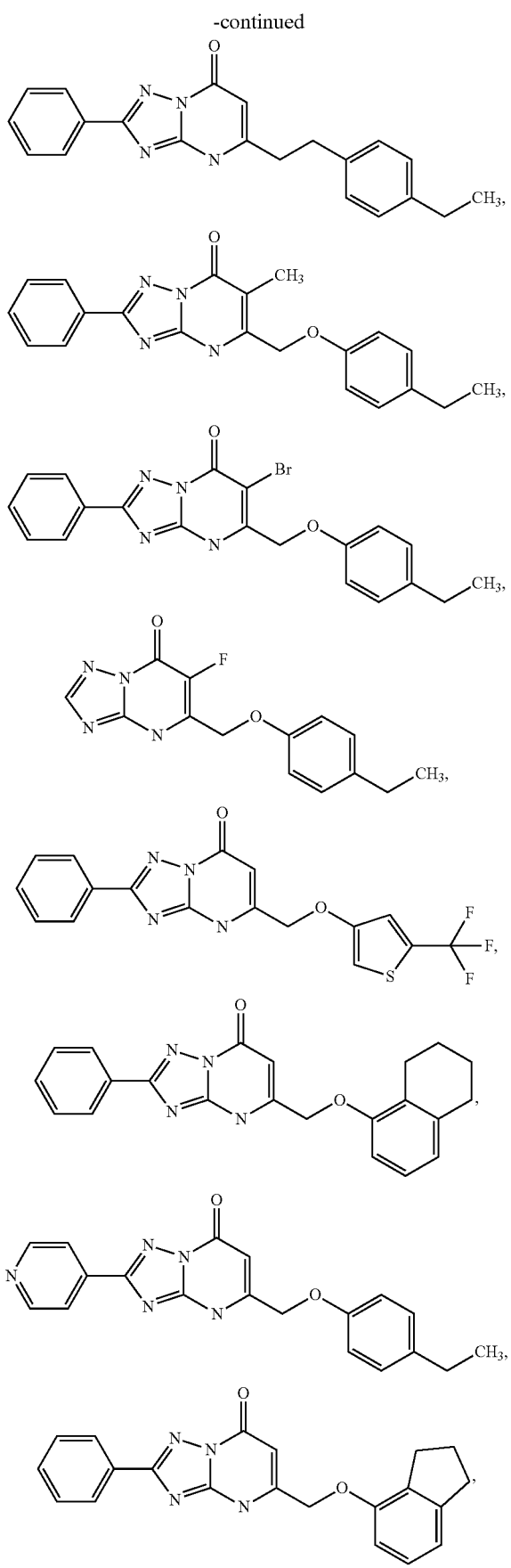
306
-continued
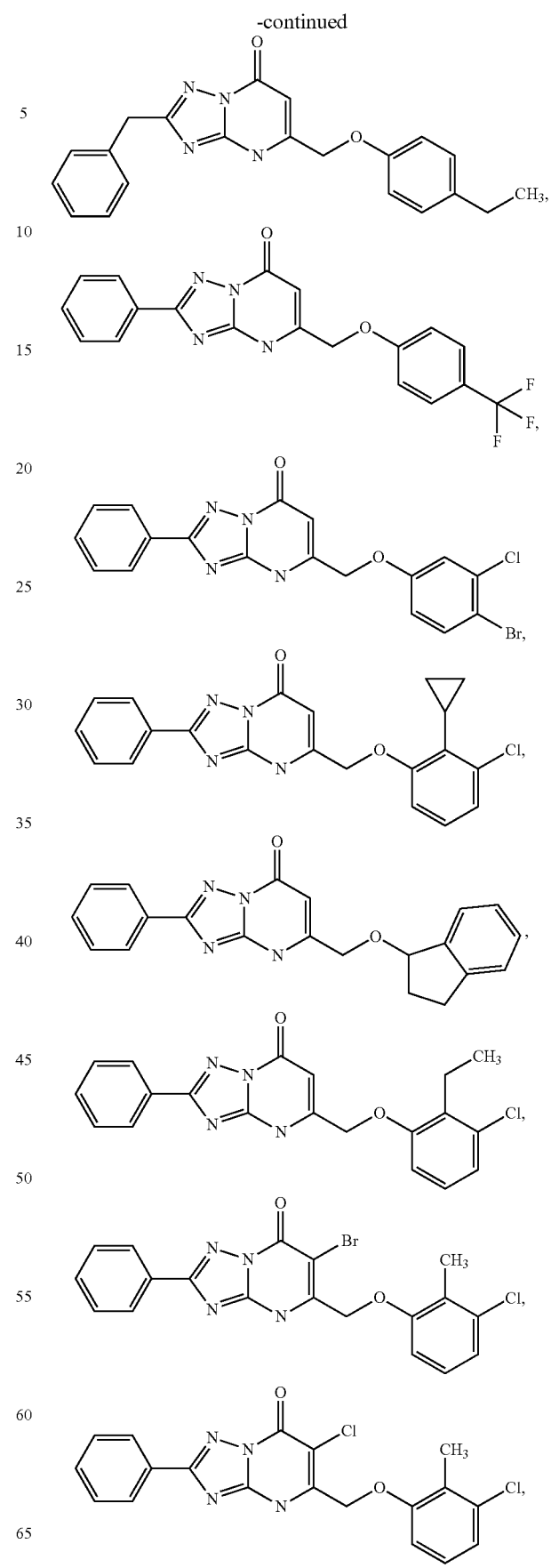

-continued
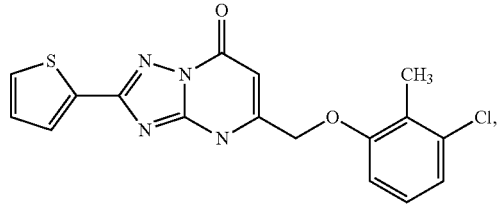
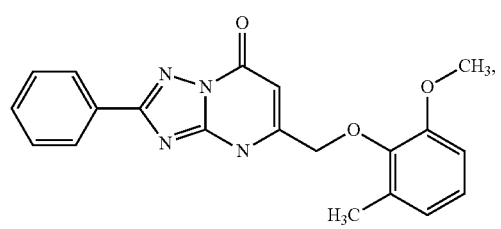
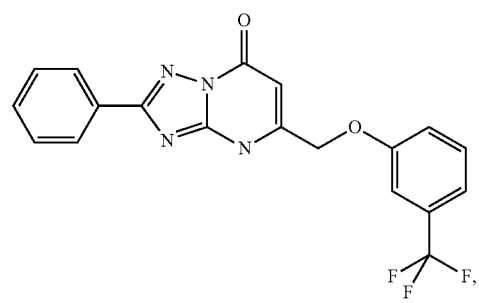
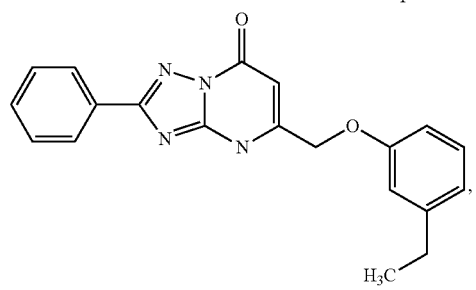
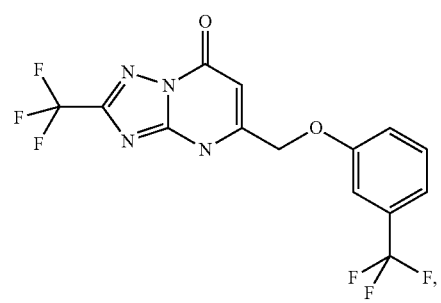
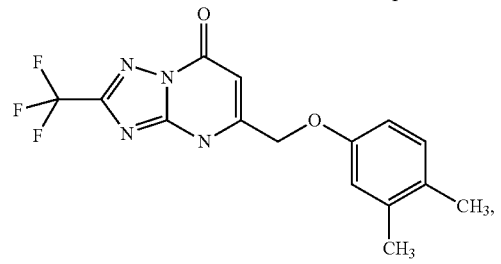
-continued
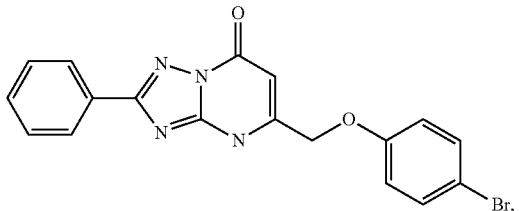
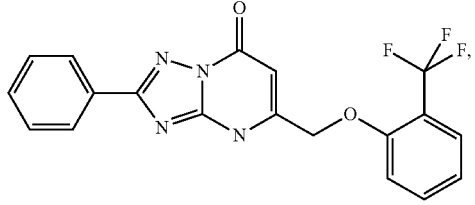
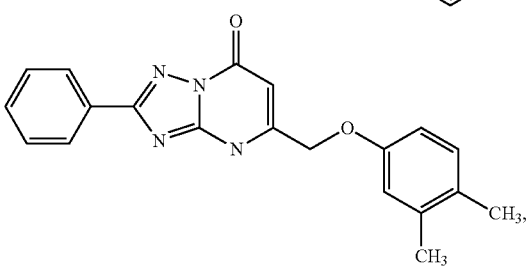
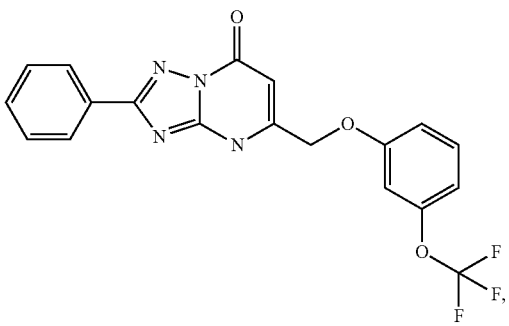
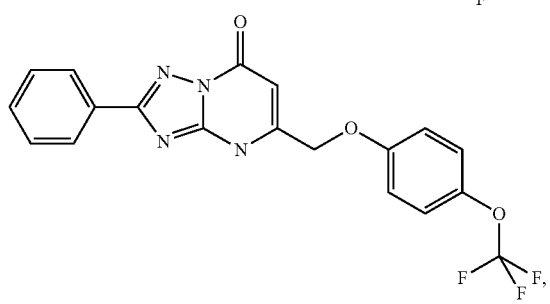
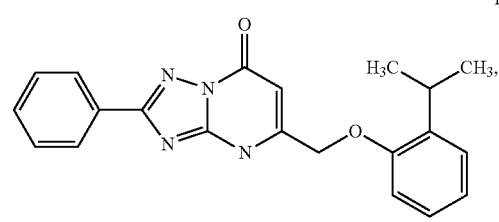
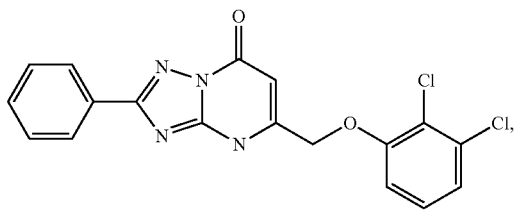

309
-continued
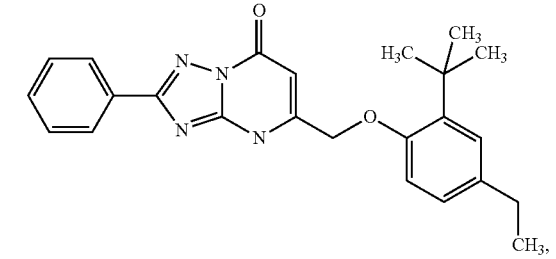
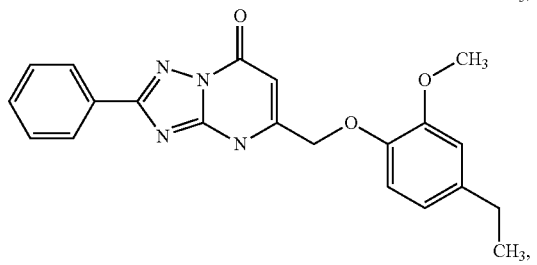
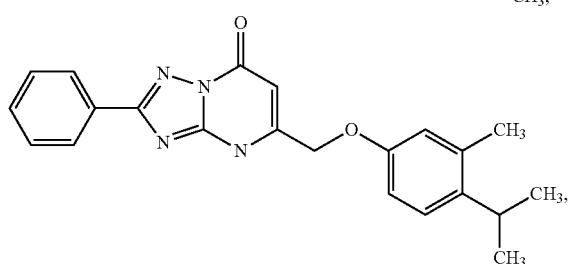
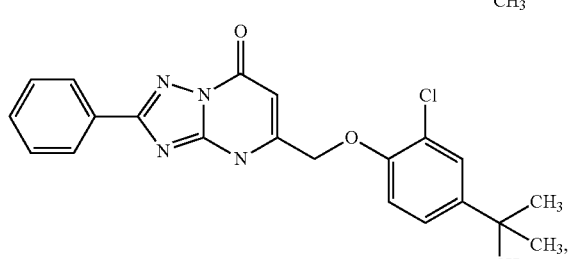
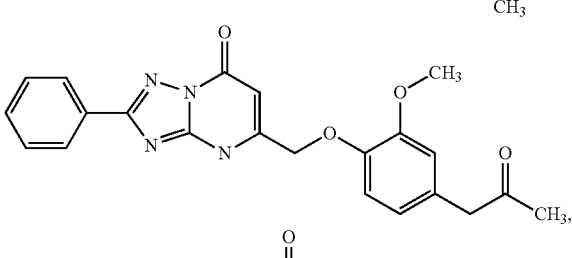
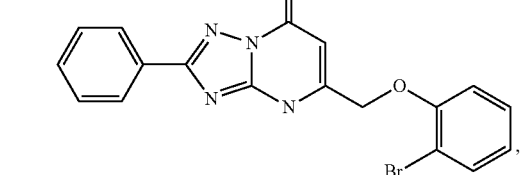
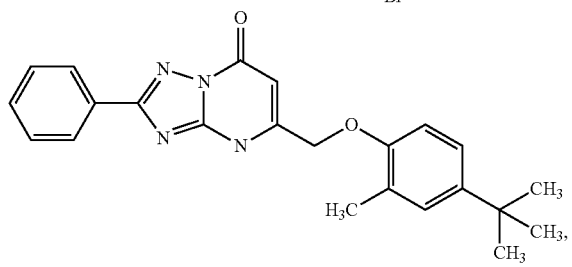
310
-continued
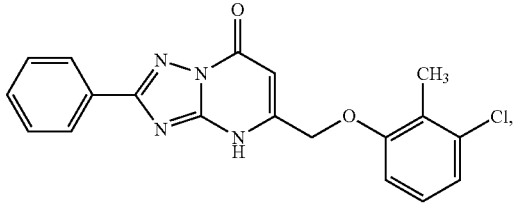
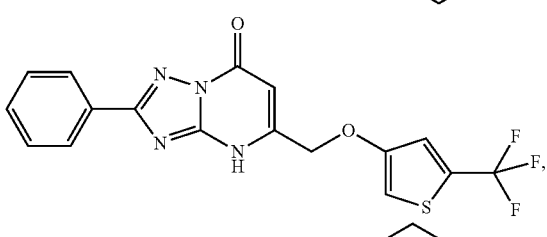
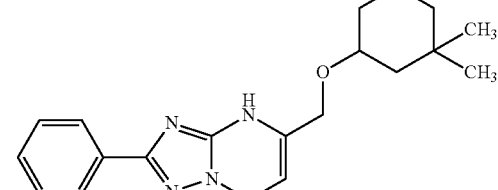
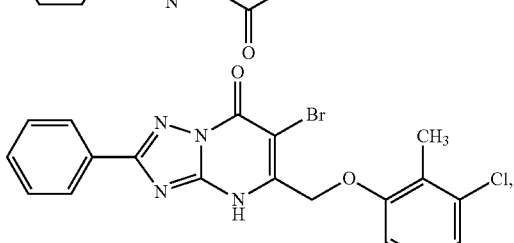
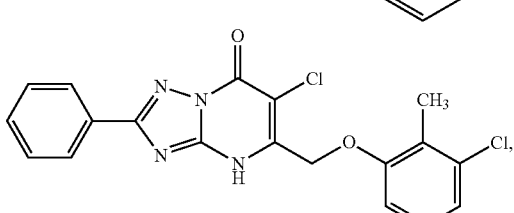
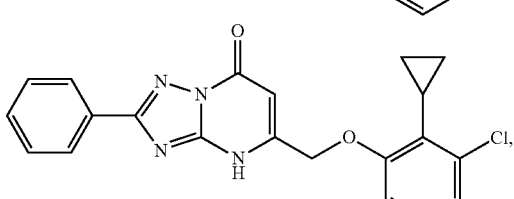
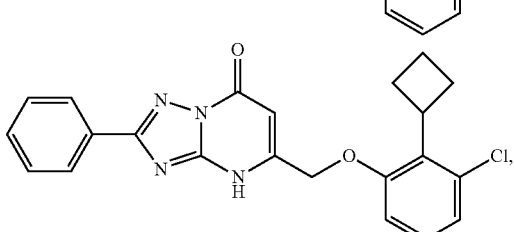
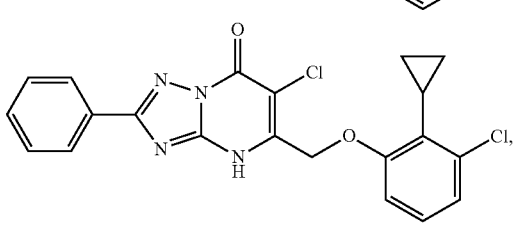

311
-continued
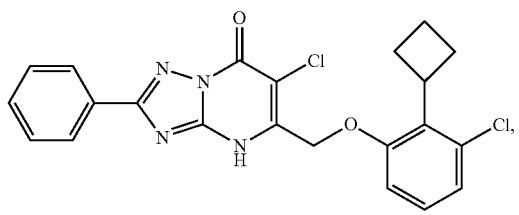
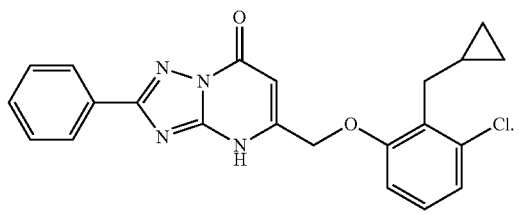
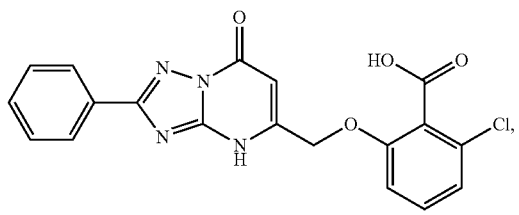
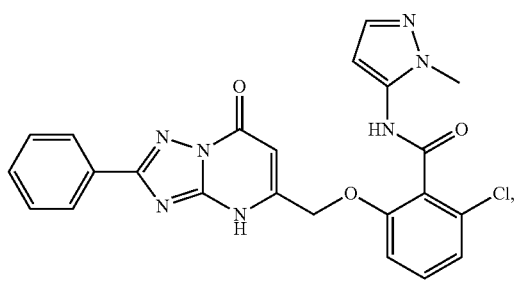
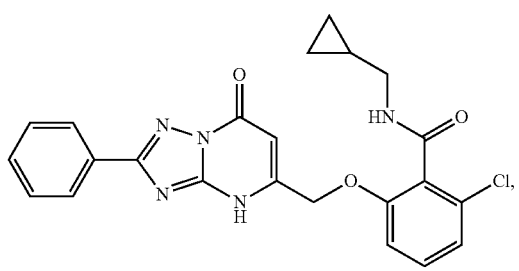
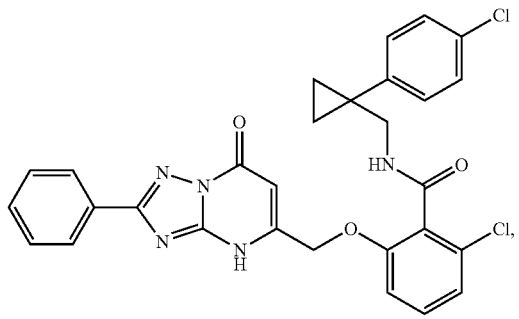
312
-continued
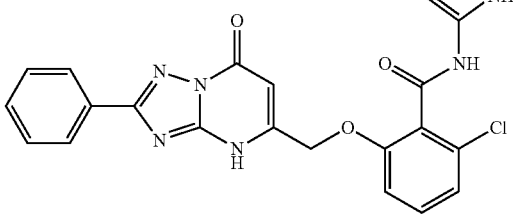
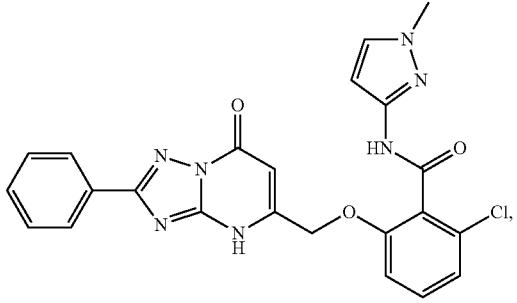
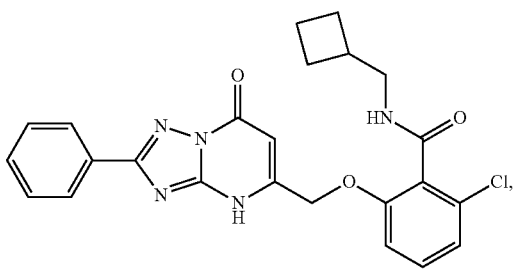
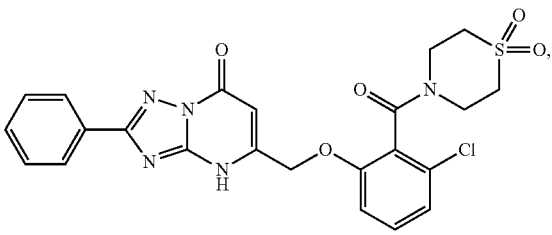
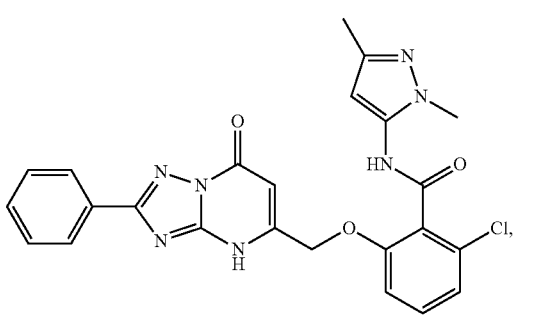

313
-continued
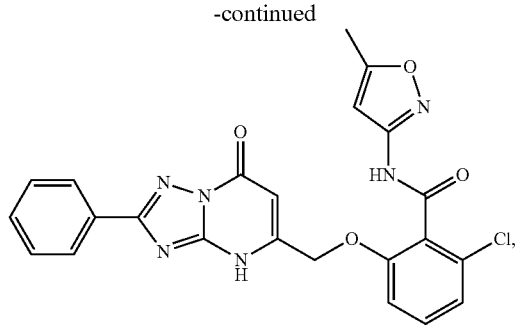
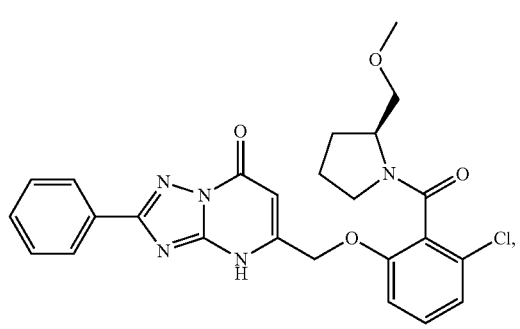
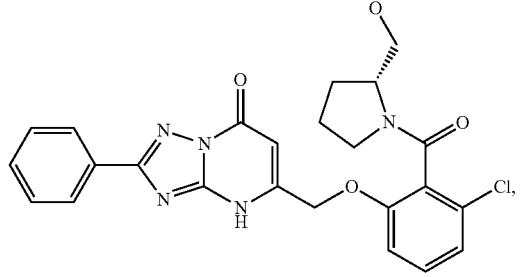
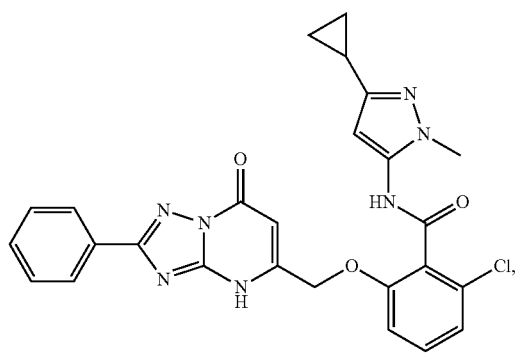
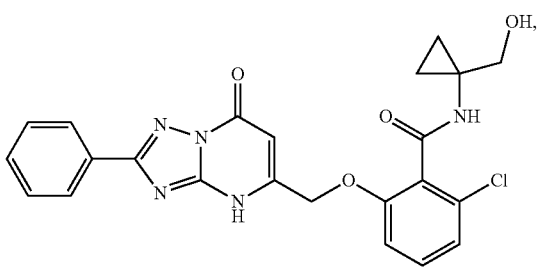
314
-continued
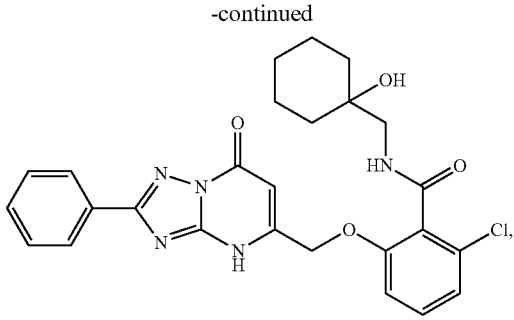
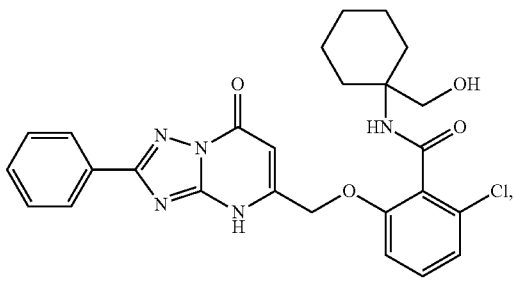
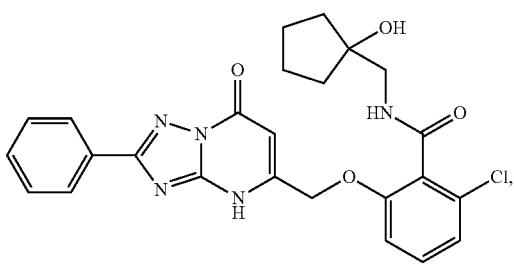
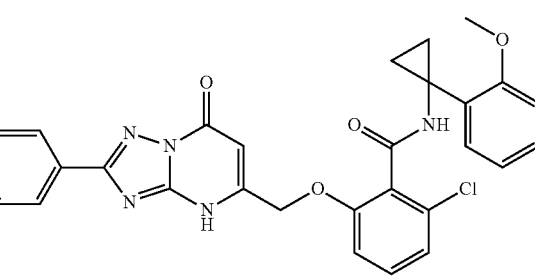
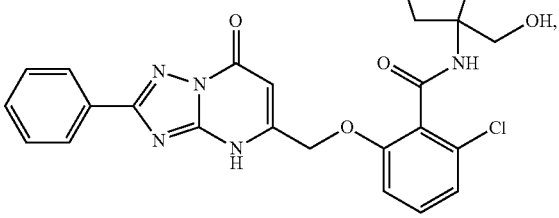
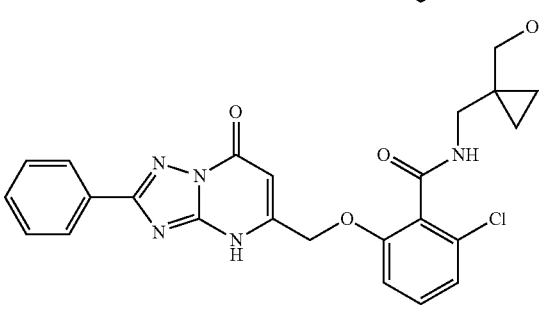

315
-continued
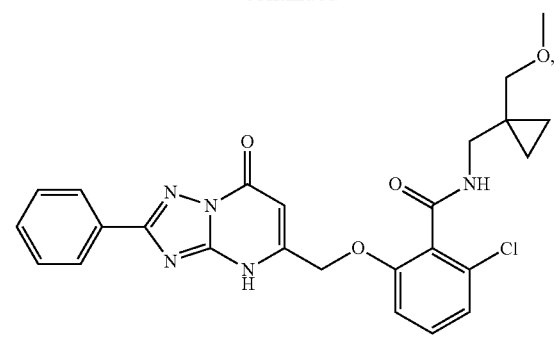
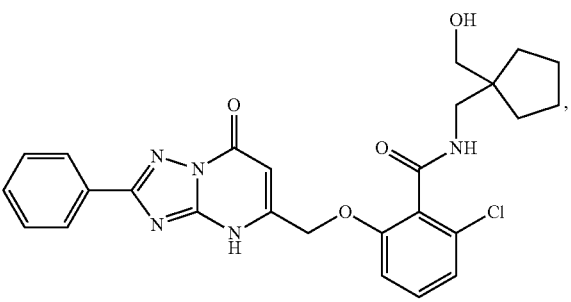
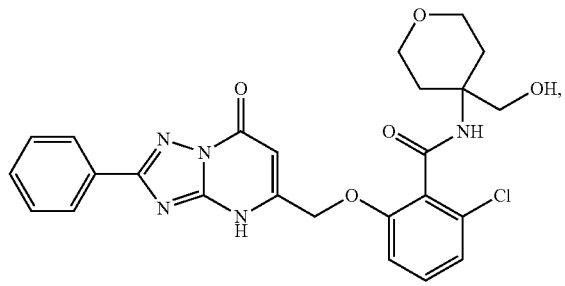
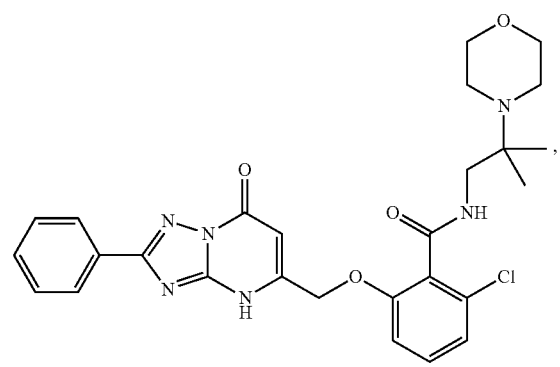
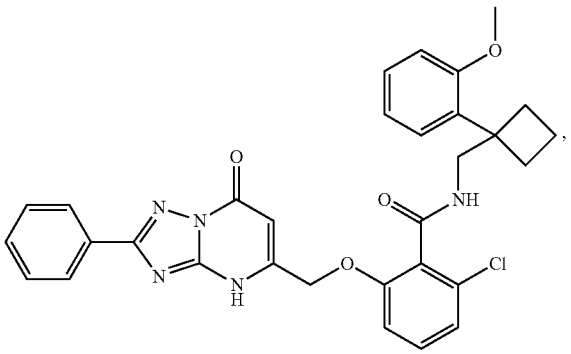
316
-continued
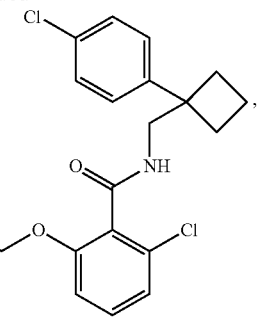
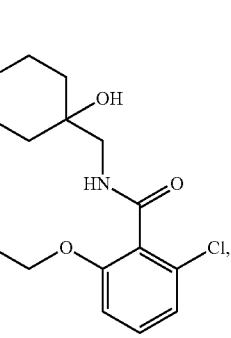
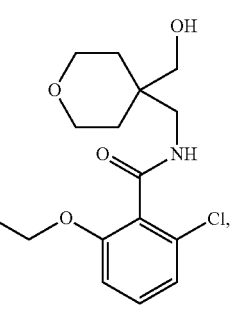
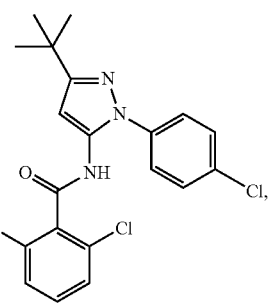
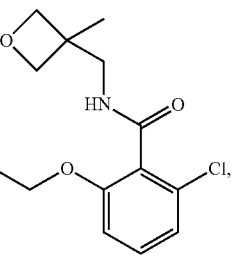

317
-continued
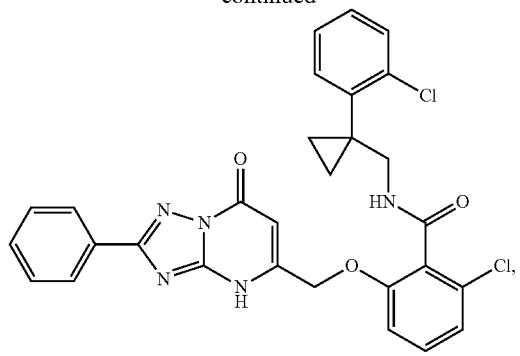
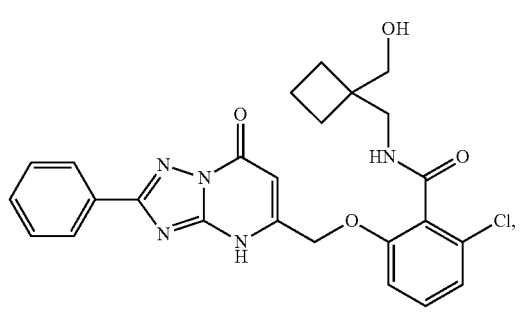
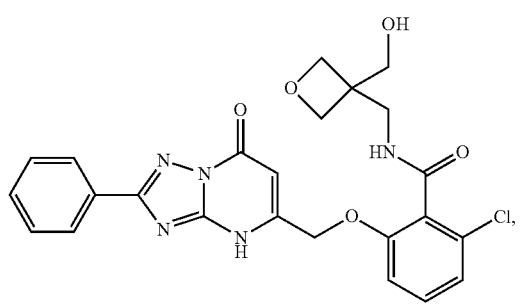
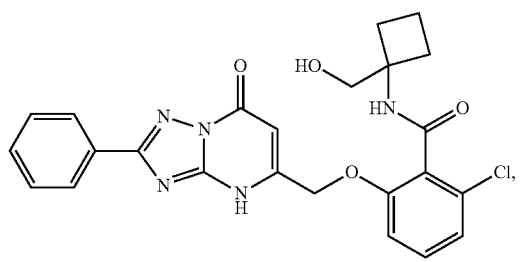
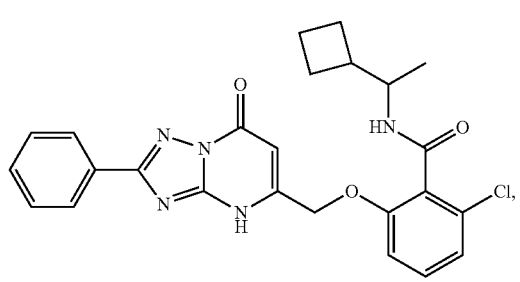
318
-continued
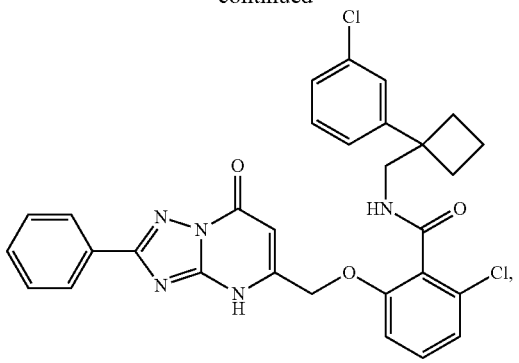
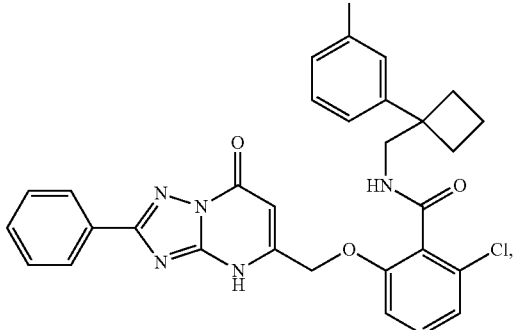
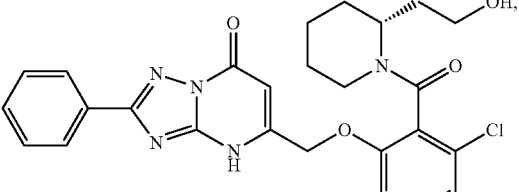
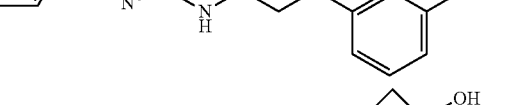
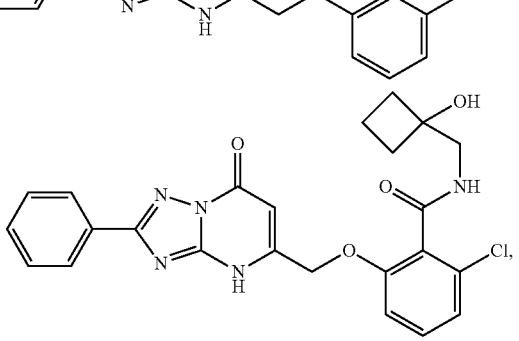
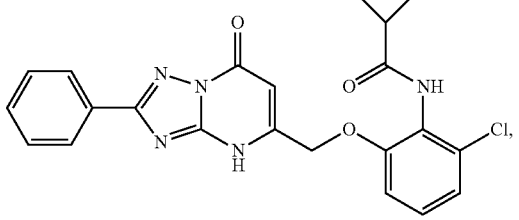

319
-continued
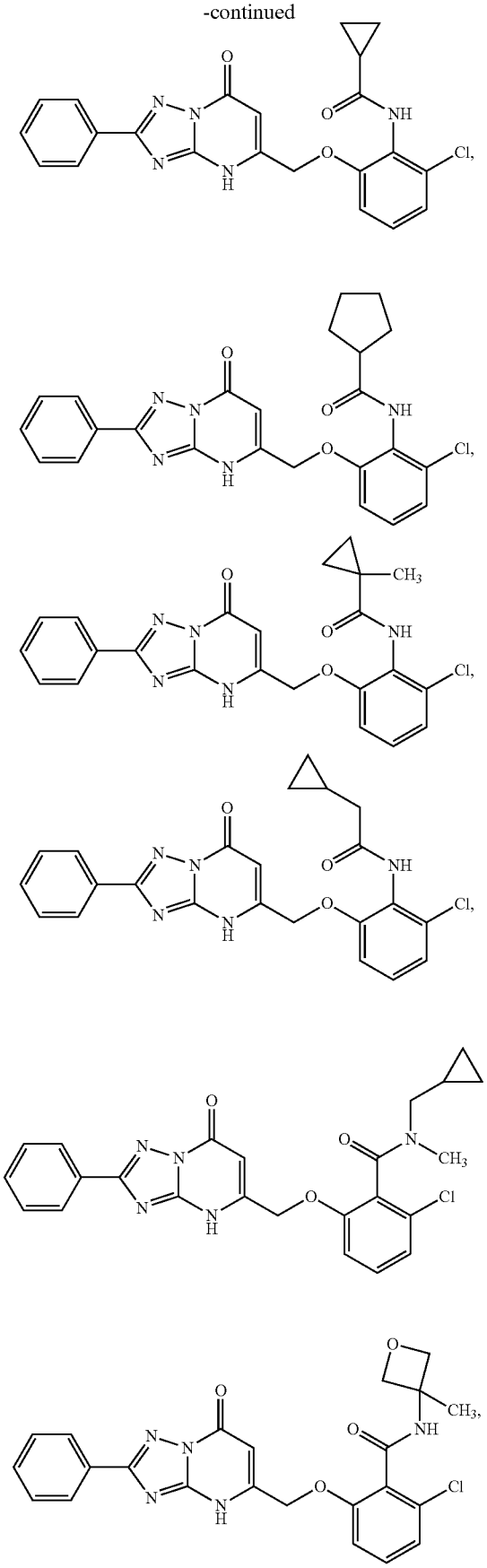
320
-continued
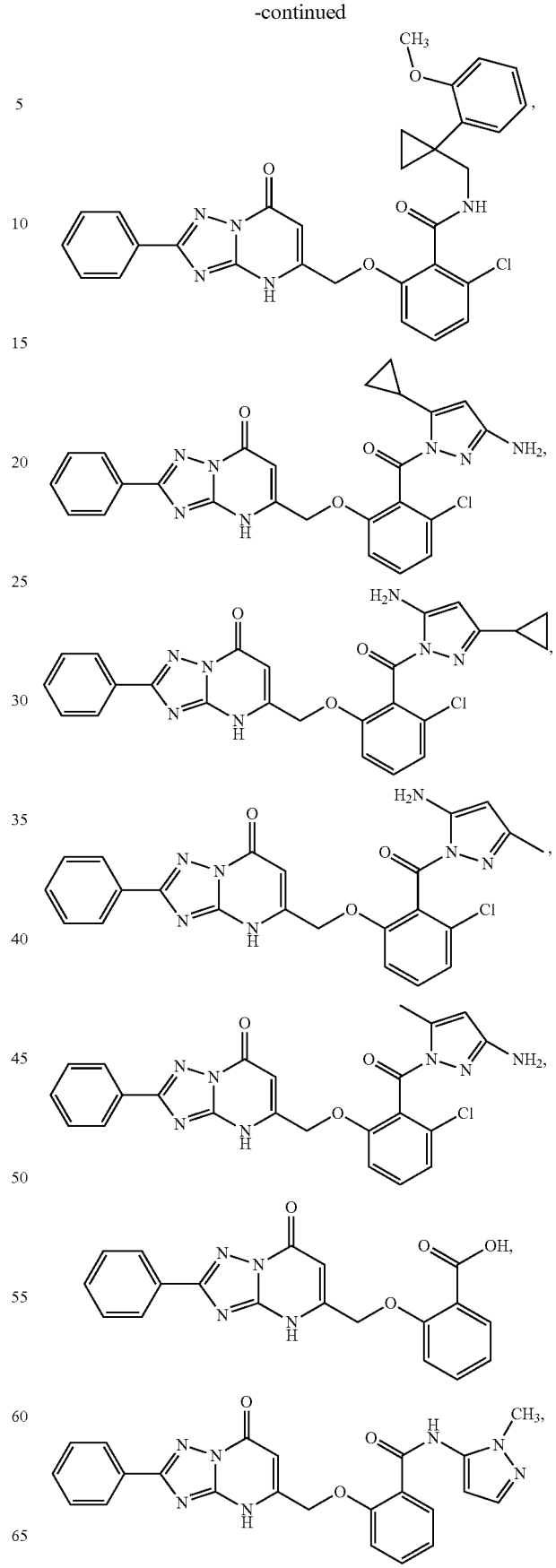

321
-continued
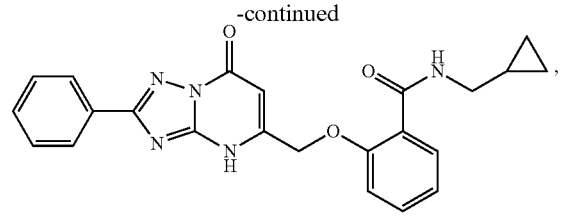
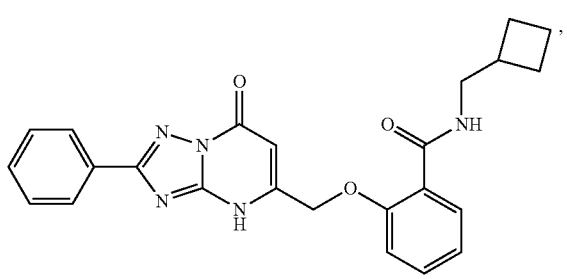
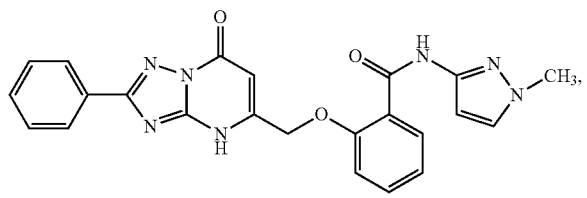
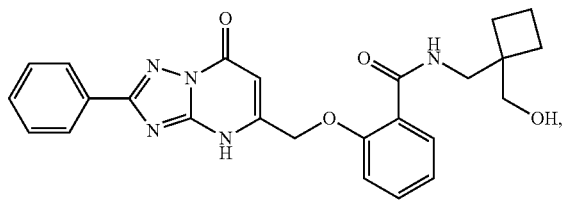
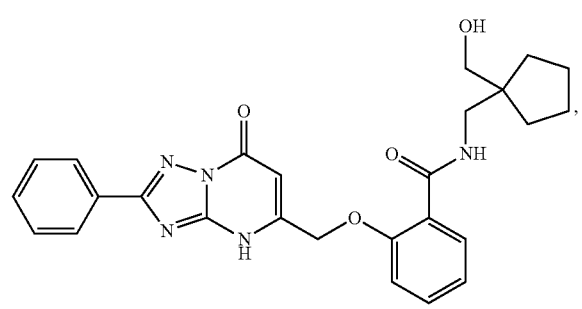
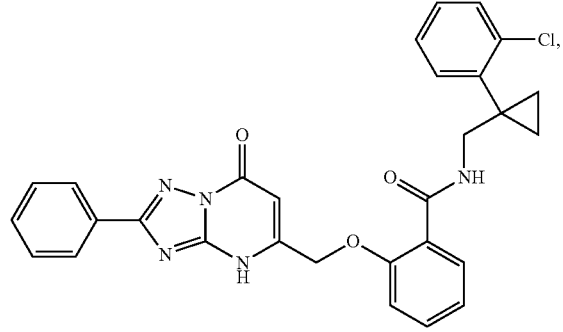
322
-continued
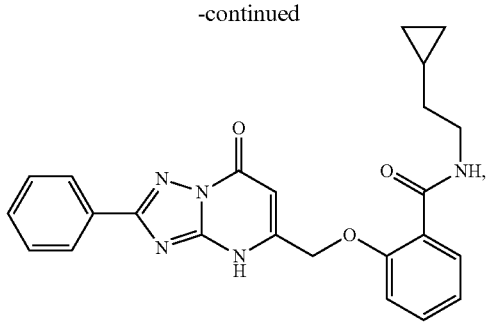
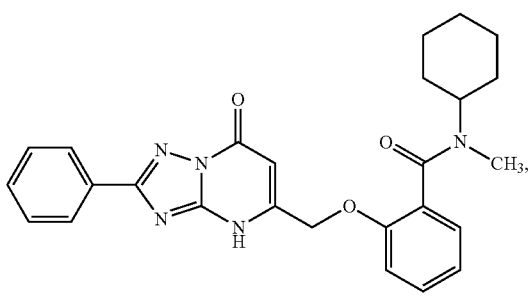
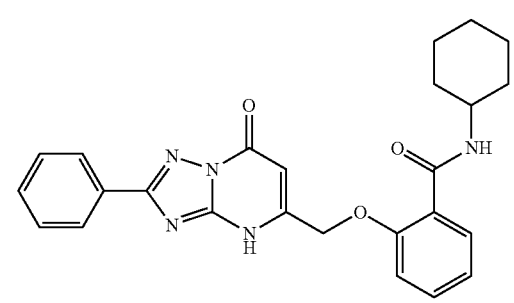
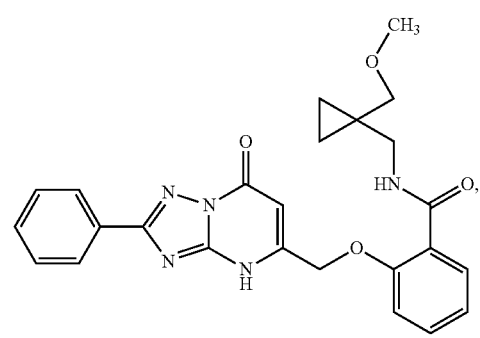
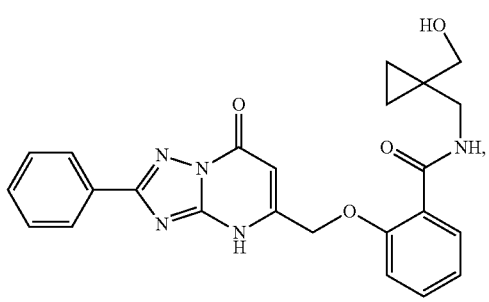

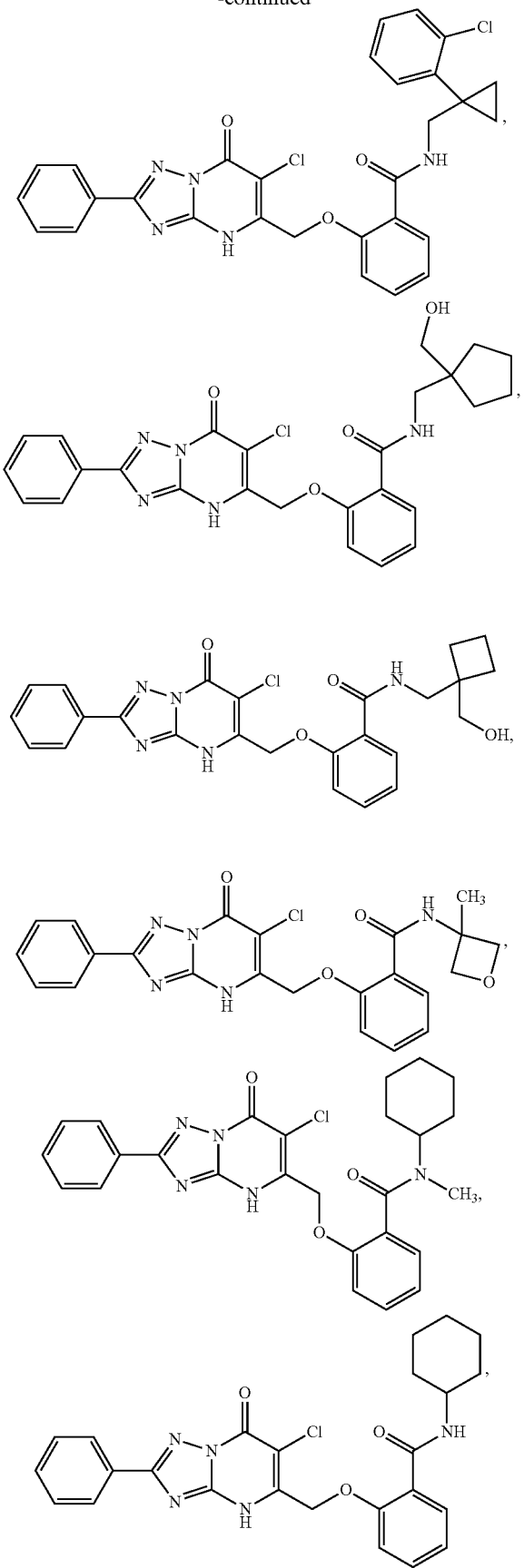
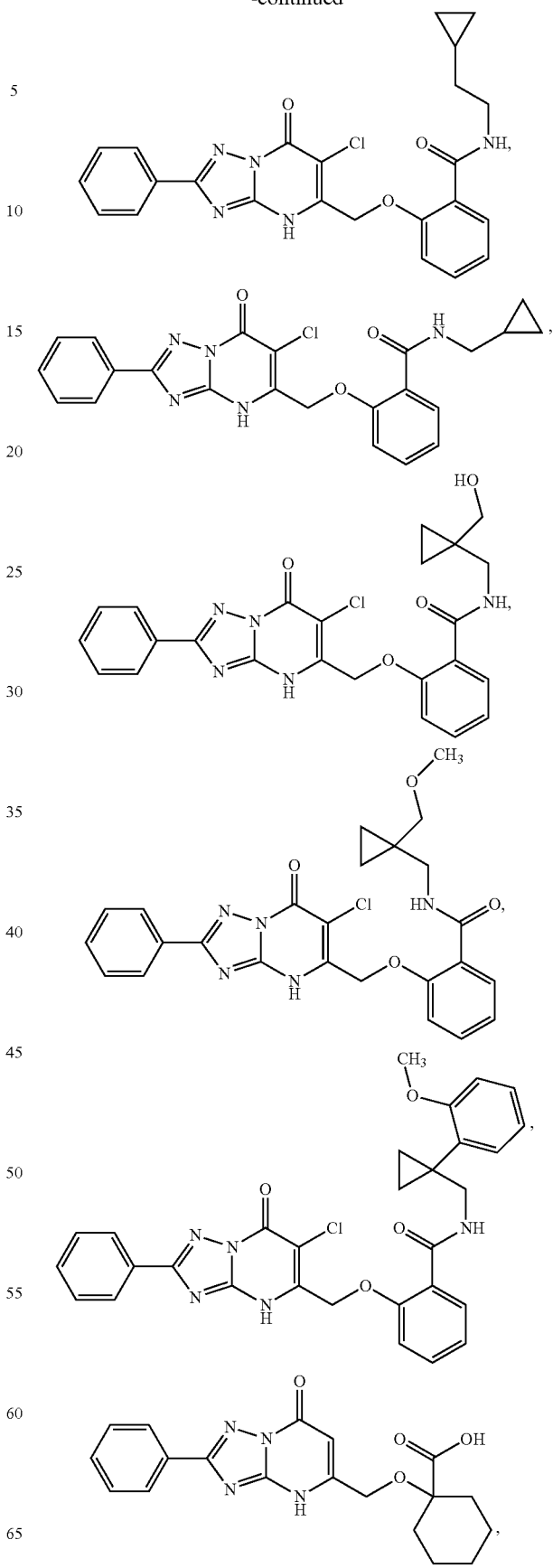

325
-continued
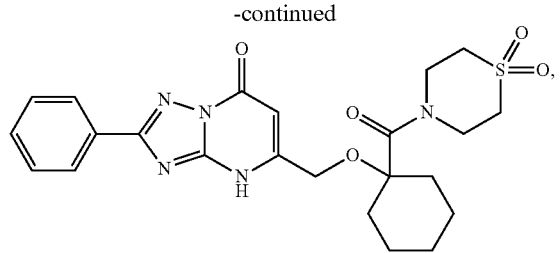
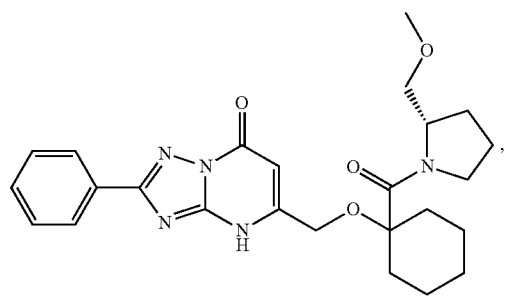
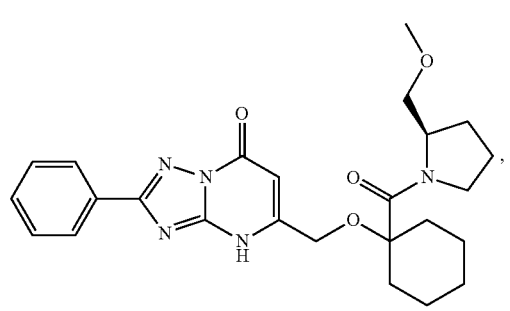
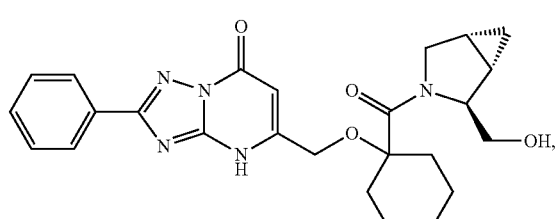
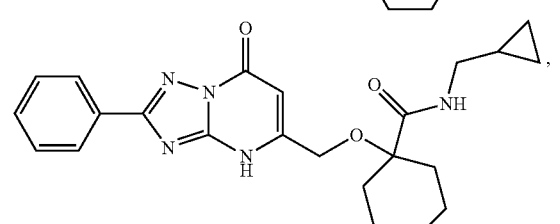
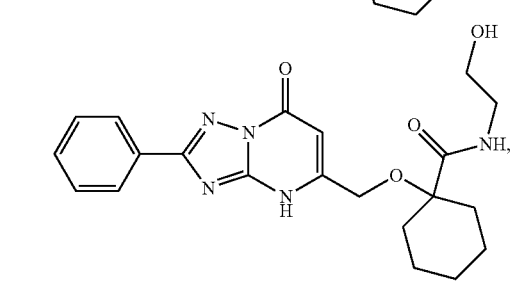
326
-continued
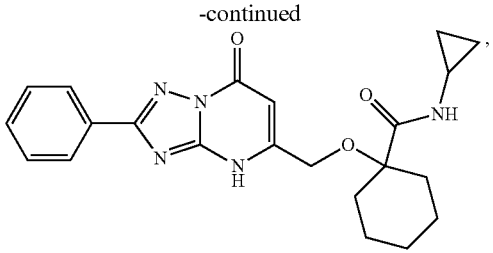
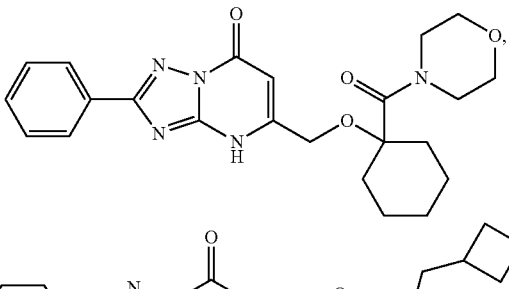
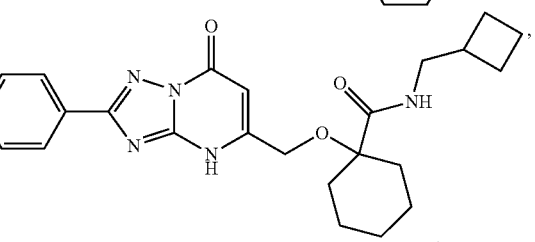
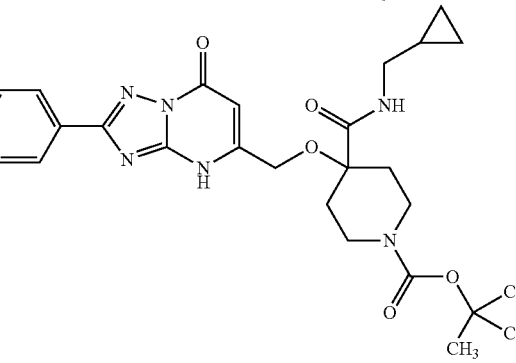
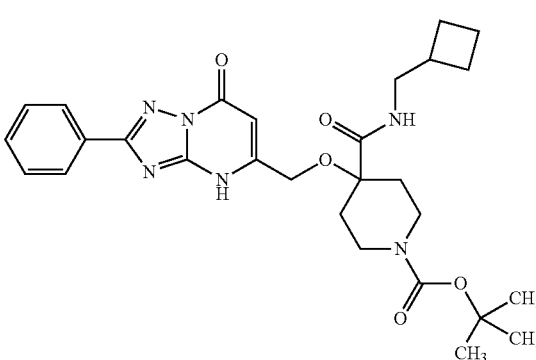
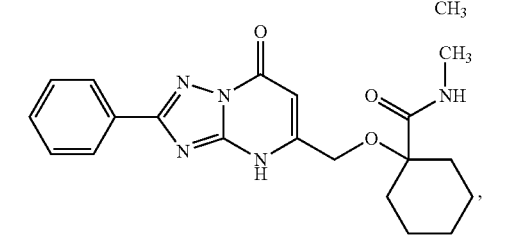

327
-continued
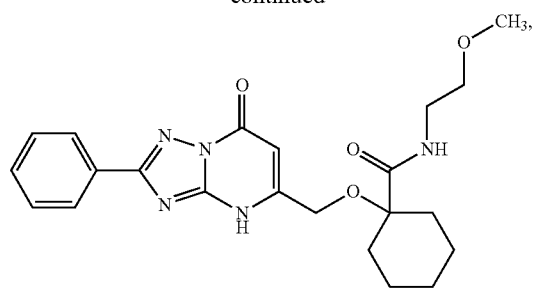
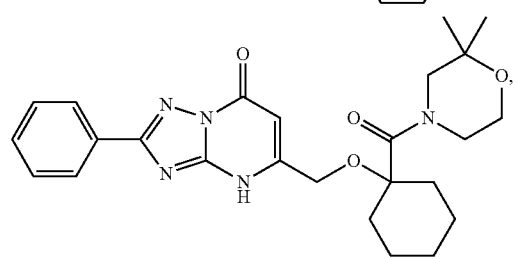
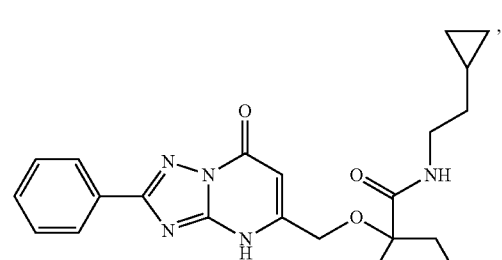
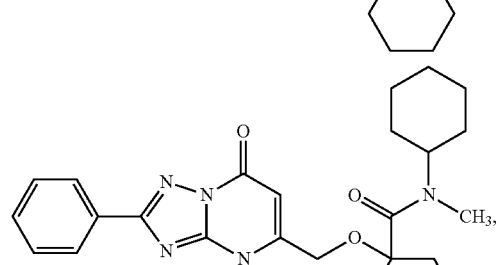
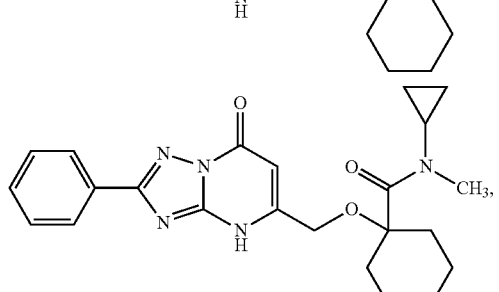
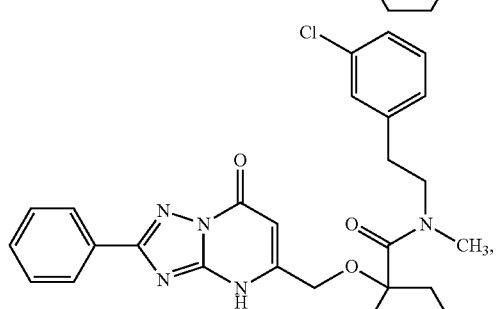
328
-continued
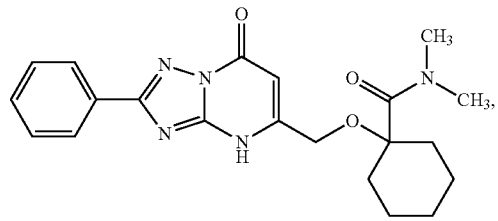
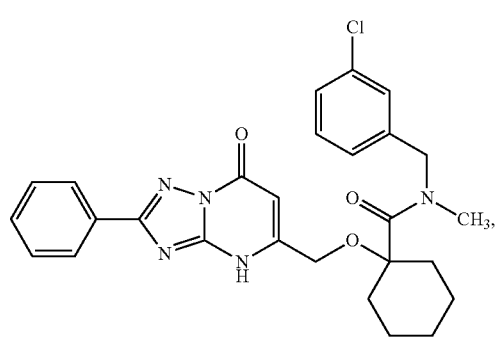
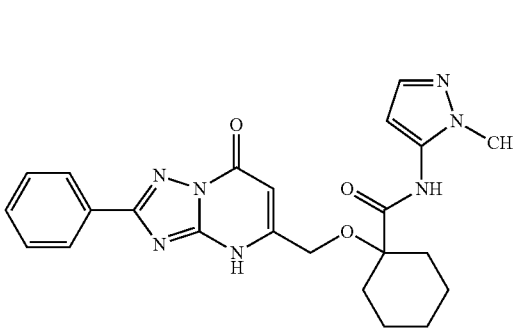
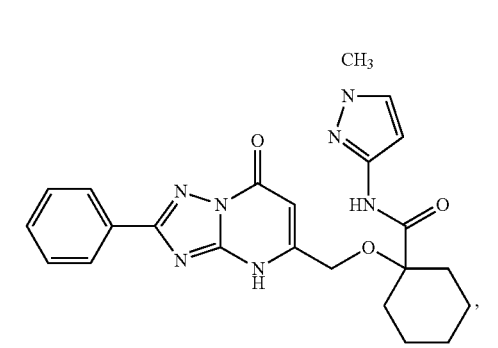
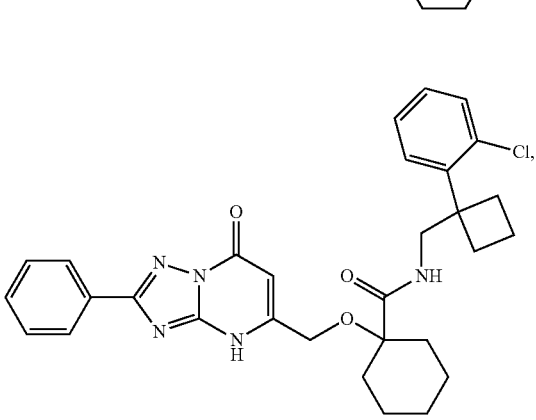

-continued
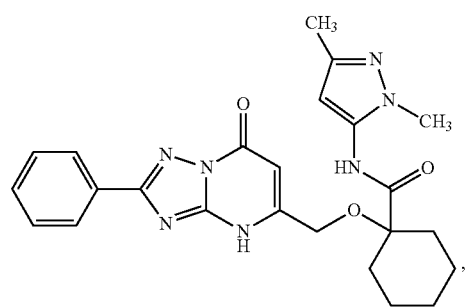
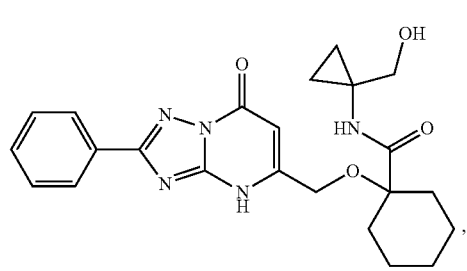
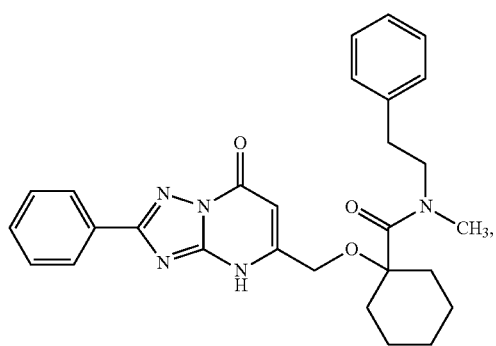
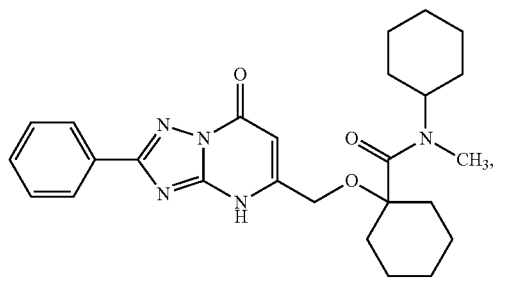
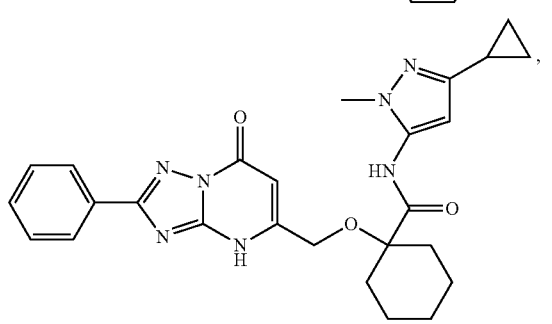
-continued
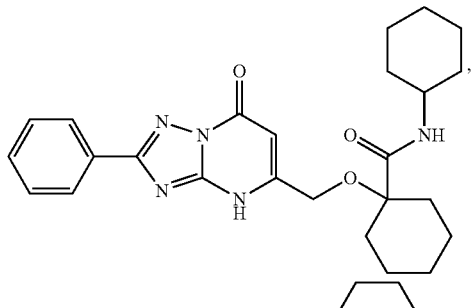
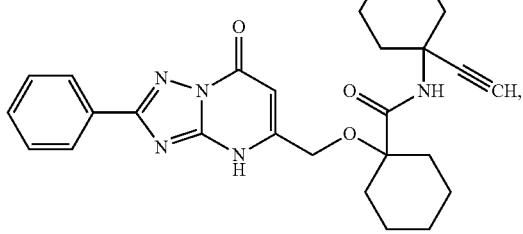
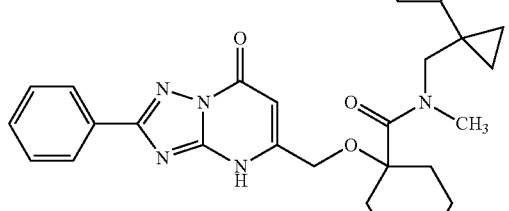
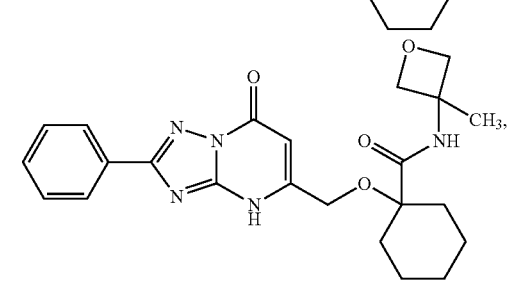
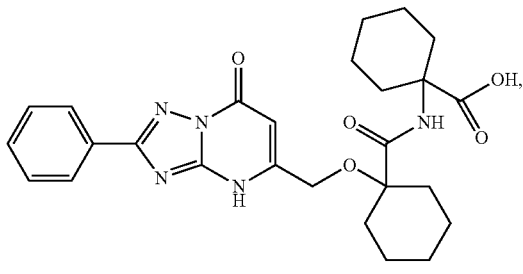
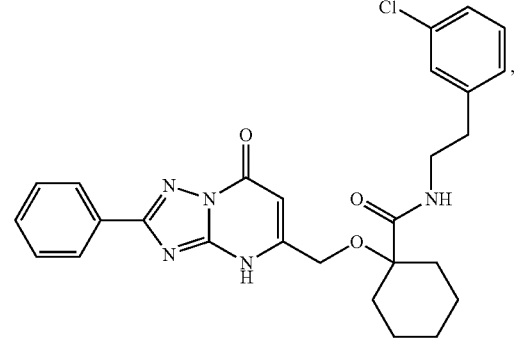

331
-continued
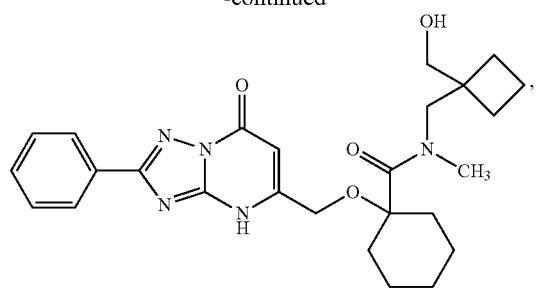
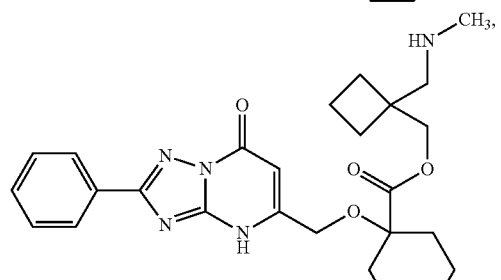
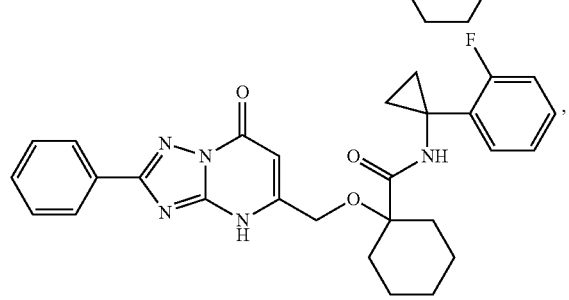
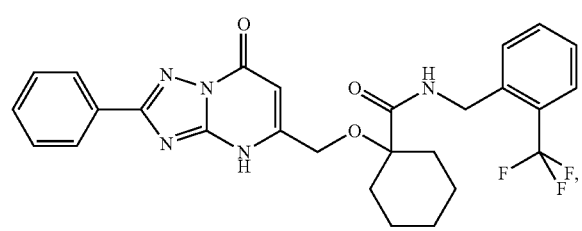
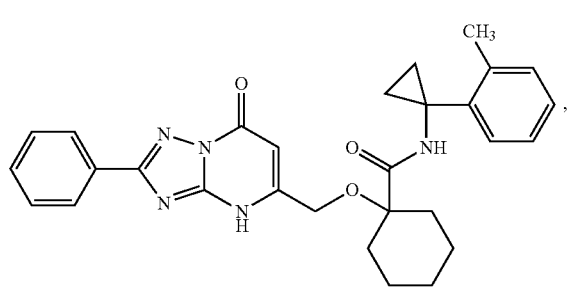
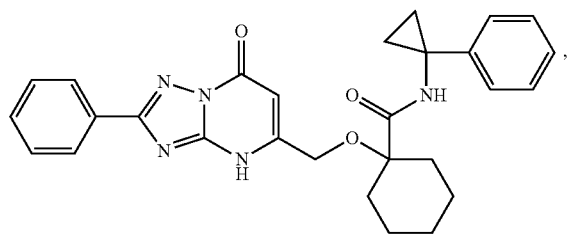
332
-continued
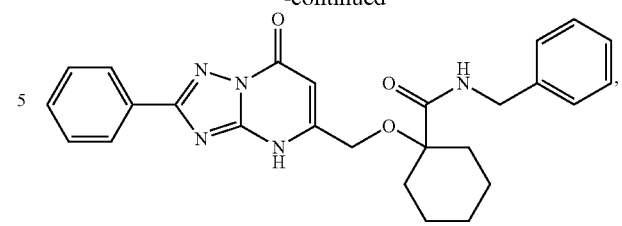
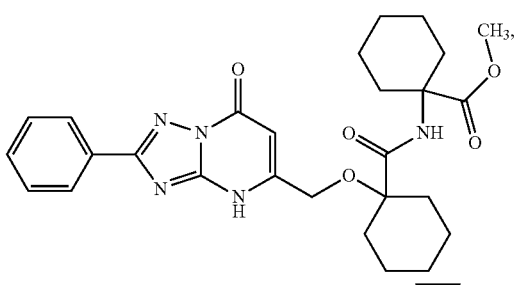
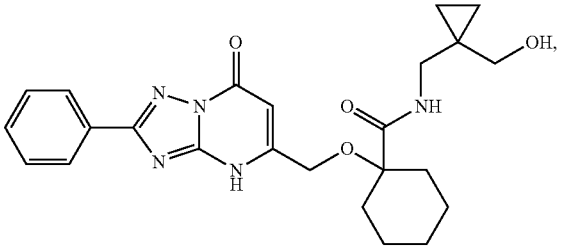
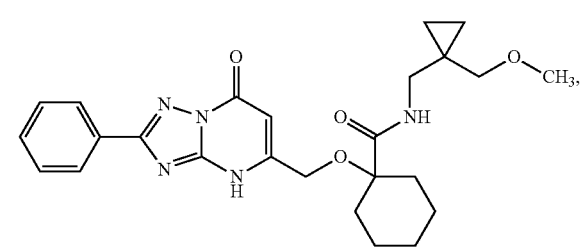
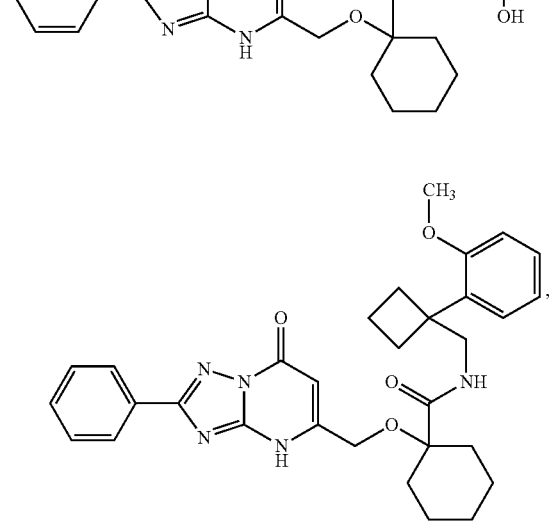

333
-continued
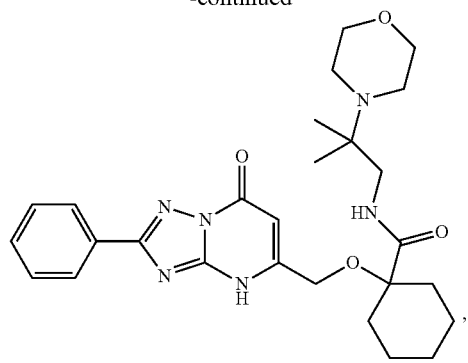
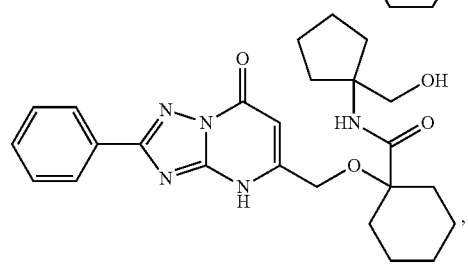
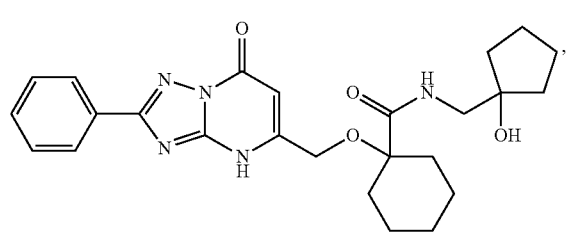
334
-continued
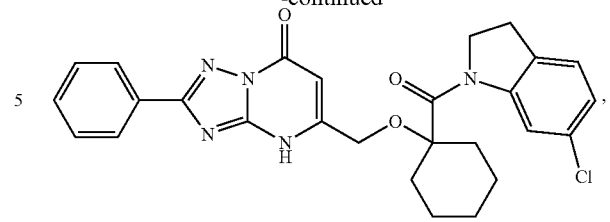
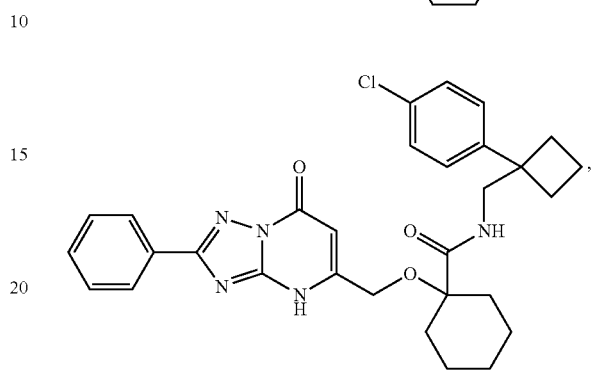
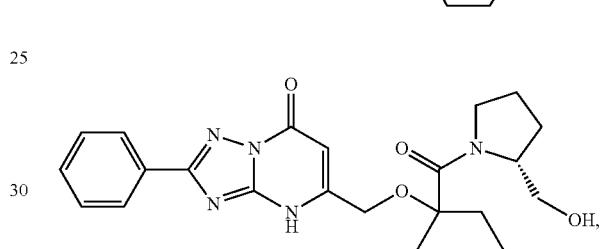
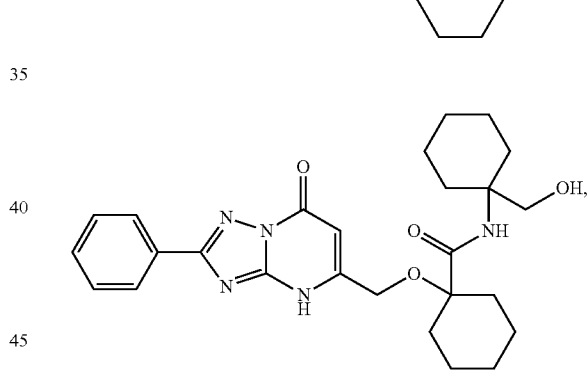
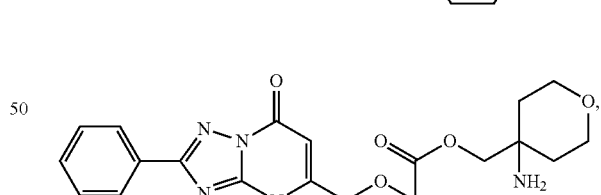
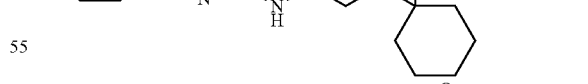
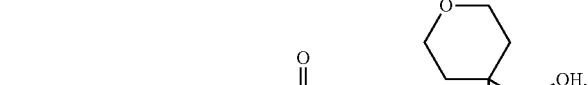

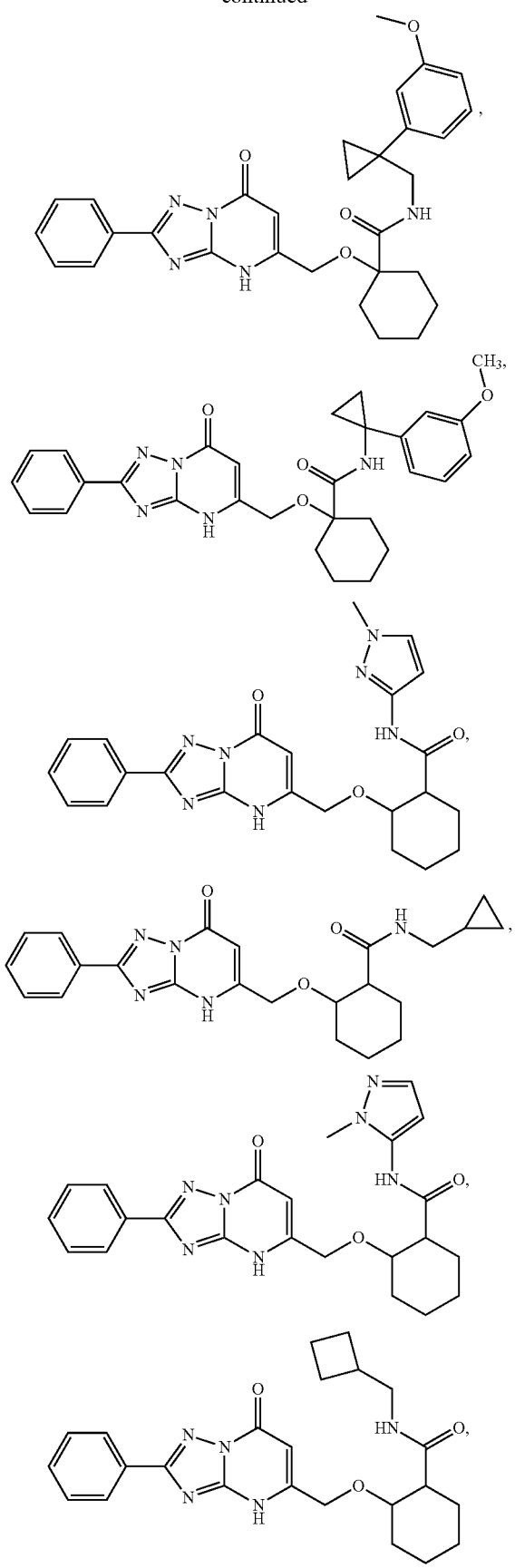
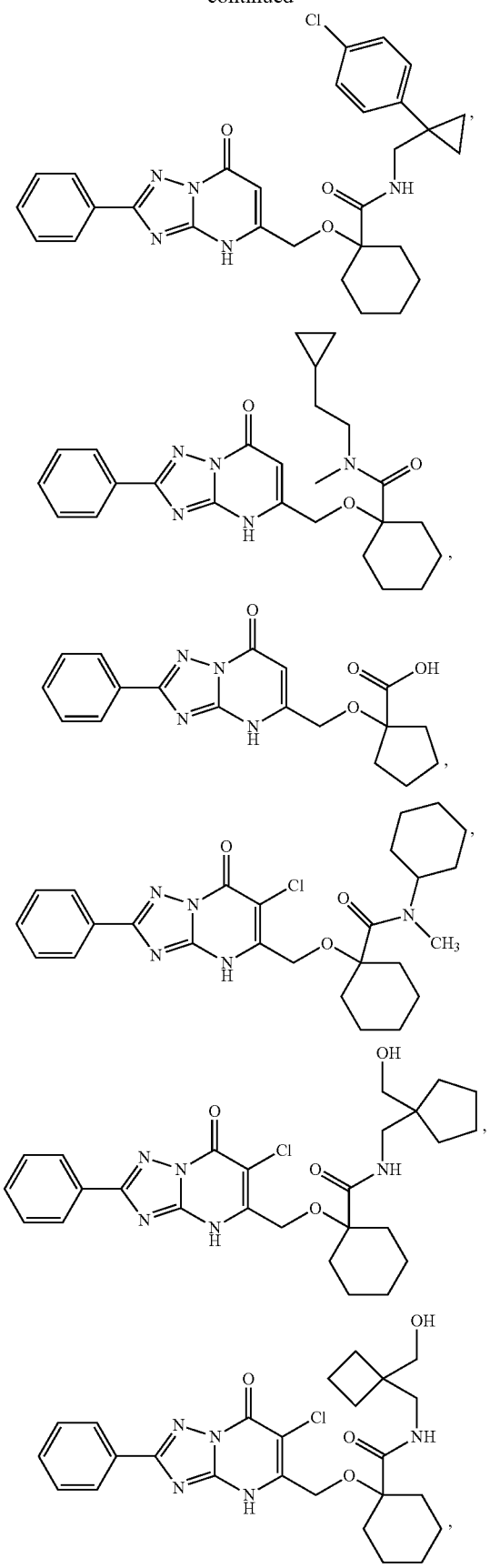

-continued

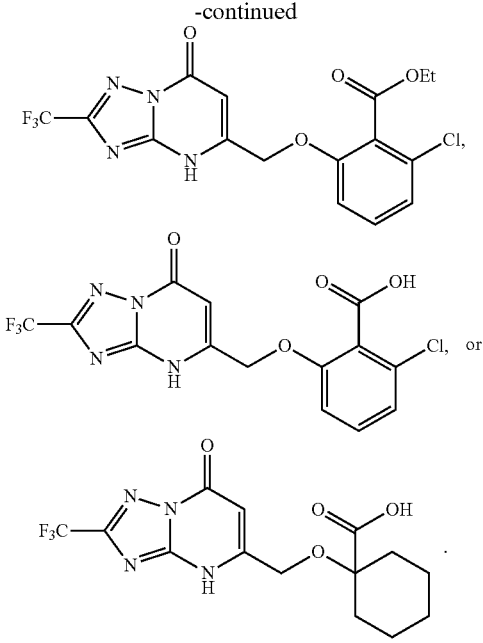

9. A pharmaceutical composition comprising an effective amount of at least one compound of claim 1 and a pharmaceutically acceptable carrier.

10. A pharmaceutical composition comprising an effective amount of at least one compound of claim 8 and a pharmaceutically acceptable carrier.

11. A compound, or a pharmaceutically acceptable salt of said compound, wherein the compound is:

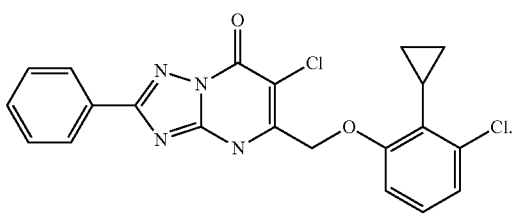 [SMILES: O=c1c(Cl)c(COc2cccc(Cl)c2C2CC2)[nH]c2nc(-c3ccccc3)nn12]

* * * * *